(12) United States Patent
Xiong et al.

(10) Patent No.: US 9,676,758 B2
(45) Date of Patent: Jun. 13, 2017

(54) 1-HETEROARYL-INDOLINE-4-CARBOXAMIDES AS MODULATORS OF GPR52 USEFUL FOR THE TREATMENT OR PREVENTION OF DISORDERS RELATED THERETO

(71) Applicant: Arena Pharmaceuticals, Inc., San Diego, CA (US)

(72) Inventors: Yifeng Xiong, San Diego, CA (US);
Andrew J. Grottick, Bonita, CA (US);
Henry Korman, Santee, CA (US);
Juerg Lehmann, San Diego, CA (US);
Albert S. Ren, San Diego, CA (US);
Graeme Semple, San Diego, CA (US);
Didier JC Bagnol, San Diego, CA (US)

(73) Assignee: Arena Pharmaceutical, Inc., San Diego, CA (US)

( * ) Notice: Subject to any disclaimer, the term of this patent is extended or adjusted under 35 U.S.C. 154(b) by 0 days.

(21) Appl. No.: 15/143,026

(22) Filed: Apr. 29, 2016

(65) Prior Publication Data

US 2016/0318911 A1    Nov. 3, 2016

Related U.S. Application Data

(60) Provisional application No. 62/154,523, filed on Apr. 29, 2015.

(51) Int. Cl.
| | | |
|---|---|---|
| C07D 405/14 | (2006.01) |
| C07D 403/04 | (2006.01) |
| C07D 413/14 | (2006.01) |
| C07D 401/14 | (2006.01) |
| C07D 401/04 | (2006.01) |

(52) U.S. Cl.
CPC ......... *C07D 405/14* (2013.01); *C07D 401/04* (2013.01); *C07D 401/14* (2013.01); *C07D 403/04* (2013.01); *C07D 413/14* (2013.01)

(58) Field of Classification Search
None
See application file for complete search history.

(56) References Cited

U.S. PATENT DOCUMENTS 8,309,721 B2 * 11/2012 Ruxer .................. C07D 401/04
544/331

FOREIGN PATENT DOCUMENTS

| EP | 2253618 A1 | 11/2010 |
| EP | 2298731 A1 | 3/2011 |
| WO | 2010018874 A1 | 2/2010 |
| WO | 2010149685 A1 | 12/2010 |

* cited by examiner

*Primary Examiner* — Brian J Davis
(74) *Attorney, Agent, or Firm* — McCarter & English, LLP; Steven G. Davis; Michael J. DeGrazia

(57) ABSTRACT

The present invention relates to compounds of Formula (Ia) and pharmaceutical compositions thereof that modulate the activity of GPR52. Compounds of the present invention and pharmaceutical compositions thereof are directed to methods useful in the treatment of a GPR52-mediated disorder (e.g., Huntington's disease, schizophrenia, bipolar disorder, attention deficit hyperactivity disorder (ADHD), or Tourette's syndrome); an extrapyramidal or movement disorder; a motor disorder; a hyperkinetic movement disorder; a psychotic disorder; catatonia; a mood disorder; a depressive disorder; an anxiety disorder; obsessive-compulsive disorder (OCD); an autism spectrum disorder; a prolactin-related disorder (e.g., hyperprolactinemia); a neurocognitive disorder; a trauma- or stressor-related disorder (e.g., post-traumatic stress disorder (PTSD)); a disruptive, impulse-control, or conduct disorder; a sleep-wake disorder; a substance-related disorder; an addictive disorder; a behavioral disorder; hypofrontality; an abnormality in the tuberoinfundibular, mesolimbic, mesocortical, or nigrostriatal pathway; decreased activity in the striatum; cortical dysfunction; neurocognitive dysfunction; and conditions related thereto.

41 Claims, 34 Drawing Sheets

General Synthetic Scheme for the Preparation of Certain Compounds of Formula (Ia) Wherein Y is -CH$_2$- and Ring A is Pyridinyl

Method D

General Synthetic Scheme for the Preparation of Certain Compounds of Formula (Ia) Wherein Y is -CH$_2$- and Ring A is Pyridinyl

General Synthetic Scheme for the Preparation of Certain Compounds of Formula (Ia) Wherein Y is -CH$_2$- and Ring A is Pyridinyl

General Synthetic Scheme for the Preparation of Certain Compounds of Formula (Ia) Wherein Y is -CH$_2$- and Ring A is Pyrazinyl General Synthetic Scheme for the Preparation of *N*-Oxides of Compounds of Formula (Ia)

Distribution and Relative Expression Levels of GPR52 mRNA in the
Cerebral Cortex and Striatum in the Rat Brain

| Structure name | Intensity | Structure name | Intensity | Structure name | Intensity |
|---|---|---|---|---|---|
| Cerebral cortex | | | | Striatum | |
| anterior olfactory nucleus | ++ | prelimbic cortex | ++ | accumbens nucleus, core | +++ |
| cingulate cortex | ++ | primary auditory cortex | ++ | accumbens nucleus, shell | +++ |
| claustrum | ++ | primary motor cortex | ++ | caudate putamen (striatum) | +++ |
| dysgranular insular cortex | + | primary somatosensory cortex | + | entopeduncular nucleus | + |
| entorhinal cortex | ++ | primary visual cortex | + | globus pallidus | + |
| granular insular cortex | ++ | retrosplenial dysgranular cortex | + | | |
| infralimbic cortex | ++ | retrosplenial granular cortex | ++ | | |
| islands of Calleja | ++ | secondary auditory cortex | ++ | | |
| lateral orbital cortex | ++ | secondary motor cortex | ++ | | |
| olfactory tubercle | +++ | secondary somatosensory cortex | + | | |
| parietal association cortex | + | temporal association cortex | ++ | | |
| perirhinal cortex | + | ventral orbital cortex | ++ | | |
| piriform cortex | ++ | | | | |

Brain structure names are based on the rat brain in stereotaxic coordinates (G. Paxinos and C. Watson, *The Rat Brain in Stereotaxic Coordinates*, 6th ed., 2007, Academic Press).

+ = low level of expression
++ = moderate level of expression
+++ = strong level of expression

FIGURE 15A

Distribution and Relative Expression Levels of GPR52 mRNA in the Hippocampus & Septum and Thalamus & Bed Nucleus of the Stria Terminalis in the Rat Brain

| Structure name | Intensity | Structure name | Intensity |
|---|---|---|---|
| Hippocampus & Septum | | Thalamus & Bed Nucleus of the Stria Terminalis | |
| dorsal pedoncular cortex | ++ | anteromedial thalamic nucleus | + |
| dorsal subiculum | ++ | centrolateral thalamic nucleus | + |
| field CA1 of the hippocampus | + | central medial thalamic nucleus | + |
| field CA2 of the hippocampus | + | laterodorsal thalamic nucleus, ventrolateral part | + |
| field CA3 of the hippocampus | + | lateral habenular nucleus | ++ |
| granular layer of the dentate gyrus | + | mediodorsal thalamic nucleus, lateral part | + |
| indusium Griseum | ++ | medial habenular nucleus | +++ |
| lateral septal nucleus | + | paraventricular thalamic nucleus | ++ |
| medial septal nucleus | + | reuniens thalamic nucleus | ++ |
| polymorph layer of the dentate gyrus | + | rhomboid thalamic nucleus | + |
| postsubiculum | ++ | reticular thalamic nucleus | ++ |
| presubiculum | ++ | ventral anterior thalamic nucleus | + |
| pyramidal cell layer of the hippocampus | + | ventromedial thalamic nucleus | + |

Brain structure names are based on the rat brain in stereotaxic coordinates (*G. Paxinos and C. Watson, The Rat Brain in Stereotaxic Coordinates, 6th ed., 2007, Academic Press*).

+ = low level of expression
++ = moderate level of expression
+++ = strong level of expression

FIGURE 15B

Distribution and Relative Expression Levels of GPR52 mRNA in the Hypothalamus and Amygdala in the Rat Brain

| Structure name | Intensity | Structure name | Intensity |
|---|---|---|---|
| Hypothalamus | | Amygdala | |
| anterior hypothalamic area | + | anterior amygdaloid area | ++ |
| arcuate hypothalamic nucleus | + | amygdalopiriform transition | ++ |
| dorsomedial hypothalamic nucleus | + | amygdalohippocampal area, posterolateral part | +++ |
| lateral hypothalamus | + | amygdalohippocampal area, posteromedial part | ++ |
| medial preoptic area | + | basolateral amygdaloid nucleus, anterior part | ++ |
| medial preoptic nucleus | +++ | basomedial amygdaloid nucleus, anterior part | ++ |
| medial mammillary nucleus, lateral part | +++ | basomedial amygdaloid nucleus, posterior part | ++ |
| medial mammillary nucleus, medial part | + | central amygdaloid nucleus | + |
| medial mammillary nucleus, median part | + | lateral amygdaloid nucleus, dorsolateral part | ++ |
| paraventricular hypothalamic nucleus | + | lateral amygdaloid nucleus, ventrolateral part | ++ |
| periventricular hypothalamic nucleus | ++ | lateral amygdaloid nucleus, ventromedial part | ++ |
| subthalamic nucleus | + | medial amygdaloid nucleus, anterodorsal part | + |
| suprachiasmatic nucleus | ++ | medial amygdaloid nucleus, anteroventral part | + |
| premammillary nucleus, dorsal part | ++ | medial amygdaloid nucleus, posterodorsal part | + |
| premammillary nucleus, ventral part | + | medial amygdaloid nucleus, posteroventral part | + |
| ventromedial hypothalamic nucleus | | posterolateral cortical amygdaloid nucleus | +++ |
| zona incerta | | posteromedial cortical amygdaloid nucleus | +++ |

Brain structure names are based on the rat brain in stereotaxic coordinates (*G. Paxinos and C. Watson, The Rat Brain in Stereotaxic Coordinates, 6th ed., 2007, Academic Press*).

+ = low level of expression, ++ = moderate level of expression, +++ = strong level of expression

FIGURE 15C

Distribution and Relative Expression Levels of GPR52 mRNA in the Midbrain, Pons & Medulla Oblongata and Cerebellum in the Rat Brain

| Structure name | Intensity | Structure name | Intensity |
|---|---|---|---|
| Midbrain, Pons & Medulla Oblongata | | Cerebellum | |
| lateral periaqueductal grey | + | All lobules | ++ |
| medial vestibular nucleus, parvicellular part | + | | |
| prepositus nucleus | + | | |
| substantia nigra, compact part | + | | |
| substantia nigra, reticular part | + | | |

Brain structure names are based on the rat brain in stereotaxic coordinates (*G. Paxinos and C. Watson, The Rat Brain in Stereotaxic Coordinates, 6th ed., 2007, Academic Press*).

+ = low level of expression
++ = moderate level of expression
+++ = strong level of expression

FIGURE 15D

Comparison of GPR52 mRNA Expression in Rat and Mouse Brain

| Structure name | Rat | Mouse | Structure name | Rat | Mouse |
|---|---|---|---|---|---|
| Cerebral cortex | | | Striatum | | |
| auditory cortex | ++ | + | accumbens nucleus | +++ | ++ |
| cingulate cortex | ++ | + | caudate putamen (striatum) | +++ | +++ |
| claustrum | ++ | ++ | Hippocampus & Septum | | |
| entorhinal cortex | ++ | ++ | field CA1-CA3 of the hippocampus | + | + |
| lateral orbital cortex | ++ | + | dorsal subiculum | ++ | + |
| limbic cortex | ++ | + | dentate gyrus | + | + |
| motor cortex | ++ | ++ | lateral septum | + | + |
| olfactory nucleus | ++ | ++ | presubiculum | ++ | ++ |
| olfactory tubercle | +++ | +++ | ventral subiculum | +++ | ++ |
| orbital cortex | ++ | + | Thalamus & Bed nucleus of the stria terminalis | | |
| parietal association cortex | + | + | centrolateral thalamic nucleus | + | + |
| perirhinal cortex | + | + | lateral habenular nucleus | ++ | ++ |
| piriform cortex | ++ | + | medial habenular nucleus | +++ | +++ |
| retrosplenial cortex | + | + | paraventricular thalamic nucleus | ++ | +++ |
| retrosplenial cortex | ++ | + | reuniens thalamic nucleus | ++ | + |
| somatosensory cortex | + | + | reticular thalamic nucleus | ++ | + |

Brain structure names are based on the rat brain in stereotaxic coordinates (G. Paxinos and C. Watson, *The Rat Brain in Stereotaxic Coordinates*, 6th ed., 2007, Academic Press).

+ = low level of expression
++ = moderate level of expression
+++ = strong level of expression

FIGURE 16A

Comparison of GPR52 mRNA Expression in Rat and Mouse Brain

| Structure name | Rat | Mouse | Structure name | Rat | Mouse |
|---|---|---|---|---|---|
| Hypothalamus | | | Amygdala | | |
| arcuate hypothalamic nucleus | + | +++ | amygdalohippocampal area | ++ | ++ |
| lateral hypothalamus | + | + | basolateral amygdaloid nucleus | ++ | ++ |
| medial mammillary nucleus, lateral part | +++ | +++ | basomedial amygdaloid nucleus | ++ | ++ |
| medial mammillary nucleus, medial part | +++ | + | lateral amygdaloid nucleus | ++ | + |
| ventromedial hypothalamic nucleus | + | + | posteromedial cortical amygdaloid nucleus | +++ | +++ |
| zona incerta | ++ | + | Midbrain, Pons & Medulla Oblongata | | |
| premammillary nucleus, dorsal part | ++ | + | lateral periaqueductal grey | + | + |
| premammillary nucleus, ventral part | ++ | +++ | substantia nigra | + | + |
| | | | Cerebellum | | |
| | | | All lobules | ++ | ++ |

Brain structure names are based on the rat brain in stereotaxic coordinates (*G. Paxinos and C. Watson, The Rat Brain in Stereotaxic Coordinates, 6th ed., 2007, Academic Press*).

+ = low level of expression
++ = moderate level of expression
+++ = strong level of expression

FIGURE 16B

Expression of GPR52 mRNA in Regions of the Human Brain

| Brain Structure | mRNA Intensity | Brain Structure | mRNA Intensity |
|---|---|---|---|
| Cortex | | Hypothalamus | |
| gyrus rectus | + | dorsomedial hypothalamic nucleus | + |
| medial orbital gyrus | + | lateral hypothalamic area | + |
| insular gyrus | + | medial mammillary nucleus, medial part | + |
| cingulate gyrus | + | perifornical nucleus | + |
| superior temporal gyrus | + | posterior hypothalamic area | + |
| inferior frontal gyrus | + | ventromedial hypothalamic nucleus | + |
| Striatum | | Hippocampus | |
| accumbens nuc., central (subventricular) part (core) | +++ | dentate gyrus | + |
| accumbens nuc., lateral (subventricular) part (core) | +++ | | |
| accumbens nuc., medial (subventricular) part (shell) | +++ | | |
| caudate fundus region | +++ | | |
| medial caudate nucleus | ++ | | |
| medial putamen dorsal part | + | | |
| lateral caudate nucleus | + | | |
| putaminal fundus region | +++ | | |

Brain structure names are based on the atlas of the human brain (Jürgen K. Mei, J. Assheneur and G. Paxinos, *Atlas of the Human Brain, 2nd ed.*, 2004, Academic Press).

+ = low level of expression
++ = moderate level of expression
+++ = strong level of expression

FIGURE 17

Percentage of Neurons Co-Expressing GPR52 and either GAD1, vGlut1, DRD1 or DRD2 in Rat and Human Brain

| | | Rat | Human |
|---|---|---|---|
| Striatum | | | |
| GPR52 | DRD2 | +++ | +++ |
| GPR52 | DRD1 | 0 | + |
| Frontal Cortex | | | |
| GPR52 | DRD2 | N.D. | + |
| GPR52 | DRD1 | +++ | ++ |
| GPR52 | vGlut1 | +++ | +++ |
| GPR52 | GAD1 | N.D. | ++ |
| vGlut1 | GPR52 | N.D. | +++ |
| GAD1 | GPR52 | N.D. | + |

0 = no co-expression
+ = low co-expression (5%-35%)
++ = moderate co-expression (35%-70%)
+++ = strong co-expression (70%-100%)
N.D. = not determined

FIGURE 18

Measurements of Intracellular Signaling in the Cortex and Striatum Following the Administration of Compound 13 in Mice

|  | ACUTE | | SUBCHRONIC | |
|---|---|---|---|---|
|  | CORTEX | STRIATUM | CORTEX | STRIATUM |
| PKA | ↑ | ↑ | N.D. | N.D. |
| c-fos | ↑ | ↑ | - | - |
| zif 268 | ↑ | ↑ | ↑ | ↑ |
| Neurotensin | N.D. | ↑ | N.D. | ↑ |
| PP2A$_C$ | - | ↑ | - | ↑ |
| pDARPP(Thr34) | N.D. | ↑ | N.D. | - |
| pCREBs133 | ↑ | ↑ | N.D. | N.D. |
| Key: N.D. = not determined, - = no change, ↑ = increased | | | | |

FIGURE 19

Intracellular Signaling Events Following Administration of Compound 13 to Mice

The Effect of Compound 13 on Amphetamine-Stimulated Locomotion in Rats

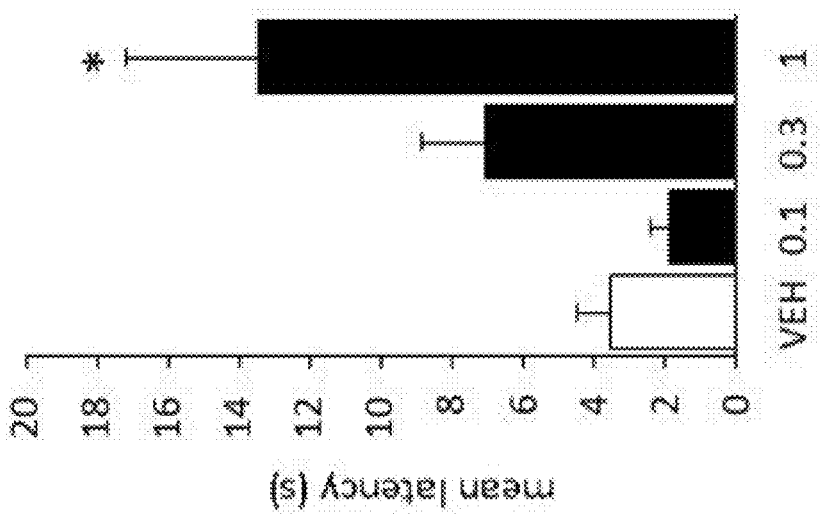
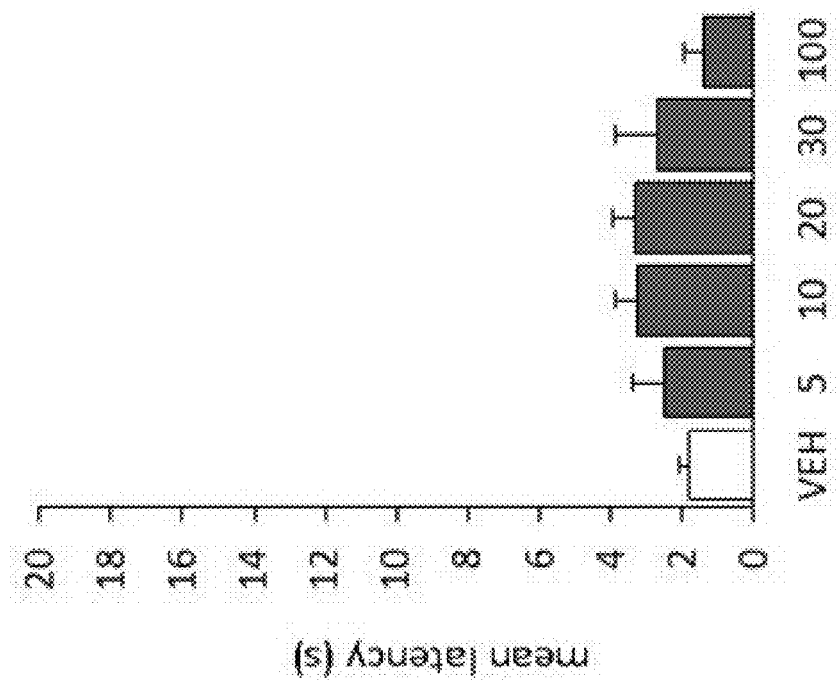
Figure 27A
Figure 27B
Measurement of Catalepsy in Rats Following Administration of Haloperidol and Compound 13

1-HETEROARYL-INDOLINE-4-CARBOXAMIDES AS MODULATORS OF GPR52 USEFUL FOR THE TREATMENT OR PREVENTION OF DISORDERS RELATED THERETO

RELATED APPLICATIONS

This application claims the benefit under 35 U.S.C §119(e) of U.S. Provisional Patent Application No. 62/154,523, filed Apr. 29, 2015. The contents of the foregoing application is hereby incorporated by reference in its entirety.

FIELD OF THE INVENTION

The present invention relates to compounds of Formula (Ia) and pharmaceutical compositions thereof that modulate the activity of GPR52. Compounds of the present invention and pharmaceutical compositions thereof are directed to methods useful in the treatment of a GPR52-mediated disorder (e.g., Huntington's disease, schizophrenia, bipolar disorder, attention deficit hyperactivity disorder (ADHD), or Tourette's syndrome); an extrapyramidal or movement disorder; a motor disorder; a hyperkinetic movement disorder; a psychotic disorder; catatonia; a mood disorder; a depressive disorder; an anxiety disorder; obsessive-compulsive disorder (OCD); an autism spectrum disorder; a prolactin-related disorder (e.g., hyperprolactinemia); a neurocognitive disorder; a trauma- or stressor-related disorder (e.g., post-traumatic stress disorder (PTSD)); a disruptive, impulse-control, or conduct disorder; a sleep-wake disorder; a substance-related disorder; an addictive disorder; a behavioral disorder; hypofrontality; an abnormality in the tuberoinfundibular, mesolimbic, mesocortical, or nigrostriatal pathway; decreased activity in the striatum; cortical dysfunction; neurocognitive dysfunction; and conditions related thereto.

BACKGROUND OF THE INVENTION

Dopamine is a biogenic amine present in the central nervous system (CNS), where it acts as a neurotransmitter. Dopamine exerts its effects by acting via five distinct G protein-coupled receptors (GPCRs) that are divided into two major groups, termed D1 (D1 and D5) and D2 (D2, D3, and D4). D1 receptors are expressed at high levels in the striatum, nucleus accumbens, substantia nigra, olfactory bulb, amygdala, and frontal cortex, and at lower levels in the hippocampus, cerebellum, thalamic areas, and hypothalamic areas. The highest levels of D2 receptors are found in the striatum, the nucleus accumbens, and the olfactory tubercle, with somewhat lower expression in the substantia nigra, ventral tegmental area, hypothalamus, cortical areas, septum, amygdala, and hippocampus. D1 receptors are generally Gs-coupled, and as such stimulate the production of the second messenger cAMP and the activity of PKA. In contrast, D2 receptors are generally Gi-coupled, and as such negatively regulate the production of cAMP and result in a decrease in PKA activity.

Dopamine has been implicated in a wide variety of biological processes ranging from voluntary movement and reward to hormonal regulation. Dopamine has also been implicated in pathological processes associated with disease states of the CNS. Pharmacological agents targeting dopaminergic neurotransmission have been used in the clinical management of several neurological and psychiatric disorders, including Parkinson's disease, schizophrenia, bipolar disorder, Huntington's disease, attention deficit hyperactivity disorder (ADHD), and Tourette's syndrome. For example, haloperidol is a potent D2 receptor antagonist widely prescribed for the treatment of acute schizophrenic symptoms.

Described herein is another GPCR with high levels of expression in the CNS-G protein-coupled receptor 52 (GPR52) (NCBI Reference Sequence: NP_005675.3). GPR52 is highly conserved in vertebrates, with the human amino acid sequence sharing over 90% identity with the chimpanzee, bovine, mouse, rat, and chicken orthologs. As seen in the studies described herein, the highest expression levels within the human CNS are found in the striatum (see FIG. 17). Lower but significant expression levels are found in many other structures in the CNS, including the cortex (see FIG. 17). GPR52 co-localizes almost exclusively with the D2 receptor in the human and rodent striatum, and with the D1 receptor in the human and rodent cortex (see FIG. 18).

Several compounds are known to function as D1 agonists in the cortex, where they increase cortical function and resolve hypofrontality. As discussed herein, GPR52 co-localizes with the D1 receptor in the cortex. Because both GPR52 and D1 receptors are Gs-coupled, a GPR52 agonist should functionally resemble a D1 agonist—and therefore exhibit effects on cortical function and hypofrontality.

The efficacy of existing antipsychotic agents is reportedly mediated by D2 antagonist activity on medium spiny neurons (MSNs) in the striatum. However, D2 antagonists produce side effects, such as motor symptoms and hyperprolactinemia. As discussed herein, GPR52 co-localizes almost exclusively with the D2 receptor in the striatum. Because GPR52 is Gs-coupled and D2 is Gi-coupled, a GPR52 agonist should functionally resemble a D2 antagonist—and therefore exhibit antipsychotic efficacy. Further, because many of the side effects associated with D2 antagonists are mediated by the D2 receptor, GPR52 agonists could avoid the side effects associated with existing D2 antagonists.

Described herein are experiments in which GPR52 agonists were found to activate intracellular signaling and immediate early genes in neurons, affect electrical activity in neurons (similar to haloperidol and several existing antipsychotics), block amphetamine-stimulated locomotor activity (which mimics a hyperdopaminergic state), improve the ability to filter sensory information, and increase object recognition. Further, described herein are experiments in which unwanted activities associated with existing antipsychotics were avoided, including extrapyramidal side effects and prolactin release. The expression levels, co-localization, intracellular signaling, and functional properties described herein suggest that GPR52 is a significant modulator of brain function with relevance for the treatment of several neurological and psychiatric disorders, including those described below.

Hypofrontality

Decreased blood flow in the prefrontal cortex (hypofrontality) is symptomatic of several neurological conditions, including schizophrenia, attention deficit hyperactivity disorder (ADHD), bipolar disorder, and major depressive disorder. Dopaminergic transmission in the prefrontal cortex is mainly mediated by D1 receptors, and D1 dysfunction has been linked to cognitive impairment and negative symptoms in schizophrenia (Goldman-Rakic P S, Castner S A, Svensson T H, Siever L J, Williams G V (2004) Targeting the dopamine D1 receptor in schizophrenia: insights for cognitive dysfunction. Psychopharmacology 174, 3-16). Increasing function in the prefrontal cortex with a GPR52 agonist is therefore useful for the treatment of symptoms associated with hypofrontality.

Movement Disorders

The striatum is involved in the control of movement. Pathology of the striatum is associated with many movement disorders, including hyperkinetic movement disorders characterized by excessive abnormal involuntary movements (known as hyperkinesias). Examples of hyperkinetic movement disorders include tremors, dystonia, chorea, ballism, athetosis, tics/Tourette's syndrome, Huntington's disease, myoclonus and startle syndromes, stereotypies, and akathisia.

In the striatum, GPR52 is almost exclusively expressed on neurons of the indirect striatal pathway. Hyperkinesias are associated with the dysfunction of inhibitory, D2-expressing neurons of this pathway. This dysfunction leads to the inability to inhibit movement, resulting in tics, chorea, vocalizations, tremors, and other hyperkinetic symptoms. For example, early hyperkinetic motor symptoms in Huntington's disease are the result of selective damage to the indirect, D2-containing pathway (Albin R L, Reiner A, Anderson K D, Penney J B, Young A B. (1990) *Striatal and nigral neuron subpopulations in rigid Huntington's disease: implications for the functional anatomy of chorea and rigidity-akinesia. Ann Neurol.* 27, 357-365). Further, D2 receptor binding in striatum is associated with the severity of Tourette syndrome symptoms (Wolf S S, Jones D W, Knable M B, Gorey J G, Lee K S, Hyde™, Coppola R, Weinberger D R (1996) *Tourette syndrome: prediction of phenotypic variation in monozygotic twins by caudate nucleus D2 receptor binding. Science* 273, 1225-1227).

The stimulation of GPR52 with agonists activates the indirect striatal pathway, leading to more inhibitory control over movement and the resolution of hyperkinetic symptoms. The GPR52 agonists disclosed herein are therefore useful for the treatment of such symptoms.

Psychotic Disorders

The psychotic symptoms of schizophrenia result from overactive presynaptic dopamine activity in the striatum (Howes O D, Kapur S (2009) *The dopamine hypothesis of schizophrenia: version III—the final common pathway. Schizophr Bull.* 35, 549-562). The clinical efficacy of existing antipsychotic drugs for treating psychotic symptoms is dependent on blockade of the D2 receptor. All known antipsychotic drugs with efficacy for the treatment of psychosis are either antagonists or partial agonists at the dopamine D2 receptor (Remington G, Kapur S (2010) *Antipsychotic dosing: how much but also how often? Schizophr Bull.* 36, 900-903). While these antipsychotic drugs can treat the positive (or psychotic) symptoms of schizophrenia, they do not treat other aspects of schizophrenia, such as the negative symptoms or cognitive impairment. These antipsychotic drugs are also associated with significant side effect profiles, including weight gain, metabolic syndrome, diabetes, hyperlipidemia, hyperglycemia, insulin resistance, extrapyramidal symptoms, hyperprolactinemia, and tardive dyskinesia. Because GPR52 agonists should functionally resemble D2 antagonists, the GPR52 agonists disclosed herein are useful for the treatment of psychotic disorders.

Other D1-Related Disorders

Several neurological and psychiatric drugs are known to function as D1 agonists, including A-86929, dinapsoline, doxanthrine, SKF-81297, SKF-82958, SKF-38393, fenoldopam, 6-Br-APB, and stepholoidine. Because GPR52 agonists should functionally resemble D1 agonists (and are co-localized), the GPR52 agonists disclosed herein are useful for the treatment of disorders treatable by D1 agonists, including but not limited to addiction (e.g., cocaine addiction), cognitive and working memory deficits in schizophrenia and schizotypal disorder, psychotic disorders, hypertension, restless leg syndrome, Parkinson's disease, and depression.

Other D2-Related Disorders

Several neurological and psychiatric drugs are known to function as D2 antagonists, including atypical antipsychotics (e.g., aripiprazole, clozapine, olanzapine, and ziprasidone), domperidone, eticlopride, fallypride, desmethoxyfallypride, L-741,626, raclopride, hydroxyzine, itopride, SV 293, typical antipsychotics, yohimibine, amisulpride, and UH-232. Because GPR52 agonists should functionally resemble D2 antagonists, the GPR52 agonists disclosed herein are useful for the treatment of disorders treatable by D2 antagonists, including but not limited to psychotic disorders, detachment, anxiety, anxiety/tension associated with psychoneurosis, acute mania, agitation, mania in bipolar disorder, dysthymia, nausea, vomiting, gastrointestinal conditions, dyspepsia, and addiction (e.g., cocaine addiction, amphetamine addiction, etc.).

There is a need for alternative compounds for the treatment of neurological and psychiatric disorders. The compounds described herein satisfy this need and provide related advantages as well.

SUMMARY OF THE INVENTION

One aspect of the present invention encompasses certain 1-heteroaryl-indoline-4-carboxamide derivatives selected from compounds of Formula (Ia) and pharmaceutically acceptable salts, solvates, hydrates, and N-oxides thereof:

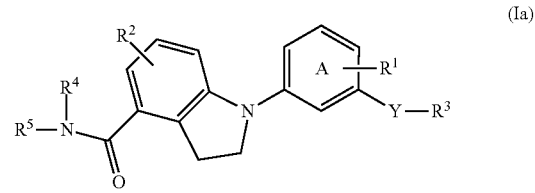

(Ia)

wherein:

Y is selected from: —$CH_2$—, —O—, and —S—;

Ring A is pyridinediyl or pyrazine-2,6-diyl;

$R^1$ is H or $C_1$-$C_6$ alkyl;

$R^2$ is H or halogen;

$R^3$ is aryl or heteroaryl, wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and the $C_1$-$C_6$ alkyl is optionally substituted with one or more groups selected independently from: $C_1$-$C_6$ alkylamino, $C_2$-$C_6$ dialkylamino, and oxo;

$R^4$ is H; and $R^5$ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

One aspect of the present invention relates to pharmaceutical products selected from: a pharmaceutical composition, a formulation, a unit dosage form, and a kit; each comprising a compound of the present invention.

One aspect of the present invention relates to pharmaceutical compositions comprising a compound of the present invention, and a pharmaceutically acceptable carrier.

One aspect of the present invention relates to methods for preparing pharmaceutical compositions comprising the step of admixing a compound of the present invention and a pharmaceutically acceptable carrier.

One aspect of the present invention relates to methods for treating or preventing a GPR52-mediated disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing an extrapyramidal or movement disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing a psychotic disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing a mood disorder, a depressive disorder, or a bipolar or related disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing attention deficit disorder (ADHD), anxiety disorder, obsessive-compulsive disorder (OCD), or autism spectrum disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing a prolactin-related disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing a neurocognitive disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing a trauma- or stressor-related disorder; a disruptive, impulse-control, or conduct disorder; or a sleep-wake disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing a substance-related disorder, an addictive disorder, or a behavioral disorder in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing hypofrontality in an individual, comprising administering to the individual in need thereof, a therapeutically effective amount of a compound of the present invention; a pharmaceutical product of the present invention; or a pharmaceutical composition of the present invention.

One aspect of the present invention relates to methods for treating or preventing an abnormality in the tuberoinfundibular pathway, mesolimbic pathway, mesocortical pathway, or nigrostriatal pathway in an individual, comprising administering to the individual in need thereof, a therapeutically effective amount of a compound of the present invention; a pharmaceutical product of the present invention; or a pharmaceutical composition of the present invention.

One aspect of the present invention relates to methods for increasing activity in the striatum in an individual, comprising administering to the individual in need thereof, a therapeutically effective amount of a compound of the present invention; a pharmaceutical product of the present invention; or a pharmaceutical composition of the present invention.

One aspect of the present invention relates to methods for improving cortical function in an individual, comprising administering to the individual in need thereof, a therapeutically effective amount of a compound of the present invention; a pharmaceutical product of the present invention; or a pharmaceutical composition of the present invention.

One aspect of the present invention relates to methods for improving neurocognitive function in an individual, comprising administering to the individual in need thereof, a therapeutically effective amount of a compound of the present invention; a pharmaceutical product of the present invention; or a pharmaceutical composition of the present invention.

One aspect of the present invention relates to uses of a compound of the present invention in the manufacture of a medicament for treating or preventing a GPR52-mediated disorder in an individual.

One aspect of the present invention relates to uses of a compound of the present invention in the manufacture of a medicament for treating or preventing an extrapyramidal or movement disorder in an individual.

One aspect of the present invention relates to uses of a compound of the present invention in the manufacture of a medicament for treating or preventing a psychotic disorder in an individual.

One aspect of the present invention relates to uses of a compound of the present invention in the manufacture of a medicament for treating or preventing a mood disorder, a depressive disorder, or a bipolar or related disorder in an individual.

One aspect of the present invention relates to uses of a compound of the present invention in the manufacture of a medicament for treating or preventing attention deficit disorder (ADHD), anxiety disorder, obsessive-compulsive disorder (OCD), or autism spectrum disorder in an individual.

One aspect of the present invention relates to uses of a compound of the present invention in the manufacture of a medicament for treating or preventing a prolactin-related disorder in an individual.

One aspect of the present invention relates to uses of a compound of the present invention in the manufacture of a medicament for treating or preventing a neurocognitive disorder in an individual.

One aspect of the present invention relates to uses of a compound of the present invention in the manufacture of a medicament for treating or preventing a trauma- or stressor-related disorder; a disruptive, impulse-control, or conduct disorder; or a sleep-wake disorder in an individual.

One aspect of the present invention relates to uses of a compound of the present invention in the manufacture of a medicament for treating or preventing a substance-related disorder, an addictive disorder, or a behavioral disorder in an individual.

One aspect of the present invention relates to uses of a compound of the present invention in the manufacture of a medicament for treating or preventing hypofrontality in an individual.

One aspect of the present invention relates to uses of a compound of the present invention in the manufacture of a medicament for treating or preventing an abnormality in the tuberoinfundibular pathway, mesolimbic pathway, mesocortical pathway, or nigrostriatal pathway in an individual.

One aspect of the present invention relates to uses of a compound of the present invention in the manufacture of a medicament for increasing activity in the striatum in an individual.

One aspect of the present invention relates to uses of a compound of the present invention in the manufacture of a medicament for improving cortical function in an individual.

One aspect of the present invention relates to uses of a compound of the present invention in the manufacture of a medicament for improving neurocognitive function in an individual.

One aspect of the present invention relates to compounds of the present invention; a pharmaceutical product of the present invention; or a pharmaceutical composition of the present invention; for use in a method of treatment of the human or animal body by therapy.

One aspect of the present invention relates to compounds of the present invention; a pharmaceutical product of the present invention; or a pharmaceutical composition of the present invention; for use in a method for treating or preventing a GPR52-mediated disorder in an individual.

One aspect of the present invention relates to compounds of the present invention; a pharmaceutical product of the present invention; or a pharmaceutical composition of the present invention; for use in a method for treating or preventing an extrapyramidal or movement disorder in an individual.

One aspect of the present invention relates to compounds of the present invention; a pharmaceutical product of the present invention; or a pharmaceutical composition of the present invention; for use in a method for treating or preventing a psychotic disorder in an individual.

One aspect of the present invention relates to compounds of the present invention; a pharmaceutical product of the present invention; or a pharmaceutical composition of the present invention; for use in a method for treating or preventing a mood disorder, a depressive disorder, or a bipolar or related disorder in an individual.

One aspect of the present invention relates to compounds of the present invention; a pharmaceutical product of the present invention; or a pharmaceutical composition of the present invention; for use in a method for treating or preventing attention deficit disorder (ADHD), anxiety disorder, obsessive-compulsive disorder (OCD), or autism spectrum disorder in an individual.

One aspect of the present invention relates to compounds of the present invention; a pharmaceutical product of the present invention; or a pharmaceutical composition of the present invention; for use in a method for treating or preventing a prolactin-related disorder in an individual.

One aspect of the present invention relates to compounds of the present invention; a pharmaceutical product of the present invention; or a pharmaceutical composition of the present invention; for use in a method for treating or preventing a neurocognitive disorder in an individual.

One aspect of the present invention relates to compounds of the present invention; a pharmaceutical product of the present invention; or a pharmaceutical composition of the present invention; for use in a method for treating or preventing a trauma- or stressor-related disorder; a disruptive, impulse-control, or conduct disorder; or a sleep-wake disorder in an individual.

One aspect of the present invention relates to compounds of the present invention; a pharmaceutical product of the present invention; or a pharmaceutical composition of the present invention; for use in a method for treating or preventing a substance-related disorder, an addictive disorder, or a behavioral disorder in an individual.

One aspect of the present invention relates to compounds of the present invention; a pharmaceutical product of the present invention; or a pharmaceutical composition of the present invention; for use in a method for treating or preventing hypofrontality in an individual.

One aspect of the present invention relates to compounds of the present invention; a pharmaceutical product of the present invention; or a pharmaceutical composition of the present invention; for use in a method for treating or preventing an abnormality in the tuberoinfundibular pathway, mesolimbic pathway, mesocortical pathway, or nigrostriatal pathway in an individual.

One aspect of the present invention relates to compounds of the present invention; a pharmaceutical product of the present invention; or a pharmaceutical composition of the present invention; for use in a method for increasing activity in the striatum in an individual.

One aspect of the present invention relates to compounds of the present invention; a pharmaceutical product of the present invention; or a pharmaceutical composition of the present invention; for use in a method for improving cortical function in an individual.

One aspect of the present invention relates to compounds of the present invention; a pharmaceutical product of the present invention; or a pharmaceutical composition of the present invention; for use in a method for improving neurocognitive function in an individual.

In some embodiments, the GPR52-mediated disorder is selected from: Huntington's disease, schizophrenia, bipolar disorder, attention deficit hyperactivity disorder (ADHD), and Tourette's syndrome.

In some embodiments, the extrapyramidal or movement disorder is selected from: akathisia, associated movements, athetosis, ataxia, ballismus, hemiballismus, chorea, Huntington's disease, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, Tourette's syndrome, tremor, and Wilson's disease.

In some embodiments, the extrapyramidal or movement disorder is a motor disorder. In some embodiments, the motor disorder is selected from: developmental coordination disorder, stereotypic movement disorder, and Tic disorder.

In some embodiments, the extrapyramidal or movement disorder is a hyperkinetic movement disorder. In some embodiments, the hyperkinetic movement disorder is selected from: Huntington's disease, Wilson's disease, restless leg syndrome, a post-stroke effect, and dentatorubral-pallidoluysian atrophy.

In some embodiments, treating or preventing an extrapyramidal or movement disorder comprises treating or preventing extrapyramidal syndrome.

In some embodiments, the psychotic disorder is selected from: schizotypal personality disorder, delusional disorder, brief psychotic disorder, schizophreniform disorder, schizophrenia, schizoaffective disorder, and substance- or medication-induced psychotic disorder.

In some embodiments, treating or preventing a psychotic disorder comprises treating or preventing a positive symptom of schizophrenia. In some embodiments, the positive symptom of schizophrenia is selected from: delusions, hallucinations, disorganized thinking, and grossly disorganized or abnormal motor behavior.

In some embodiments, treating or preventing a psychotic disorder comprises treating or preventing a negative symptom of schizophrenia. In some embodiments, the negative symptom of schizophrenia is selected from: diminished emotional expression, avolition, alogia, anhedonia, and asociality.

In some embodiments, the psychotic disorder comprises a schizophrenia spectrum domain selected from: delusions, hallucinations, disorganized thinking, grossly disorganized or abnormal motor behavior, and negative symptoms.

In some embodiments, the psychotic disorder is characterized by catatonia.

In some embodiments, the depressive disorder is major depressive disorder.

In some embodiments, the bipolar or related disorder is selected from: bipolar I disorder, bipolar II disorder, cyclothymic disorder, substance- or medication-induced bipolar and related disorders, and bipolar and related disorders due to another medical condition.

In some embodiments, the anxiety disorder is selected from: separation anxiety disorder, selective mutism, specific phobia, social anxiety disorder, panic disorder, agoraphobia, generalized anxiety disorder, substance- or medication-induced anxiety disorder, and anxiety disorder due to another medical condition.

In some embodiments, the prolactin-related disorder is hyperprolactinemia.

In some embodiments, the neurocognitive disorder is selected from: delirium, major neurocognitive disorder, and minor neurocognitive disorder.

In some embodiments, the neurocognitive disorder is selected from: amnesia, dementia, and delirium.

In some embodiments, the trauma- or stressor-related disorder is posttraumatic stress disorder (PTSD).

In some embodiments, the substance is selected from: alcohol, caffeine, *cannabis*, a hallucinogen, an inhalant, an opioid, a sedative, a hypnotic, an anxiolytic, a stimulant, and tobacco.

In some embodiments, the hypofrontality is associated with at least one disorder selected from: schizophrenia, attention deficit hyperactivity disorder (ADHD), bipolar disorder, and major depressive disorder.

In some embodiments, the cortical function is selected from: executive function, attention, and memory.

In some embodiments, the neurocognitive function is at least one domain selected from: complex attention, executive function, learning and memory, language, perceptual-motor, and social cognition.

In some embodiments, the individual in need of treatment is an adult. In some embodiments, the individual in need of treatment is an adolescent. In some embodiments, the individual in need of treatment is a child. In some embodiments, the individual in need of treatment is aged 13-17 years. In some embodiments, the individual in need of treatment is aged 10-17 years. In some embodiments, the individual in need of treatment is aged 5-16 years.

In some embodiments, the compounds disclosed herein are not administered to individuals with dementia-related psychosis. In certain embodiments, the individuals with dementia-related psychosis are elderly patients. In some embodiments, individuals who are administered the compounds disclosed herein are monitored for suicidal thoughts and behaviors. In some embodiments, individuals who are administered an antidepressant and a compound disclosed herein are monitored for suicidal thoughts and behaviors. In certain embodiments, the individual being monitored is a child, an adolescent, or a young adult.

In some embodiments, the compounds disclosed herein are for use in acute treatment. In some embodiments, the compounds disclosed herein are for use in short-term treatment. In some embodiments, the compounds disclosed herein are for use in chronic treatment. In some embodiments, the compounds disclosed herein are for use in the treatment of a first episode. In some embodiments, the compounds disclosed herein are for use in the treatment of recurrent episodes. In some embodiments, the compounds disclosed herein are for use in maintenance treatment.

In some embodiments, the compounds disclosed herein are for use in monotherapy. In some embodiments, the compounds disclosed herein are for use in combination therapy. In some embodiments, the compounds disclosed herein are for use as an adjunct therapy. In certain embodiments, the compounds disclosed herein are for use in combination with an antipsychotic. In certain embodiments, the compounds disclosed herein are for use in combination with an antidepressant. In certain embodiments, the compounds disclosed herein are for use in combination with mood stabilizers or antidepressants. In certain embodiments, the compounds disclosed herein are for use in combination with lithium or valproate. In certain embodiments, the compounds disclosed herein are for use in combination with haloperidol for the treatment or prevention of schizophrenia. In certain embodiments, the compounds disclosed herein are for use as an adjunct to an antipsychotic. In certain embodiments, the compounds disclosed herein are for as an adjunct to an antidepressant. In certain embodiments, the compounds disclosed herein are for use as an adjunct to mood stabilizers or antidepressants. In certain embodiments, the compounds disclosed herein are for use as an adjunct to lithium or valproate. In certain embodiments, the compounds disclosed herein are used as an adjunct for the treatment or prevention of a major depressive disorder. In certain embodiments, the compounds disclosed herein are used as an adjunct to haloperidol for the treatment or prevention of schizophrenia. In certain embodiments, the compounds disclosed herein are used as a monotherapy for a first indication, and as an adjunct therapy for a second indication. For example, in certain embodiments, the first indication is schizophrenia, and the second indication is bipolar disorder.

In some embodiments, the compounds disclosed herein are for use in the treatment or prevention of a disorder that is known to be treated by a D1 agonist. In some embodiments, the compounds disclosed herein are for use in the treatment or prevention of a disorder that is known to be treated by a D2 antagonist. In certain embodiments, the compounds disclosed herein are useful for the treatment of schizophrenia, bipolar disorder, major depressive disorder, agitation associated with dementia, anxiety disorder, autism spectrum disorder, or obsessive-compulsive disorder. In some embodiments, the compounds disclosed herein are for use in the treatment or prevention of a disorder known to be treated by an antipsychotic, such as the treatment or prevention of a disorder for which the FDA has approved an antipsychotic. In certain embodiments, the disorder is schizophrenia, schizoaffective disorder, irritability associated with autistic disorder, bipolar I disorder, bipolar mania, manic or mixed episodes associated with bipolar I disorder, bipolar depression, depressive episodes associated with bipolar disorder, depressive episodes associated with bipolar I disorder, major depressive disorder, agitation associated with schizophrenia or bipolar I disorder, or treatment-resistant depression. In some embodiments, the compounds disclosed herein are useful for treatment with reduced side effects compared to an existing antipsychotic, such as reduced side effects compared to an antipsychotic approved by the FDA. In certain embodiments, the side effect is prolactin hypersecretion, an extrapyramidal symptom, or tardive dyskinesia.

These and other aspects of the invention disclosed herein will be set forth in greater detail as the patent disclosure proceeds.

BRIEF DESCRIPTION OF THE DRAWINGS

FIG. 15A shows the distribution and relative expression levels of GPR52 mRNA in regions of the cerebral cortex and striatum in the rat brain.

FIG. 15B shows the distribution and relative expression levels of GPR52 mRNA in regions of the hippocampus, septum, thalamus, and bed nucleus of the stria terminalis in the rat brain.

FIG. 15C shows the distribution and relative expression levels of GPR52 mRNA in regions of the hypothalamus and amygdala in the rat brain.

FIG. 15D shows the distribution and relative expression levels of GPR52 mRNA in regions of the midbrain, pons, medulla oblongata, and cerebellum in the rat brain.

FIG. 16A shows a comparison of GPR52 mRNA expression levels in regions of the cerebral cortex, striatum, hippocampus, septum, thalamus, and bed nucleus of the stria terminalis in the rat and mouse brain.

FIG. 16B shows a comparison of GPR52 mRNA expression levels in regions of the hypothalamus, amygdala, midbrain, pons, medulla oblongata, and cerebellum in the rat and mouse brain.

FIG. 17 shows relative expression levels of GPR52 mRNA in regions of the human brain.

FIG. 18 shows the percentage of neurons co-expressing GPR52 and either GAD1, vGlut1, DRD1, or DRD2 in the rat and human brain.

FIG. 19 shows intracellular signaling markers in the cortex and striatum following the administration of Compound 13 to mice.

FIGS. 27A-B show the measurement of catalepsy in rats following the administration of vehicle, haloperidol, or Compound 13.

DETAILED DESCRIPTION OF THE INVENTION

Definitions

Figure 1:
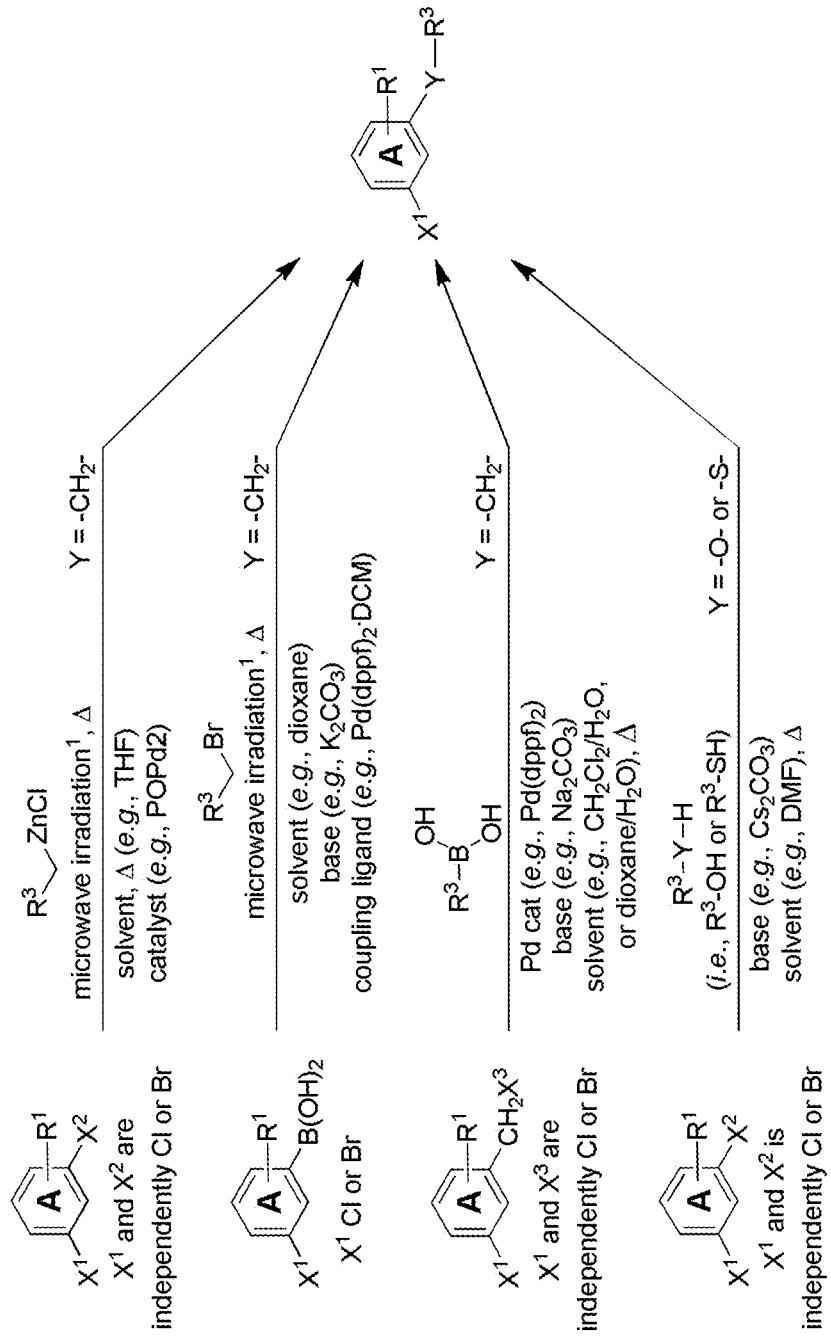
FIG. 1 shows a general synthetic scheme for the preparation of intermediates useful in preparing compounds of Formula (Ia), wherein Y, Ring A, $R^1$, and $R^3$ have the same definitions as used throughout this disclosure. Four separate methods are shown to introduce a variety of Y and $R^3$ groups.
Figure 2:
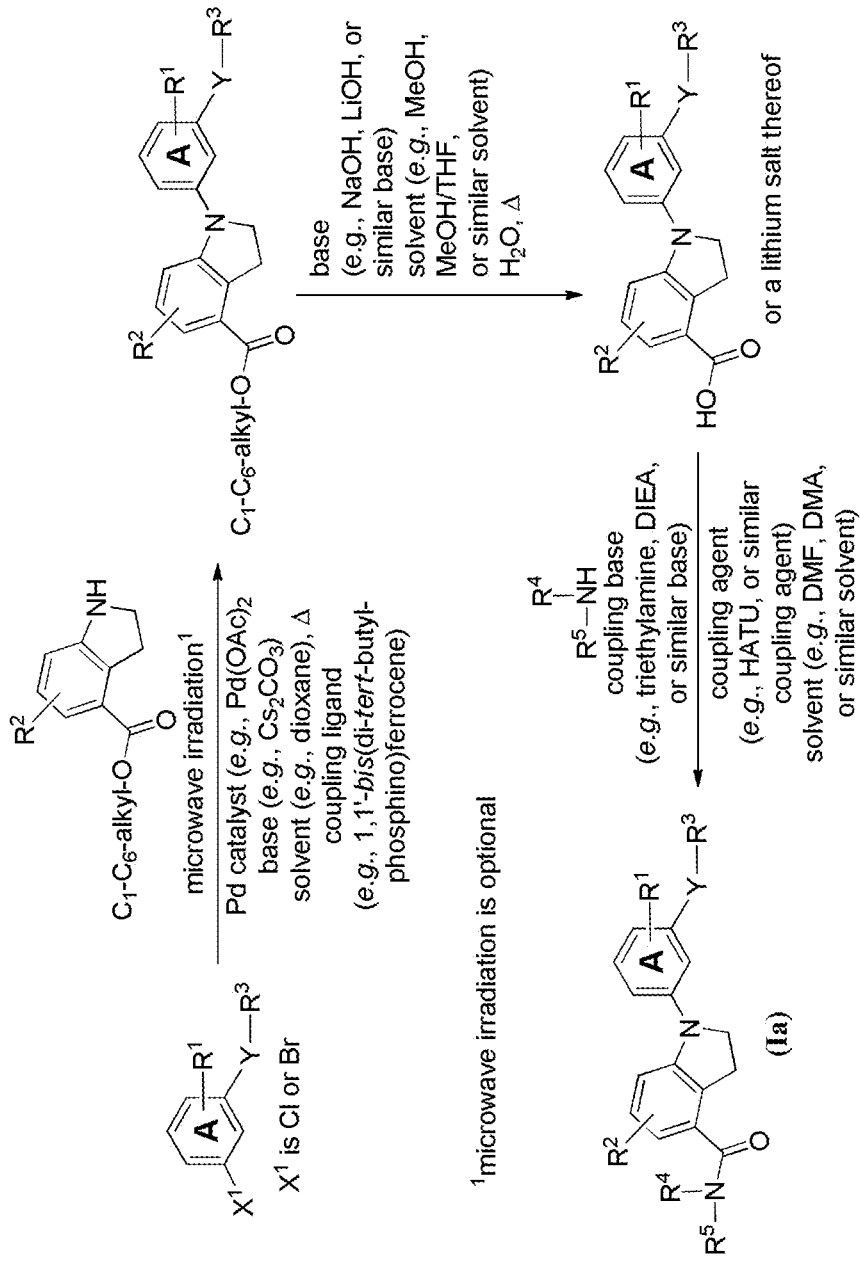
FIG. 2 shows a general synthetic scheme for the preparation of compounds of Formula (Ia), wherein Y, Ring A, $R^1$, $R^2$, $R^3$, $R^4$, and $R^5$ have the same definitions as used throughout this disclosure. A variety of $R^4$ and $R^5$ groups can be introduced via coupling reactions.
Figure 3:
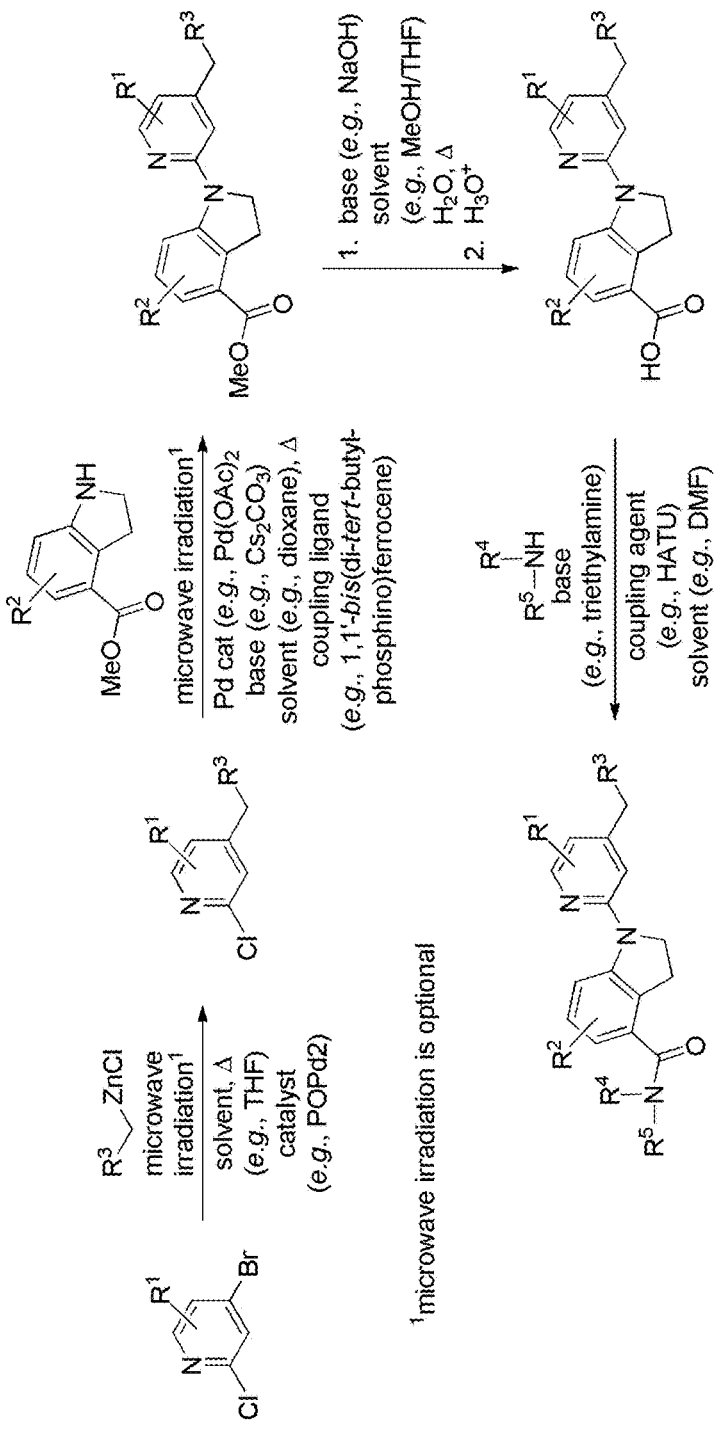
FIG. 3 shows a general synthetic scheme for the preparation of certain compounds of Formula (Ia) referred to Method A herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.6.
Figure 4:
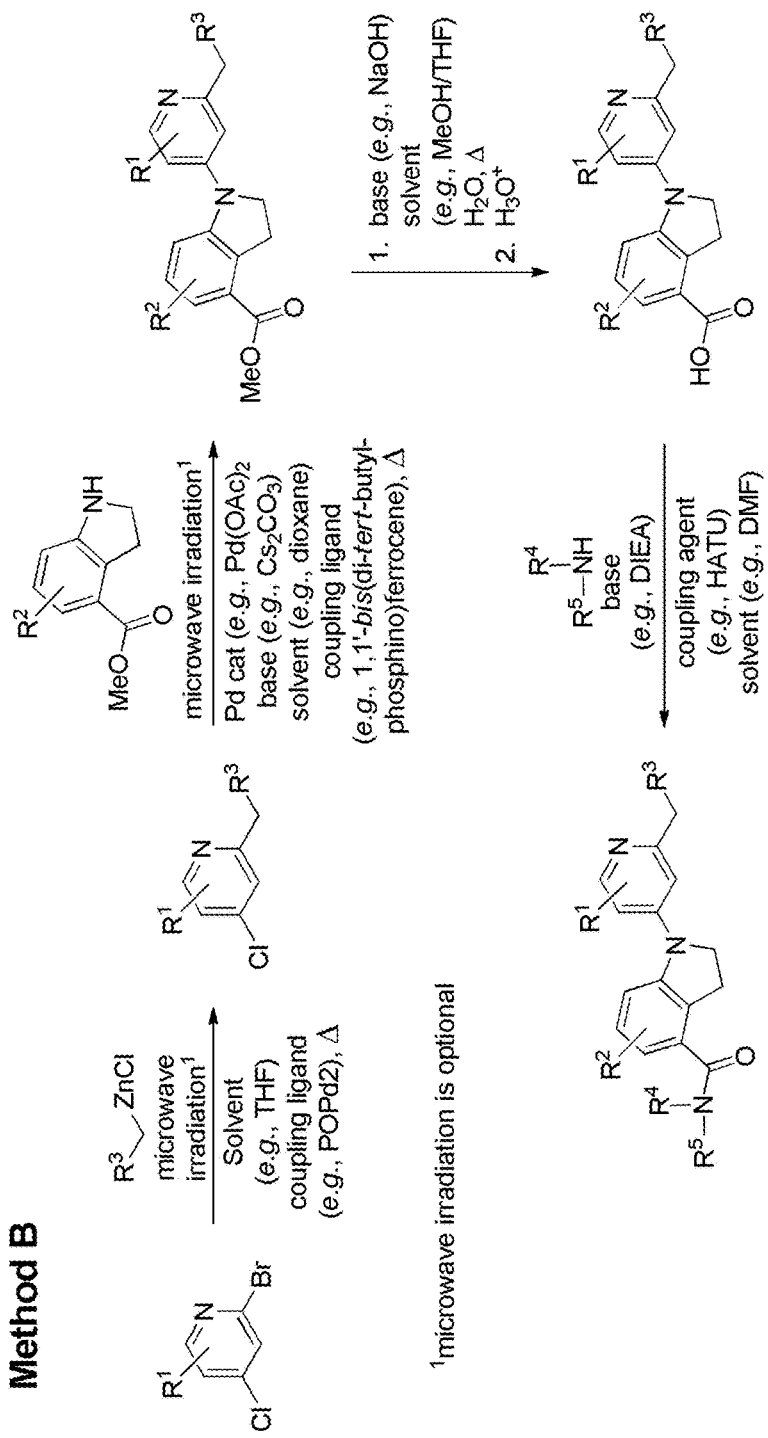
FIG. 4 shows a general synthetic scheme for the preparation of certain compounds of Formula (Ia) referred to Method B herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.7.
Figure 5:
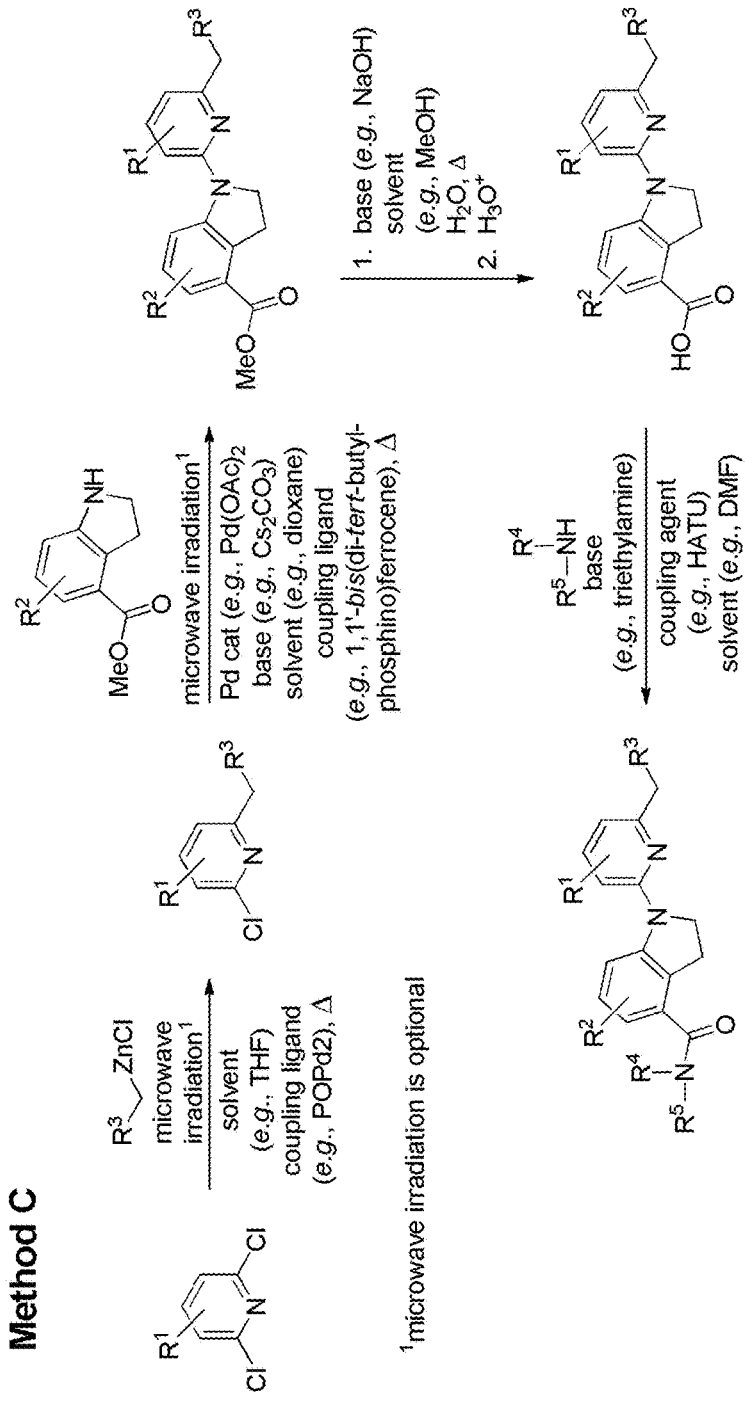
FIG. 5 shows a general synthetic scheme for the preparation of certain compounds of Formula (Ia) referred to Method C herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.8.
Figure 6:
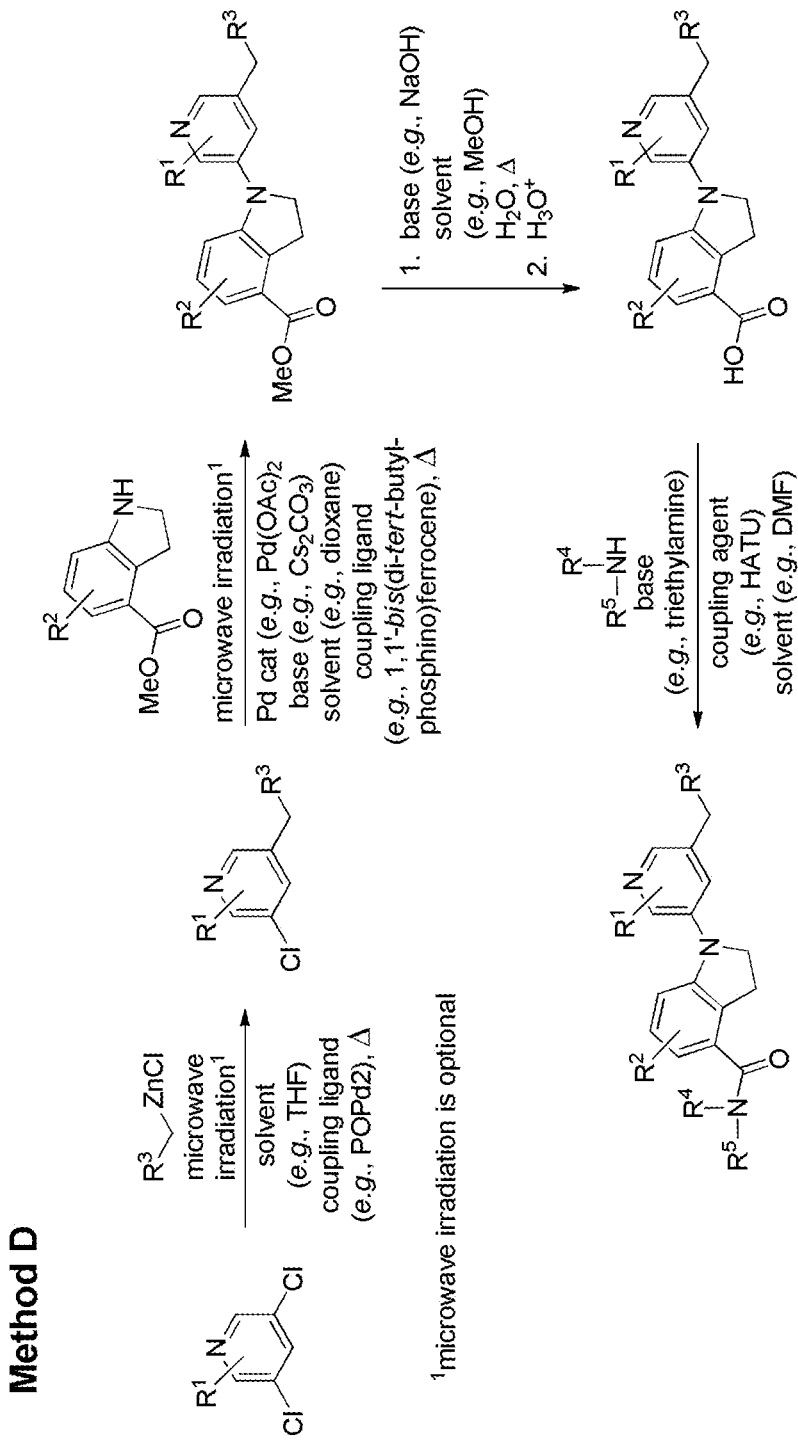
FIG. 6 shows a general synthetic scheme for the preparation of certain compounds of Formula (Ia) referred to Method D herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.9.
Figure 7:
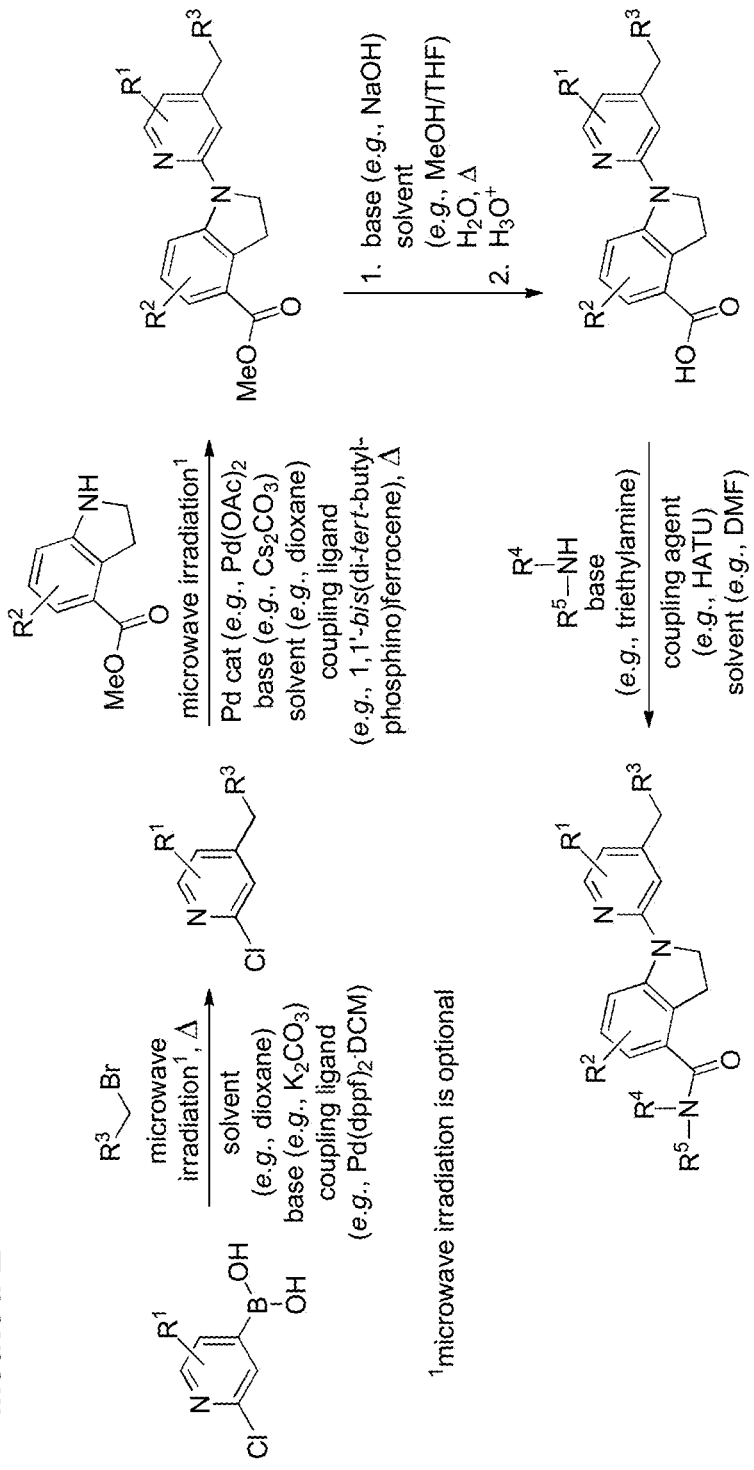
FIG. 7 shows a general synthetic scheme for the preparation of certain compounds of Formula (Ia) referred to Method E herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.10.
Figure 8:
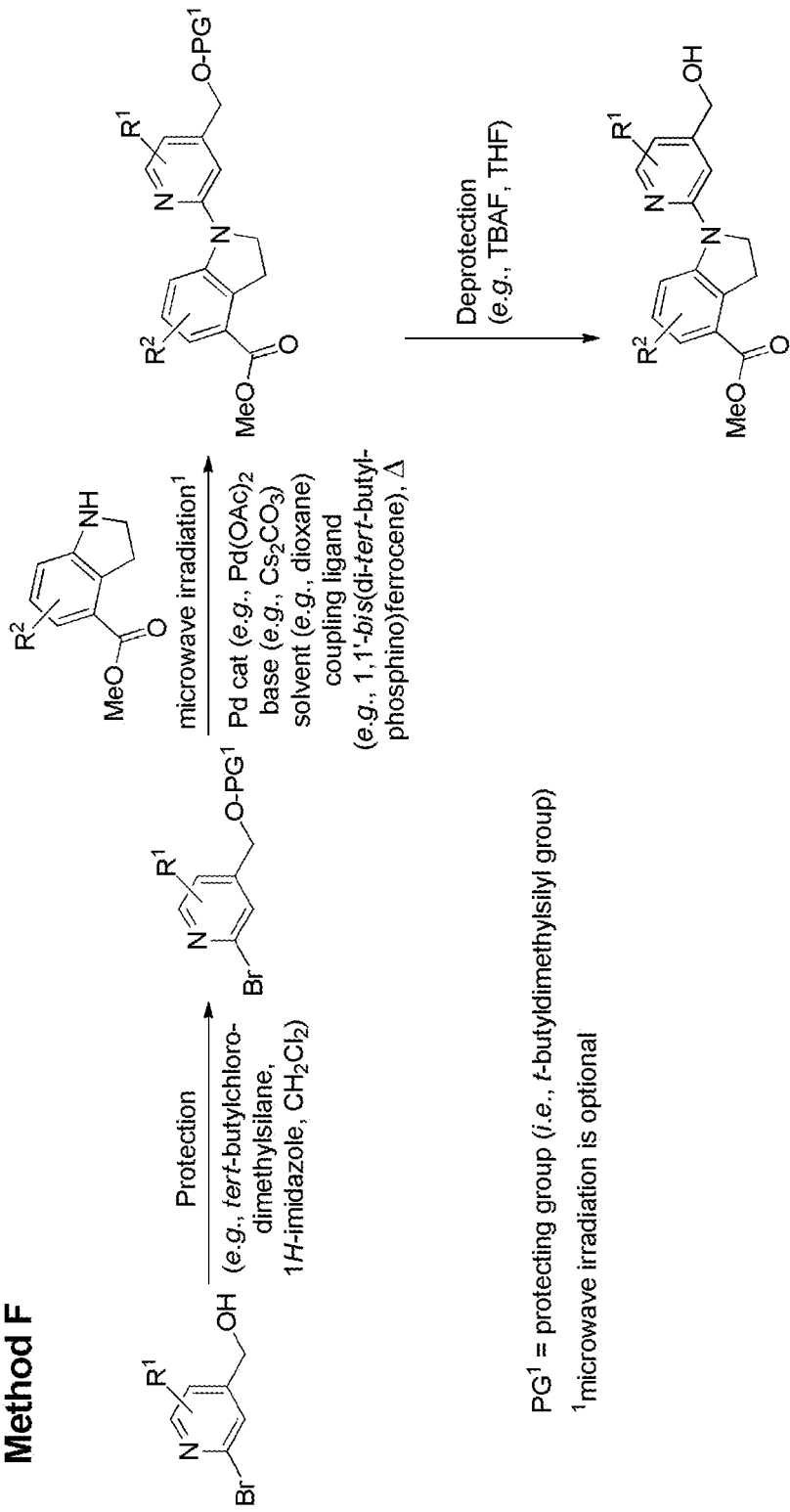
FIG. 8 shows a general synthetic scheme for the preparation of intermediates useful in preparing certain compounds of Formula (Ia) referred to Method F herein, wherein: Y is —$CH_2$—, Ring A is pyridinediyl, $R^1$ and $R^2$ have the same definitions as used throughout this disclosure and $PG^1$ refers to a protection group for the benzyl alcohol, one example includes the use of the t-BDMS (i.e., tert-butyldimethylsilyl) group. For illustrative purposes, see Example 1.5.
Figure 9:
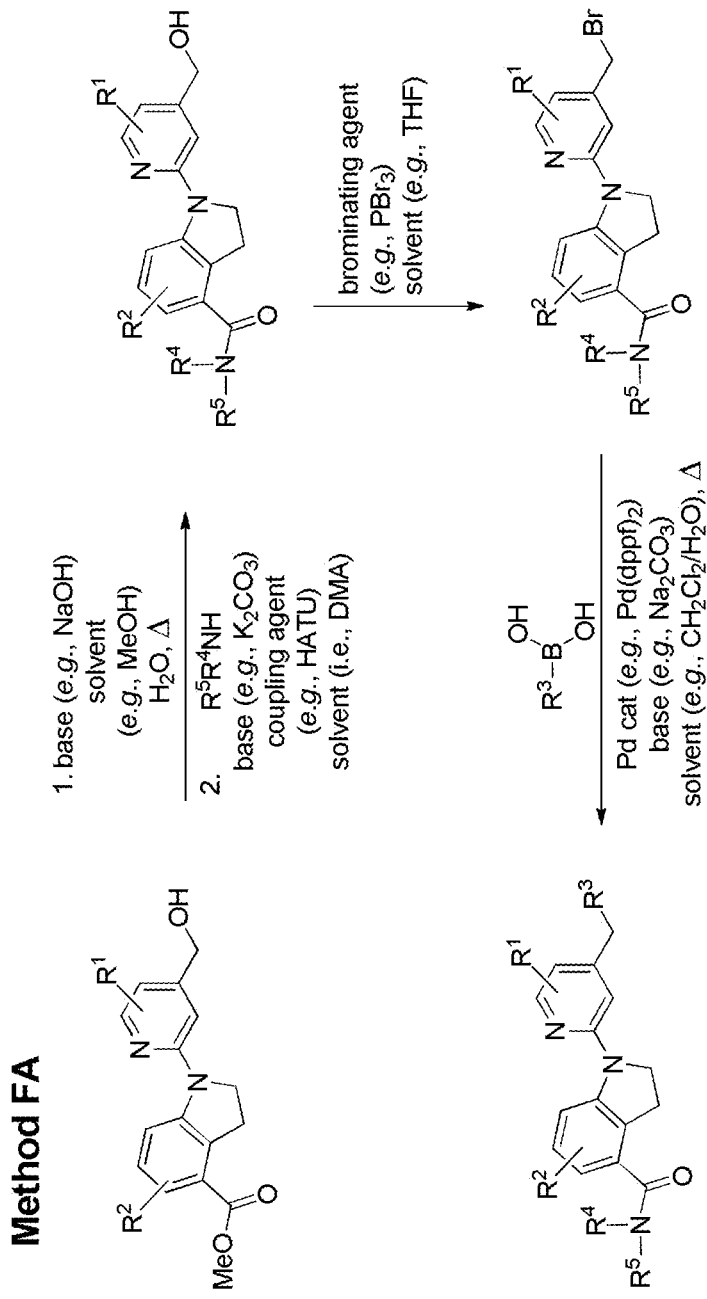
FIG. 9 shows a general synthetic scheme for the preparation of certain compounds of Formula (Ia) referred to Method FA herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.11.
Figure 10:
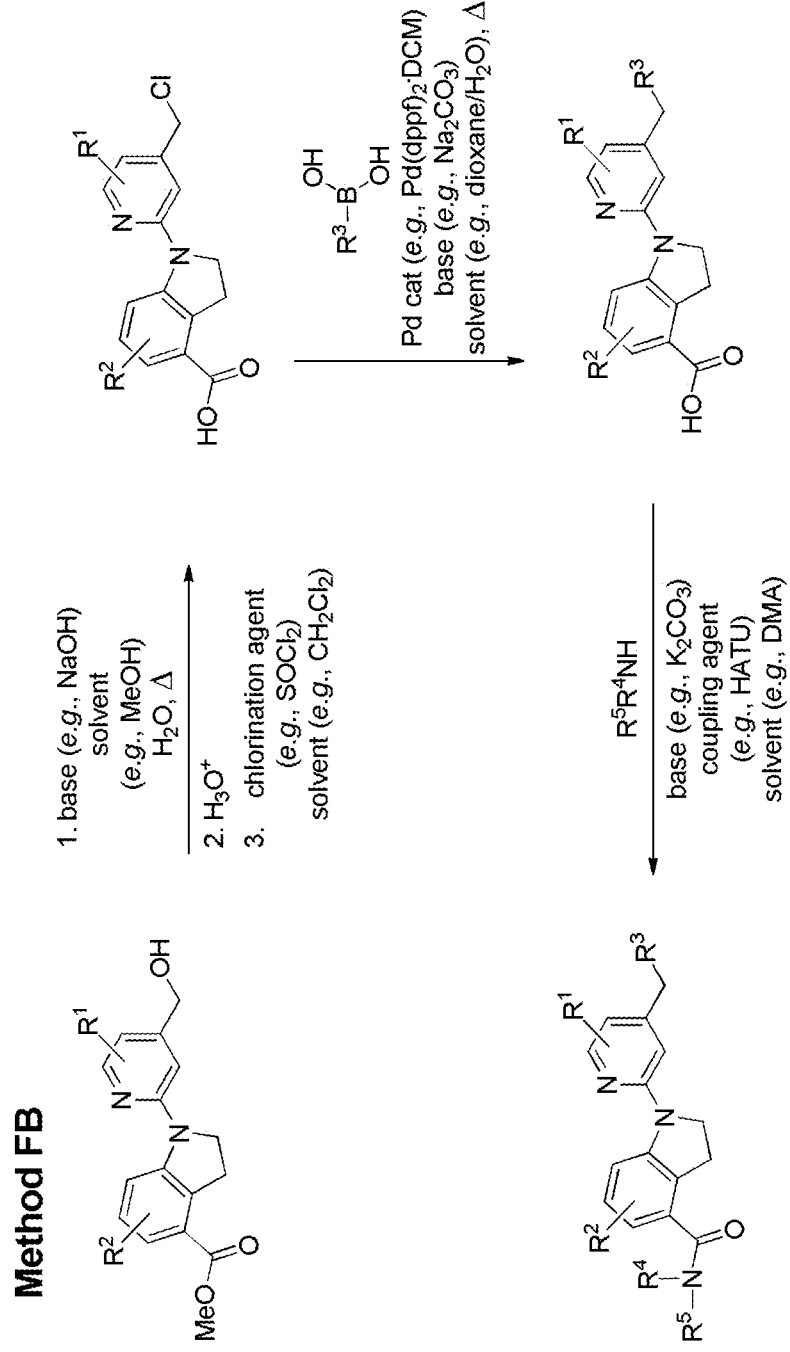
FIG. 10 shows a general synthetic scheme for the preparation of certain compounds of Formula (Ia) referred to Method FB herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.12.
Figure 11:
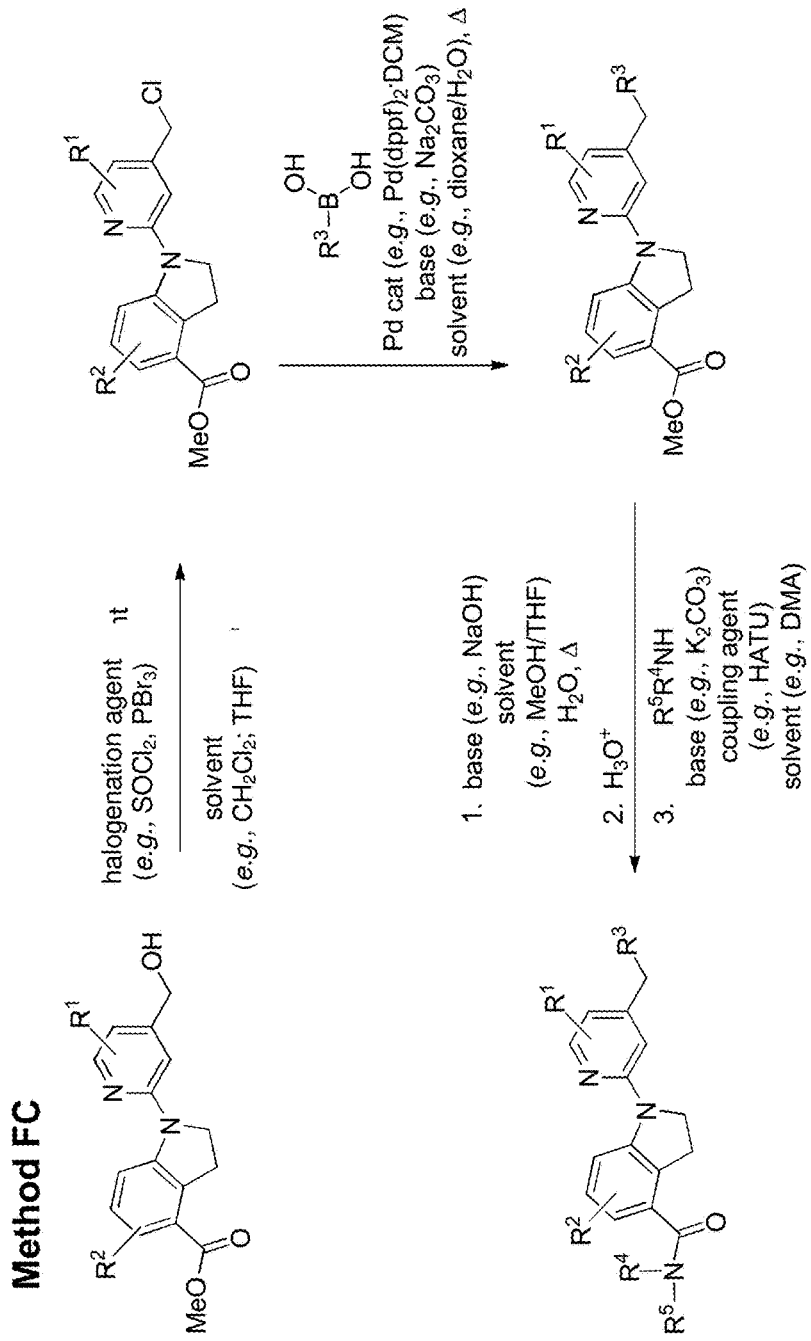
FIG. 11 shows a general synthetic scheme for the preparation of certain compounds of Formula (Ia) referred to Method FC herein, wherein: Y is —$CH_2$—, Ring A is pyridinediyl, $R^1$, $R^2$, $R^3$, $R^4$, and $R^5$ have the same definitions as used throughout this disclosure. For illustrative purposes, see Example 1.13.
Figure 12:
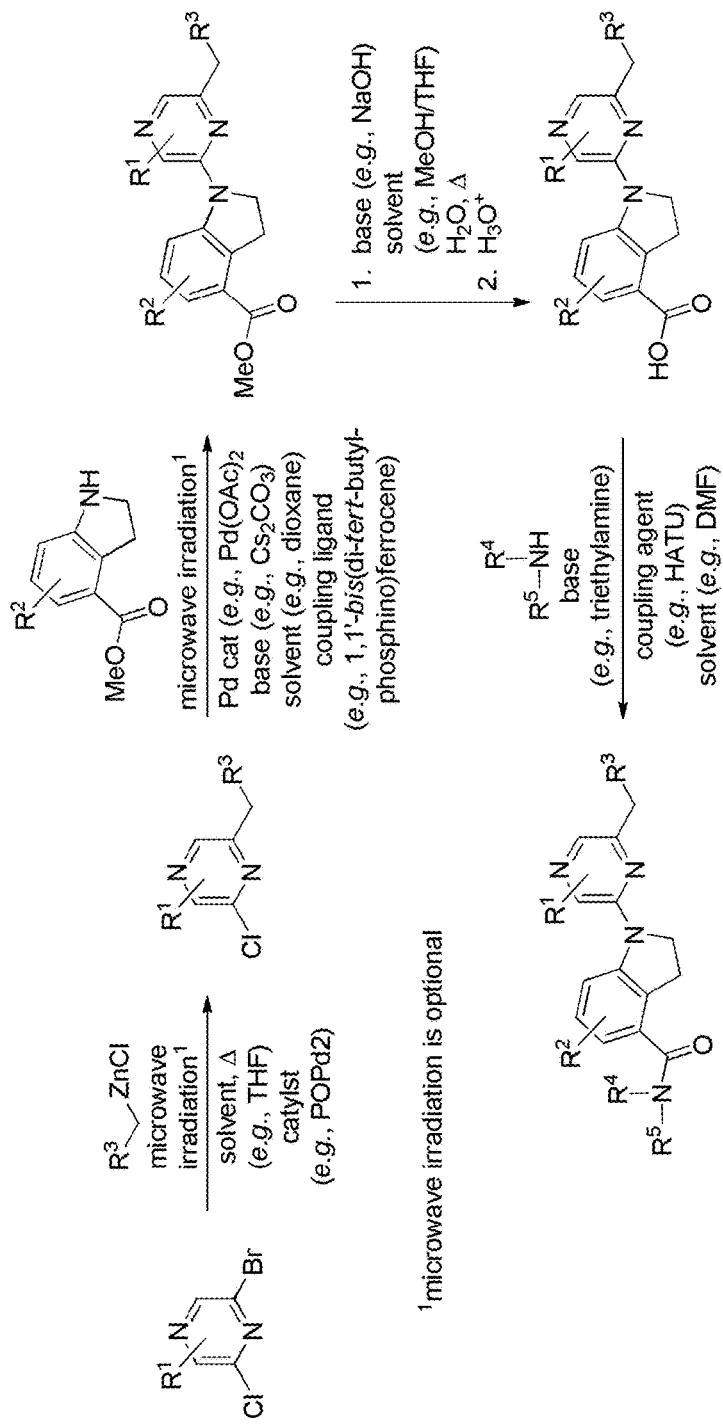
FIG. 12 shows a general synthetic scheme for the preparation of certain compounds of Formula (Ia), wherein: Y is —$CH_2$—, Ring A is pyrazine-2,6-diyl, $R^1$, $R^2$, $R^3$, $R^4$, and $R^5$ have the same definitions as used throughout this disclosure.
Figure 13:
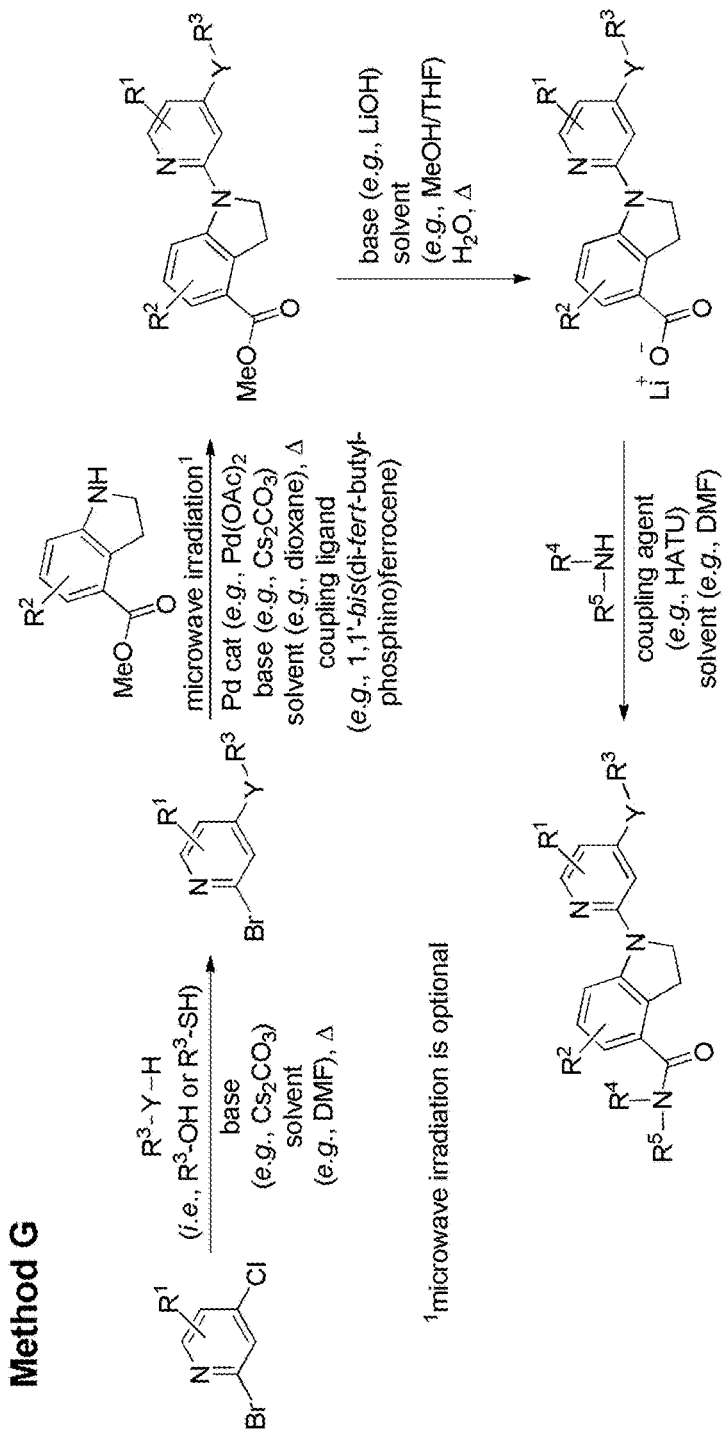
FIG. 13 shows a general synthetic scheme for the preparation of certain compounds of Formula (Ia) referred to Method G herein, wherein: Y is —O— or —S—, Ring A is pyridinediyl, $R^1$, $R^2$, $R^3$, $R^4$, and $R^5$ have the same definitions as used throughout this disclosure. For illustrative purposes, see Example 1.14.
Figure 14:
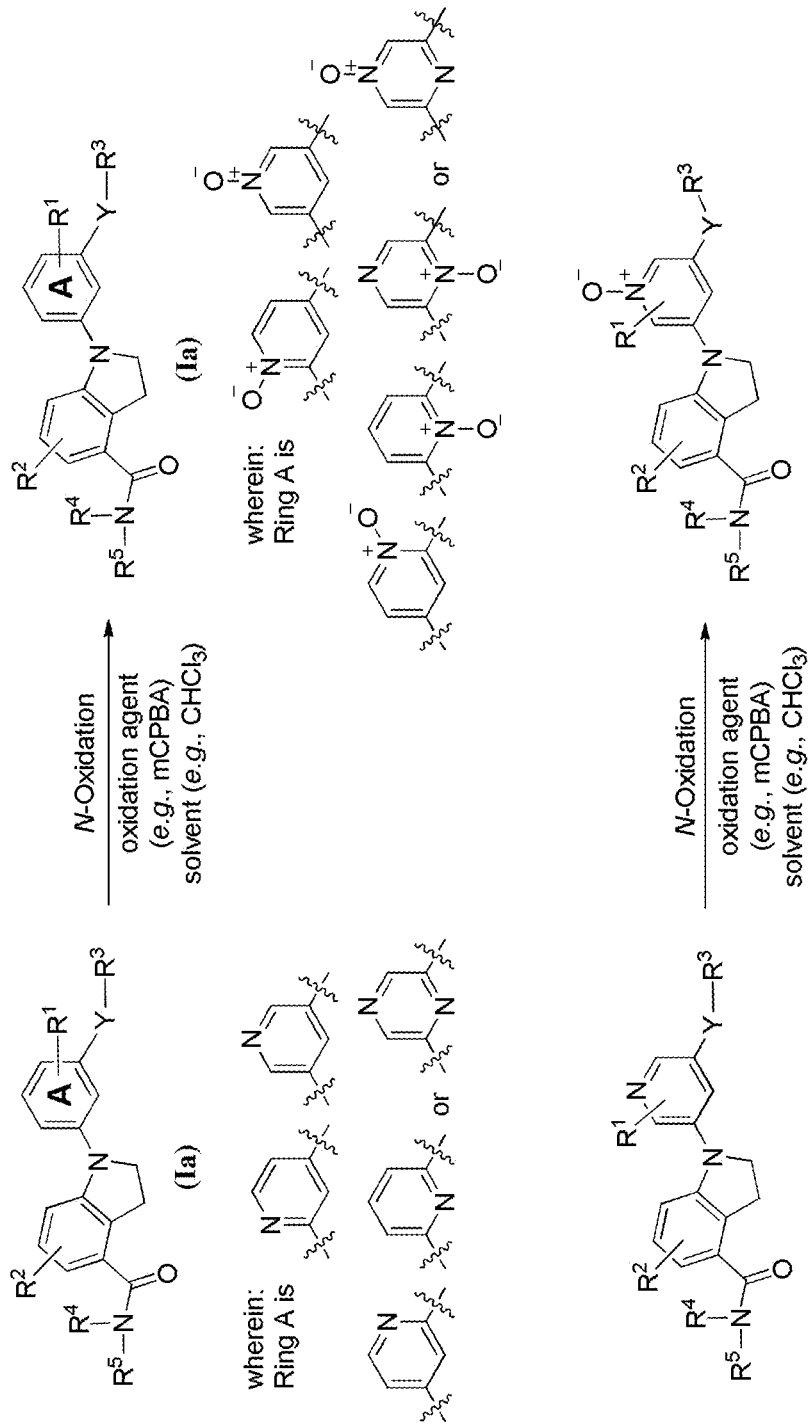
FIG. 14 shows a general synthetic scheme for the preparation of N-oxides of compounds of Formula (Ia) referred to Method H herein, wherein Y, Ring A, $R^1$, $R^2$, $R^3$, $R^4$, and $R^5$ have the same definitions as used throughout this disclosure. For illustrative purposes, see Example 1.15.

For clarity and consistency, the following definitions will be used throughout this patent document.

The term "administering" as used herein means to provide a compound or other therapy, remedy, or treatment. For example, a health care provider can directly provide a compound to an individual in the form of a sample, or can indirectly provide a compound to an individual by providing an oral or written prescription for the compound. Also, for example, an individual can obtain a compound by themself without the involvement of a health care provider. Administration of the compound may or may not involve the individual actually internalizing the compound.

The term "agonist" refers to a moiety that interacts with and activates a G-protein-coupled receptor, for instance a GPR52 receptor, and can thereby initiate a physiological or pharmacological response characteristic of that receptor. For example, an agonist may activate an intracellular response upon binding to a receptor, or enhance GTP binding to a membrane.

The term "composition" refers to a compound or crystalline form thereof, including but not limited to, salts, solvates, and hydrates of a compound of the present invention, in combination with at least one additional component, such as, a composition obtained/prepared during synthesis, pre-formulation, in-process testing (i.e., TLC, HPLC, NMR samples), and the like.

The term "hydrate" as used herein means a compound of the invention or a salt thereof that further includes a stoichiometric or non-stoichiometric amount of water bound by non-covalent intermolecular forces.

The term "in need of treatment" and the term "in need thereof" when referring to treatment are used interchangeably to mean a judgment made by a caregiver (e.g. physician, nurse, nurse practitioner, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit, or ameliorate the disease, condition, or disorder.

The term "individual" refers to any animal, including mammals, such as, mice, rats, other rodents, rabbits, dogs, cats, swine, cattle, sheep, horses, primates, and humans. In some embodiment "individual" refers to humans.

The term "pharmaceutical composition" refers to a specific composition comprising at least one active ingredient; including but not limited to, salts, solvates, and hydrates of compounds of the present invention, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The phrase "pharmaceutically acceptable salts, solvates, and hydrates" when referring to a compound/compounds as described herein embraces pharmaceutically acceptable solvates and/or hydrates of the compound/compounds, pharmaceutically acceptable salts of the compound/compounds, as well as pharmaceutically acceptable solvates and/or hydrates of pharmaceutically acceptable salts of the compound/compounds. It is also understood that when the phrase "pharmaceutically acceptable solvates and hydrates" or the phrase "pharmaceutically acceptable solvate or hydrate" is used when referring to a compound/compounds as described herein that are salts, it embraces pharmaceutically acceptable solvates and/or hydrates of such salts. It is also understood by a person of ordinary skill in the art that hydrates are a subgenus of solvates.

The term "prescribing" refers to order, authorize, or recommend the use of a drug or other therapy, remedy, or treatment. In some embodiments, a health care provider orally advises, recommends, or authorizes the use of a compound, dosage regimen, or other treatment to an individual. The health care provider may or may not provide a written prescription for the compound, dosage regimen, or treatment. Further, the health care provider may or may not provide the compound or treatment to the individual. For example, the health care provider can advise the individual where to obtain the compound without providing the compound. In some embodiments, a health care provider can provide a written prescription for the compound, dosage regimen, or treatment to the individual. A prescription can be written on paper or recorded on electronic media. In addition, a prescription can be called in (oral) or faxed in (written) to a pharmacy or a dispensary. In some embodiments, a sample of the compound or treatment is given to the individual. As used herein, giving a sample of a compound constitutes an implicit prescription for the compound. Different health care systems around the world use different methods for prescribing and administering compounds or treatments, and these methods are encompassed by the disclosure herein.

A health care provider can include, for example, a physician, nurse, nurse practitioner, or other health care professional who can prescribe or administer compounds (drugs) for the disorders disclosed herein. In addition, a health care provider can include anyone who can recommend, prescribe, administer, or prevent an individual from receiving a compound or drug, including, for example, an insurance provider.

The terms "prevent," "preventing," and "prevention" refer to the elimination or reduction of the occurrence or onset of one or more symptoms associated with a particular disorder. For example, the terms "prevent," "preventing," and "prevention" can refer to the administration of therapy on a prophylactic or preventative basis to an individual who may ultimately manifest at least one symptom of a disorder but who has not yet done so; also referred to as "prophylactic treatment". Such individuals can be identified on the basis of risk factors that are known to correlate with the subsequent occurrence of the disease, such as the presence of a biomarker. Alternatively, prevention therapy, or prophylactic treatment, can be administered as a prophylactic measure without prior identification of a risk factor. Delaying the onset of the at least one episode and/or symptom of a disorder can also be considered prevention or prophylactic treatment.

The term "solvate" as used herein means a compound of the invention or a salt thereof that further includes a stoichiometric or non-stoichiometric amount of a solvent bound by non-covalent intermolecular forces. Preferred solvents are volatile, non-toxic, and/or acceptable for administration to humans in trace amounts.

The terms "treat," "treating," and "treatment" refer to the administration of therapy to an individual who already manifests, or who has previously manifested, at least one symptom of a disease, disorder, condition, dependence, or behavior; also referred to as "therapeutic treatment". For example, "treating" or "therapeutic treatment" can include any of the following with respect to a disease, disorder, condition, dependence, or behavior: alleviating, abating, ameliorating, improving, inhibiting (e.g., arresting the development), relieving, or causing regression. "Treating" can also include treating the symptoms, preventing additional symptoms, preventing the underlying physiological causes of the symptoms, or stopping the symptoms (either prophylactically and/or therapeutically) of a disease, disorder, condition, dependence, or behavior. For example, the term "treating" in reference to a disorder means a reduction in severity of one or more symptoms associated with a particular disorder. Therefore, treating a disorder does not necessarily mean a reduction in severity of all symptoms associated with a disorder and does not necessarily mean a complete reduction in the severity of one or more symptoms associated with a disorder. "Treating" or "treatment can include prophylactic treatment or therapeutic treatment of a subject in need thereof. In one aspect of the invention, "treating" comprises therapeutic treatment. In another aspect of the invention, "treating" comprises prophylactic treatment of a subject in need thereof.

The term "therapeutically effective amount" refers to the amount of active compound or pharmaceutical agent that elicits the biological or medicinal response in a tissue, system, animal, or human that is being sought by an individual, researcher, veterinarian, medical doctor, or other clinician or caregiver, which can include one or more of the following:

(1) preventing the disorder, for example, preventing a disease, condition, or disorder in an individual who may be predisposed to the disease, condition, or disorder but does not yet experience or display the relevant pathology or symptomatology;

(2) inhibiting the disorder, for example, inhibiting a disease, condition, or disorder in an individual who is experiencing or displaying the relevant pathology or symptomatology (i.e., arresting further development of the pathology and/or symptomatology); and (3) ameliorating the disorder, for example, ameliorating a disease, condition, or disorder in an individual who is experiencing or displaying the relevant pathology or symptomatology (i.e., reversing the pathology and/or symptomatology).

Chemical Group, Moiety or Radical

The term "$C_1$-$C_6$ acyl" refers to a radical comprising a $C_1$-$C_6$ alkyl group attached to the carbon of a carbonyl group, wherein $C_1$-$C_6$ alkyl has the same definition as found herein. Examples include, but are not limited to acetyl, propionyl, butyryl, isobutyryl, pivaloyl, and the like.

The term "$C_1$-$C_6$ acyloxy" refers to a radical comprising a $C_1$-$C_6$ acyl group attached to an oxygen, wherein $C_1$-$C_6$ acyl has the same definition as found herein. $C_1$-$C_6$ acyloxy has the following formula:

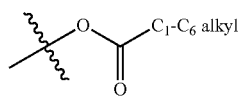

Examples of $C_1$-$C_6$ acyloxy include, but are not limited to, acetoxy, propionyloxy, butyryloxy, isobutyryloxy, pivaloyloxy, and the like.

The term "amino" refers to the group —$NH_2$.

The term "aryl" refers to a ring system containing 6 to 10 carbon atoms that may contain a single ring or two fused rings, and wherein at least one ring is aromatic. Examples include phenyl, indanyl, tetrahydronaphthalene, and naphthyl.

The term "$C_1$-$C_6$ alkoxy" refers to a radical comprising a $C_1$-$C_6$ alkyl group attached directly to an oxygen atom, wherein $C_1$-$C_6$ alkyl has the same definition as found herein. Some embodiments contain 1 to 5 carbons (i.e., $C_1$-$C_5$ alkoxy). Some embodiments contain 1 to 4 carbons (i.e., $C_1$-$C_4$ alkoxy). Some embodiments contain 1 to 3 carbons (i.e., $C_1$-$C_3$ alkoxy). Some embodiments contain 1 or 2 carbons. Examples include, but are not limited to methoxy, ethoxy, n-propoxy, isopropoxy, n-butoxy, t-butoxy, isobutoxy, s-butoxy, and the like.

The term "$C_1$-$C_6$ alkyl" refers to a straight or branched carbon radical containing 1 to 6 carbons. Some embodiments are 1 to 5 carbons (i.e., $C_1$-$C_5$ alkyl), some embodiments are 1 to 4 carbons (i.e., $C_1$-$C_4$ alkyl), some embodiments are 1 to 3 carbons (i.e., $C_1$-$C_3$ alkyl), and some embodiments are 1 or 2 carbons. Examples of an alkyl include, but are not limited to, methyl, ethyl, n-propyl, isopropyl, n-butyl, sec-butyl, isobutyl, tert-butyl, pentyl, isopentyl, tert-pentyl, neo-pentyl, 1-methylbutyl [i.e., —CH($CH_3$)$CH_2CH_2CH_3$], 2-methylbutyl [i.e., —$CH_2$CH($CH_3$)$CH_2CH_3$], n-hexyl and the like.

The term "$C_1$-$C_6$ alkylamino" refers to mean a radical comprising one $C_1$-$C_4$ alkyl group attached to an NH group, wherein $C_1$-$C_6$ alkyl has the same meaning as described herein. Some examples include, but are not limited to, methylamino, ethylamino, n-propylamino, isopropylamino, n-butylamino, s-butylamino, isobutylamino, t-butylamino, and the like. Some embodiments are "$C_1$-$C_2$ alkylamino."

The term "$C_1$-$C_6$ alkylcarboxamide" refers to mean a single $C_1$-$C_6$ alkyl group attached to either the carbon or the nitrogen of an amide group, wherein $C_1$-$C_6$ alkyl has the same definition as found herein. The $C_1$-$C_6$ alkylcarboxamido group may be represented by the following:

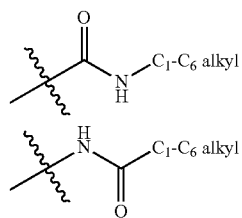

Examples include, but are not limited to, N-methylcarboxamide, N-ethylcarboxamide, N-n-propylcarboxamide, N-isopropylcarboxamide, N-n-butylcarboxamide, N-s-butylcarboxamide, N-isobutylcarboxamide, N-t-butylcarboxamide, and the like.

The term "cyano" refers to the group —CN.

The term "$C_2$-$C_6$ dialkylamino" refers to a radical comprising an amino group substituted with two of the same or different $C_1$-$C_3$ alkyl groups, wherein $C_1$-$C_3$ alkyl has the same definition as found herein. Some examples include, but are not limited to, dimethylamino, methylethylamino, diethylamino, methylpropylamino, methylisopropylamino, ethylpropylamino, ethylisopropylamino, dipropylamino, propylisopropylamino, and the like. Some embodiments are $C_2$-$C_4$ dialkylamino.

The term "$C_1$-$C_6$ haloalkoxy" refers to a radical comprising a $C_1$-$C_6$ haloalkyl group directly attached to an oxygen atom, wherein $C_1$-$C_6$ haloalkyl has the same definition as found herein. Examples include, but are not limited to, difluoromethoxy, trifluoromethoxy, 2,2,2-trifluoroethoxy, pentafluoroethoxy, and the like.

The term "$C_1$-$C_6$ haloalkyl" refers to a radical comprising a $C_1$-$C_6$ alkyl group substituted with one or more halogens, wherein $C_1$-$C_6$ alkyl has the same definition as found herein. The $C_1$-$C_6$ haloalkyl may be fully substituted in which case it can be represented by the formula $C_nL_{2n+1}$, wherein L is a halogen and "n" is 1, 2, 3, 4, 5, or 6. When more than one halogen is present then they may be the same or different and selected from: fluorine, chlorine, bromine, and iodine. In some embodiments, haloalkyl contains 1 to 5 carbons (i.e., $C_1$-$C_5$ haloalkyl). In some embodiments, haloalkyl contains 1 to 4 carbons (i.e., $C_1$-$C_4$ haloalkyl). In some embodiments, haloalkyl contains 1 to 3 carbons (i.e., $C_1$-$C_3$ haloalkyl). In some embodiments, haloalkyl contains 1 or 2 carbons. Examples of haloalkyl groups include, but are not limited to, fluoromethyl, difluoromethyl, trifluoromethyl, chlorodifluoromethyl, 2,2,2-trifluoroethyl, pentafluoroethyl, and the like.

The term "halogen" refers to fluoro, chloro, bromo, or iodo group.

The term "heteroaryl" refers to a ring system containing 5 to 10 ring atoms, that may contain a single ring, two fused rings or three fused rings, and wherein at least one ring is aromatic and at least one ring atom is a heteroatom selected from, for example: O, S, and N, wherein N is optionally substituted with H, $C_1$-$C_4$ acyl, $C_1$-$C_4$ alkyl, or oxide (i.e., an aromatic ring nitrogen and oxide form an N-oxide). Some embodiments contain 5 to 6 ring atoms for example furanyl, thienyl, pyrrolyl, imidazolyl, oxazolyl, thiazolyl, isoxazolyl, pyrazolyl, isothiazolyl, oxadiazolyl, triazolyl, tetrazolyl, thiadiazolyl, pyridinyl, pyrazinyl, pyrimidinyl, pyridazinyl, triazinyl, and the like. Some embodiments contain 8 to 10 ring atoms for example quinolizinyl, quinolinyl, isoquinolinyl, cinnolinyl, phthalazinyl, quinazolinyl, quinoxalinyl, triazinyl, indolyl, isoindolyl, indazolyl, indolizinyl, purinyl, naphthyridinyl, pteridinyl, carbazolyl, acridinyl. phenazinyl, phenothiazinyl, phenoxazinyl, benzoxazolyl, benzothiazolyl, 1H-benzimidazolyl, imidazopyridinyl, benzothienyl, benzofuranyl, isobenzofuran, 2,3-dihydrobenzofuranyl, 4H-benzo[1,3]dioxinyl, 3,4-dihydro-1H-isoquinolinyl, 1,4,6,7-tetrahydro-imidazo[4,5-c]pyridinyl, 7,8-dihydro-5H-[1,6]naphthyridinyl, 5,6-dihydro-8H-[1,2,4]triazolo[4,3-a]pyrazinyl, benzo[1,3]dioxolyl, pyrazolo[1,5-a]pyrimidinyl, 1,2,3,4-tetrahydroquinolinyl, and the like.

In some embodiments, "heteroaryl" is selected from the group: pyrazolyl, imidazolyl, indolyl, 2,3-dihydrobenzofuranyl, 3,4-dihydro-2H-benzo[b][1,4]dioxepinyl, benzo[d][1,3]dioxolyl, benzofuranyl, furanyl, isoxazolyl, pyridinyl, pyrimidinyl, and quinolinyl. In some embodiments, "heteroaryl" is selected from the group: 1H-pyrazol-4-yl, 1H-imidazol-1-yl, 1H-imidazol-5-yl, 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, pyridin-2-yl, pyridin-3-yl, pyridin-4-yl, pyrimidin-5-yl, quinolin-3-yl, and quinolin-5-yl.

The term "heterocyclyl" refers to a non-aromatic ring radical containing 3 to 8 ring atoms, wherein one, two, or three of the ring atoms are heteroatoms selected from, for example: O, S, and N, wherein N is optionally substituted with H, $C_1$-$C_4$ acyl, or $C_1$-$C_4$ alkyl, and S is optionally substituted with one or two oxygens. In some embodiments, "heterocyclyl" refers to a non-aromatic ring radical containing 3 to 8 ring atoms, wherein one or two of the ring atoms are heteroatoms selected from, for example: O, S, and NH. Examples of a heterocyclyl group include, but are not limited to, aziridinyl, azetidinyl, piperidinyl, morpholinyl, oxetanyl, imidazolidinyl, piperazinyl, pyrrolidinyl, thiomorpholinyl, [1,4]oxazepanyl, 1,1-dioxothiomorpholinyl, azepanyl, tetrahydrofuranyl, tetrahydropyranyl, tetrahydrothiopyranyl, and the like.

In some embodiments, "heterocyclyl" is selected from the group: oxetanyl, imidazolidinyl, pyrrolidinyl, piperidinyl, and tetrahydrofuranyl. In some embodiments, "heterocyclyl" is selected from the group: oxetan-3-yl, imidazolidin-1-yl, pyrrolidin-1-yl, piperidin-3-yl, piperidin-4-yl, pyrrolidin-3-yl, and tetrahydrofuran-3-yl.

The term "heterocyclyl-$C_1$-$C_6$ alkyl" refers to a radical consisting of a heterocyclyl group attached to a $C_1$-$C_6$ alkyl radical, wherein heterocyclyl and $C_1$-$C_6$ alkyl have the same definitions as described herein. Examples of a heterocyclyl-$C_1$-$C_6$ alkyl group include, but not limited to, (oxetanyl)methyl, (oxetanyl)ethyl, (imidazolidinyl)methyl, (imidazolidinyl)ethyl, (pyrrolidinyl)methyl, (pyrrolidinyl)ethyl, (piperidinyl)methyl, (piperidinyl)ethyl, (tetrahydrofuranyl)methyl, and (tetrahydrofuranyl)ethyl. In some embodiments, "heterocyclyl-$C_1$-$C_6$ alkyl" is selected from the group: (oxetanyl)methyl, 2-(imidazolidinyl)ethyl, and 2-(pyrrolidinyl)ethyl. In some embodiments, "heterocyclyl-$C_1$-$C_6$ alkyl" is selected from the group: (oxetan-3-yl)methyl, 2-(imidazolidin-1-yl)ethyl, and 2-(pyrrolidin-1-yl)ethyl.

The term "hydroxyl" refers to the group —OH.

The term "hydroxy-$C_1$-$C_6$-alkoxy" refers to a radical consisting of a hydroxyl group attached to a $C_1$-$C_6$-alkoxy radical, wherein hydroxyl and $C_1$-$C_6$-alkoxy have the same definitions as described herein. Examples include, but are not limited to 2-hydroxyethoxy, 2-hydroxypropoxy, 3-hydroxypropoxy, 2-hydroxybutoxy, 3-hydroxybutoxy, 4-hydroxybutoxy, and the like.

The term "hydroxy-$C_1$-$C_6$-alkyl" refers to a radical consisting of a hydroxyl group attached to a $C_1$-$C_6$ alkyl radical, wherein hydroxyl and $C_1$-$C_6$ alkyl have the same definitions as described herein. Examples include, but are not limited to hydroxymethyl, 2-hydroxyethyl, 1-hydroxyethyl, and the like.

The term "oxo" refers to the diradical =O.

The term "pyridinediyl" refers to the di-radical of pyridine.

The term "pyrazine-2,6-diyl" refers to the 2,6-di-radical of pyrazine.

Compounds of the Invention

One aspect of the present invention encompasses, inter alia, certain 1-heteroaryl-indoline-4-carboxamide derivatives selected from compounds of Formula (Ia) and pharmaceutically acceptable salts, solvates, hydrates, and N-oxides thereof:

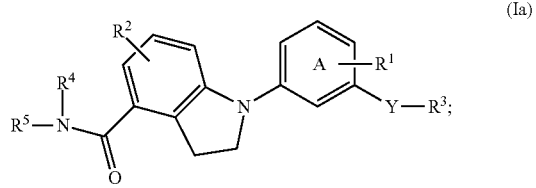

(Ia)

wherein: Ring A, Y, $R^1$, $R^2$, $R^3$, $R^4$, and $R^5$, have the same definitions as described herein, supra and infra. Compounds of Formula (Ia) include anhydrous (i.e., unsolvated), solvated and hydrated forms of uncharged compounds, and further include anhydrous (i.e., unsolvated), solvated and hydrated forms of salts of the compounds. It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables (e.g., Ring A, Y, $R^1$, $R^2$, $R^3$, $R^4$, and $R^5$) contained within the generic chemical formulae described herein, for example, Formulae (Ia), (Ic), (Ie), (Ig), (Ii), (Ik), (Im), (Io), (Iq), (Is), (Iu), (Iw), and the formulae disclosed in the figures, are specifically embraced by the present invention just as if each and every combination was individually and explicitly recited, to the extent that such combinations embrace compounds that result in stable compounds (i.e., compounds that can be isolated, characterized, and tested for biological activity). In addition, all subcombinations of the chemical groups listed in the embodiments describing such variables, as well as all subcombinations of uses and medical indications described herein, are also specifically embraced by the present invention just as if each and every subcombination of chemical groups and subcombination of uses and medical indications was individually and explicitly recited herein.

As used herein, "substituted" indicates that at least one hydrogen atom of the chemical group is replaced by a non-hydrogen substituent or group, the non-hydrogen substituent or group can be monovalent or divalent. When the substituent or group is divalent, then it is understood that this group is further substituted with another substituent or group. When a chemical group herein is "substituted" it may have up to the full valence of substitution; for example, a methyl group can be substituted by 1, 2, or 3 substituents, a methylene group can be substituted by 1 or 2 substituents, a phenyl group can be substituted by 1, 2, 3, 4, or 5 substituents, a naphthyl group can be substituted by 1, 2, 3, 4, 5, 6, or 7 substituents, and the like. Likewise, "substituted with one or more substituents" refers to the substitution of a group with one substituent up to the total number of substituents physically allowed by the group. Further, when a group is substituted with more than one group they can be identical or they can be different.

Compounds of the invention can also include tautomeric forms, such as keto-enol tautomers and the like. Tautomeric forms can be in equilibrium or sterically locked into one form by appropriate substitution. It is understood that the various tautomeric forms are within the scope of the compounds of the present invention.

It is understood and appreciated that compounds of Formula (Ia) and formulae related thereto may have one or more chiral centers and therefore can exist as enantiomers and/or diastereoisomers. The invention is understood to extend to and embrace all such enantiomers, diastereoisomers and mixtures thereof, including but not limited to racemates. It is understood that compounds of Formula (Ia) and formulae used throughout this disclosure represent all individual enantiomers and mixtures thereof, unless specifically stated or shown otherwise.

The Y Group

In some embodiments, Y is selected from: —$CH_2$—, —O—, and —S—.

In some embodiments, Y is —$CH_2$—.

In some embodiments, Y is —O—.

In some embodiments, Y is —S—.

Ring A

In some embodiments, Ring A is pyridinediyl or pyrazine-2,6-diyl.

In some embodiments, Ring A is pyridinediyl.
In some embodiments, Ring A is:

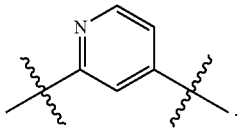

In some embodiments, Ring A is:

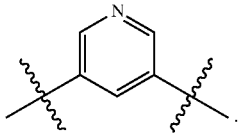 [SMILES: *c1cncc(*)c1]

In some embodiments, Ring A is:

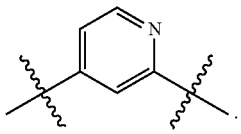 [SMILES: *c1ccnc(*)c1]

In some embodiments, Ring A is:

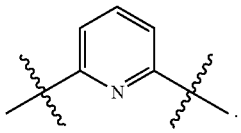 [SMILES: *c1cccc(*)n1]

In some embodiments, Ring A is pyrazine-2,6-diyl of the formula:

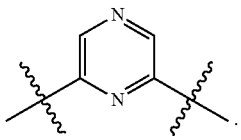 [SMILES: *c1cncc(*)n1]

The $R^1$ Group
In some embodiments, $R^1$ is H or $C_1$-$C_6$ alkyl.
In some embodiments, $R^1$ is H or methyl.
In some embodiments, $R^1$ is H.
In some embodiments, $R^1$ is $C_1$-$C_6$ alkyl.
In some embodiments, $R^1$ is methyl.
The $R^2$ Group
In some embodiments, $R^2$ is H or halogen.
In some embodiments, $R^2$ is H or fluoro.
In some embodiments, $R^2$ is H.
In some embodiments, $R^2$ is halogen.
In some embodiments, $R^2$ is fluoro.
The $R^3$ Group
In some embodiments, $R^3$ is aryl or heteroaryl, wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and the $C_1$-$C_6$ alkyl is optionally substituted with one or more groups selected independently from: $C_1$-$C_6$ alkylamino, $C_2$-$C_6$ dialkylamino, and oxo.

In some embodiments, $R^3$ is aryl or heteroaryl, wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

In some embodiments, $R^3$ is aryl optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

In some embodiments, $R^3$ is heteroaryl optionally substituted with one or more groups selected independently from: chloro, cyano, fluoro, methoxy, methyl, and trifluoromethyl.

In some embodiments, $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein the $C_1$-$C_6$ alkyl is optionally substituted with one or more groups selected independently from: $C_1$-$C_6$ alkylamino, $C_2$-$C_6$ dialkylamino, and oxo.

In some embodiments, $R^3$ is phenyl optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein the $C_1$-$C_6$ alkyl is optionally substituted with one or more groups selected independently from: $C_1$-$C_6$ alkylamino, $C_2$-$C_6$ dialkylamino, and oxo.

In some embodiments, $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ alkoxy, $C_1$-$C_6$ alkyl, cyano, $C_1$-$C_6$ haloalkyl, and halogen.

In some embodiments, $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

In some embodiments, $R^3$ is phenyl optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

In some embodiments, $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: chloro, cyano, fluoro, methoxy, methyl, and trifluoromethyl.

In some embodiments, $R^3$ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl.

In some embodiments, $R^3$ is selected from: 3-((dimethylamino)methyl)phenyl, 3-(trifluoromethoxy)phenyl, 3-(trifluoromethyl)phenyl, 3,4,5-trifluorophenyl, 3,4-difluorophenyl, 3,5-difluoro-4-methoxyphenyl, 3,5-difluorophenyl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, and 4-methoxy-3-methylphenyl.

In some embodiments, $R^3$ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3,4-dihydro-2H-benzo[b][1,4]dioxepin-7-yl, 3,5-dimethylisoxazol-4-yl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl.

In some embodiments, $R^3$ is 1H-indol-4-yl. In some embodiments, $R^3$ is 2-(trifluoromethyl)pyridin-4-yl. In some embodiments, $R^3$ is 2,3-dihydrobenzofuran-5-yl. In some embodiments, $R^3$ is 2-chloropyrimidin-5-yl. In some embodiments, $R^3$ is 2-methoxypyrimidin-5-yl. In some embodiments, $R^3$ is 3-((dimethylamino)methyl)phenyl. In some embodiments, $R^3$ is 3-(trifluoromethoxy)phenyl. In some embodiments, $R^3$ is 3-(trifluoromethyl)phenyl. In some embodiments, $R^3$ is 3,4,5-trifluorophenyl. In some embodiments, $R^3$ is 3,4-difluorophenyl. In some embodiments, $R^3$ is 3,4-dihydro-2H-benzo[b][1,4]dioxepin-7-yl. In some embodiments, $R^3$ is 3,5-difluoro-4-methoxyphenyl. In some embodiments, $R^3$ is 3,5-difluorophenyl. In some embodiments, $R^3$ is 3,5-dimethylisoxazol-4-yl. In some embodiments, $R^3$ is 3-acetoxyphenyl. In some embodiments, $R^3$ is 3-acetyl-4-fluorophenyl. In some embodiments, $R^3$ is 3-acetylphenyl. In some embodiments, $R^3$ is 3-chloro-4-fluorophenyl. In some embodiments, $R^3$ is 3-chloro-4-methoxyphenyl. In some embodiments, $R^3$ is 3-chloro-5-fluorophenyl. In some embodiments, $R^3$ is 3-chloro-5-methoxyphenyl. In some embodiments, $R^3$ is 3-cyano-4-fluorophenyl. In some embodiments, $R^3$ is 3-cyano-5-fluorophenyl. In some embodiments, $R^3$ is 3-fluoro-4-(hydroxymethyl)phenyl. In some embodiments, $R^3$ is 3-fluoro-4-hydroxyphenyl. In some embodiments, $R^3$ is 3-fluoro-4-methoxyphenyl. In some embodiments, $R^3$ is 3-fluoro-5-(trifluoromethyl)phenyl. In some embodiments, $R^3$ is 3-fluoro-5-methoxyphenyl. In some embodiments, $R^3$ is 3-methoxyphenyl. In some embodiments, $R^3$ is 4-acetyl-3-fluorophenyl. In some embodiments, $R^3$ is 4-acetylphenyl. In some embodiments, $R^3$ is 4-chloro-3-fluorophenyl. In some embodiments, $R^3$ is 4-chloro-3-methoxyphenyl. In some embodiments, $R^3$ is 4-cyano-3-fluorophenyl. In some embodiments, $R^3$ is 4-ethoxy-3-fluorophenyl. In some embodiments, $R^3$ is 4-fluoro-3-(hydroxymethyl)phenyl. In some embodiments, $R^3$ is 4-fluoro-3-(methylcarbamoyl)phenyl. In some embodiments, $R^3$ is 4-fluoro-3-(trifluoromethyl)phenyl. In some embodiments, $R^3$ is 4-fluoro-3-hydroxyphenyl. In some embodiments, $R^3$ is 4-fluoro-3-methoxyphenyl. In some embodiments, $R^3$ is 4-methoxy-3-(trifluoromethyl)phenyl. In some embodiments, $R^3$ is 4-methoxy-3-methylphenyl. In some embodiments, $R^3$ is 5-(trifluoromethyl)pyridin-3-yl. In some embodiments, $R^3$ is 5,6-difluoropyridin-3-yl. In some embodiments, $R^3$ is 5-chloro-6-fluoropyridin-3-yl. In some embodiments, $R^3$ is 5-chloro-6-methoxypyridin-3-yl. In some embodiments, $R^3$ is 5-chloropyridin-3-yl. In some embodiments, $R^3$ is 5-fluoro-6-methoxypyridin-3-yl. In some embodiments, $R^3$ is 6-(trifluoromethyl)pyridin-2-yl. In some embodiments, $R^3$ is 6-cyanopyridin-3-yl. In some embodiments, $R^3$ is 6-fluoro-5-methylpyridin-3-yl. In some embodiments, $R^3$ is 6-methoxypyridin-3-yl. In some embodiments, $R^3$ is benzo[d][1,3]dioxol-5-yl. In some embodiments, $R^3$ is benzofuran-2-yl. In some embodiments, $R^3$ is benzofuran-5-yl. In some embodiments, $R^3$ is furan-2-yl. In some embodiments, $R^3$ is furan-3-yl. In some embodiments, $R^3$ is quinolin-3-yl. In some embodiments, $R^3$ is quinolin-5-yl.

The $R^4$ Group

In some embodiments, $R^4$ is H.

The $R^5$ Group

In some embodiments, $R^5$ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

In some embodiments, $R^5$ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

In some embodiments, $R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

In some embodiments, $R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

In some embodiments, $R^5$ is selected from: H, (3-(hydroxymethyl)oxetan-3-yl)methyl, (dimethylamino)ethyl, 1-(2-hydroxyethyl)-1H-pyrazol-4-yl, 1-(2-hydroxyethyl)piperidin-4-yl, 1,3-dihydroxybutan-2-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2,3-dihydroxypropyl, 2-acetamidoethyl, 2-cyanoethyl, 2-fluoro-3-hydroxypropyl, 2-fluoroethyl, 2-hydroxy-2-(pyridin-2-yl)ethyl, 2-hydroxy-2-(pyridin-3-yl)ethyl, 2-hydroxy-2-(pyridin-4-yl)ethyl, 2-hydroxy-3-methoxypropyl, 2-hydroxyethyl, 2-hydroxypropyl, 2-morpholinoethyl, 2-oxopyrrolidin-3-yl, 2-oxotetrahydrofuran-3-yl, 3-(dimethylamino)-2-hydroxypropyl, 3-(methylamino)-3-oxopropyl, 3,3,3-trifluoro-2-hydroxypropyl, 3-fluoro-2-hydroxypropyl, 3-hydroxypropyl, 6-oxopiperidin-3-yl, cyanomethyl, methyl, pyridin-4-yl, and tetrahydrofuran-3-yl.

In some embodiments, $R^5$ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

In some embodiments, $R^5$ is H. In some embodiments, $R^5$ is (2R,3S)-1,3-dihydroxybutan-2-yl. In some embodiments, $R^5$ is (3-(hydroxymethyl)oxetan-3-yl)methyl. In some embodiments, $R^5$ is (dimethylamino)ethyl. In some embodiments, $R^5$ is (R)-2,3-dihydroxypropyl. In some embodiments, $R^5$ is (R)-2-fluoro-3-hydroxypropyl. In some embodiments, $R^5$ is (R)-2-hydroxy-2-(pyridin-3-yl)ethyl. In some embodiments, $R^5$ is (R)-2-hydroxy-3-methoxypropyl. In some embodiments, $R^5$ is (R)-2-hydroxypropyl. In some embodiments, $R^5$ is (R)-2-oxopyrrolidin-3-yl. In some embodiments, $R^5$ is (R)-2-oxotetrahydrofuran-3-yl. In some embodiments, $R^5$ is (S)-2,3-dihydroxypropyl. In some embodiments, $R^5$ is (S)-2-fluoro-3-hydroxypropyl. In some embodiments, $R^5$ is (S)-2-hydroxy-2-(pyridin-3-yl)ethyl. In some embodiments, $R^5$ is (S)-2-hydroxy-3-methoxypropyl. In some embodiments, $R^5$ is (S)-2-hydroxypropyl. In some embodiments, $R^5$ is (S)-2-oxopyrrolidin-3-yl. In some embodiments, $R^5$ is (S)-2-oxotetrahydrofuran-3-yl. In some embodiments, $R^5$ is (S)-3,3,3-trifluoro-2-hydroxypropyl. In some embodiments, $R^5$ is (S)-3-fluoro-2-hydroxypropyl. In some embodiments, $R^5$ is (S)-tetrahydrofuran-3-yl. In some embodiments, $R^5$ is 1-(2-hydroxyethyl)-1H-pyrazol-4-yl. In some embodiments, $R^5$ is 1-(2-hydroxyethyl)piperidin-4-yl. In some embodiments, $R^5$ is 1,3-dihydroxybutan-2-yl. In some embodiments, $R^5$ is 1,3-dihydroxypropan-2-yl. In some embodiments, $R^5$ is 1,3-dimethoxypropan-2-yl. In some embodiments, $R^5$ is 1-methyl-1H-pyrazol-4-yl. In some embodiments, $R^5$ is 1-methylpiperidin-4-yl. In some embodiments, $R^5$ is 2-(1H-imidazol-1-yl)ethyl. In some embodiments, $R^5$ is 2-(1H-imidazol-5-yl)ethyl. In some embodiments, $R^5$ is 2-(2-hydroxyethoxy)ethyl. In some embodiments, $R^5$ is 2-(2-oxoimidazolidin-1-yl)ethyl. In some embodiments, $R^5$ is 2-(2-oxopyrrolidin-1-yl)ethyl. In some embodiments, $R^5$ is 2-(pyrrolidin-1-yl)ethyl. In some embodiments, $R^5$ is 2,3-dihydroxypropyl. In some embodiments, $R^5$ is 2-acetamidoethyl. In some embodiments, $R^5$ is 2-cyanoethyl. In some embodiments, $R^5$ is 2-fluoro-3-hydroxypropyl. In some embodiments, $R^5$ is 2-fluoroethyl. In some embodiments, $R^5$ is 2-hydroxy-2-(pyridin-2-yl)ethyl. In some embodiments, $R^5$ is 2-hydroxy-2-(pyridin-3-yl)ethyl. In some embodiments, $R^5$ is 2-hydroxy-2-(pyridin-4-yl)ethyl. In some embodiments, $R^5$ is 2-hydroxy-3-methoxypropyl. In some embodiments, $R^5$ is 2-hydroxyethyl. In some embodiments, $R^5$ is 2-hydroxypropyl. In some embodiments, $R^5$ is 2-morpholinoethyl. In some embodiments, $R^5$ is 2-oxopyrrolidin-3-yl. In some embodiments, $R^5$ is 2-oxotetrahydrofuran-3-yl. In some embodiments, $R^5$ is 3-(dimethylamino)-2-hydroxypropyl. In some embodiments, $R^5$ is 3-(methylamino)-3-oxopropyl. In some embodiments, $R^5$ is 3,3,3-trifluoro-2-hydroxypropyl. In some embodiments, $R^5$ is 3-fluoro-2-hydroxypropyl. In some embodiments, $R^5$ is 3-hydroxypropyl. In some embodiments, $R^5$ is 6-oxopiperidin-3-yl. In some embodiments, $R^5$ is cyanomethyl. In some embodiments, $R^5$ is methyl. In some embodiments, $R^5$ is pyridin-4-yl. In some embodiments, $R^5$ is tetrahydrofuran-3-yl.

Stereochemical Designation

In some embodiments, compounds of the present invention have one chiral carbon and the chiral carbon has the (S)

stereochemical designation. In some embodiments, compounds of the present invention have one chiral carbon and the chiral carbon has the (R) stereochemical designation. In some embodiments, the one chiral carbon is present in the $R^3$ group. In some embodiments, the one chiral carbon is present in the $R^5$ group.

In some embodiments, compounds of the present invention have two chiral carbons and the chiral carbons have the (R,R) stereochemical designations. In some embodiments, compounds of the present invention have two chiral carbons and the chiral carbons have the (R,S) stereochemical designations. In some embodiments, compounds of the present invention have two chiral carbons and the chiral carbons have the (S,S) stereochemical designations. In some embodiments, compounds of the present invention have two chiral carbons and the chiral carbons have the (S,R) stereochemical designations. In some embodiments, the two chiral carbons are present in the $R^3$ group. In some embodiments, the two chiral carbons are present in the $R^5$ group.

It is understood that each chiral carbon designated by (R) or (S) is determined in accordance to the system by which the substituents are each assigned a priority based on atomic number defined by the Cahn-Ingold-Prelog priority rules (i.e., CIP).

Certain Combinations

One aspect of the present invention pertains to compounds of Formula (Ic) and pharmaceutically acceptable salts, solvates, hydrates, and N-oxides thereof:

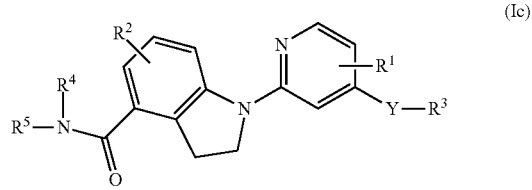

(Ic)

wherein Y, $R^1$, $R^2$, $R^3$, $R^4$, and $R^5$, have the same definitions as described herein, supra and infra.

One aspect of the present invention pertains to compounds of Formula (Im) and pharmaceutically acceptable salts, solvates, hydrates, and N-oxides thereof:

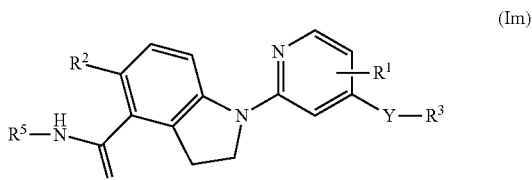

(Im)

wherein:
Y is selected from: —CH₂—, —O—, and —S—;
$R^1$ is H or $C_1$-$C_6$ alkyl;
$R^2$ is H or halogen;
$R^3$ is aryl or heteroaryl, wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and
$R^5$ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: 2-hydroxyethyl, acetamido, cyano, dimethylamino, fluoro, hydroxy, hydroxymethyl, methoxy, methyl, methylamino, oxo, and trifluoromethyl.

One aspect of the present invention pertains to compounds of Formula (Im) and pharmaceutically acceptable salts, solvates, hydrates, and N-oxides thereof:

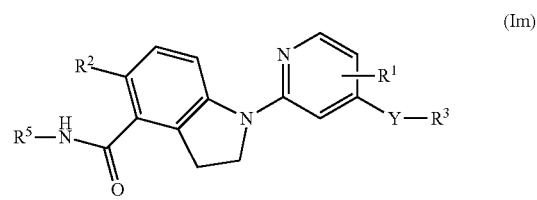

(Im)

wherein:
Y is selected from: —CH₂—, —O—, and —S—;
$R^1$ is H or $C_1$-$C_6$ alkyl;
$R^2$ is H or halogen;
$R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein the $C_1$-$C_6$ alkyl is optionally substituted with one or more groups selected independently from: $C_1$-$C_6$ alkylamino, $C_2$-$C_6$ dialkylamino, and oxo; and
$R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

One aspect of the present invention pertains to compounds of Formula (Im) and pharmaceutically acceptable salts, solvates, hydrates, and N-oxides thereof:

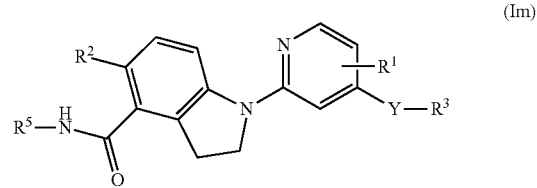

(Im)

wherein:
Y is selected from: —CH₂—, —O—, and —S—;
$R^1$ is H or methyl;
$R^2$ is H or fluoro;

R³ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and R⁵ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

One aspect of the present invention pertains to compounds of Formula (Im) and pharmaceutically acceptable salts, solvates, hydrates, and N-oxides thereof:

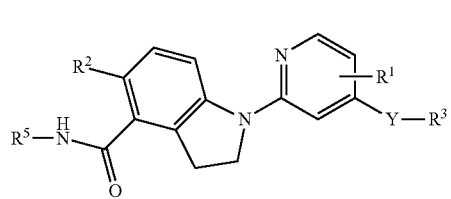

(Im)

wherein:
Y is selected from: —CH₂—, —O—, and —S—;
R¹ is H or methyl;
R² is H or fluoro;
R³ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl; and R⁵ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

One aspect of the present invention pertains to compounds of Formula (Io) and pharmaceutically acceptable salts, solvates, hydrates, and N-oxides thereof:

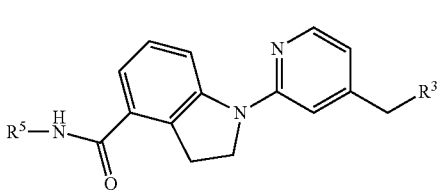

(Io)

wherein:
R³ is aryl or heteroaryl, wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and R⁵ is selected from: H, C₁-C₆ alkyl, heteroaryl, heteroaryl-C₁-C₆ alkyl, heterocyclyl, heterocyclyl-C₁-C₆ alkyl, and hydroxy-C₁-C₆-alkyl; and each group is optionally substituted with one or more groups selected independently from: 2-hydroxyethyl, acetamido, cyano, dimethylamino, fluoro, hydroxy, hydroxymethyl, methoxy, methyl, methylamino, oxo, and trifluoromethyl.

One aspect of the present invention pertains to compounds of Formula (Io) and pharmaceutically acceptable salts, solvates, hydrates, and N-oxides thereof:

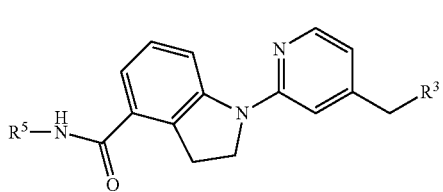

(Io)

wherein:

R³ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein the $C_1$-$C_6$ alkyl is optionally substituted with one or more groups selected independently from: $C_1$-$C_6$ alkylamino, $C_2$-$C_6$ dialkylamino, and oxo; and R⁵ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

One aspect of the present invention pertains to compounds of Formula (Io) and pharmaceutically acceptable salts, solvates, hydrates, and N-oxides thereof:

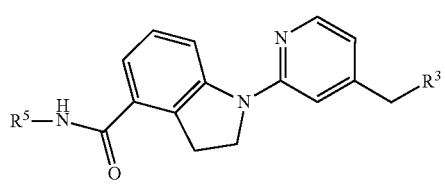

(Io)

wherein:

R³ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and R⁵ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

One aspect of the present invention pertains to compounds of Formula (Io) and pharmaceutically acceptable salts, solvates, hydrates, and N-oxides thereof:

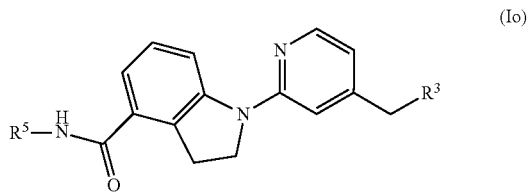

(Io)

wherein:

R³ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl; and R⁵ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

One aspect of the present invention pertains to compounds of Formula (Ie) and pharmaceutically acceptable salts, solvates, hydrates, and N-oxides thereof:

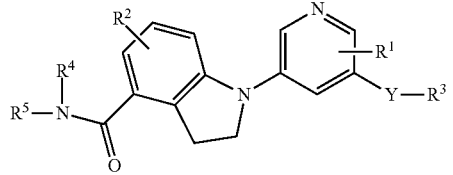

(Ie)

wherein Y, R¹, R², R³, R⁴, and R⁵, have the same definitions as described herein, supra and infra.

One aspect of the present invention pertains to compounds of Formula (Iq) and pharmaceutically acceptable salts, solvates, hydrates, and N-oxides thereof:

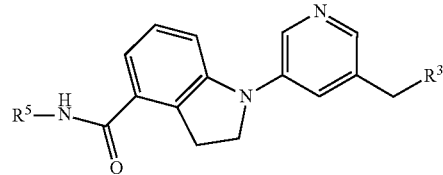

(Iq)

wherein:
R³ is aryl optionally substituted with $C_1$-$C_6$ haloalkyl; and
R⁵ is selected from: H, $C_1$-$C_6$ alkyl, and heterocyclyl; and
$C_1$-$C_6$ alkyl is optionally substituted with hydroxyl.

One aspect of the present invention pertains to compounds of Formula (Iq) and pharmaceutically acceptable salts, solvates, hydrates, and N-oxides thereof:

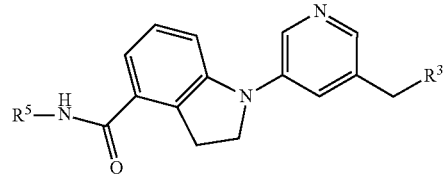

(Iq)

wherein:
R³ is phenyl optionally substituted with trifluoromethyl; and
R⁵ is selected from: H, methyl, ethyl, and tetrahydrofuranyl; and ethyl is optionally substituted with hydroxyl.

One aspect of the present invention pertains to compounds of Formula (Iq) and pharmaceutically acceptable salts, solvates, hydrates, and N-oxides thereof:

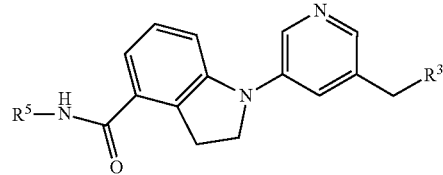

(Iq)

wherein:
R³ is 3-(trifluoromethyl)phenyl; and
R⁵ is selected from: H, methyl, 2-hydroxyethyl, and tetrahydrofuran-3-yl.

One aspect of the present invention pertains to compounds of Formula (Ig) and pharmaceutically acceptable salts, solvates, hydrates, and N-oxides thereof:

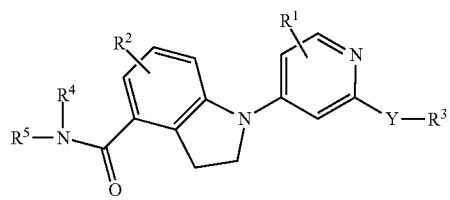

(Ig)

wherein Y, R¹, R², R³, R⁴, and R⁵, have the same definitions as described herein, supra and infra.

One aspect of the present invention pertains to compounds of Formula (Is) and pharmaceutically acceptable salts, solvates, hydrates, and N-oxides thereof:

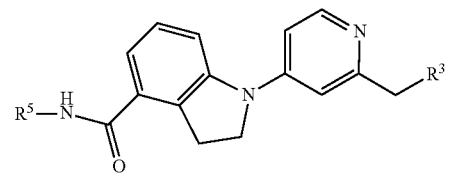

(Is)

wherein:
R³ is aryl is optionally substituted with one or more groups selected independently from: $C_1$-$C_6$ acyl, $C_1$-$C_6$ alkoxy, $C_1$-$C_6$ haloalkyl, and halogen; and
R⁵ is selected from: H, $C_1$-$C_6$ alkyl, and heterocyclyl; and $C_1$-$C_6$ alkyl and heterocyclyl are each optionally substituted with one or more groups selected independently from: $C_1$-$C_6$ alkoxy, halogen, hydroxyl, and oxo.

One aspect of the present invention pertains to compounds of Formula (Is) and pharmaceutically acceptable salts, solvates, hydrates, and N-oxides thereof:

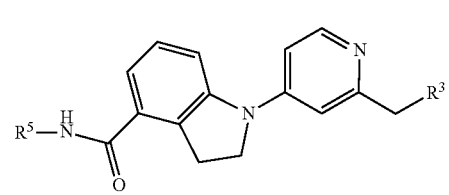

(Is)

wherein:
R³ is phenyl is optionally substituted with one or more groups selected independently from: acetyl, methoxy, trifluoromethyl, chloro, and fluoro; and
R⁵ is selected from: H, ethyl, pyrrolidinyl, and tetrahydrofuranyl; and ethyl and pyrrolidinyl are each optionally substituted with one or more groups selected independently from: methoxy, fluoro, hydroxyl, and oxo.

One aspect of the present invention pertains to compounds of Formula (Is) and pharmaceutically acceptable salts, solvates, hydrates, and N-oxides thereof:

(Is)

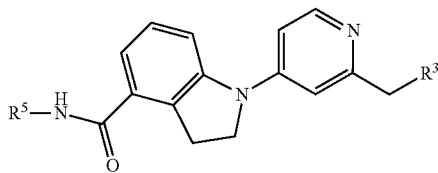

wherein:

R³ is 3-(trifluoromethyl)phenyl, 3-acetylphenyl, 3,4,5-trifluorophenyl, 3-chloro-5-fluorophenyl, 4-fluoro-3-(trifluoromethyl)phenyl, and 3-fluoro-4-methoxyphenyl; and R⁵ is selected from: H, 2-fluoro-3-hydroxypropyl, 2-hydroxy-3-methoxypropyl, 2-oxopyrrolidin-3-yl, 2-hydroxypropyl, 3-fluoro-2-hydroxypropyl, tetrahydrofuran-3-yl, 2-fluoroethyl, and 2-hydroxyethyl.

One aspect of the present invention pertains to compounds of Formula (Ii) and pharmaceutically acceptable salts, solvates, hydrates, and N-oxides thereof:

(Ii)

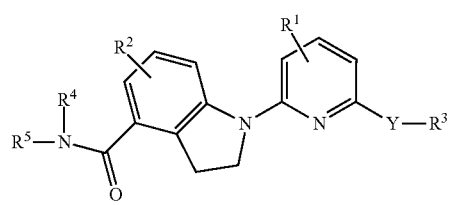

wherein Y, R¹, R², R³, R⁴, and R⁵, have the same definitions as described herein, supra and infra.

One aspect of the present invention pertains to compounds of Formula (Iu) and pharmaceutically acceptable salts, solvates, hydrates, and N-oxides thereof:

(Iu)

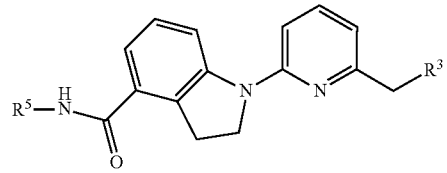

wherein:

R³ is aryl optionally substituted with $C_1$-$C_6$ haloalkyl; and

R⁵ is selected from: H and heterocyclyl.

One aspect of the present invention pertains to compounds of Formula (Iu) and pharmaceutically acceptable salts, solvates, hydrates, and N-oxides thereof:

(Iu)

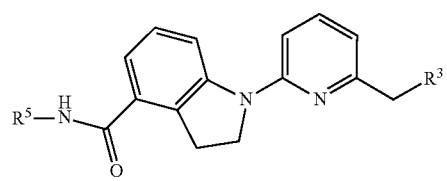

wherein:

R³ is phenyl optionally substituted with trifluoromethyl; and

R⁵ is selected from: H and tetrahydrofuranyl.

One aspect of the present invention pertains to compounds of Formula (Iu) and pharmaceutically acceptable salts, solvates, hydrates, and N-oxides thereof:

(Iu)

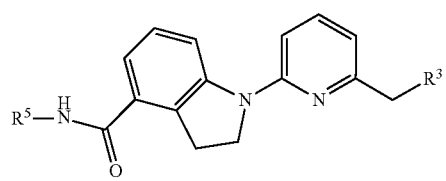

wherein:

R³ is 3-(trifluoromethyl)phenyl; and

R⁵ is selected from: H and tetrahydrofuran-3-yl.

One aspect of the present invention pertains to compounds of Formula (Ik) and pharmaceutically acceptable salts, solvates, hydrates, and N-oxides thereof:

(Ik)

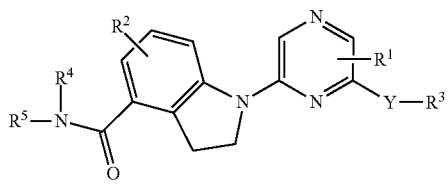

wherein Y, R¹, R², R³, R⁴, and R⁵, have the same definitions as described herein, supra and infra.

One aspect of the present invention pertains to compounds of Formula (Iw) and pharmaceutically acceptable salts, solvates, hydrates, and N-oxides thereof:

(Iw)

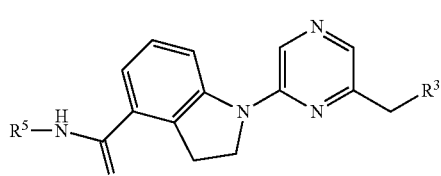

wherein:

R³ is aryl optionally substituted with $C_1$-$C_6$ haloalkyl; and

R⁵ is selected from: H and $C_1$-$C_6$ alkyl; and $C_1$-$C_6$ alkyl is optionally substituted with hydroxyl.

One aspect of the present invention pertains to compounds of Formula (Iw) and pharmaceutically acceptable salts, solvates, hydrates, and N-oxides thereof:

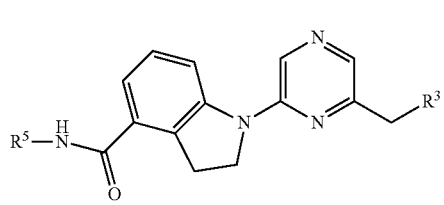

(Iw)

wherein:
R³ is phenyl optionally substituted with trifluoromethyl; and
R⁵ is selected from: H and ethyl; and ethyl is optionally substituted with hydroxyl.

One aspect of the present invention pertains to compounds of Formula (Iw) and pharmaceutically acceptable salts, solvates, hydrates, and N-oxides thereof:

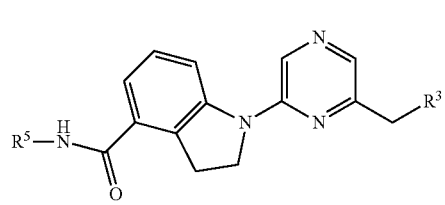

(Iw)

wherein:
R³ is 3-(trifluoromethyl)phenyl; and
R⁵ is selected from: H and 2-hydroxyethyl.

Some embodiments of the present invention include every combination of one or more compounds and pharmaceutically acceptable salts, solvates, hydrates, and N-oxides thereof selected from the following group shown in Table A.

TABLE A

| Cmpd No. | Chemical Structure | Chemical Name |
|---|---|---|
| 1 | 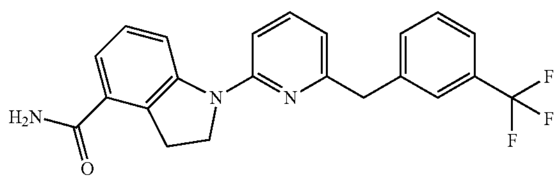 | 1-(6-(3-(Trifluoromethyl)benzyl)pyridin-2-yl)indoline-4-carboxamide |
| 2 | 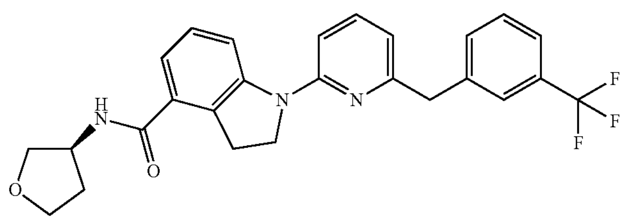 [SMILES: O=C(N[C@H]1CCOC1)c1cccc2c1CCN2c1cccc(Cc2cccc(C(F)(F)F)c2)n1] | (S)-N-(Tetrahydrofuran-3-yl)-1-(6-(3-(trifluoromethyl)benzyl)pyridin-2-yl)indoline-4-carboxamide |
| 3 | 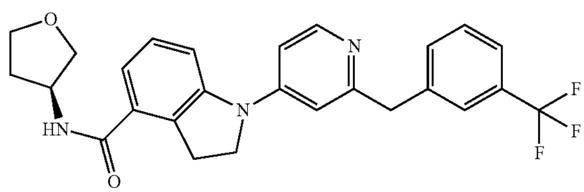 [SMILES: O=C(N[C@H]1CCOC1)c1cccc2c1CCN2c1ccnc(Cc2cccc(C(F)(F)F)c2)c1] | (S)-N-(Tetrahydrofuran-3-yl)-1-(2-(3-(trifluoromethyl)benzyl)pyridin-4-yl)indoline-4-carboxamide |
| 4 | 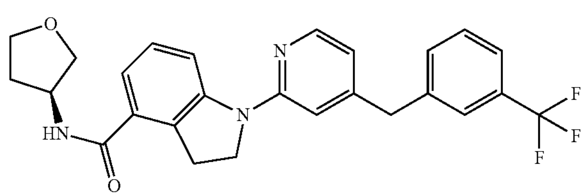 [SMILES: O=C(N[C@H]1CCOC1)c1cccc2c1CCN2c1cc(Cc2cccc(C(F)(F)F)c2)ccn1] | (S)-N-(Tetrahydrofuran-3-yl)-1-(4-(3-(trifluoromethyl)benzyl)pyridin-2-yl)indoline-4-carboxamide |
| 5 | 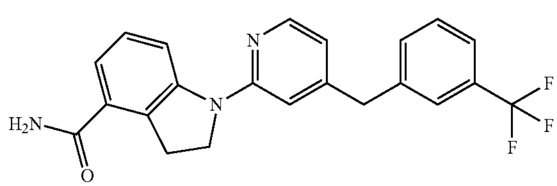 [SMILES: NC(=O)c1cccc2c1CCN2c1cc(Cc2cccc(C(F)(F)F)c2)ccn1] | 1-(4-(3-(Trifluoromethyl)benzyl)pyridin-2-yl)indoline-4-carboxamide |

TABLE A-continued

| Cmpd No. | Chemical Structure | Chemical Name |
|---|---|---|
| 6 | 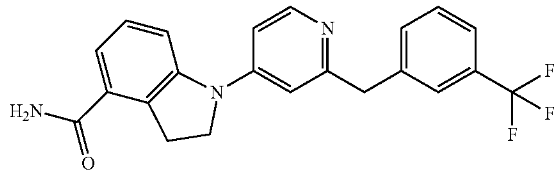 [SMILES: NC(=O)c1cccc2c1CCN2c1ccnc(Cc2cccc(C(F)(F)F)c2)c1] | 1-(2-(3-(Trifluoromethyl)benzyl)pyridin-4-yl)indoline-4-carboxamide |
| 7 | 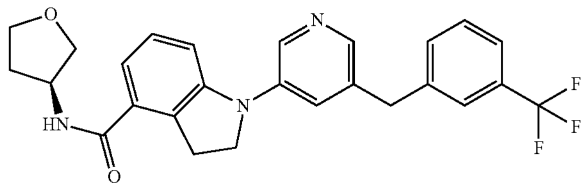 [SMILES: O=C(N[C@H]1CCOC1)c1cccc2c1CCN2c1cncc(Cc2cccc(C(F)(F)F)c2)c1] | (S)-N-(Tetrahydrofuran-3-yl)-1-(5-(3-(trifluoromethyl)benzyl)pyridin-3-yl)indoline-4-carboxamide |
| 8 | 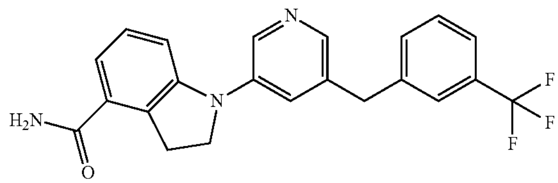 [SMILES: NC(=O)c1cccc2c1CCN2c1cncc(Cc2cccc(C(F)(F)F)c2)c1] | 1-(5-(3-(Trifluoromethyl)benzyl)pyridin-3-yl)indoline-4-carboxamide |
| 9 | 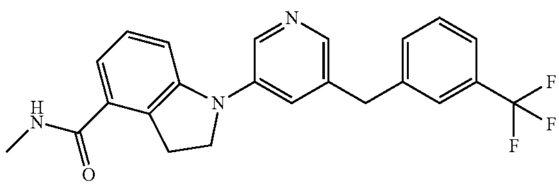 [SMILES: CNC(=O)c1cccc2c1CCN2c1cncc(Cc2cccc(C(F)(F)F)c2)c1] | N-Methyl-1-(5-(3-(trifluoromethyl)benzyl)pyridin-3-yl)indoline-4-carboxamide |
| 10 | 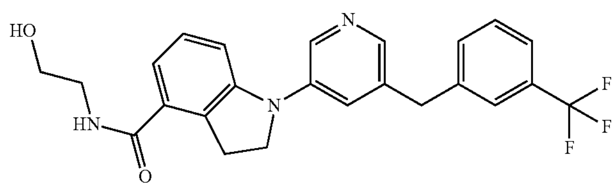 [SMILES: O=C(NCCO)c1cccc2c1CCN2c1cncc(Cc2cccc(C(F)(F)F)c2)c1] | N-(2-Hydroxyethyl)-1-(5-(3-(trifluoromethyl)benzyl)pyridin-3-yl)indoline-4-carboxamide |
| 11 | 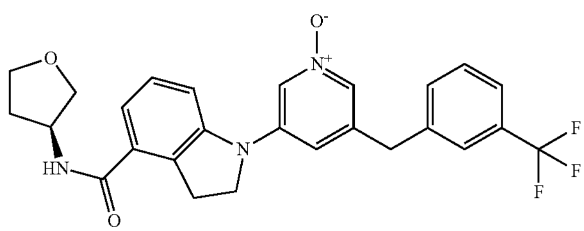 [SMILES: O=C(N[C@H]1CCOC1)c1cccc2c1CCN2c1cc(Cc2cccc(C(F)(F)F)c2)c[n+]([O-])c1] | (S)-3-(4-(Tetrahydrofuran-3-ylcarbamoyl)indolin-1-yl)-5-(3-(trifluoromethyl)benzyl)pyridine 1-oxide |
| 12 | 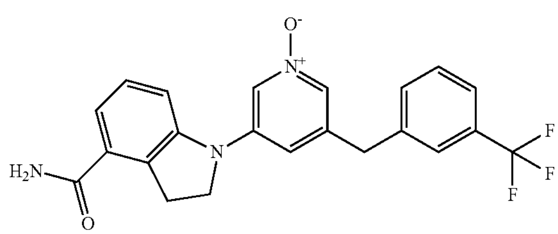 [SMILES: NC(=O)c1cccc2c1CCN2c1cc(Cc2cccc(C(F)(F)F)c2)c[n+]([O-])c1] | 3-(4-Carbamoylindolin-1-yl)-5-(3-(trifluoromethyl)benzyl)pyridine 1-oxide |
| 13 | 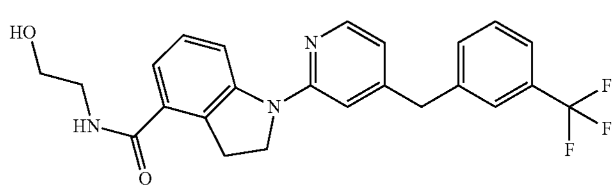 [SMILES: O=C(NCCO)c1cccc2c1CCN2c1cc(Cc2cccc(C(F)(F)F)c2)ccn1] | N-(2-Hydroxyethyl)-1-(4-(3-(trifluoromethyl)benzyl)pyridin-2-yl)indoline-4-carboxamide |

TABLE A-continued

| Cmpd No. | Chemical Structure | Chemical Name |
|---|---|---|
| 14 | 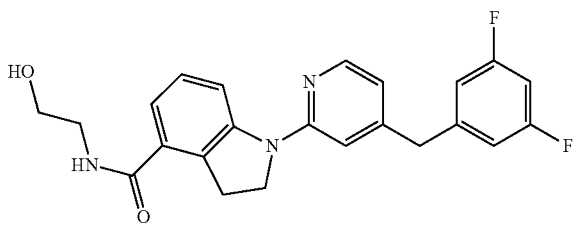 [SMILES: O=C(NCCO)c1cccc2c1CCN2c1cc(Cc2cc(F)cc(F)c2)ccn1] | 1-(4-(3,5-Difluorobenzyl)pyridin-2-yl)-N-(2-hydroxyethyl)indoline-4-carboxamide |
| 15 | 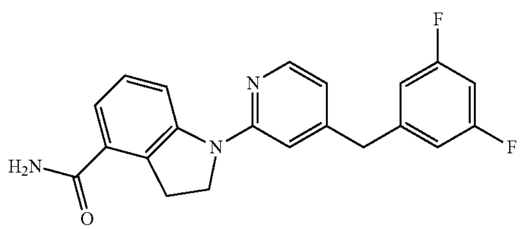 [SMILES: NC(=O)c1cccc2c1CCN2c1cc(Cc2cc(F)cc(F)c2)ccn1] | 1-(4-(3,5-Difluorobenzyl)pyridin-2-yl)indoline-4-carboxamide |
| 16 | 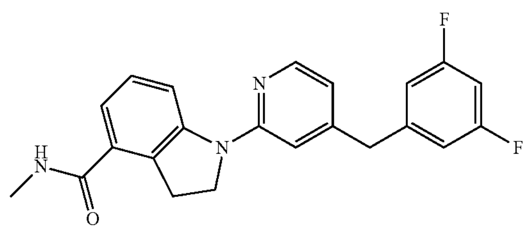 [SMILES: CNC(=O)c1cccc2c1CCN2c1cc(Cc2cc(F)cc(F)c2)ccn1] | 1-(4-(3,5-Difluorobenzyl)pyridin-2-yl)-N-methylindoline-4-carboxamide |
| 17 | 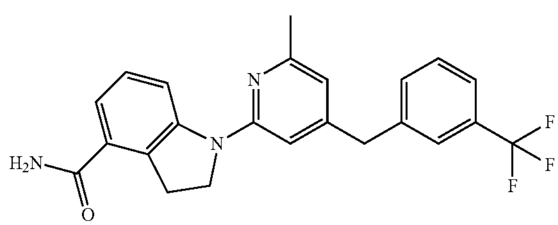 [SMILES: Cc1cc(Cc2cccc(C(F)(F)F)c2)cc(N2CCc3c(C(N)=O)cccc32)n1] | 1-(6-Methyl-4-(3-(trifluoromethyl)benzyl)pyridin-2-yl)indoline-4-carboxamide |
| 18 | 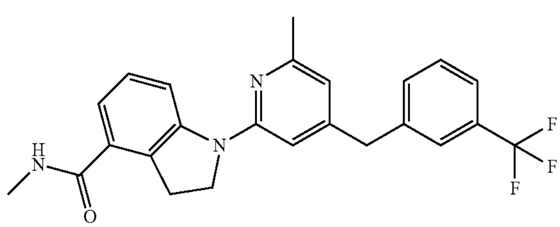 [SMILES: CNC(=O)c1cccc2c1CCN2c1cc(Cc2cccc(C(F)(F)F)c2)cc(C)n1] | N-Methyl-1-(6-methyl-4-(3-(trifluoromethyl)benzyl)pyridin-2-yl)indoline-4-carboxamide |
| 19 | 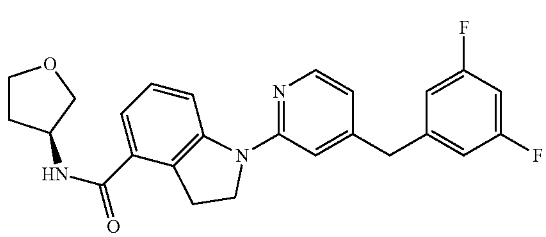 [SMILES: O=C(N[C@H]1CCOC1)c1cccc2c1CCN2c1cc(Cc2cc(F)cc(F)c2)ccn1] | (S)-1-(4-(3,5-Difluorobenzyl)pyridin-2-yl)-N-(tetrahydrofuran-3-yl)indoline-4-carboxamide |

TABLE A-continued

| Cmpd No. | Chemical Structure | Chemical Name |
|---|---|---|
| 20 | 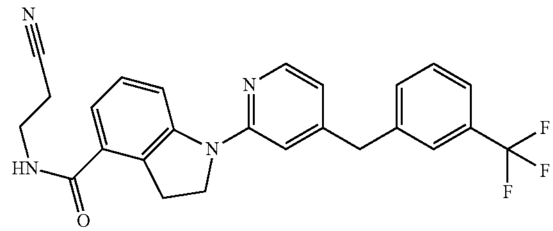 [SMILES: N#CCCNC(=O)c1cccc2c1CCN2c1cc(Cc2cccc(C(F)(F)F)c2)ccn1] | N-(2-Cyanoethyl)-1-(4-(3-(trifluoromethyl)benzyl)pyridin-2-yl)indoline-4-carboxamide |
| 21 | 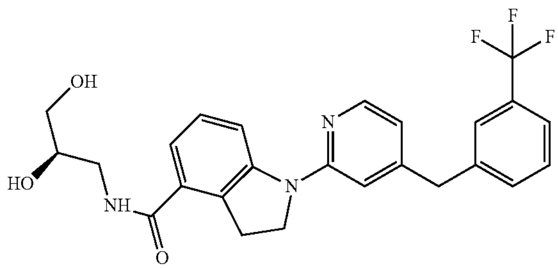 [SMILES: O=C(NC[C@@H](O)CO)c1cccc2c1CCN2c1cc(Cc2cccc(C(F)(F)F)c2)ccn1] | (R)-N-(2,3-Dihydroxypropyl)-1-(4-(3-(trifluoromethyl)benzyl)pyridin-2-yl)indoline-4-carboxamide |
| 22 | 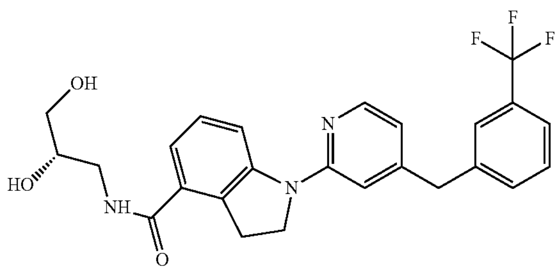 [SMILES: O=C(NC[C@H](O)CO)c1cccc2c1CCN2c1cc(Cc2cccc(C(F)(F)F)c2)ccn1] | (S)-N-(2,3-Dihydroxypropyl)-1-(4-(3-(trifluoromethyl)benzyl)pyridin-2-yl)indoline-4-carboxamide |
| 23 | 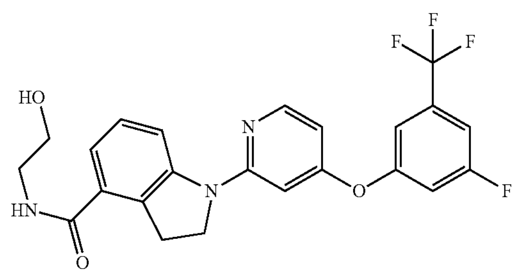 [SMILES: O=C(NCCO)c1cccc2c1CCN2c1cc(Oc2cc(F)cc(C(F)(F)F)c2)ccn1] | 1-(4-(3-Fluoro-5-(trifluoromethyl)phenoxy)pyridin-2-yl)-N-(2-hydroxyethyl)indoline-4-carboxamide |
| 24 | 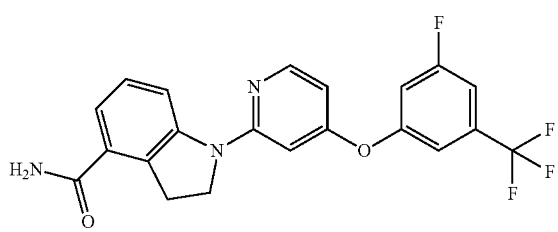 [SMILES: NC(=O)c1cccc2c1CCN2c1cc(Oc2cc(F)cc(C(F)(F)F)c2)ccn1] | 1-(4-(3-Fluoro-5-(trifluoromethyl)phenoxy)pyridin-2-yl)indoline-4-carboxamide |
| 25 | 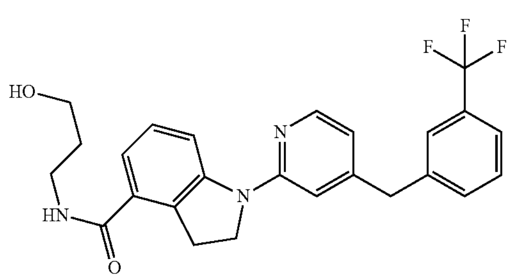 [SMILES: O=C(NCCCO)c1cccc2c1CCN2c1cc(Cc2cccc(C(F)(F)F)c2)ccn1] | N-(3-Hydroxypropyl)-1-(4-(3-(trifluoromethyl)benzyl)pyridin-2-yl)indoline-4-carboxamide |

TABLE A-continued

| Cmpd No. | Chemical Structure | Chemical Name |
|---|---|---|
| 26 | 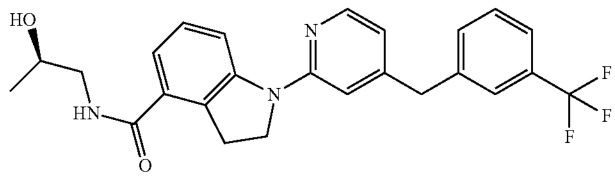 [SMILES: C[C@@H](O)CNC(=O)c1cccc2c1CCN2c1cc(Cc2cccc(C(F)(F)F)c2)ccn1] | (R)-N-(2-Hydroxypropyl)-1-(4-(3-(trifluoromethyl)benzyl)pyridin-2-yl)indoline-4-carboxamide |
| 27 | 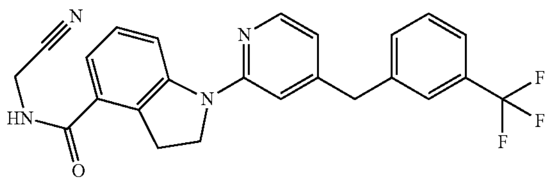 [SMILES: N#CCNC(=O)c1cccc2c1CCN2c1cc(Cc2cccc(C(F)(F)F)c2)ccn1] | N-(Cyanomethyl)-1-(4-(3-(trifluoromethyl)benzyl)pyridin-2-yl)indoline-4-carboxamide |
| 28 | 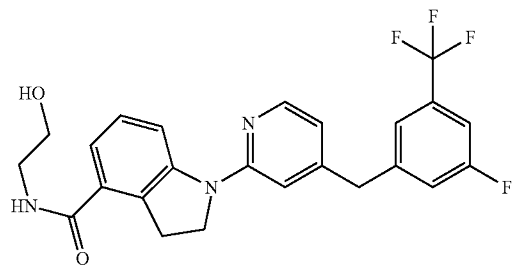 [SMILES: O=C(NCCO)c1cccc2c1CCN2c1cc(Cc2cc(F)cc(C(F)(F)F)c2)ccn1] | 1-(4-(3-Fluoro-5-(trifluoromethyl)benzyl)pyridin-2-yl)-N-(2-hydroxyethyl)indoline-4-carboxamide |
| 29 | 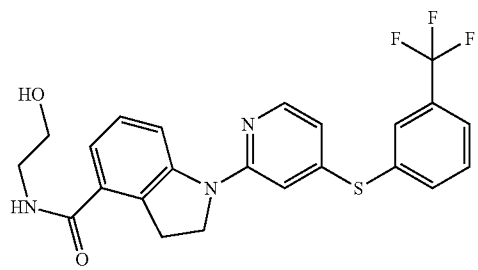 [SMILES: O=C(NCCO)c1cccc2c1CCN2c1cc(Sc2cccc(C(F)(F)F)c2)ccn1] | N-(2-Hydroxyethyl)-1-(4-(3-(trifluoromethyl)phenyl)pyridin-2-yl)indoline-4-carboxamide |
| 30 | 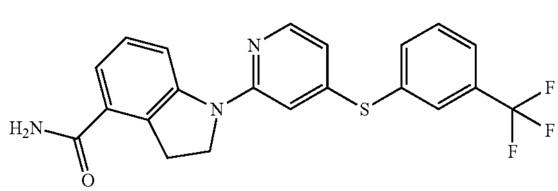 | 1-(4-(3-(Trifluoromethyl)phenylthio)pyridin-2-yl)indoline-4-carboxamide |
| 31 | 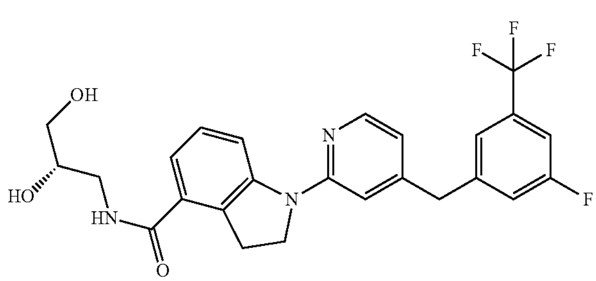 [SMILES: O=C(NC[C@H](O)CO)c1cccc2c1CCN2c1cc(Cc2cc(F)cc(C(F)(F)F)c2)ccn1] | (S)-N-(2,3-Dihydroxypropyl)-1-(4-(3-fluoro-5-(trifluoromethyl)benzyl)pyridin-2-yl)indoline-4-carboxamide |

TABLE A-continued

| Cmpd No. | Chemical Structure | Chemical Name |
|---|---|---|
| 32 | 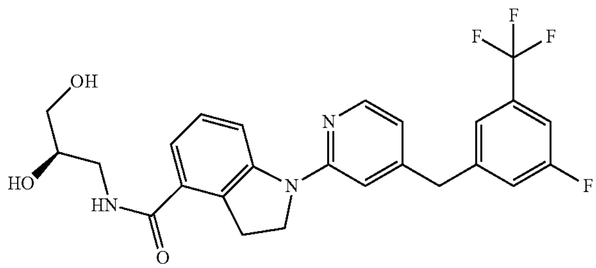 [SMILES: O=C(NC[C@@H](O)CO)c1cccc2c1CCN2c1cc(Cc2cc(F)cc(C(F)(F)F)c2)ccn1] | (R)-N-(2,3-Dihydroxypropyl)-1-(4-(3-fluoro-5-(trifluoromethyl)benzyl)pyridin-2-yl)indoline-4-carboxamide |
| 33 | 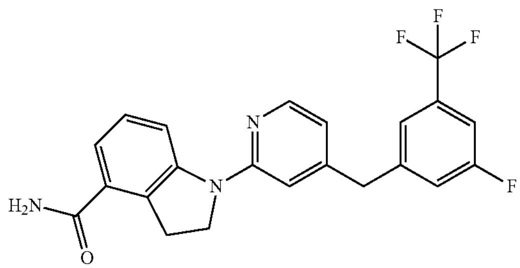 [SMILES: NC(=O)c1cccc2c1CCN2c1cc(Cc2cc(F)cc(C(F)(F)F)c2)ccn1] | 1-(4-(3-Fluoro-5-(trifluoromethyl)benzyl)pyridin-2-yl)indoline-4-carboxamide |
| 34 | 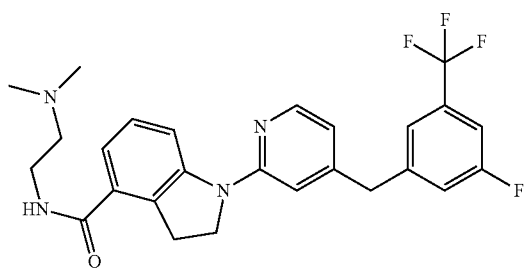 [SMILES: CN(C)CCNC(=O)c1cccc2c1CCN2c1cc(Cc2cc(F)cc(C(F)(F)F)c2)ccn1] | N-(2-(Dimethylamino)ethyl)-1-(4-(3-fluoro-5-(trifluoromethyl)benzyl)pyridin-2-yl)indoline-4-carboxamide |
| 35 | 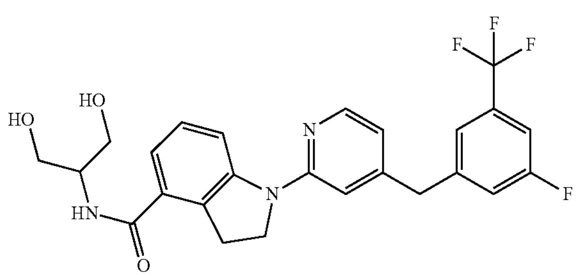 [SMILES: O=C(NC(CO)CO)c1cccc2c1CCN2c1cc(Cc2cc(F)cc(C(F)(F)F)c2)ccn1] | N-(1,3-Dihydroxypropan-2-yl)-1-(4-(3-fluoro-5-(trifluoromethyl)benzyl)pyridin-2-yl)indoline-4-carboxamide |
| 36 | 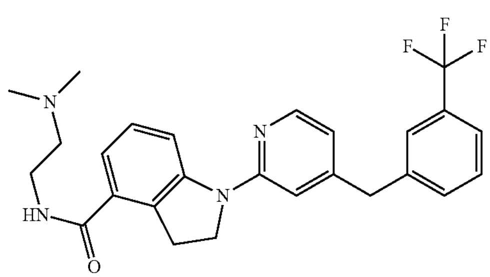 [SMILES: CN(C)CCNC(=O)c1cccc2c1CCN2c1cc(Cc2cccc(C(F)(F)F)c2)ccn1] | N-(2-(Dimethylamino)ethyl)-1-(4-(3-(trifluoromethyl)benzyl)pyridin-2-yl)indoline-4-carboxamide |

TABLE A-continued

| Cmpd No. | Chemical Structure | Chemical Name |
|---|---|---|
| 37 | 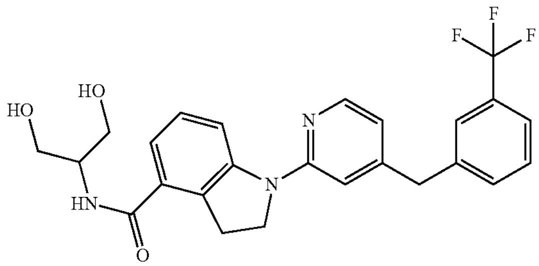 [SMILES: O=C(NC(CO)CO)c1cccc2c1CCN2c1cc(Cc2cccc(C(F)(F)F)c2)ccn1] | N-(1,3-Dihydroxypropan-2-yl)-1-(4-(3-(trifluoromethyl)benzyl)pyridin-2-yl)indoline-4-carboxamide |
| 38 | 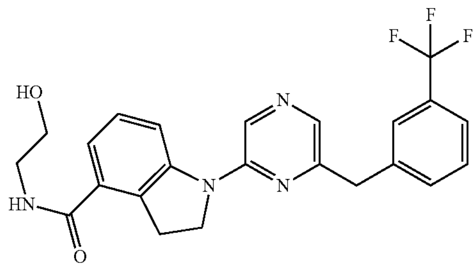 [SMILES: O=C(NCCO)c1cccc2c1CCN2c1cncc(Cc2cccc(C(F)(F)F)c2)n1] | N-(2-Hydroxyethyl)-1-(6-(3-(trifluoromethyl)benzyl)pyrazin-2-yl)indoline-4-carboxamide |
| 39 | 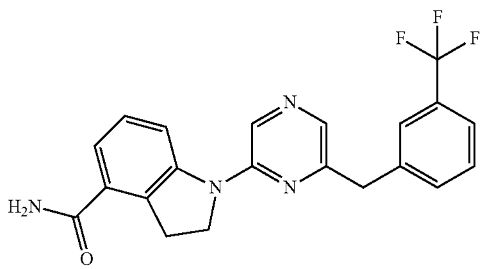 [SMILES: NC(=O)c1cccc2c1CCN2c1cncc(Cc2cccc(C(F)(F)F)c2)n1] | 1-(6-(3-(Trifluoromethyl)benzyl)pyrazin-2-yl)indoline-4-carboxamide |
| 40 | 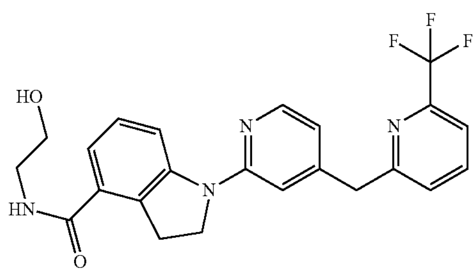 | N-(2-Hydroxyethyl)-1-(4-((6-(trifluoromethyl)pyridin-2-yl)methyl)pyridin-2-yl)indoline-4-carboxamide |
| 41 | 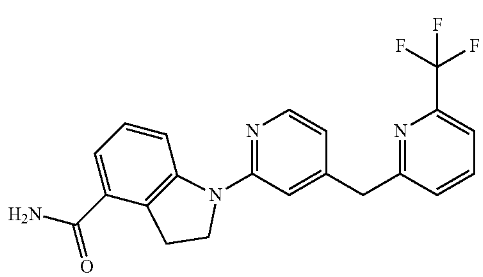 | 1-(4-((6-(Trifluoromethyl)pyridin-2-yl)methyl)pyridin-2-yl)indoline-4-carboxamide |
| 42 | 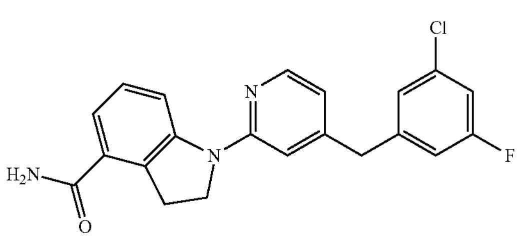 [SMILES: NC(=O)c1cccc2c1CCN2c1cc(Cc2cc(F)cc(Cl)c2)ccn1] | 1-(4-(3-Chloro-5-fluorobenzyl)pyridin-2-yl)indoline-4-carboxamide |

TABLE A-continued

| Cmpd No. | Chemical Structure | Chemical Name |
|---|---|---|
| 43 | 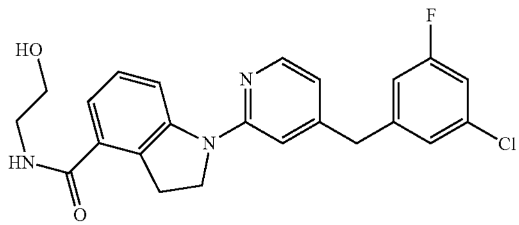 [SMILES: O=C(NCCO)c1cccc2c1CCN2c1cc(Cc2cc(F)cc(Cl)c2)ccn1] | 1-(4-(3-Chloro-5-fluorobenzyl)pyridin-2-yl)-N-(2-hydroxyethyl)indoline-4-carboxamide |
| 44 | 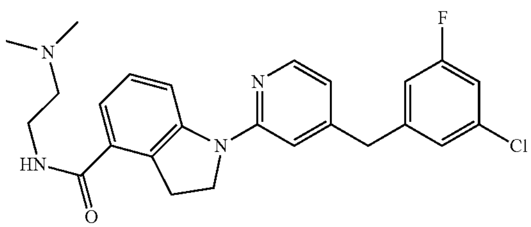 [SMILES: CN(C)CCNC(=O)c1cccc2c1CCN2c1cc(Cc2cc(F)cc(Cl)c2)ccn1] | 1-(4-(3-Chloro-5-fluorobenzyl)pyridin-2-yl)-N-(2-(dimethylamino)ethyl)indoline-4-carboxamide |
| 45 | 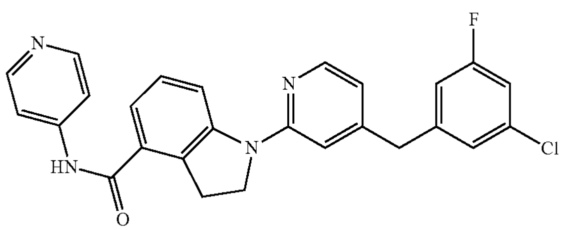 [SMILES: O=C(Nc1ccncc1)c1cccc2c1CCN2c1cc(Cc2cc(F)cc(Cl)c2)ccn1] | 1-(4-(3-Chloro-5-fluorobenzyl)pyridin-2-yl)-N-(pyridin-4-yl)indoline-4-carboxamide |
| 46 | 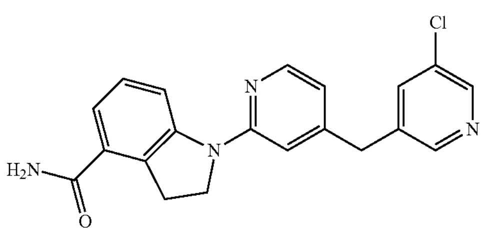 [SMILES: NC(=O)c1cccc2c1CCN2c1cc(Cc2cncc(Cl)c2)ccn1] | 1-(4-((5-Chloropyridin-3-yl)methyl)pyridin-2-yl)indoline-4-carboxamide |
| 47 | 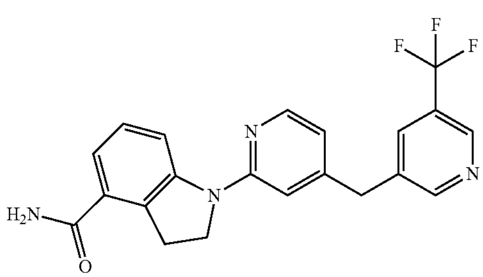 [SMILES: NC(=O)c1cccc2c1CCN2c1cc(Cc2cncc(C(F)(F)F)c2)ccn1] | 1-(4-((5-(Trifluoromethyl)pyridin-3-yl)methyl)pyridin-2-yl)indoline-4-carboxamide |
| 48 | 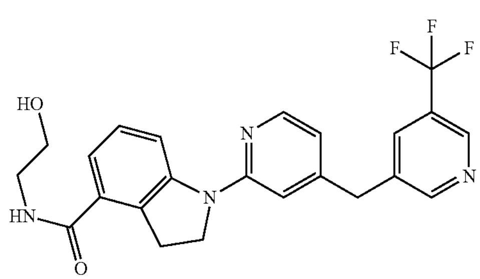 [SMILES: O=C(NCCO)c1cccc2c1CCN2c1cc(Cc2cncc(C(F)(F)F)c2)ccn1] | N-(2-Hydroxyethyl)-1-(4-((5-(trifluoromethyl)pyridin-3-yl)methyl)pyridin-2-yl)indoline-4-carboxamide |

TABLE A-continued

| Cmpd No. | Chemical Structure | Chemical Name |
|---|---|---|
| 49 | 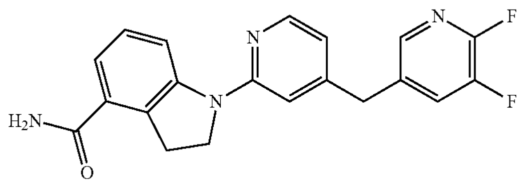 [SMILES: NC(=O)c1cccc2c1CCN2c1cc(Cc2cnc(F)c(F)c2)ccn1] | 1-(4-((5,6-Difluoropyridin-3-yl)methyl)pyridin-2-yl)indoline-4-carboxamide |
| 50 | 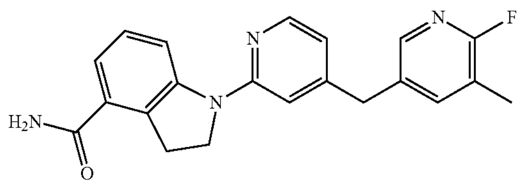 [SMILES: Cc1cc(Cc2ccnc(N3CCc4c(C(N)=O)cccc43)c2)cnc1F] | 1-(4-((6-Fluoro-5-methylpyridin-3-yl)methyl)pyridin-2-yl)indoline-4-carboxamide |
| 51 | 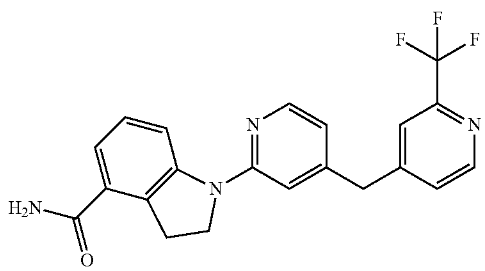 [SMILES: NC(=O)c1cccc2c1CCN2c1cc(Cc2ccnc(C(F)(F)F)c2)ccn1] | 1-(4-((2-(Trifluoromethyl)pyridin-4-yl)methyl)pyridin-2-yl)indoline-4-carboxamide |
| 52 | 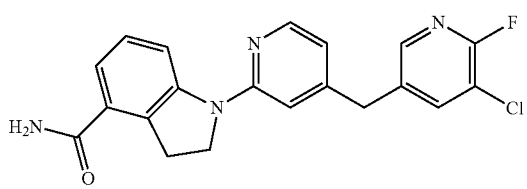 [SMILES: NC(=O)c1cccc2c1CCN2c1cc(Cc2cnc(F)c(Cl)c2)ccn1] | 1-(4-((5-Chloro-6-fluoropyridin-3-yl)methyl)pyridin-2-yl)indoline-4-carboxamide |
| 53 | 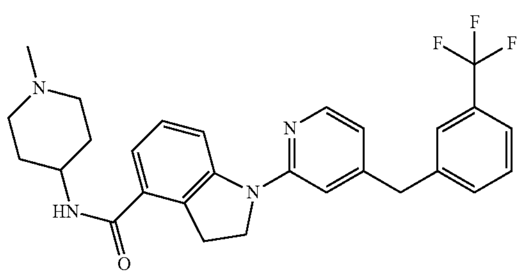 [SMILES: CN1CCC(NC(=O)c2cccc3c2CCN3c2cc(Cc3cccc(C(F)(F)F)c3)ccn2)CC1] | N-(1-Methylpiperidin-4-yl)-1-(4-(3-(trifluoromethyl)benzyl)pyridin-2-yl)indoline-4-carboxamide |
| 54 | 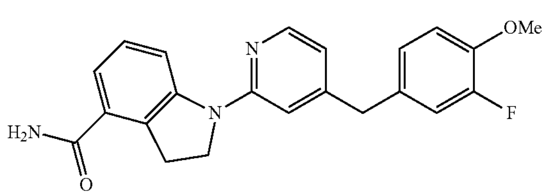 | 1-(4-(3-Fluoro-4-methoxybenzyl)pyridin-2-yl)indoline-4-carboxamide |
| 55 | 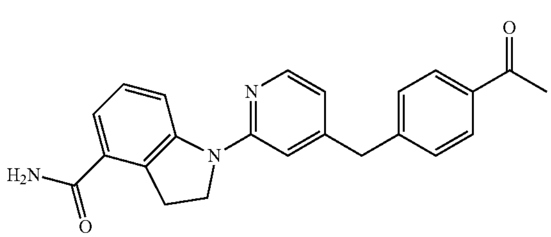 [SMILES: CC(=O)c1ccc(Cc2ccnc(N3CCc4c(C(N)=O)cccc43)c2)cc1] | 1-(4-(4-Acetylbenzyl)pyridin-2-yl)indoline-4-carboxamide |

TABLE A-continued

| Cmpd No. | Chemical Structure | Chemical Name |
|---|---|---|
| 56 | 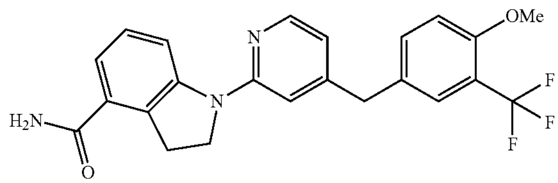 [SMILES: COc1ccc(Cc2ccnc(N3CCc4c(C(N)=O)cccc43)c2)cc1C(F)(F)F] | 1-(4-(4-Methoxy-3-(trifluoromethyl)benzyl)pyridin-2-yl)indoline-4-carboxamide |
| 57 | 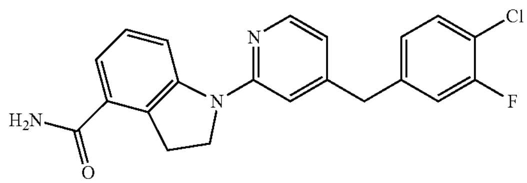 [SMILES: NC(=O)c1cccc2c1CCN2c1cc(Cc2ccc(Cl)c(F)c2)ccn1] | 1-(4-(4-Chloro-3-fluorobenzyl)pyridin-2-yl)indoline-4-carboxamide |
| 58 | 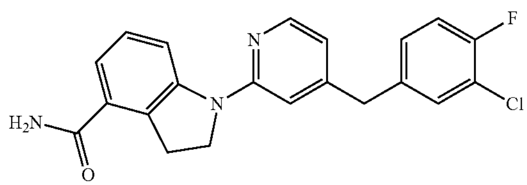 [SMILES: NC(=O)c1cccc2c1CCN2c1cc(Cc2ccc(F)c(Cl)c2)ccn1] | 1-(4-(3-Chloro-4-fluorobenzyl)pyridin-2-yl)indoline-4-carboxamide |
| 59 | 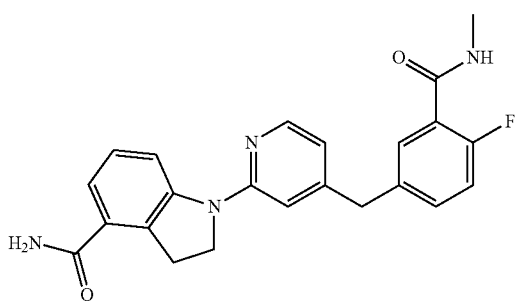 [SMILES: CNC(=O)c1cc(Cc2ccnc(N3CCc4c(C(N)=O)cccc43)c2)ccc1F] | 1-(4-(4-Fluoro-3-(methylcarbamoyl)benzyl)pyridin-2-yl)indoline-4-carboxamide |
| 60 | 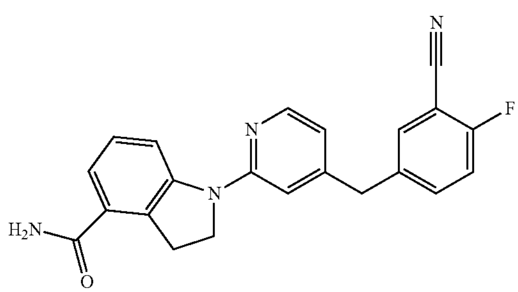 [SMILES: N#Cc1cc(Cc2ccnc(N3CCc4c(C(N)=O)cccc43)c2)ccc1F] | 1-(4-(3-Cyano-4-fluorobenzyl)pyridin-2-yl)indoline-4-carboxamide |
| 61 | 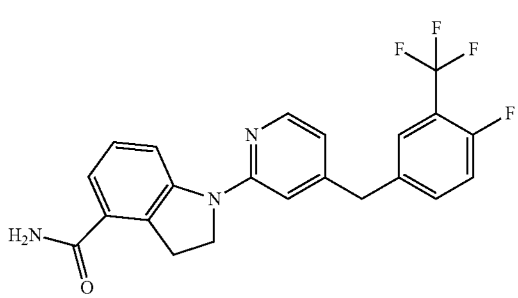 [SMILES: NC(=O)c1cccc2c1CCN2c1cc(Cc2ccc(F)c(C(F)(F)F)c2)ccn1] | 1-(4-(4-Fluoro-3-(trifluoromethyl)benzyl)pyridin-2-yl)indoline-4-carboxamide |

TABLE A-continued

| Cmpd No. | Chemical Structure | Chemical Name |
|---|---|---|
| 62 | 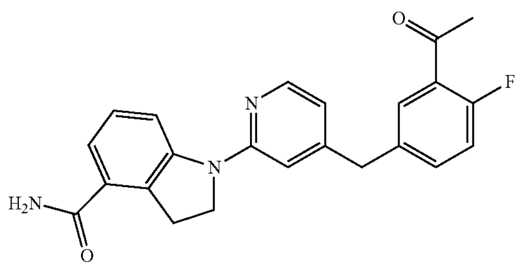 [SMILES: CC(=O)c1cc(Cc2ccnc(N3CCc4c(C(N)=O)cccc43)c2)ccc1F] | 1-(4-(3-Acetyl-4-fluorobenzyl)pyridin-2-yl)indoline-4-carboxamide |
| 63 | 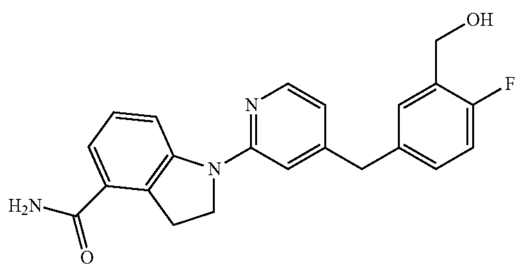 [SMILES: NC(=O)c1cccc2c1CCN2c1cc(Cc2ccc(F)c(CO)c2)ccn1] | 1-(4-(4-Fluoro-3-(hydroxymethyl)benzyl)pyridin-2-yl)indoline-4-carboxamide |
| 64 | 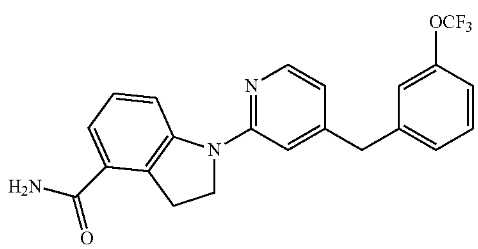 [SMILES: NC(=O)c1cccc2c1CCN2c1cc(Cc2cccc(OC(F)(F)F)c2)ccn1] | 1-(4-(3-(Trifluoromethoxy)benzyl)pyridin-2-yl)indoline-4-carboxamide |
| 65 | 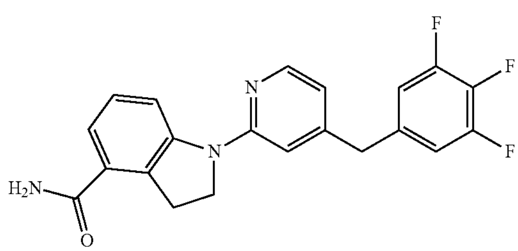 [SMILES: NC(=O)c1cccc2c1CCN2c1cc(Cc2cc(F)c(F)c(F)c2)ccn1] | 1-(4-(3,4,5-Trifluorobenzyl)pyridin-2-yl)indoline-4-carboxamide |
| 66 | 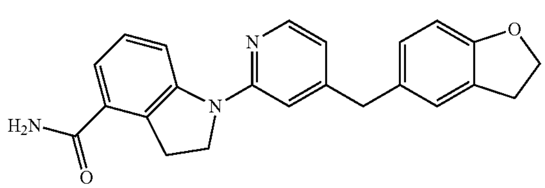 [SMILES: NC(=O)c1cccc2c1CCN2c1cc(Cc2ccc3c(c2)CCO3)ccn1] | 1-(4-((2,3-Dihydrobenzofuran-5-yl)methyl)pyridin-2-yl)indoline-4-carboxamide |
| 67 | 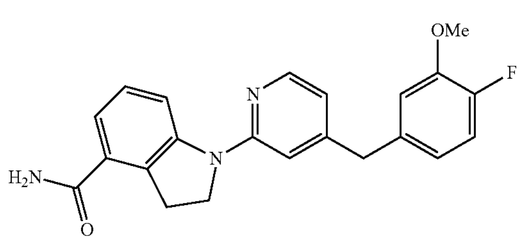 [SMILES: COc1cc(Cc2ccnc(N3CCc4c(C(N)=O)cccc43)c2)ccc1F] | 1-(4-(4-Fluoro-3-methoxybenzyl)pyridin-2-yl)indoline-4-carboxamide |

TABLE A-continued

| Cmpd No. | Chemical Structure | Chemical Name |
|---|---|---|
| 68 | 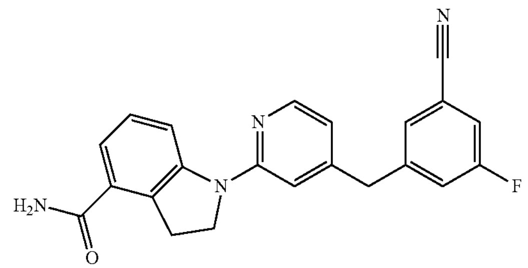 [SMILES: N#Cc1cc(F)cc(Cc2ccnc(N3CCc4c(C(N)=O)cccc43)c2)c1] | 1-(4-(3-Cyano-5-fluorobenzyl)pyridin-2-yl)indoline-4-carboxamide |
| 69 | 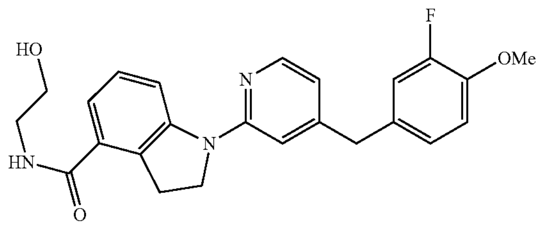 [SMILES: COc1ccc(Cc2ccnc(N3CCc4c(C(=O)NCCO)cccc43)c2)cc1F] | 1-(4-(3-Fluoro-4-methoxybenzyl)pyridin-2-yl)-N-(2-hydroxyethyl)indoline-4-carboxamide |
| 70 | 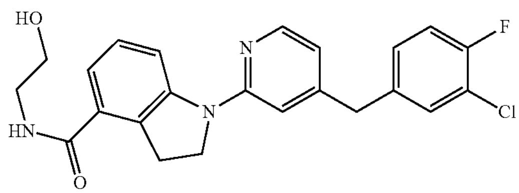 [SMILES: O=C(NCCO)c1cccc2c1CCN2c1cc(Cc2ccc(F)c(Cl)c2)ccn1] | 1-(4-(3-Chloro-4-fluorobenzyl)pyridin-2-yl)-N-(2-hydroxyethyl)indoline-4-carboxamide |
| 71 | 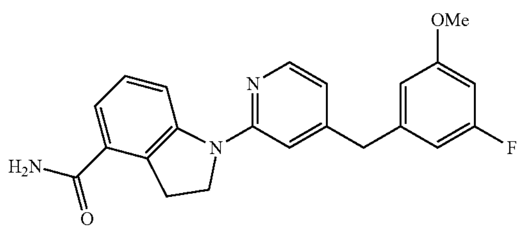 [SMILES: COc1cc(F)cc(Cc2ccnc(N3CCc4c(C(N)=O)cccc43)c2)c1] | 1-(4-(3-Fluoro-5-methoxybenzyl)pyridin-2-yl)indoline-4-carboxamide |
| 72 | 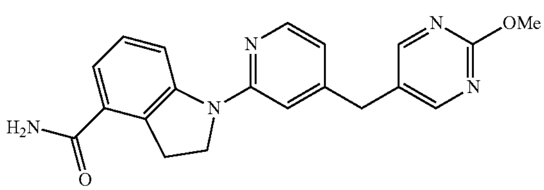 [SMILES: COc1ncc(Cc2ccnc(N3CCc4c(C(N)=O)cccc43)c2)cn1] | 1-(4-((2-Methoxypyrimidin-5-yl)methyl)pyridin-2-yl)indoline-4-carboxamide |
| 73 | 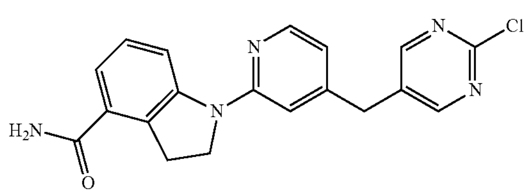 [SMILES: NC(=O)c1cccc2c1CCN2c1cc(Cc2cnc(Cl)nc2)ccn1] | 1-(4-((2-Chloropyrimidin-5-yl)methyl)pyridin-2-yl)indoline-4-carboxamide |
| 74 | 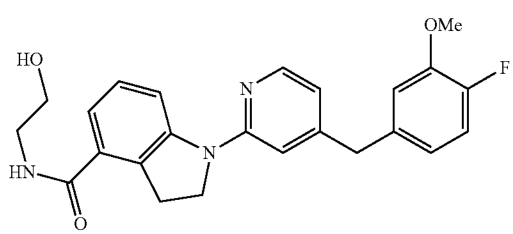 [SMILES: COc1cc(Cc2ccnc(N3CCc4c(C(=O)NCCO)cccc43)c2)ccc1F] | 1-(4-(4-Fluoro-3-methoxybenzyl)pyridin-2-yl)-N-(2-hydroxyethyl)indoline-4-carboxamide |

TABLE A-continued

| Cmpd No. | Chemical Structure | Chemical Name |
|---|---|---|
| 75 | 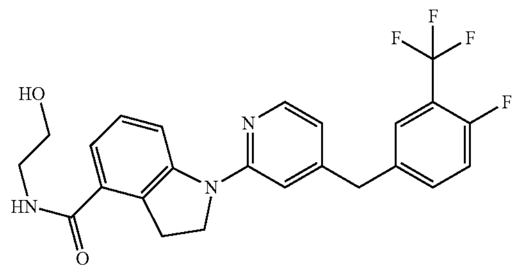 [SMILES: O=C(NCCO)c1cccc2c1CCN2c1cc(Cc2ccc(F)c(C(F)(F)F)c2)ccn1] | 1-(4-(4-Fluoro-3-(trifluoromethyl)benzyl)pyridin-2-yl)-N-(2-hydroxyethyl)indoline-4-carboxamide |
| 76 | 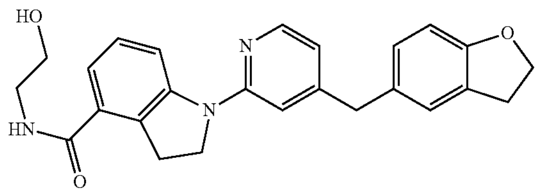 [SMILES: O=C(NCCO)c1cccc2c1CCN2c1cc(Cc2ccc3c(c2)CCO3)ccn1] | 1-(4-((2,3-Dihydrobenzofuran-5-yl)methyl)pyridin-2-yl)-N-(2-hydroxyethyl)indoline-4-carboxamide |
| 77 | 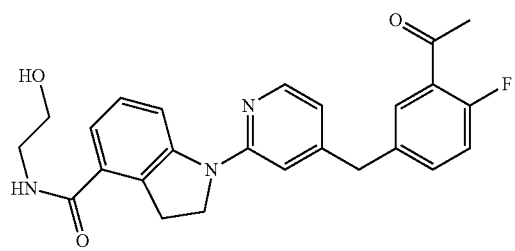 [SMILES: CC(=O)c1cc(Cc2ccnc(N3CCc4c(C(=O)NCCO)cccc43)c2)ccc1F] | 1-(4-(3-Acetyl-4-fluorobenzyl)pyridin-2-yl)-N-(2-hydroxyethyl)indoline-4-carboxamide |
| 78 | 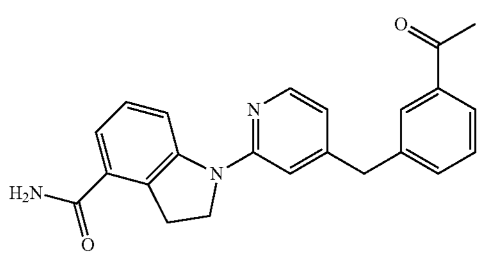 [SMILES: CC(=O)c1cccc(Cc2ccnc(N3CCc4c(C(N)=O)cccc43)c2)c1] | 1-(4-(3-Acetylbenzyl)pyridin-2-yl)indoline-4-carboxamide |
| 79 | 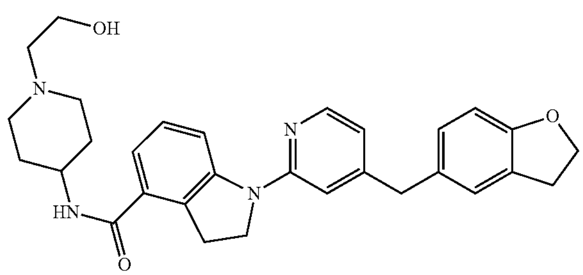 [SMILES: O=C(NC1CCN(CCO)CC1)c1cccc2c1CCN2c1cc(Cc2ccc3c(c2)CCO3)ccn1] | 1-(4-((2,3-Dihydrobenzofuran-5-yl)methyl)pyridin-2-yl)-N-(1-(2-hydroxyethyl)piperidin-4-yl)indoline-4-carboxamide |
| 80 | 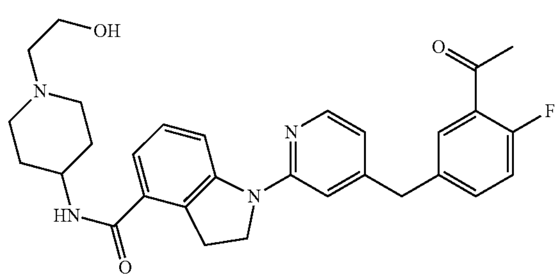 [SMILES: CC(=O)c1cc(Cc2ccnc(N3CCc4c(C(=O)NC5CCN(CCO)CC5)cccc43)c2)ccc1F] | 1-(4-(3-Acetyl-4-fluorobenzyl)pyridin-2-yl)-N-(1-(2-hydroxyethyl)piperidin-4-yl)indoline-4-carboxamide |

TABLE A-continued

| Cmpd No. | Chemical Structure | Chemical Name |
|---|---|---|
| 81 | 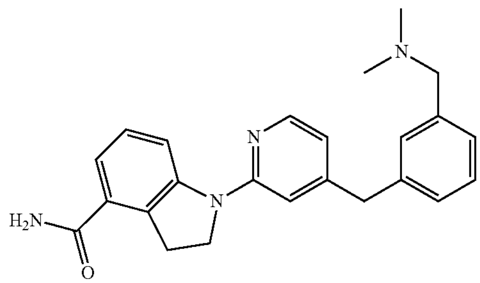 [SMILES: CN(C)Cc1cccc(Cc2ccnc(N3CCc4c(C(N)=O)cccc43)c2)c1] | 1-(4-(3-((Dimethylamino)methyl)benzyl)pyridin-2-yl)indoline-4-carboxamide |
| 82 | 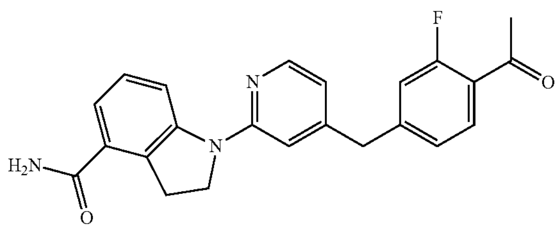 [SMILES: CC(=O)c1ccc(Cc2ccnc(N3CCc4c(C(N)=O)cccc43)c2)cc1F] | 1-(4-(4-Acetyl-3-fluorobenzyl)pyridin-2-yl)indoline-4-carboxamide |
| 83 | 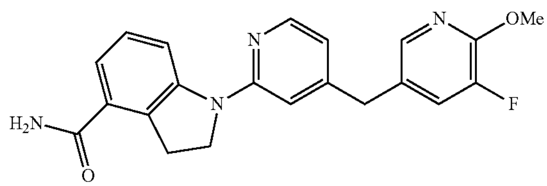 [SMILES: COc1ncc(Cc2ccnc(N3CCc4c(C(N)=O)cccc43)c2)cc1F] | 1-(4-((5-Fluoro-6-methoxypyridin-3-yl)methyl)pyridin-2-yl)indoline-4-carboxamide |
| 84 | 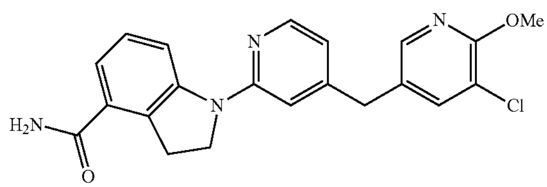 [SMILES: COc1ncc(Cc2ccnc(N3CCc4c(C(N)=O)cccc43)c2)cc1Cl] | 1-(4-((5-Chloro-6-methoxypyridin-3-yl)methyl)pyridin-2-yl)indoline-4-carboxamide |
| 85 | 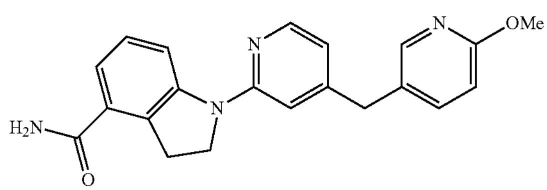 [SMILES: COc1ccc(Cc2ccnc(N3CCc4c(C(N)=O)cccc43)c2)cn1] | 1-(4-((6-Methoxypyridin-3-yl)methyl)pyridin-2-yl)indoline-4-carboxamide |
| 86 | 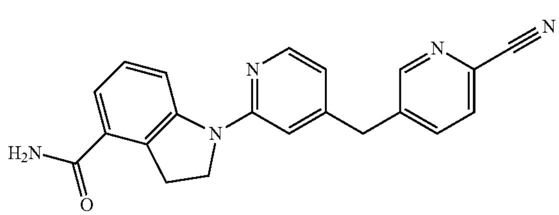 [SMILES: N#Cc1ccc(Cc2ccnc(N3CCc4c(C(N)=O)cccc43)c2)cn1] | 1-(4-((6-Cyanopyridin-3-yl)methyl)pyridin-2-yl)indoline-4-carboxamide |
| 87 | 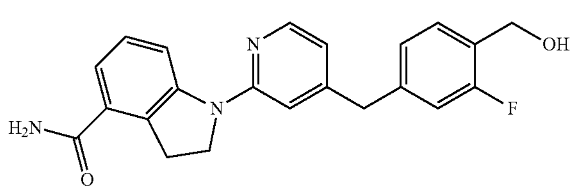 [SMILES: NC(=O)c1cccc2c1CCN2c1cc(Cc2ccc(CO)c(F)c2)ccn1] | 1-(4-(3-Fluoro-4-(hydroxymethyl)benzyl)pyridin-2-yl)indoline-4-carboxamide |

TABLE A-continued

| Cmpd No. | Chemical Structure | Chemical Name |
|---|---|---|
| 88 | 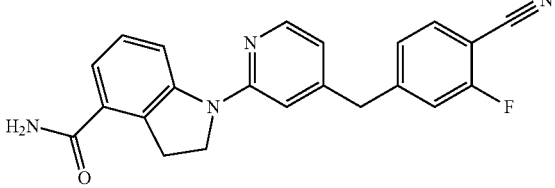 | 1-(4-(4-Cyano-3-fluorobenzyl)pyridin-2-yl)indoline-4-carboxamide |
| 89 | 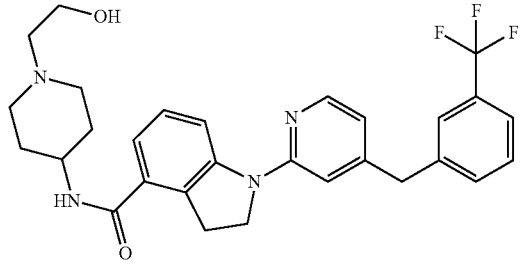 [SMILES: O=C(NC1CCN(CCO)CC1)c1cccc2c1CCN2c1cc(Cc2cccc(C(F)(F)F)c2)ccn1] | N-(1-(2-Hydroxyethyl)piperidin-4-yl)-1-(4-(3-(trifluoromethyl)benzyl)pyridin-2-yl)indoline-4-carboxamide |
| 90 | 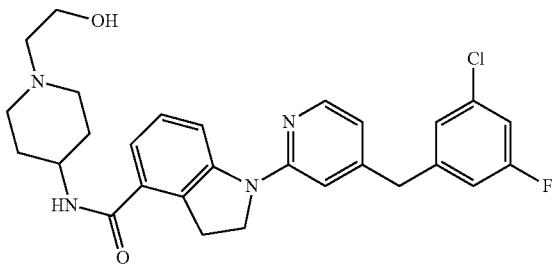 [SMILES: O=C(NC1CCN(CCO)CC1)c1cccc2c1CCN2c1cc(Cc2cc(F)cc(Cl)c2)ccn1] | 1-(4-(3-Chloro-5-fluorobenzyl)pyridin-2-yl)-N-(1-(2-hydroxyethyl)piperidin-4-yl)indoline-4-carboxamide |
| 91 | 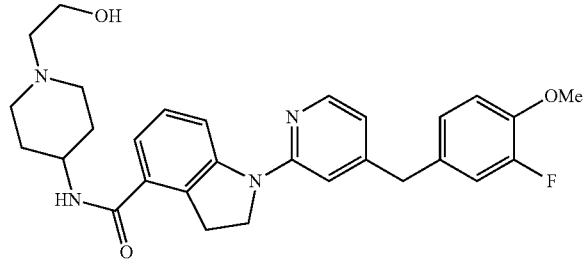 [SMILES: COc1ccc(Cc2ccnc(N3CCc4c(C(=O)NC5CCN(CCO)CC5)cccc43)c2)cc1F] | 1-(4-(3-Fluoro-4-methoxybenzyl)pyridin-2-yl)-N-(1-(2-hydroxyethyl)piperidin-4-yl)indoline-4-carboxamide |
| 92 | 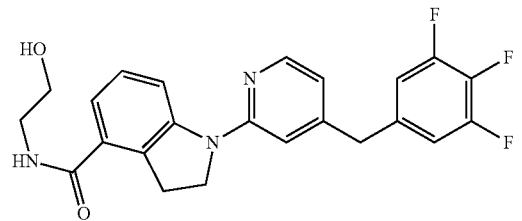 [SMILES: O=C(NCCO)c1cccc2c1CCN2c1cc(Cc2cc(F)c(F)c(F)c2)ccn1] | N-(2-Hydroxyethyl)-1-(4-(3,4,5-trifluorobenzyl)pyridin-2-yl)indoline-4-carboxamide |
| 93 | 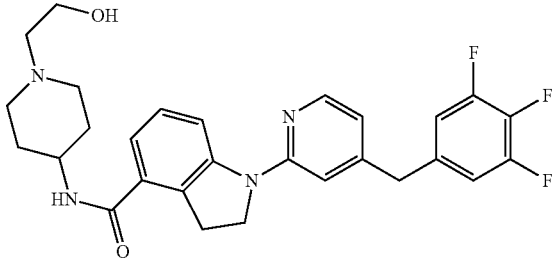 [SMILES: O=C(NC1CCN(CCO)CC1)c1cccc2c1CCN2c1cc(Cc2cc(F)c(F)c(F)c2)ccn1] | N-(1-(2-Hydroxyethyl)piperidin-4-yl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 94 | 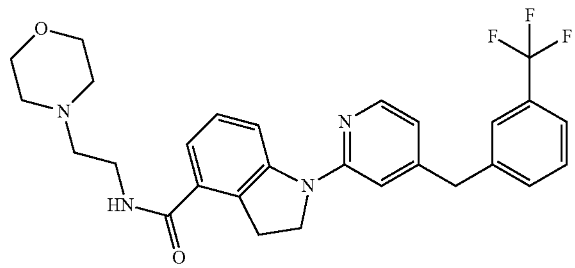 [SMILES: O=C(NCCN1CCOCC1)c1cccc2c1CCN2c1cc(Cc2cccc(C(F)(F)F)c2)ccn1] | N-(2-Morpholinoethyl)-1-(4-(3-(trifluoromethyl)benzyl)pyridin-2-yl)indoline-4-carboxamide |
| 95 | 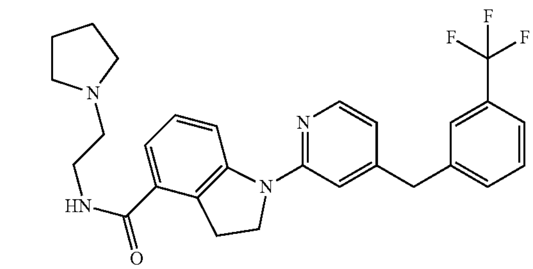 [SMILES: O=C(NCCN1CCCC1)c1cccc2c1CCN2c1cc(Cc2cccc(C(F)(F)F)c2)ccn1] | N-(2-(Pyrrolidin-1-yl)ethyl)-1-(4-(3-(trifluoromethyl)benzyl)pyridin-2-yl)indoline-4-carboxamide |
| 96 | 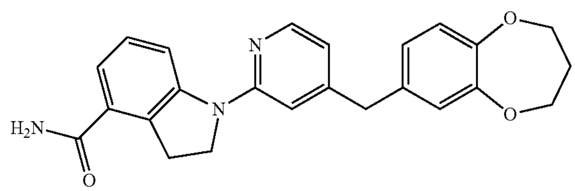 [SMILES: NC(=O)c1cccc2c1CCN2c1cc(Cc2ccc3c(c2)OCCCO3)ccn1] | 1-(4-((3,4-Dihydro-2H-benzo[b][1,4]dioxepin-7-yl)methyl)pyridin-2-yl)indoline-4-carboxamide |
| 97 | 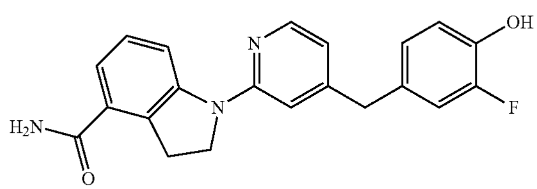 [SMILES: NC(=O)c1cccc2c1CCN2c1cc(Cc2ccc(O)c(F)c2)ccn1] | 1-(4-(3-Fluoro-4-hydroxybenzyl)pyridin-2-yl)indoline-4-carboxamide |
| 98 | 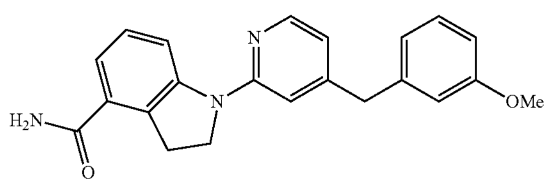 [SMILES: COc1cccc(Cc2ccnc(N3CCc4c(C(N)=O)cccc43)c2)c1] | 1-(4-(3-Methoxybenzyl)pyridin-2-yl)indoline-4-carboxamide |
| 99 | 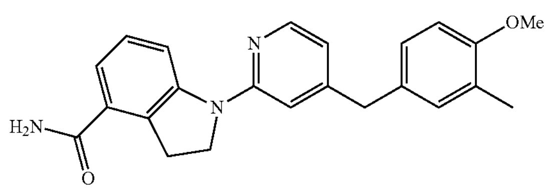 [SMILES: COc1ccc(Cc2ccnc(N3CCc4c(C(N)=O)cccc43)c2)cc1C] | 1-(4-(4-Methoxy-3-methylbenzyl)pyridin-2-yl)indoline-4-carboxamide |
| 100 | 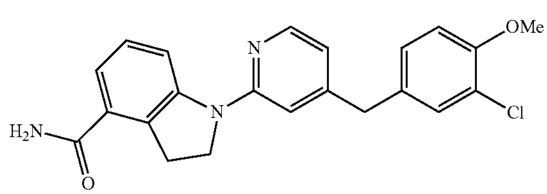 [SMILES: COc1ccc(Cc2ccnc(N3CCc4c(C(N)=O)cccc43)c2)cc1Cl] | 1-(4-(3-Chloro-4-methoxybenzyl)pyridin-2-yl)indoline-4-carboxamide |

TABLE A-continued

| Cmpd No. | Chemical Structure | Chemical Name |
|---|---|---|
| 101 | 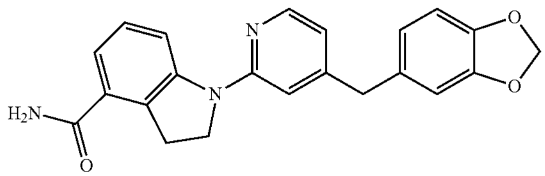 [SMILES: NC(=O)c1cccc2c1CCN2c1cc(Cc2ccc3c(c2)OCO3)ccn1] | 1-(4-(Benzo[d][1,3]dioxol-5-ylmethyl)pyridin-2-yl)indoline-4-carboxamide |
| 102 | 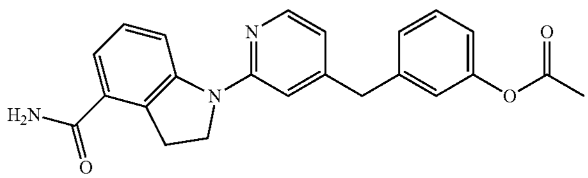 [SMILES: CC(=O)Oc1cccc(Cc2ccnc(N3CCc4c(C(N)=O)cccc43)c2)c1] | 3-((2-(4-Carbamoylindolin-1-yl)pyridin-4-yl)methyl)phenyl acetate |
| 103 | 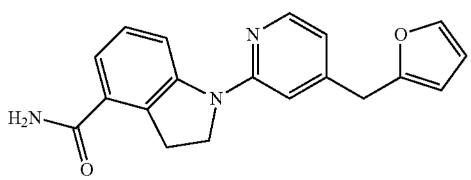 [SMILES: NC(=O)c1cccc2c1CCN2c1cc(Cc2ccco2)ccn1] | 1-(4-(Furan-2-ylmethyl)pyridin-2-yl)indoline-4-carboxamide |
| 104 | 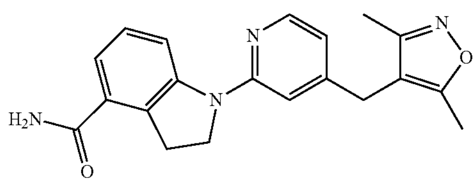 [SMILES: Cc1noc(C)c1Cc1ccnc(N2CCc3c(C(N)=O)cccc32)c1] | 1-(4-((3,5-Dimethylisoxazol-4-yl)methyl)pyridin-2-yl)indoline-4-carboxamide |
| 105 | 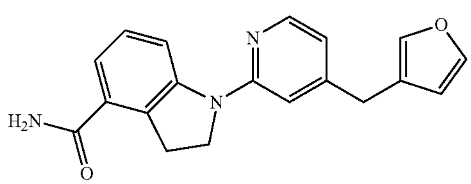 [SMILES: NC(=O)c1cccc2c1CCN2c1cc(Cc2ccoc2)ccn1] | 1-(4-(Furan-3-ylmethyl)pyridin-2-yl)indoline-4-carboxamide |
| 106 | 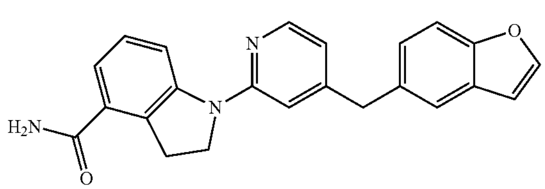 [SMILES: NC(=O)c1cccc2c1CCN2c1cc(Cc2ccc3occc3c2)ccn1] | 1-(4-(Benzofuran-5-ylmethyl)pyridin-2-yl)indoline-4-carboxamide |
| 107 | 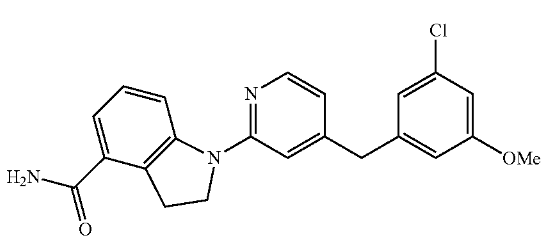 [SMILES: COc1cc(Cl)cc(Cc2ccnc(N3CCc4c(C(N)=O)cccc43)c2)c1] | 1-(4-(3-Chloro-5-methoxybenzyl)pyridin-2-yl)indoline-4-carboxamide |

TABLE A-continued

| Cmpd No. | Chemical Structure | Chemical Name |
|---|---|---|
| 108 | 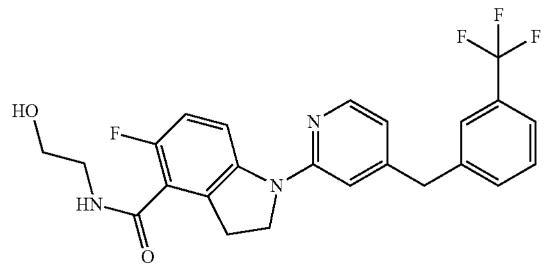 [SMILES: O=C(NCCO)c1c(F)ccc2c1CCN2c1cc(Cc2cccc(C(F)(F)F)c2)ccn1] | 5-Fluoro-N-(2-hydroxyethyl)-1-(4-(3-(trifluoromethyl)benzyl)pyridin-2-yl)indoline-4-carboxamide |
| 109 | 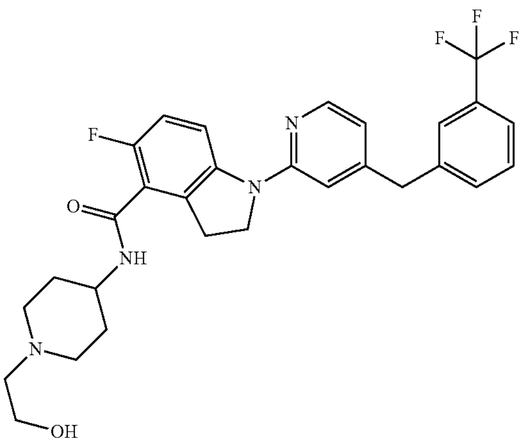 [SMILES: O=C(NC1CCN(CCO)CC1)c1c(F)ccc2c1CCN2c1cc(Cc2cccc(C(F)(F)F)c2)ccn1] | 5-Fluoro-N-(1-(2-hydroxyethyl)piperidin-4-yl)-1-(4-(3-(trifluoromethyl)benzyl)pyridin-2-yl)indoline-4-carboxamide |
| 110 | 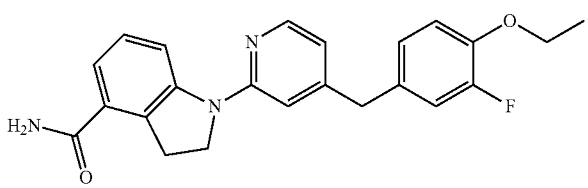 [SMILES: CCOc1ccc(Cc2ccnc(N3CCc4c(C(N)=O)cccc43)c2)cc1F] | 1-(4-(4-Ethoxy-3-fluorobenzyl)pyridin-2-yl)indoline-4-carboxamide |
| 111 | 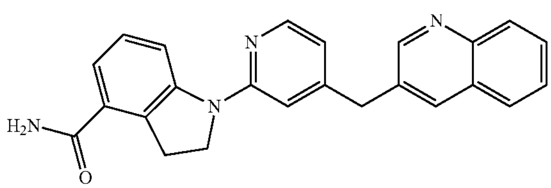 [SMILES: NC(=O)c1cccc2c1CCN2c1cc(Cc2cnc3ccccc3c2)ccn1] | 1-(4-(Quinolin-3-ylmethyl)pyridin-2-yl)indoline-4-carboxamide |
| 112 | 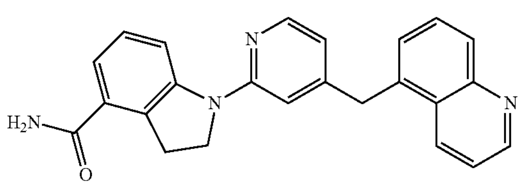 [SMILES: NC(=O)c1cccc2c1CCN2c1cc(Cc2cccc3ncccc23)ccn1] | 1-(4-(Quinolin-5-ylmethyl)pyridin-2-yl)indoline-4-carboxamide |
| 113 | 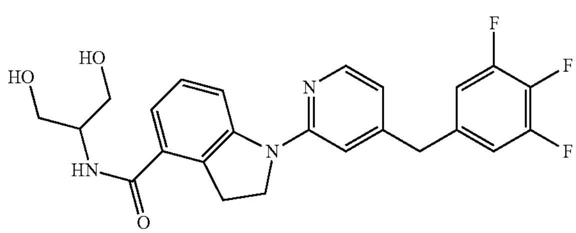 [SMILES: O=C(NC(CO)CO)c1cccc2c1CCN2c1cc(Cc2cc(F)c(F)c(F)c2)ccn1] | N-(1,3-Dihydroxypropan-2-yl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 114 | 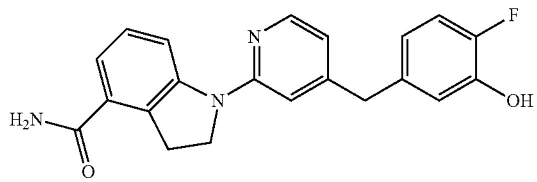 [SMILES: NC(=O)c1cccc2c1CCN2c1cc(Cc2ccc(F)c(O)c2)ccn1] | 1-(4-(4-Fluoro-3-hydroxybenzyl)pyridin-2-yl)indoline-4-carboxamide |
| 115 | 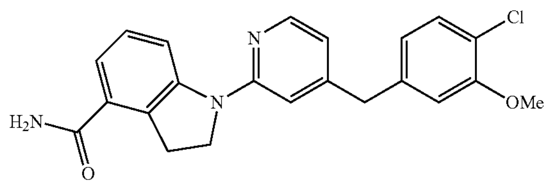 [SMILES: COc1cc(Cc2ccnc(N3CCc4c(C(N)=O)cccc43)c2)ccc1Cl] | 1-(4-(4-Chloro-3-methoxybenzyl)pyridin-2-yl)indoline-4-carboxamide |
| 116 | 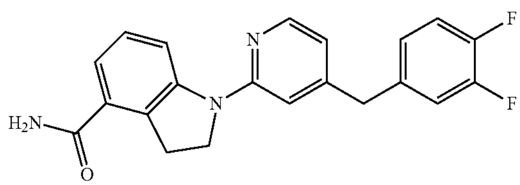 [SMILES: NC(=O)c1cccc2c1CCN2c1cc(Cc2ccc(F)c(F)c2)ccn1] | 1-(4-(3,4-Difluorobenzyl)pyridin-2-yl)indoline-4-carboxamide |
| 117 | 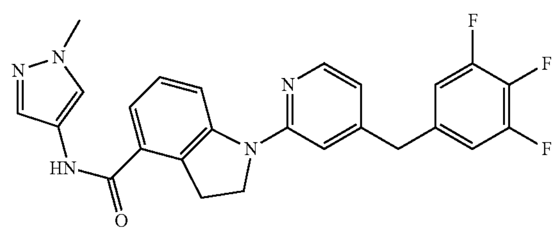 [SMILES: Cn1cc(NC(=O)c2cccc3c2CCN3c2cc(Cc3cc(F)c(F)c(F)c3)ccn2)cn1] | N-(1-Methyl-1H-pyrazol-4-yl)-1-(4-(3,4,5-trifluorobenzyl)pyridin-2-yl)indoline-4-carboxamide |
| 118 | 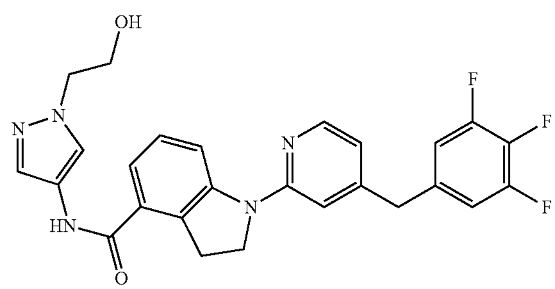 [SMILES: O=C(Nc1cnn(CCO)c1)c1cccc2c1CCN2c1cc(Cc2cc(F)c(F)c(F)c2)ccn1] | N-(1-(2-Hydroxyethyl)-1H-pyrazol-4-yl)-1-(4-(3,4,5-trifluorobenzyl)pyridin-2-yl)indoline-4-carboxamide |
| 119 | 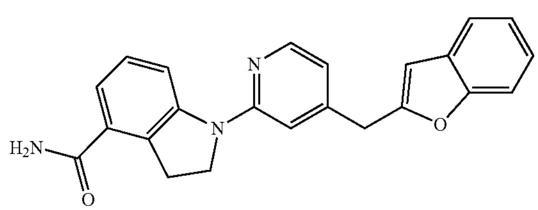 [SMILES: NC(=O)c1cccc2c1CCN2c1cc(Cc2cc3ccccc3o2)ccn1] | 1-(4-(Benzofuran-2-ylmethyl)pyridin-2-yl)indoline-4-carboxamide |
| 120 | 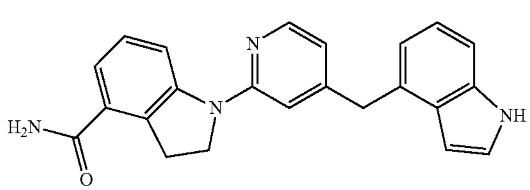 [SMILES: NC(=O)c1cccc2c1CCN2c1cc(Cc2cccc3[nH]ccc23)ccn1] | 1-(4-((1H-Indol-4-yl)methyl)pyridin-2-yl)indoline-4-carboxamide |

TABLE A-continued

| Cmpd No. | Chemical Structure | Chemical Name |
|---|---|---|
| 121 | 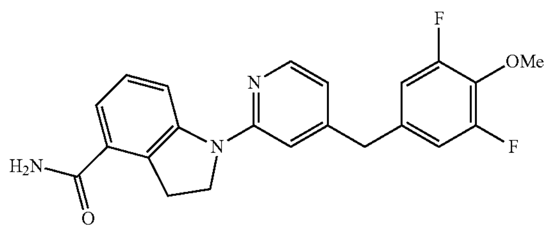 [SMILES: COc1c(F)cc(Cc2ccnc(N3CCc4c(C(N)=O)cccc43)c2)cc1F] | 1-(4-(3,5-Difluoro-4-methoxybenzyl)pyridin-2-yl)indoline-4-carboxamide |
| 122 | 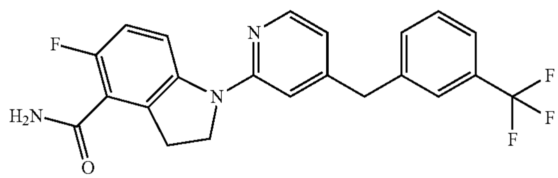 [SMILES: NC(=O)c1c(F)ccc2c1CCN2c1cc(Cc2cccc(C(F)(F)F)c2)ccn1] | 5-Fluoro-1-(4-(3-(trifluoromethyl)benzyl)pyridin-2-yl)indoline-4-carboxamide |
| 123 | 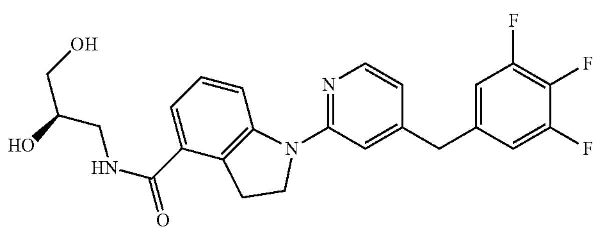 [SMILES: O=C(NC[C@@H](O)CO)c1cccc2c1CCN2c1cc(Cc2cc(F)c(F)c(F)c2)ccn1] | (R)-N-(2,3-Dihydroxypropyl)-1-(4-(3,4,5-trifluorobenzyl)pyridin-2-yl)indoline-4-carboxamide |
| 124 | 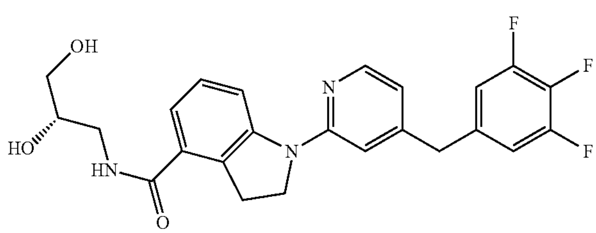 [SMILES: O=C(NC[C@H](O)CO)c1cccc2c1CCN2c1cc(Cc2cc(F)c(F)c(F)c2)ccn1] | (S)-N-(2,3-dihydroxypropyl)-1-(4-(3,4,5-trifluorobenzyl)pyridin-2-yl)indoline-4-carboxamide |
| 125 | 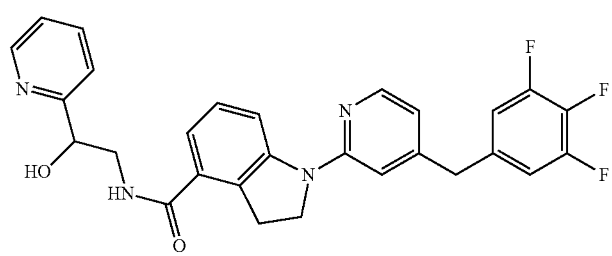 [SMILES: O=C(NCC(O)c1ccccn1)c1cccc2c1CCN2c1cc(Cc2cc(F)c(F)c(F)c2)ccn1] | N-(2-Hydroxy-2-(pyridin-2-yl)ethyl)-1-(4-(3,4,5-trifluorobenzyl)pyridin-2-yl)indoline-4-carboxamide |
| 126 | 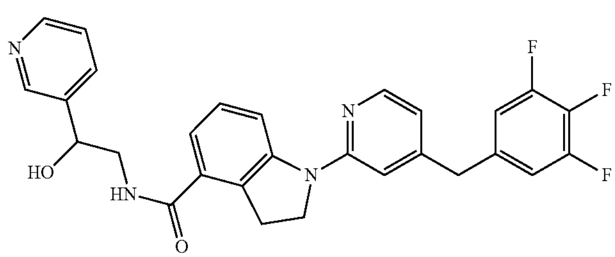 | N-(2-Hydroxy-2-(pyridin-3-yl)ethyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 127 | 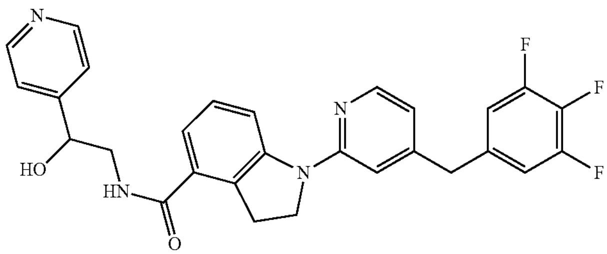 [SMILES: O=C(NCC(O)c1ccncc1)c1cccc2c1CCN2c1cc(Cc2cc(F)c(F)c(F)c2)ccn1] | N-(2-Hydroxy-2-(pyridin-4-yl)ethyl)-1-(4-(3,4,5-trifluorobenzyl)pyridin-2-yl)indoline-4-carboxamide |
| 128 | 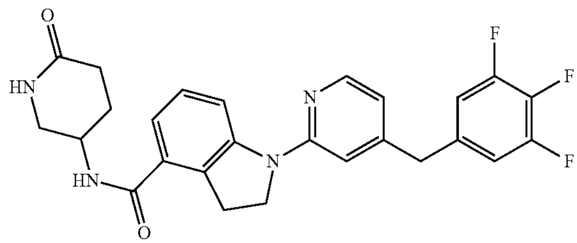 [SMILES: O=C1CCC(NC(=O)c2cccc3c2CCN3c2cc(Cc3cc(F)c(F)c(F)c3)ccn2)CN1] | N-(6-Oxopiperidin-3-yl)-1-(4-(3,4,5-trifluorobenzyl)pyridin-2-yl)indoline-4-carboxamide |
| 129 | 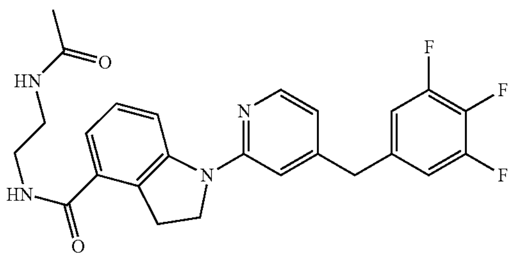 [SMILES: CC(=O)NCCNC(=O)c1cccc2c1CCN2c1cc(Cc2cc(F)c(F)c(F)c2)ccn1] | N-(2-Acetamidoethyl)-1-(4-(3,4,5-trifluorobenzyl)pyridin-2-yl)indoline-4-carboxamide |
| 130 | 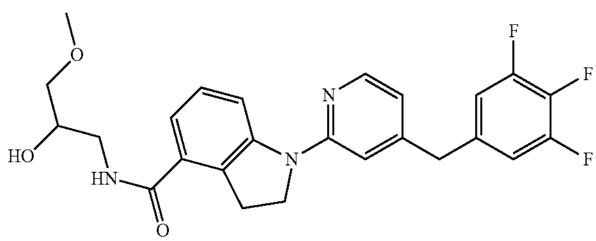 [SMILES: COCC(O)CNC(=O)c1cccc2c1CCN2c1cc(Cc2cc(F)c(F)c(F)c2)ccn1] | N-(2-Hydroxy-3-methoxypropyl)-1-(4-(3,4,5-trifluorobenzyl)pyridin-2-yl)indoline-4-carboxamide |
| 131 | 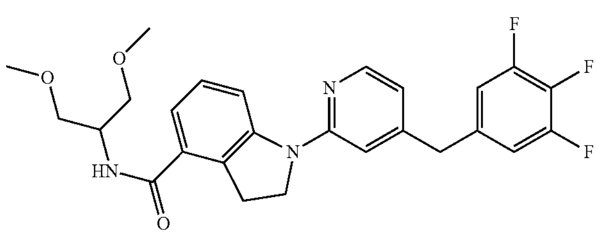 [SMILES: COCC(COC)NC(=O)c1cccc2c1CCN2c1cc(Cc2cc(F)c(F)c(F)c2)ccn1] | N-(1,3-Dimethoxypropan-2-yl)-1-(4-(3,4,5-trifluorobenzyl)pyridin-2-yl)indoline-4-carboxamide |
| 132 | 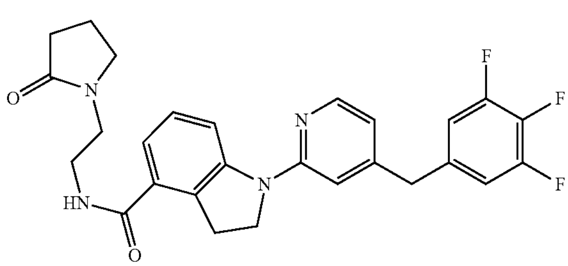 [SMILES: O=C(NCCN1CCCC1=O)c1cccc2c1CCN2c1cc(Cc2cc(F)c(F)c(F)c2)ccn1] | N-(2-(2-Oxopyrrolidin-1-yl)ethyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 133 | 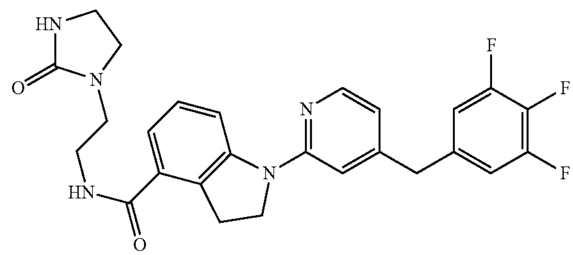 [SMILES: O=C(NCCN1CCNC1=O)c1cccc2c1CCN2c1cc(Cc2cc(F)c(F)c(F)c2)ccn1] | N-(2-(2-Oxoimidazolidin-1-yl)ethyl)-1-(4-(3,4,5-trifluorobenzyl)pyridin-2-yl)indoline-4-carboxamide |
| 134 | 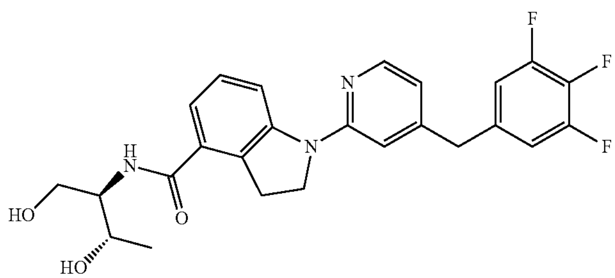 [SMILES: C[C@H](O)[C@@H](CO)NC(=O)c1cccc2c1CCN2c1cc(Cc2cc(F)c(F)c(F)c2)ccn1] | N-((2R,3S)-1,3-Dihydroxybutan-2-yl)-1-(4-(3,4,5-trifluorobenzyl)pyridin-2-yl)indoline-4-carboxamide |
| 135 | 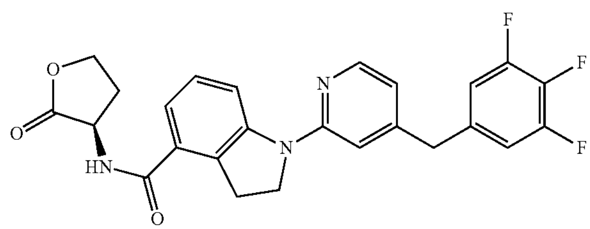 [SMILES: O=C(N[C@@H]1CCOC1=O)c1cccc2c1CCN2c1cc(Cc2cc(F)c(F)c(F)c2)ccn1] | (R)-N-(2-Oxotetrahydrofuran-3-yl)-1-(4-(3,4,5-trifluorobenzyl)pyridin-2-yl)indoline-4-carboxamide |
| 136 | 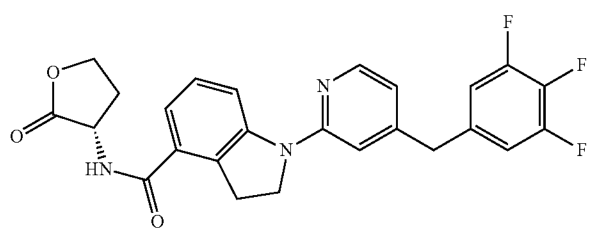 [SMILES: O=C(N[C@H]1CCOC1=O)c1cccc2c1CCN2c1cc(Cc2cc(F)c(F)c(F)c2)ccn1] | (S)-N-(2-Oxotetrahydrofuran-3-yl)-1-(4-(3,4,5-trifluorobenzyl)pyridin-2-yl)indoline-4-carboxamide |
| 137 | 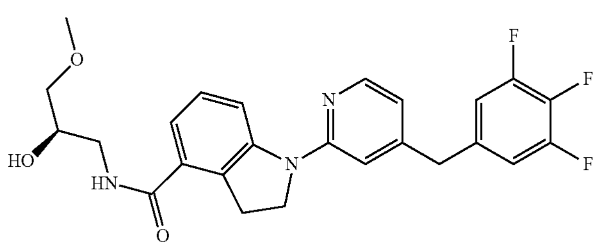 [SMILES: COC[C@H](O)CNC(=O)c1cccc2c1CCN2c1cc(Cc2cc(F)c(F)c(F)c2)ccn1] | (R)-N-(2-Hydroxy-3-methoxypropyl)-1-(4-(3,4,5-trifluorobenzyl)pyridin-2-yl)indoline-4-carboxamide |
| 138 | 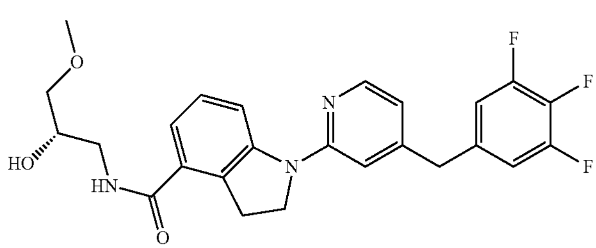 [SMILES: COC[C@@H](O)CNC(=O)c1cccc2c1CCN2c1cc(Cc2cc(F)c(F)c(F)c2)ccn1] | (S)-N-(2-Hydroxy-3-methoxypropyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 139 | 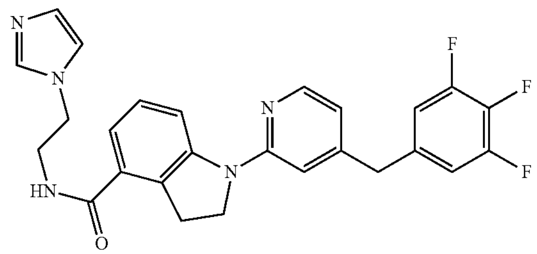 [SMILES: O=C(NCCn1ccnc1)c1cccc2c1CCN2c1cc(Cc2cc(F)c(F)c(F)c2)ccn1] | N-(2-(1H-Imidazol-1-yl)ethyl)-1-(4-(3,4,5-trifluorobenzyl)pyridin-2-yl)indoline-4-carboxamide |
| 140 | 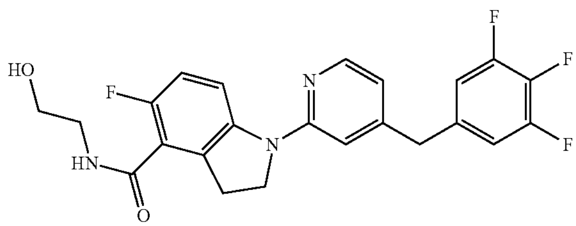 [SMILES: O=C(NCCO)c1c(F)ccc2c1CCN2c1cc(Cc2cc(F)c(F)c(F)c2)ccn1] | 5-Fluoro-N-(2-hydroxyethyl)-1-(4-(3,4,5-trifluorobenzyl)pyridin-2-yl)indoline-4-carboxamide |
| 141 | 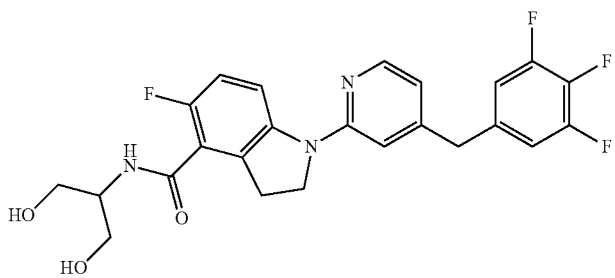 [SMILES: O=C(NC(CO)CO)c1c(F)ccc2c1CCN2c1cc(Cc2cc(F)c(F)c(F)c2)ccn1] | N-(1,3-Dihydroxypropan-2-yl)-5-fluoro-1-(4-(3,4,5-trifluorobenzyl)pyridin-2-yl)indoline-4-carboxamide |
| 142 | 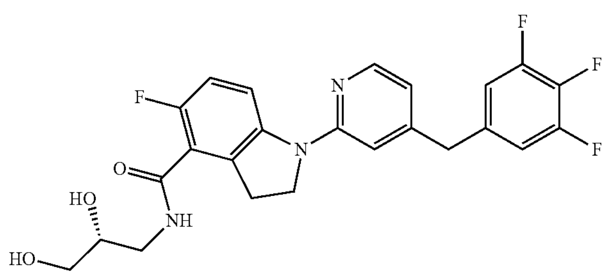 [SMILES: O=C(NC[C@@H](O)CO)c1c(F)ccc2c1CCN2c1cc(Cc2cc(F)c(F)c(F)c2)ccn1] | (R)-N-(2,3-Dihydroxypropyl)-5-fluoro-1-(4-(3,4,5-trifluorobenzyl)pyridin-2-yl)indoline-4-carboxamide |
| 143 | 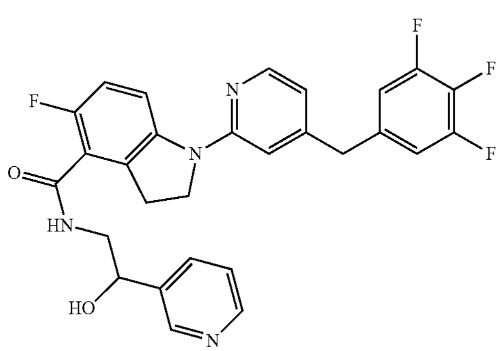 [SMILES: O=C(NCC(O)c1cccnc1)c1c(F)ccc2c1CCN2c1cc(Cc2cc(F)c(F)c(F)c2)ccn1] | 5-Fluoro-N-(2-hydroxy-2-(pyridin-3-yl)ethyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 144 | 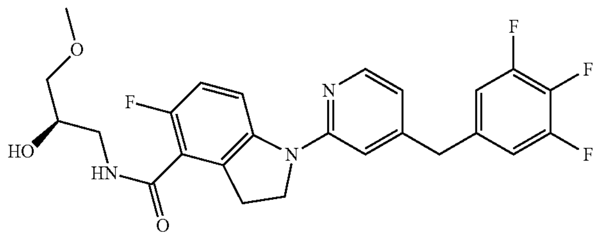 [SMILES: COC[C@H](O)CNC(=O)c1c(F)ccc2c1CCN2c1cc(Cc2cc(F)c(F)c(F)c2)ccn1] | (R)-5-Fluoro-N-(2-hydroxy-3-methoxypropyl)-1-(4-(3,4,5-trifluorobenzyl)pyridin-2-yl)indoline-4-carboxamide |
| 145 | 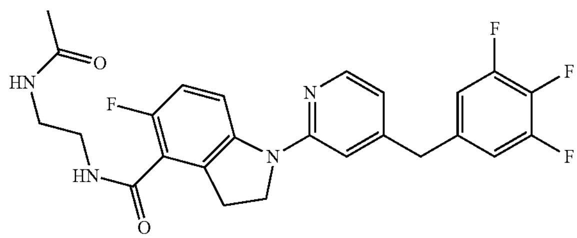 [SMILES: CC(=O)NCCNC(=O)c1c(F)ccc2c1CCN2c1cc(Cc2cc(F)c(F)c(F)c2)ccn1] | N-(2-Acetamidoethyl)-5-fluoro-1-(4-(3,4,5-trifluorobenzyl)pyridin-2-yl)indoline-4-carboxamide |
| 146 | 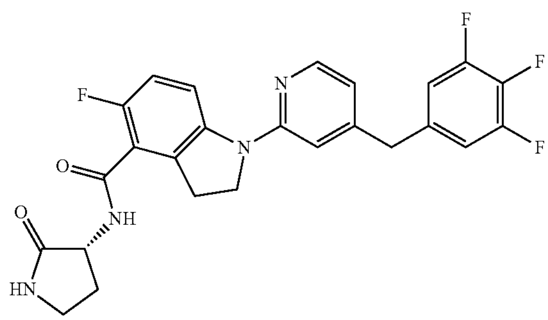 [SMILES: O=C(N[C@@H]1CCNC1=O)c1c(F)ccc2c1CCN2c1cc(Cc2cc(F)c(F)c(F)c2)ccn1] | (R)-5-Fluoro-N-(2-oxopyrrolidin-3-yl)-1-(4-(3,4,5-trifluorobenzyl)pyridin-2-yl)indoline-4-carboxamide |
| 147 | 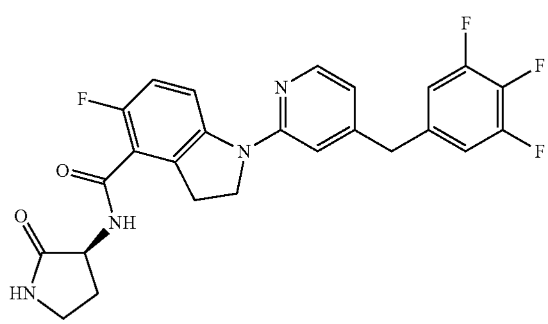 [SMILES: O=C(N[C@H]1CCNC1=O)c1c(F)ccc2c1CCN2c1cc(Cc2cc(F)c(F)c(F)c2)ccn1] | (S)-5-Fluoro-N-(2-oxopyrrolidin-3-yl)-1-(4-(3,4,5-trifluorobenzyl)pyridin-2-yl)indoline-4-carboxamide |
| 148 | 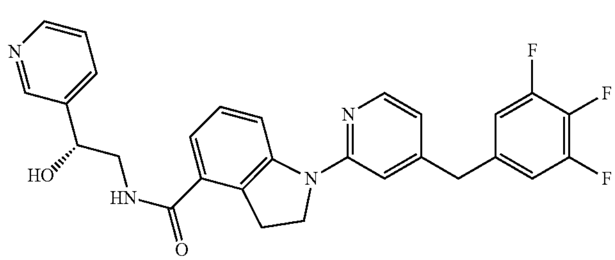 | (R)-N-(2-Hydroxy-2-(pyridin-3-yl)ethyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 149 | 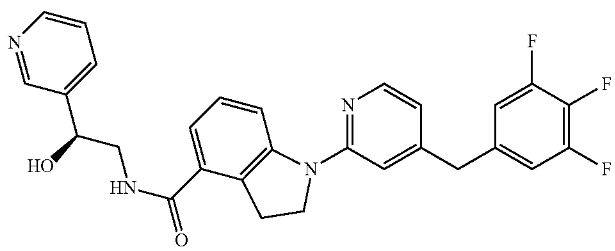 [SMILES: O=C(NC[C@@H](O)c1cccnc1)c1cccc2c1CCN2c1cc(Cc2cc(F)c(F)c(F)c2)ccn1] | (S)-N-(2-Hydroxy-2-(pyridin-3-yl)ethyl)-1-(4-(3,4,5-trifluorobenzyl)pyridin-2-yl)indoline-4-carboxamide |
| 150 | 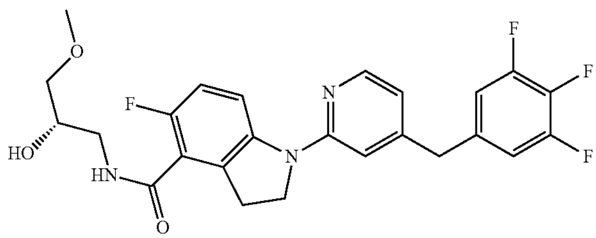 [SMILES: COC[C@@H](O)CNC(=O)c1c(F)ccc2c1CCN2c1cc(Cc2cc(F)c(F)c(F)c2)ccn1] | (S)-5-Fluoro-N-(2-hydroxy-3-methoxypropyl)-1-(4-(3,4,5-trifluorobenzyl)pyridin-2-yl)indoline-4-carboxamide |
| 151 | 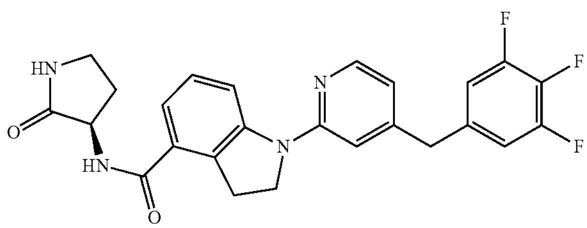 [SMILES: O=C(N[C@@H]1CCNC1=O)c1cccc2c1CCN2c1cc(Cc2cc(F)c(F)c(F)c2)ccn1] | (R)-N-(2-Oxopyrrolidin-3-yl)-1-(4-(3,4,5-trifluorobenzyl)pyridin-2-yl)indoline-4-carboxamide |
| 152 | 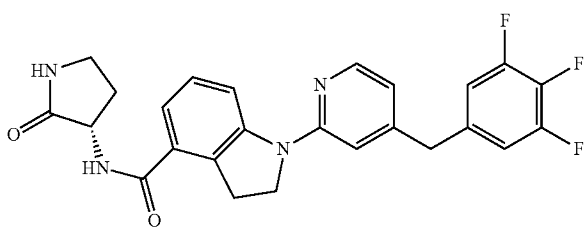 [SMILES: O=C(N[C@H]1CCNC1=O)c1cccc2c1CCN2c1cc(Cc2cc(F)c(F)c(F)c2)ccn1] | (S)-N-(2-Oxopyrrolidin-3-yl)-1-(4-(3,4,5-trifluorobenzyl)pyridin-2-yl)indoline-4-carboxamide |
| 153 | 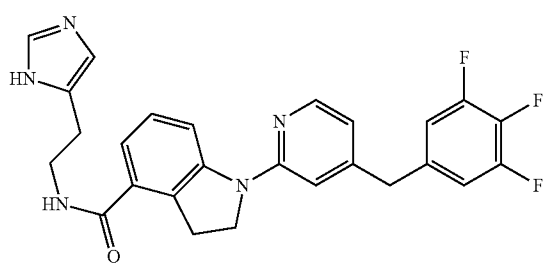 [SMILES: O=C(NCCc1cnc[nH]1)c1cccc2c1CCN2c1cc(Cc2cc(F)c(F)c(F)c2)ccn1] | N-(2-(1H-Imidazol-5-yl)ethyl)-1-(4-(3,4,5-trifluorobenzyl)pyridin-2-yl)indoline-4-carboxamide |
| 154 | 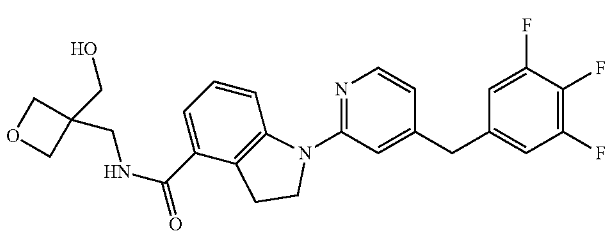 [SMILES: O=C(NCC1(CO)COC1)c1cccc2c1CCN2c1cc(Cc2cc(F)c(F)c(F)c2)ccn1] | N-((3-(Hydroxymethyl)oxetan-3-yl)methyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 155 | 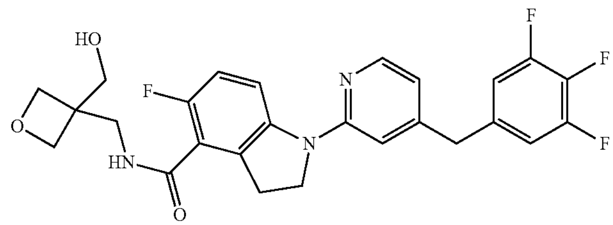 [SMILES: O=C(NCC1(CO)COC1)c1c(F)ccc2c1CCN2c1cc(Cc2cc(F)c(F)c(F)c2)ccn1] | 5-Fluoro-N-((3-(hydroxymethyl)oxetan-3-yl)methyl)-1-(4-(3,4,5-trifluorobenzyl)pyridin-2-yl)indoline-4-carboxamide |
| 156 | 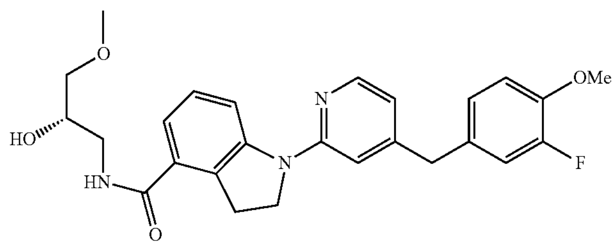 [SMILES: COC[C@@H](O)CNC(=O)c1cccc2c1CCN2c1cc(Cc2ccc(OC)c(F)c2)ccn1] | (S)-1-(4-(3-Fluoro-4-methoxybenzyl)pyridin-2-yl)-N-(2-hydroxy-3-methoxypropyl)indoline-4-carboxamide |
| 157 | 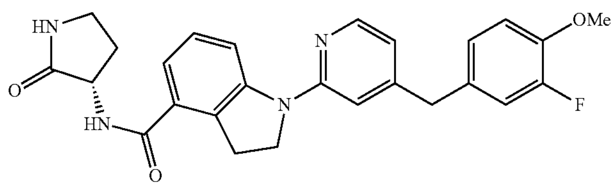 [SMILES: COc1ccc(Cc2ccnc(N3CCc4c(C(=O)N[C@H]5CCNC5=O)cccc43)c2)cc1F] | (S)-1-(4-(3-Fluoro-4-methoxybenzyl)pyridin-2-yl)-N-(2-oxopyrrolidin-3-yl)indoline-4-carboxamide |
| 158 | 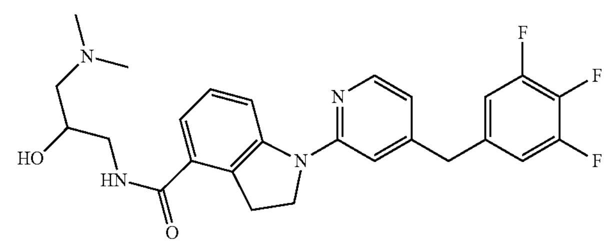 [SMILES: CN(C)CC(O)CNC(=O)c1cccc2c1CCN2c1cc(Cc2cc(F)c(F)c(F)c2)ccn1] | N-(3-(Dimethylamino)-2-hydroxypropyl)-1-(4-(3,4,5-trifluorobenzyl)pyridin-2-yl)indoline-4-carboxamide |
| 159 | 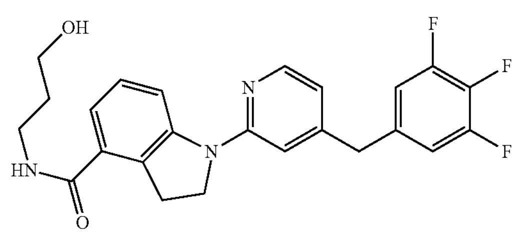 [SMILES: O=C(NCCCO)c1cccc2c1CCN2c1cc(Cc2cc(F)c(F)c(F)c2)ccn1] | N-(3-Hydroxypropyl)-1-(4-(3,4,5-trifluorobenzyl)pyridin-2-yl)indoline-4-carboxamide |
| 160 | 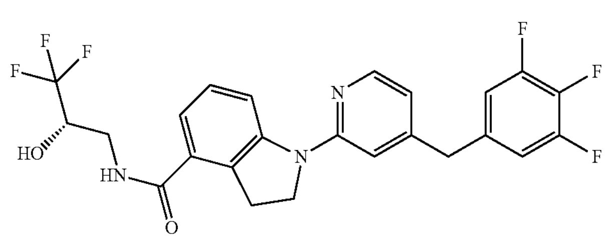 [SMILES: O=C(NC[C@H](O)C(F)(F)F)c1cccc2c1CCN2c1cc(Cc2cc(F)c(F)c(F)c2)ccn1] | (S)-N-(3,3,3-Trifluoro-2-hydroxypropyl)-1-(4-(3,4,5-trifluorobenzyl)pyridin-2-yl)indoline-4-carboxamide |

TABLE A-continued

| Cmpd No. | Chemical Name |
|---|---|
| 161 | N-(2-Fluoroethyl)-1-(4-(3,4,5-trifluorobenzyl)pyridin-2-yl)indoline-4-carboxamide |
| 162 | 5-Fluoro-1-(4-(3-fluoro-4-methoxybenzyl)pyridin-2-yl)-N-(2-hydroxyethyl)indoline-4-carboxamide |
| 163 | 5-Fluoro-1-(4-(3-fluoro-4-methoxybenzyl)pyridin-2-yl)-N-(2-fluoroethyl)indoline-4-carboxamide |
| 164 | N-(2-Acetamidoethyl)-5-fluoro-1-(4-(3-fluoro-4-methoxybenzyl)pyridin-2-yl)indoline-4-carboxamide |
| 165 | N-(3-Fluoro-2-hydroxypropyl)-1-(4-(3,4,5-trifluorobenzyl)pyridin-2-yl)indoline-4-carboxamide |
| 166 | (R)-N-(2-Fluoro-3-hydroxypropyl)-1-(4-(3,4,5-trifluorobenzyl)pyridin-2-yl)indoline-4-carboxamide |
| 167 | (R)-5-Fluoro-N-(2-fluoro-3-hydroxypropyl)-1-(4-(3-fluoro-4-methoxybenzyl)pyridin-2-yl)indoline-4-carboxamide |

TABLE A-continued

| Cmpd No. | Chemical Structure | Chemical Name |
|---|---|---|
| 168 | 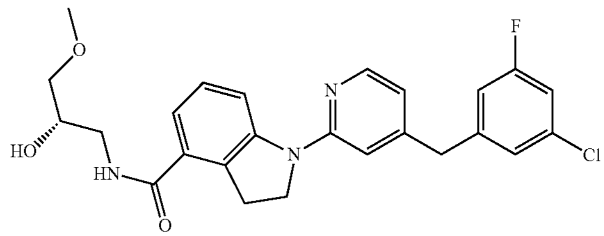 [SMILES: COC[C@@H](O)CNC(=O)c1cccc2c1CCN2c1cc(Cc2cc(F)cc(Cl)c2)ccn1] | (S)-1-(4-(3-Chloro-5-fluorobenzyl)pyridin-2-yl)-N-(2-hydroxy-3-methoxypropyl)indoline-4-carboxamide |
| 169 | 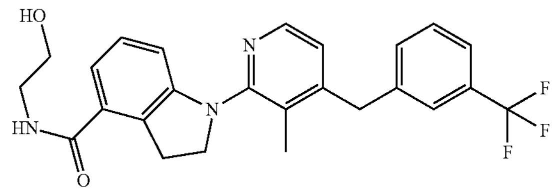 [SMILES: Cc1c(Cc2cccc(C(F)(F)F)c2)ccnc1N1CCc2c(C(=O)NCCO)cccc21] | N-(2-Hydroxyethyl)-1-(3-methyl-4-(3-(trifluoromethyl)benzyl)pyridin-2-yl)indoline-4-carboxamide |
| 170 | 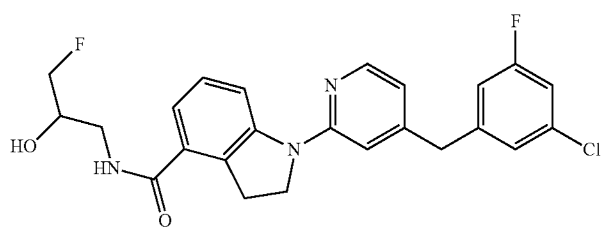 [SMILES: O=C(NCC(O)CF)c1cccc2c1CCN2c1cc(Cc2cc(F)cc(Cl)c2)ccn1] | 1-(4-(3-Chloro-5-fluorobenzyl)pyridin-2-yl)-N-(3-fluoro-2-hydroxypropyl)indoline-4-carboxamide |
| 171 | 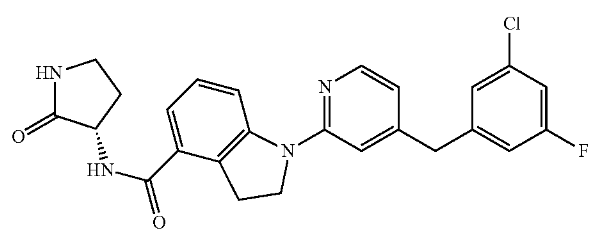 [SMILES: O=C(N[C@H]1CCNC1=O)c1cccc2c1CCN2c1cc(Cc2cc(F)cc(Cl)c2)ccn1] | (S)-1-(4-(3-Chloro-5-fluorobenzyl)pyridin-2-yl)-N-(2-oxopyrrolidin-3-yl)indoline-4-carboxamide |
| 172 | 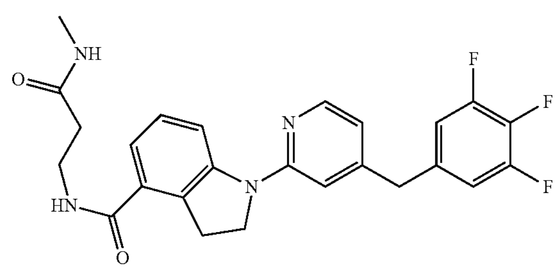 [SMILES: CNC(=O)CCNC(=O)c1cccc2c1CCN2c1cc(Cc2cc(F)c(F)c(F)c2)ccn1] | N-(3-Methylamino)-3-oxopropyl)-1-(4-(3,4,5-trifluorobenzyl)pyridin-2-yl)indoline-4-carboxamide |
| 173 | 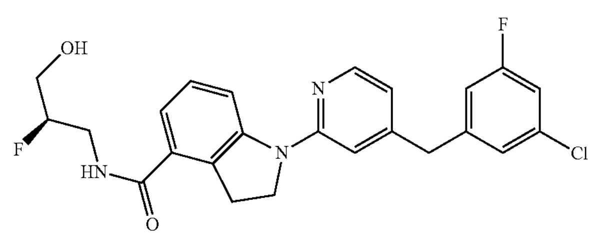 [SMILES: O=C(NC[C@@H](F)CO)c1cccc2c1CCN2c1cc(Cc2cc(F)cc(Cl)c2)ccn1] | (R)-1-(4-(3-Chloro-5-fluorobenzyl)pyridin-2-yl)-N-(2-fluoro-3-hydroxypropyl)indoline-4-carboxamide |

TABLE A-continued

| Cmpd No. | Chemical Structure | Chemical Name |
|---|---|---|
| 174 | 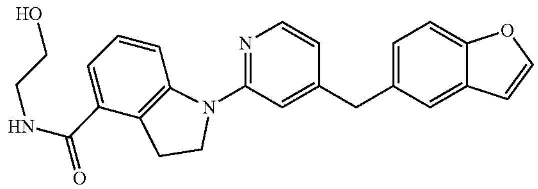 [SMILES: O=C(NCCO)c1cccc2c1CCN2c1cc(Cc2ccc3occc3c2)ccn1] | 1-(4-(Benzofuran-5-ylmethyl)pyridin-2-yl)-N-(2-hydroxyethyl)indoline-4-carboxamide |
| 175 | 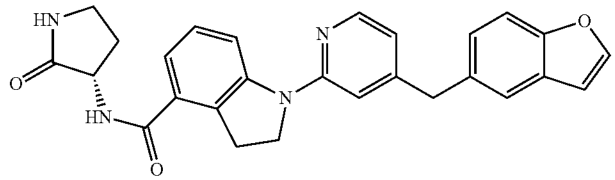 [SMILES: O=C(N[C@H]1CCNC1=O)c1cccc2c1CCN2c1cc(Cc2ccc3occc3c2)ccn1] | (S)-1-(4-(Benzofuran-5-ylmethyl)pyridin-2-yl)-N-(2-oxopyrrolidin-3-yl)indoline-4-carboxamide |
| 176 | 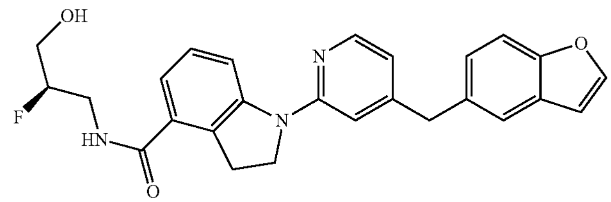 [SMILES: O=C(NC[C@@H](F)CO)c1cccc2c1CCN2c1cc(Cc2ccc3occc3c2)ccn1] | (R)-1-(4-(Benzofuran-5-ylmethyl)pyridin-2-yl)-N-(2-fluoro-3-hydroxypropyl)indoline-4-carboxamide |
| 177 | 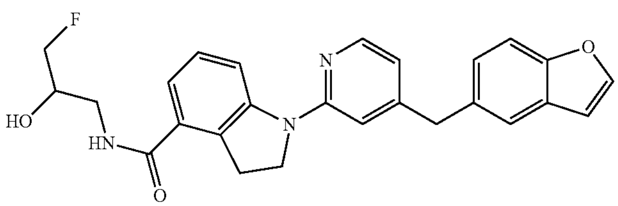 [SMILES: O=C(NCC(O)CF)c1cccc2c1CCN2c1cc(Cc2ccc3occc3c2)ccn1] | 1-(4-(Benzofuran-5-ylmethyl)pyridin-2-yl)-N-(3-fluoro-2-hydroxypropyl)indoline-4-carboxamide |
| 178 | 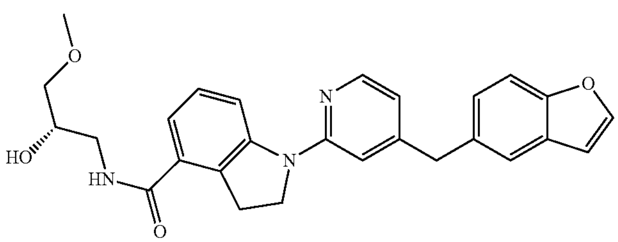 [SMILES: COC[C@@H](O)CNC(=O)c1cccc2c1CCN2c1cc(Cc2ccc3occc3c2)ccn1] | (S)-1-(4-(Benzofuran-5-ylmethyl)pyridin-2-yl)-N-(2-hydroxy-3-methoxypropyl)indoline-4-carboxamide |
| 179 | 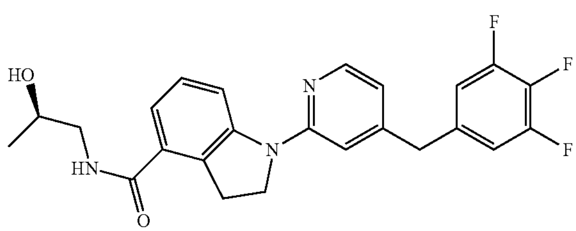 [SMILES: C[C@@H](O)CNC(=O)c1cccc2c1CCN2c1cc(Cc2cc(F)c(F)c(F)c2)ccn1] | (R)-N-(2-Hydroxypropyl)-1-(4-(3,4,5-trifluorobenzyl)pyridin-2-yl)indoline-4-carboxamide |
| 180 | 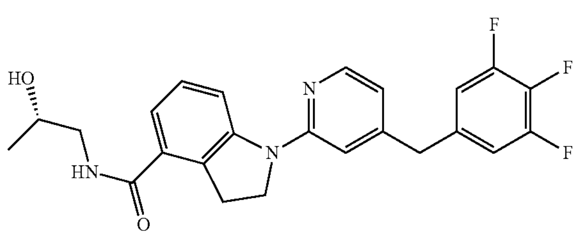 [SMILES: C[C@H](O)CNC(=O)c1cccc2c1CCN2c1cc(Cc2cc(F)c(F)c(F)c2)ccn1] | (S)-N-(2-Hydroxypropyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 181 | 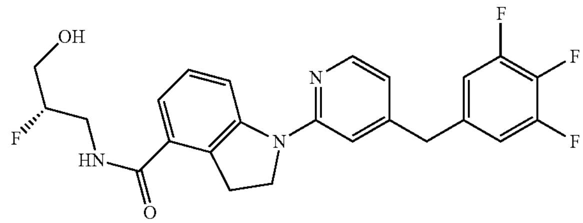 [SMILES: O=C(NC[C@H](F)CO)c1cccc2c1CCN2c1cc(Cc2cc(F)c(F)c(F)c2)ccn1] | (S)-N-(2-Fluoro-3-hydroxypropyl)-1-(4-(3,4,5-trifluorobenzyl)pyridin-2-yl)indoline-4-carboxamide |
| 182 | 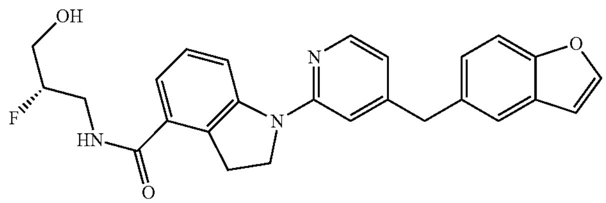 [SMILES: O=C(NC[C@H](F)CO)c1cccc2c1CCN2c1cc(Cc2ccc3occc3c2)ccn1] | (S)-1-(4-(Benzofuran-5-ylmethyl)pyridin-2-yl)-N-(2-fluoro-3-hydroxypropyl)indoline-4-carboxamide |
| 183 | 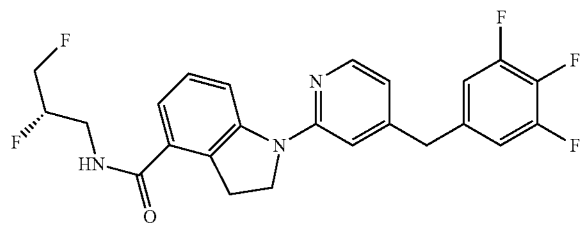 [SMILES: O=C(NC[C@H](F)CF)c1cccc2c1CCN2c1cc(Cc2cc(F)c(F)c(F)c2)ccn1] | (S)-N-(3-Fluoro-2-hydroxypropyl)-1-(4-(3,4,5-trifluorobenzyl)pyridin-2-yl)indoline-4-carboxamide |
| 184 | 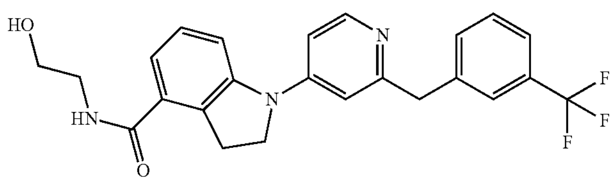 [SMILES: O=C(NCCO)c1cccc2c1CCN2c1ccnc(Cc2cccc(C(F)(F)F)c2)c1] | N-(2-Hydroxyethyl)-1-(2-(3-(trifluoromethyl)benzyl)pyridin-4-yl)indoline-4-carboxamide |
| 185 | 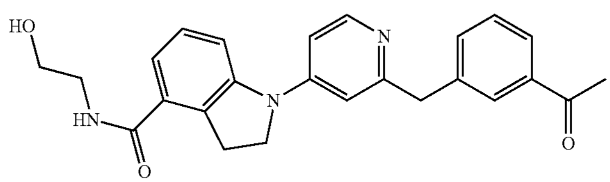 [SMILES: CC(=O)c1cccc(Cc2cc(N3CCc4c(C(=O)NCCO)cccc43)ccn2)c1] | 1-(2-(3-Acetylbenzyl)pyridin-4-yl)-N-(2-hydroxyethyl)indoline-4-carboxamide |
| 186 | 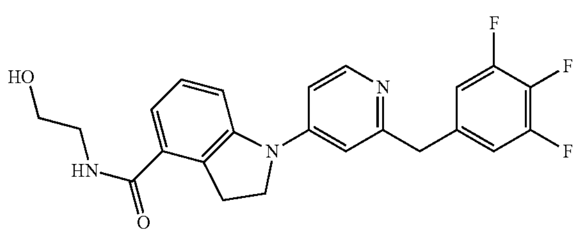 [SMILES: O=C(NCCO)c1cccc2c1CCN2c1ccnc(Cc2cc(F)c(F)c(F)c2)c1] | N-(2-Hydroxyethyl)-1-(2-(3,4,5-trifluorobenzyl)pyridin-4-yl)indoline-4-carboxamide |
| 187 | 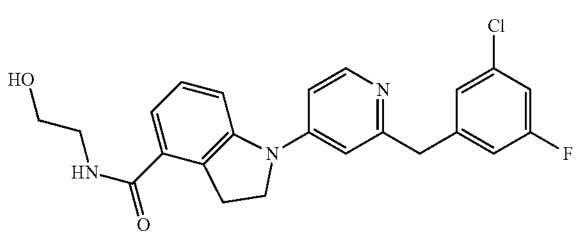 [SMILES: O=C(NCCO)c1cccc2c1CCN2c1ccnc(Cc2cc(F)cc(Cl)c2)c1] | 1-(2-(3-Chloro-5-fluorobenzyl)pyridin-4-yl)-N-(2-hydroxyethyl)indoline-4-carboxamide |

TABLE A-continued

| Cmpd No. | Chemical Structure | Chemical Name |
|---|---|---|
| 188 | 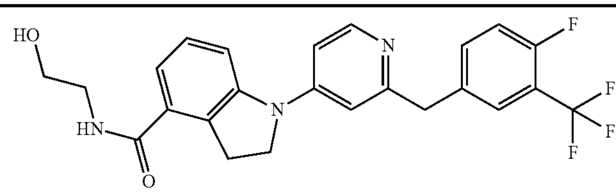 | 1-(2-(4-Fluoro-3-(trifluoromethyl)benzyl)pyridin-4-yl)-N-(2-hydroxyethyl)indoline-4-carboxamide |
| 189 | 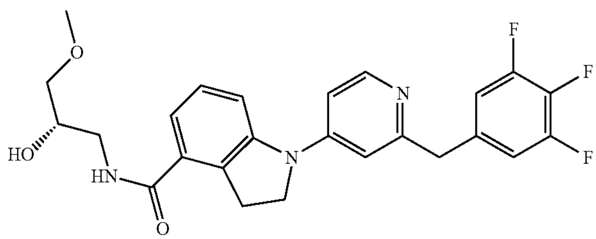 [SMILES: COC[C@@H](O)CNC(=O)c1cccc2c1CCN2c1ccnc(Cc2cc(F)c(F)c(F)c2)c1] | (S)-N-(2-Hydroxy-3-methoxypropyl)-1-(2-(3,4,5-trifluorobenzyl)pyridin-4-yl)indoline-4-carboxamide |
| 190 | 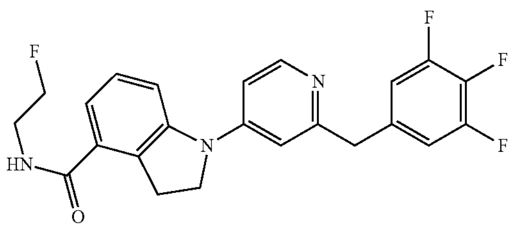 [SMILES: O=C(NCCF)c1cccc2c1CCN2c1ccnc(Cc2cc(F)c(F)c(F)c2)c1] | N-(2-Fluoroethyl)-1-(2-(3,4,5-trifluorobenzyl)pyridin-4-yl)indoline-4-carboxamide |
| 191 | 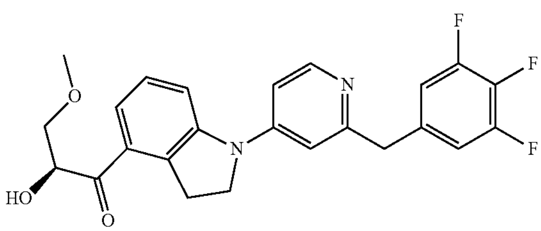 [SMILES: COC[C@H](O)C(=O)c1cccc2c1CCN2c1ccnc(Cc2cc(F)c(F)c(F)c2)c1] | (R)-N-(2-Hydroxy-3-methoxypropyl)-1-(2-(3,4,5-trifluorobenzyl)pyridin-4-yl)indoline-4-carboxamide |
| 192 | 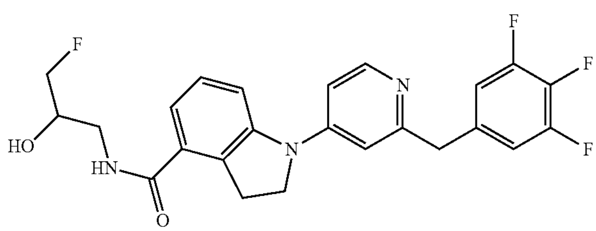 [SMILES: O=C(NCC(O)CF)c1cccc2c1CCN2c1ccnc(Cc2cc(F)c(F)c(F)c2)c1] | N-(3-Fluoro-2-hydroxypropyl)-1-(2-(3,4,5-trifluorobenzyl)pyridin-4-yl)indoline-4-carboxamide |
| 193 | 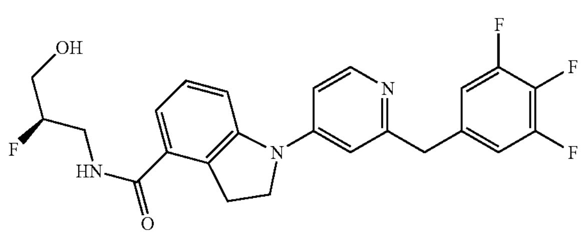 [SMILES: O=C(NC[C@@H](F)CO)c1cccc2c1CCN2c1ccnc(Cc2cc(F)c(F)c(F)c2)c1] | (R)-N-(2-Fluoro-3-hydroxypropyl)-1-(2-(3,4,5-trifluorobenzyl)pyridin-4-yl)indoline-4-carboxamide |
| 194 | 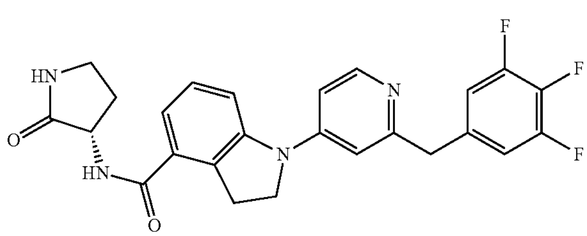 [SMILES: O=C(N[C@H]1CCNC1=O)c1cccc2c1CCN2c1ccnc(Cc2cc(F)c(F)c(F)c2)c1] | (S)-N-(2-Oxopyrrolidin-3-yl)-1-(2-(3,4,5-trifluorobenzyl)pyridin-4-yl)indoline-4-carboxamide |

TABLE A-continued

| Cmpd No. | Chemical Structure | Chemical Name |
|---|---|---|
| 195 | 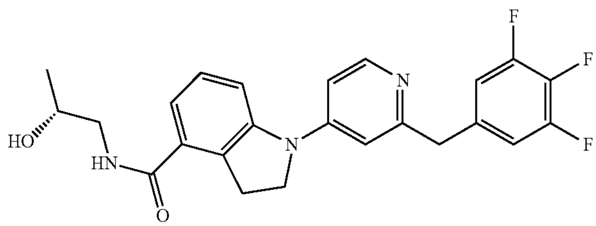 [SMILES: C[C@@H](O)CNC(=O)c1cccc2c1CCN2c1ccnc(Cc2cc(F)c(F)c(F)c2)c1] | (R)-N-(2-Hydroxypropyl)-1-(2-(3,4,5-trifluorobenzyl)pyridin-4-yl)indoline-4-carboxamide |
| 196 | 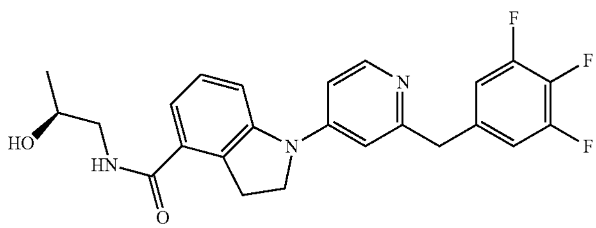 [SMILES: C[C@H](O)CNC(=O)c1cccc2c1CCN2c1ccnc(Cc2cc(F)c(F)c(F)c2)c1] | (S)-N-(2-Hydroxypropyl)-1-(2-(3,4,5-trifluorobenzyl)pyridin-4-yl)indoline-4-carboxamide |
| 197 | 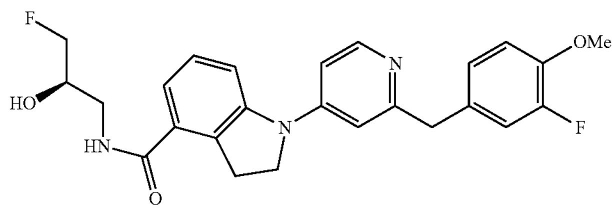 [SMILES: COc1ccc(Cc2cc(N3CCc4c(C(=O)NC[C@@H](O)CF)cccc43)ccn2)cc1F] | (R)-N-(3-fluoro-2-hydroxypropyl)-1-(4-(3-fluoro-4-methoxybenzyl)pyridin-2-yl)indoline-4-carboxamide |
| 198 | 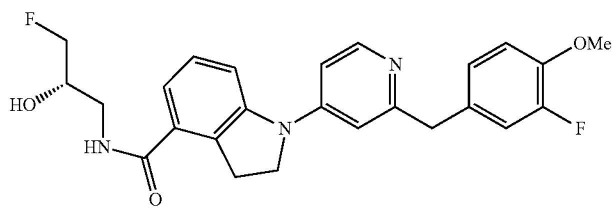 [SMILES: COc1ccc(Cc2cc(N3CCc4c(C(=O)NC[C@H](O)CF)cccc43)ccn2)cc1F] | (S)-N-(3-fluoro-2-hydroxyporpyl)-1-(4-(3-fluoro-4-methoxybenzyl)pyridin-2-yl)indoline-4-carboxamide |
| 199 | 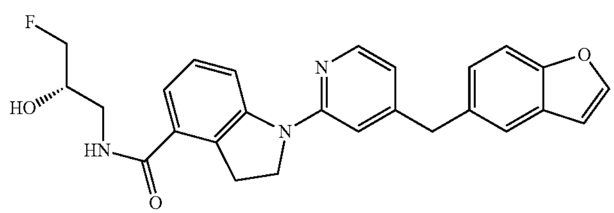 [SMILES: O=C(NC[C@H](O)CF)c1cccc2c1CCN2c1cc(Cc2ccc3occc3c2)ccn1] | (S)-1-(4-(benzofuran-5-ylmethyl)pyridin-2-yl)-N-(3-fluoro-2-hydroxypropyl)indoline-4-carboxamide |
| 200 | 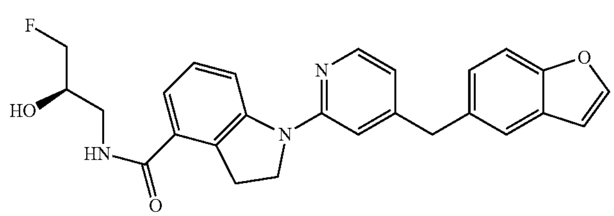 [SMILES: O=C(NC[C@@H](O)CF)c1cccc2c1CCN2c1cc(Cc2ccc3occc3c2)ccn1] | (R)-1-(4-(benzofuran-5-ylmethyl)pyridin-2-yl)-N-(3-fluoro-2-hydroxypropyl)indoline-4-carboxamide |
| 201 | 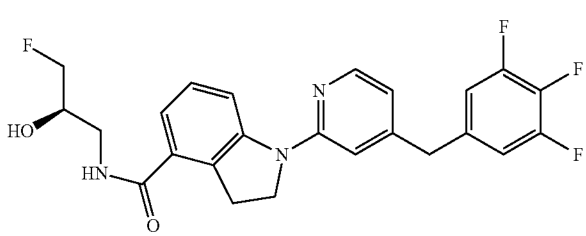 [SMILES: O=C(NC[C@@H](O)CF)c1cccc2c1CCN2c1cc(Cc2cc(F)c(F)c(F)c2)ccn1] | (R)-N-(3-fluoro-2-hydroxypropyl)-1-(4-(3,4,5-trifluorobenzyl)pyridin-2-yl)indoline-4-carboxamide |

TABLE A-continued

| Cmpd No. | Chemical Structure | Chemical Name |
|---|---|---|
| 202 | 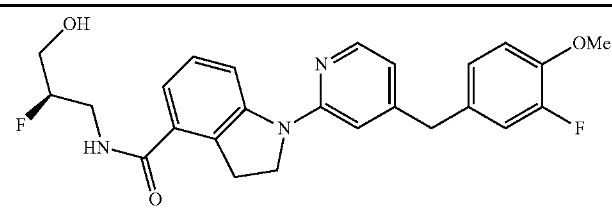 | (R)-N-(2-fluoro-3-hydroxypropyl)-1-(4-(3-fluoro-4-methoxybenzyl)pyridin-2-yl)indoline-4-carboxamide |
| 203 | 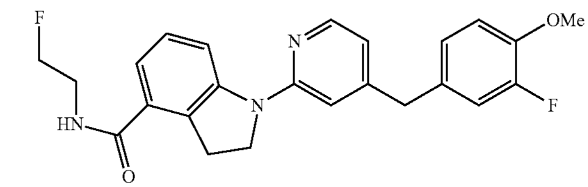 [SMILES: COc1ccc(Cc2ccnc(N3CCc4c(C(=O)NCCF)cccc43)c2)cc1F] | 1-(4-(3-fluoro-4-methoxybenzyl)pyridin-2-yl)-N-(2-fluoroethyl)indoline-4-carboxamide |
| 204 | 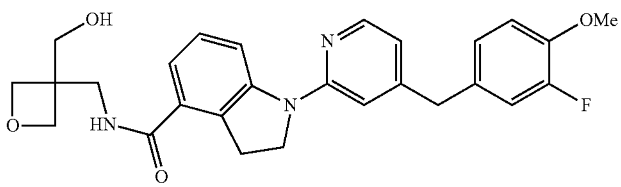 [SMILES: COc1ccc(Cc2ccnc(N3CCc4c(C(=O)NCC5(CO)COC5)cccc43)c2)cc1F] | 1-(4-(3-fluoro-4-methoxybenzyl)pyridin-2-yl)-N-((3-(hydroxymethyl)oxetan-3-yl)methyl)indoline-4-carboxamide |
| 205 | 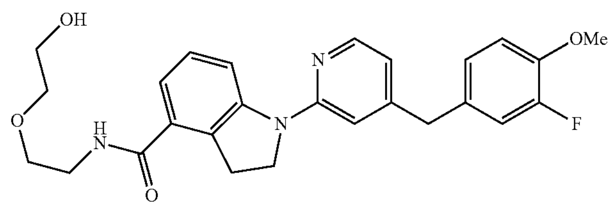 [SMILES: COc1ccc(Cc2ccnc(N3CCc4c(C(=O)NCCOCCO)cccc43)c2)cc1F] | 1-(4-(3-fluoro-4-methoxybenzyl)pyridin-2-yl)-N-(2-(2-hydroxyethoxy)ethyl)indoline-4-carboxamide |
| 206 | 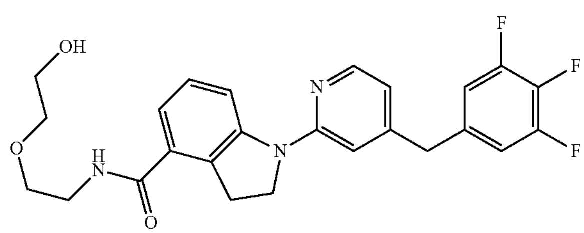 [SMILES: O=C(NCCOCCO)c1cccc2c1CCN2c1cc(Cc2cc(F)c(F)c(F)c2)ccn1] | N-(2-(2-hydroxyethoxy)ethyl)-1-(4-(3,4,5-trifluorobenzyl)pyridin-2-yl)indoline-4-carboxamide |
| 207 | 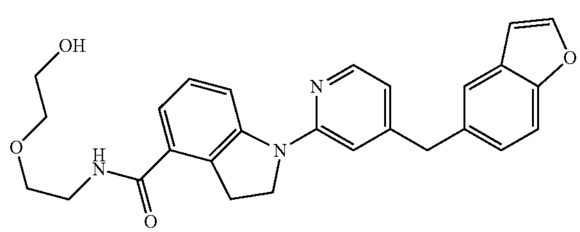 [SMILES: O=C(NCCOCCO)c1cccc2c1CCN2c1cc(Cc2ccc3occc3c2)ccn1] | 1-(4-(benzofuran-5-ylmethyl)pyridin-2-yl)-N-(2-(2-hydroxyethoxy)ethyl)indoline-4-carboxamide |
| 208 | 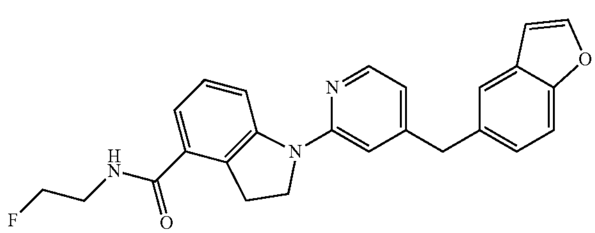 [SMILES: O=C(NCCF)c1cccc2c1CCN2c1cc(Cc2ccc3occc3c2)ccn1] | 1-(4-(benzofuran-5-ylmethyl)pyridin-2-yl)-N-(2-fluoroethyl)indoline-4-carboxamide |

Additionally, individual compounds and chemical genera of the present invention, for example those compounds found in Table A including, isomers, diastereoisomers, and enantiomers thereof, encompass all pharmaceutically acceptable salts, solvates, hydrates, and N-oxides thereof. For the avoidance of doubt, compounds of the invention may exist in an uncharged form, a salt form, or a mixture thereof. The uncharged compounds may form solvates or hydrates, or may be anhydrous (i.e., unsolvated). Likewise, salts of the compounds of Formula (Ia) may exist in the form of solvates or hydrates, as well as anhydrous (i.e., unsolvated) forms.

The compounds of Formula (Ia) of the present invention may be prepared according to relevant published literature procedures that are used by one skilled in the art. Exemplary reagents and procedures for these reactions appear hereinafter in the working Examples. Protection and deprotection may be carried out by procedures generally known in the art (see, for example, Greene, T. W. and Wuts, P. G. M., *Protecting Groups in Organic Synthesis*, 3$^{rd}$ Edition, 1999 [Wiley]).

It is understood that the present invention embraces, each isomer, each diastereoisomer, each enantiomer and mixtures thereof of each compound and generic formulae disclosed herein just as if they were each individually disclosed with the specific stereochemical designation for each chiral carbon. Separation of the individual isomers and enantiomers (such as, by HPLC (including, normal phase, reverse phase, and chiral), recrystallization of diastereoisomeric mixtures, and the like) or selective synthesis (such as, by enantiomeric selective syntheses and the like) of the individual isomers can be accomplished by application of various methods which are well known to practitioners in the art.

Disorders and Methods of Treatment

The compounds disclosed herein are useful in the treatment or prevention of several diseases, disorders, conditions, and/or indications (which are cumulatively referred to herein as "disorders"). One of skill in the art will recognize that when a disorder, or a method of treatment or prevention, is disclosed herein, such disclosure encompasses second medical uses (e.g., a compound for use in the treatment of the disorder, use of a compound for the treatment of the disorder, and/or use of a compound in the manufacture of a medicament for the treatment of the disorder).

In some embodiments, the compounds disclosed herein are useful for the treatment or prevention of a disorder. In some embodiments, the compounds disclosed herein are useful for the treatment or prevention of a subtype of a disorder. In some embodiments, the compounds disclosed herein are useful for the treatment or prevention of a symptom of a disorder.

Provided herein are methods for treating or preventing a GPR52-mediated disorder. In some embodiments, the compounds disclosed herein are useful for the prevention of a GPR52-mediated disorder. In some embodiments, the compounds disclosed herein are useful for the treatment or prevention of a GPR52-mediated disorder. In some embodiments, the GPR52-mediated disorder is a brain disorder. In some embodiments, the GPR52-mediated disorder is a mental disorder. In some embodiments, the GPR52-mediated disorder is a neurologic disorder. In some embodiments, the GPR52-mediated disorder is a psychiatric disorder. In some embodiments, the GPR52-mediated disorder is a disorder of the central nervous system (CNS). In some embodiments, the GPR52-mediated disorder is a treatment resistant disorder.

In some embodiments, the compounds described herein are useful for improving cortical function. In certain embodiments, the cortical function is prefrontal cortical function. In certain embodiments, the cortical function is selected from: executive function, attention, and memory. In some embodiments, the GPR52-mediated disorder is hypofrontality. In certain embodiments, the hypofrontality is associated with a condition selected from at least one of: schizophrenia, attention deficit hyperactivity disorder (ADHD), bipolar disorder, and major depressive disorder. In certain embodiments, the compounds disclosed herein are useful for the treatment or prevention of at least one negative symptom of schizophrenia. In certain embodiments, the compounds disclosed herein are useful for improving memory deficits. In certain embodiments, the compounds disclosed herein are useful for improving executive function. In certain embodiments, the compounds disclosed herein increase cerebral blood flow in the prefrontal cortex. In certain embodiments, the compounds disclosed herein increase utilization of glucose in the prefrontal cortex. One of skill in the art will recognize that hypofrontality can be determined using a number of imaging techniques. For example, hypofrontality can be determined using functional magnetic resonance imaging (fMRI).

In some embodiments, the GPR52-mediated disorder is an extrapyramidal or movement disorder. In certain embodiments, the extrapyramidal or movement disorder is selected from: akathisia, associated movements, athetosis, ataxia, ballismus (including hemiballismus), chorea (e.g., Huntington's disease), choreoathetosis, dyskinesia (e.g., tardive dyskinesia or neuroleptic-induced dyskinesia), myoclonus, mirror movement disorder, paroxysmal kinesigenic dyskinesia, restless legs syndrome, spasms, stereotypic movement disorder, sterotypy, Tic disorder (e.g., Tourette's syndrome), tremor, and Wilson's disease. In some embodiments, the GPR52-mediated disorder is Parkinson's disease. In some embodiments, the GPR52-mediated disorder is extrapyramidal syndrome. In some embodiments, the GPR52-mediated disorder is a motor disorder. In certain embodiments, the motor disorder is selected from: developmental coordination disorder, stereotypic movement disorder, and Tic disorder. In certain embodiments, the motor disorder is selected from: Tourette's disorder, persistent (chronic) motor or vocal tic disorder, and provisional tic disorder. In certain embodiments, the GPR52-mediated disorder is a medication-induced movement disorder. In certain embodiments, the medication-induced movement disorder is induced by a medication for Parkinson's disease. In certain embodiments, the medication-induced movement disorder is induced by an antipsychotic. In certain embodiments, the GPR52-mediated disorder is a hyperkinetic movement disorder. In certain embodiments, the hyperkinetic movement disorder is associated with at least one of the following: Huntington's disease, Wilson's disease, restless leg syndrome, post-stroke effects, and dentatorubral-pallidoluysian atrophy. In certain embodiments, the hyperkinetic movement disorder is Huntington's disease. In certain embodiments, the compounds disclosed herein are useful for the treatment or prevention of at least one of the following: ataxia, athetosis, chorea, dystonia, hemiballismus, hemifacial spasm, myoclonus, steretypies, tardive dyskinesia, tardive dystonia, tics, tremor, and volitional hyperkinesia.

In some embodiments, the GPR52-mediated disorder is a psychotic disorder. In certain embodiments, the GPR52-mediated disorder is selected from: schizotypal (personality) disorder, delusional disorder, brief psychotic disorder, schizophreniform disorder, schizophrenia, schizoaffective disorder, and substance- or medication-induced psychotic disorder. In certain embodiments, the GPR52-mediated disorder is schizophrenia. In certain embodiments, the GPR52-mediated disorder is a positive symptom of schizophrenia. In certain embodiments, the positive symptom is selected from: delusions, hallucinations, disorganized thinking, and grossly disorganized or abnormal motor behavior. In certain embodiments, the GPR52-mediated disorder is a negative symptom of schizophrenia. In certain embodiments, the negative symptom is induced by the administration of an antipsychotic. In certain embodiments, the compounds disclosed herein are useful for the treatment or prevention of at least one positive symptom of schizophrenia. In certain embodiments, the compounds disclosed herein are useful for the treatment or prevention of at least one negative symptom of schizophrenia. In certain embodiments, the negative symptom is selected from: diminished emotional expression, avolition, alogia, anhedonia, and asociality. In certain embodiments, the compounds disclosed herein are useful for the treatment or prevention of at least one schizophrenia spectrum domain selected from: delusions, hallucinations, disorganized thinking, grossly disorganized or abnormal motor behavior, or negative symptoms. In certain embodiments, the disorganized thinking is inferred from an individual's speech. In certain embodiments, the psychotic disorder is characterized by catatonia. In certain embodiments, the GPR52-mediated disorder is catatonia. In certain embodiments, the grossly disorganized or abnormal motor behavior includes catatonia. In certain embodiments, the catatonia is associated with another mental disorder. In certain embodiments, the psychotic disorder is due to another medical condition. In certain embodiments, the compounds disclosed herein are useful for the treatment or prevention of schizoaffective disorder. In certain embodiments, the compounds disclosed herein are useful for the treatment or prevention of a delusional disorder subtype selected from at least one of the following: erotomanic type, grandiose type, jealous type, persecutory type, somatic type, and mixed type. In certain embodiments, the substance-induced psychotic disorder involves the use of alcohol; *cannabis*; phencyclidine; another hallucinogen; an inhalant; a sedative, hypnotic, or anxiolytic; amphetamine or another stimulant; or cocaine. In certain embodiments, the GPR52-mediated disorder is a schizophrenia subtype selected from: paranoid type, disorganized type, catatonic type, undifferentiated type, and residual type. In certain embodiments, the psychotic disorder is characterized by psychosis. In certain embodiments, the GPR52-mediated disorder is psychosis. In certain embodiments, the psychosis is excitative psychosis. In certain embodiments, the GPR52-mediated disorder is psychosomatic disorder. In certain embodiments, the compounds disclosed herein are useful for a treatment-resistant psychotic disorder. In certain embodiments, the compounds disclosed herein are useful for the treatment or prevention of the first episode of a psychotic disorder. In certain embodiments, the compounds disclosed herein are useful for the treatment or prevention of the second or subsequent episode of a psychotic disorder. In certain embodiments, the compounds disclosed herein are useful for the treatment or prevention of a continuous psychotic disorder.

In some embodiments, the GPR52-mediated disorder is a mood disorder. In some embodiments, the GPR52-mediated disorder is a depressive disorder. In certain embodiments, the depressive disorder is selected from: disruptive mood dysregulation disorder, major depressive disorder, persistent depressive disorder (dysthymia), premenstrual dysphoric disorder, substance- or medication-induced depressive disorder, and depressive disorder due to another medical condition. In certain embodiments, the GPR52-mediated disorder is major depressive disorder. In certain embodiments, the GPR52-mediated disorder is selected from bipolar and related disorders. In certain embodiments, the bipolar or related disorder is selected from: bipolar I disorder, bipolar II disorder, cyclothymic disorder, substance- or medication-induced bipolar and related disorders, and bipolar and related disorders due to another medical condition. In certain embodiments, the substance-induced bipolar or related disorder involves the use of alcohol; phencyclidine; another hallucinogen; a sedative, hypnotic, or anxiolytic; amphetamine or another stimulant; or cocaine. In certain embodiments, the bipolar disorder is bipolar I disorder. In certain embodiments, the bipolar disorder is bipolar II disorder. In certain embodiments, the compounds disclosed herein are useful for the treatment or prevention of bipolar mania. In certain embodiments, the compounds disclosed herein are useful for the treatment or prevention of bipolar hypomania. In certain embodiments, the compounds disclosed herein are useful for the treatment or prevention of bipolar depression. In certain embodiments, the compounds disclosed herein are useful for the treatment or prevention of a major depressive episode. In certain embodiments, the compounds disclosed herein are useful for the treatment or prevention of depressive episodes associated with bipolar I disorder. In certain embodiments, the compounds disclosed herein are useful for acute treatment of manic or mixed episodes associated with bipolar I disorder. In certain embodiments, the compounds disclosed herein are useful for treatment-resistant bipolar disorder. In certain embodiments, the compounds disclosed herein are useful for maintenance treatment of bipolar I disorder.

In some embodiments, the GPR52-mediated disorder is attention deficit disorder (ADD) or attention deficit hyperactivity disorder (ADHD). In certain embodiments, the compounds disclosed herein are useful for the treatment or prevention of a subtype of ADHD selected from: ADHD predominantly inattentive presentation, ADHD predominantly hyperactive/impulsive presentation, and ADHD combined presentation.

In some embodiments, the GPR52-mediated disorder is an anxiety disorder. In certain embodiments, the anxiety disorder is selected from: separation anxiety disorder, selective mutism, specific phobia, social anxiety disorder (social phobia), panic disorder, agoraphobia, generalized anxiety disorder, substance- or medication-induced anxiety disorder, and anxiety disorder due to another medical condition. In some embodiments, the compounds disclosed herein are useful for the treatment or prevention of nausea. In some embodiments, the compounds disclosed herein are useful for the treatment or prevention of vomiting.

In some embodiments, the GPR52-mediated disorder is a prolactin-related disorder. In certain embodiments, the prolactin-related disorder is hyperprolactinemia or hypoprolactinemia. In certain embodiments, the hyperprolactinemia is caused by a pituitary tumor, hypothyroidism, or medication. In certain embodiments, the hyperprolactinemia is medication-induced. In certain embodiments, the prolactin-related disorder is selected from: hypoestrogenism, anovulatory infertility, oligomenorrhoea, amenorrhoea, galactorrhea, atrophy of the ovary or uterus, sterility, loss of libido, and erectile dysfunction. In certain embodiments, the hypoprolactinemia is medication-induced. In certain embodiments, the prolactin-related disorder is selected from: ovarian dysfunction, menopausal symptoms, metabolic syndrome, anxiety, arteriogenic erectile dysfunction, premature ejaculation, oligozoospermia, asthenospermia, hypofunction of seminal vesicles, and hypoandrogenism. In certain embodiments, the prolactin-related disorder is associated with stress. In certain embodiments, the prolactin-related disorder is associated with a sleep disorder.

In some embodiments, the GPR52-mediated disorder is a neurocognitive disorder. In certain embodiments, the compounds disclosed herein are useful for improving a neurocognitive domain selected from: complex attention, executive function, learning and memory, language, perceptual-motor, and social cognition. In certain embodiments, the compounds disclosed herein improve an assessment of at least one of the following: sustained attention, selective attention, divided attention, planning, decision making, working memory, feedback/error utilization, overriding habits/inhibition, mental/cognitive flexibility, immediate memory span, recent memory, expressive language, grammar and syntax, receptive language, visual perception, visuoconstructional, perceptual-motor, praxis, gnosis, recognition of emotions, and theory of mind. In certain embodiments, the neurocognitive disorder is selected from: delirium, major neurocognitive disorder, and minor neurocognitive disorder. In certain embodiments, the delirium is selected from: substance intoxication delirium, substance withdrawal delirium, medication-induced delirium, and delirium due to another medical condition. In some embodiments, the neurocognitive disorder is due to at least one of the following: Alzheimer's disease, frontotemporal lobar degeneration, Lewy body disease, vascular disease, traumatic brain injury, substance/medication use, HIV infection, prion disease, Parkinson's disease, and Huntington's disease. In certain embodiments, the neurocognitive disorder is major or minor frontotemporal neurocognitive disorder. In certain embodiments, the GPR52-mediated disorder is selected from: amnesia, dementia, and delirium. In certain embodiments, the GPR52-mediated disorder is dementia.

In some embodiments, the GPR52-mediated disorder is a trauma- or stressor-related disorder. In certain embodiments, the trauma- or stressor-related disorder is selected from: reactive attachment disorder, disinhibited social engagement disorder, posttraumatic stress disorder (PTSD), acute stress disorder, and adjustment disorder. In certain embodiments, the GPR52-mediated disorder is PTSD.

In some embodiments, the GPR52-mediated disorder is obsessive-compulsive (OCD) or a related disorder. In certain embodiments, the obsessive-compulsive or related disorder is selected from: obsessive-compulsive disorder, body dysmorphic disorder, hoarding disorder, trichotillomania, and excoriation disorder. In certain embodiments, the GPR52-mediated disorder is obsessive-compulsive disorder.

In some embodiments, the GPR52-mediated disorder is a disruptive, impulse-control, or conduct disorder. In certain embodiments, the GPR52-mediated disorder is selected from: oppositional defiant disorder, intermittent explosive disorder, conduct disorder, antisocial personality disorder, pyromania, and kleptomania. In some embodiments, the GPR52-mediated disorder is aggression.

In some embodiments, the GPR52-mediated disorder is a substance-related or addictive disorder. In certain embodiments, the substance-related disorder is a substance use disorder or substance-induced disorder. In certain embodiments, the GPR52-mediated disorder is selected from: an alcohol-related disorder; a caffeine-related disorder; a *cannabis*-related disorder; a hallucinogen-related disorder; an inhalant-related disorder; an opioid-related disorder; a sedative-, hypnotic-, or anxiolytic-related disorder; a stimulant-related disorder, and a tobacco-related disorder. In certain embodiments, the GPR52-mediated disorder is selected from: a substance use disorder, intoxication, and withdrawal. In certain embodiments, the substance-related disorder is selected from: alcohol use disorder; *cannabis* use disorder; hallucinogen use disorder; phencyclidine use disorder; inhalant use disorder; opioid use disorder; sedative, hypnotic, or anxiolytic use disorder; stimulant use disorder; and tobacco use disorder. In certain embodiments, the substance use disorder is a mild substance use disorder. In certain embodiments, the substance use disorder is a moderate substance use disorder. In certain embodiments, the substance use disorder is a severe substance use disorder. In certain embodiments, the substance-induced disorder is selected from: substance intoxication, substance withdrawal, and a substance/medication-induced mental disorder. In certain embodiments, the substance-related disorder is selected from: alcohol abuse, alcohol addiction, alcohol dependence, alcohol misuse, drug abuse, drug addiction, drug dependence, drug misuse, illegal drug abuse, illegal drug addiction, illegal drug dependence, illegal drug misuse, nicotine abuse, nicotine addiction, nicotine dependence, nicotine misuse, prescription drug abuse, prescription drug addiction, prescription drug dependence, prescription drug misuse, substance abuse, substance addiction, substance dependence, and substance misuse. In certain embodiments, the substance is selected from: alcohol, caffeine, *cannabis*, a hallucinogen, an inhalant, an opioid, a sedative, a hypnotic, an anxiolytic, a stimulant, and tobacco. In certain embodiments, the substance is phencyclidine. In certain embodiments, the substance is amphetamine. In certain embodiments, the substance is cocaine. In certain embodiments, the substance is nicotine. In certain embodiments, the compounds disclosed herein are useful for smoking cessation. In certain embodiments, the substance is a prescription drug. In certain embodiments, the substance is a drug of abuse. In certain embodiments, the substance-related or addictive disorder involves the use of more than one substance. In some embodiments, the GPR52-mediated disorder is a behavioral disorder or addiction. In certain embodiments, the behavioral disorder is a gambling disorder.

In some embodiments, the GPR52-mediated disorder is a striatal disorder. In certain embodiments, the striatal disorder is a frontostriatal disorder. In certain embodiments, the frontostriatal disorder is selected from: schizophrenia, OCD, ADHD, autism spectrum disorder, Tourette's syndrome, and depression. In certain embodiments, the GPR52-mediated disorder is autism. In certain embodiments, the striatal disorder is an orbitofrontal-striatal disorder.

In some embodiments, the GPR52-mediated disorder is an abnormality in the tuberoinfundibular pathway. In certain embodiments, the abnormality in the tuberoinfundibular pathway is associated with a prolactin-related disorder. In certain embodiments, the abnormality in the tuberoinfundibular pathway is selected from: acromegaly or Cushing's syndrome. In some embodiments, the GPR52-mediated disorder is an abnormality in the mesencephalostriatal pathway. In certain embodiments, the abnormality in the mesencephalostriatal pathway is associated with hyperprolactinemia. In certain embodiments, the abnormality in the mesencephalostriatal pathway is associated with Parkinson's disease. In some embodiments, the GPR52-mediated disorder is an abnormality in the mesolimbic pathway. In certain embodiments, the abnormality in the mesolimbic pathway is associated with addiction or a positive symptom of schizophrenia. In certain embodiments, the abnormality in the mesolimbic pathway is associated with a positive symptom of schizophrenia. In some embodiments, the GPR52-mediated disorder is an abnormality in the mesocortical pathway. In certain embodiments, the abnormality in the mesocortical pathway is associated with a negative symptom of schizophrenia. In certain embodiments, the abnormality in the mesocortical pathway is associated with a cognitive symptom. In some embodiments, the GPR52-mediated disorder is an abnormality in the nigrostriatal pathway. In certain embodiments, the abnormality in the nigrostriatal pathway is associated with Parkinson's disease or tardive dyskinesia. In certain embodiments, the abnormality in the nigrostriatal pathway is associated with an extrapyramidal symptom. In some embodiments, the compounds disclosed herein are useful for increasing activity in the striatum. In certain embodiments, the compounds disclosed herein are useful for increasing activity in the dorsomedial region of the brain. In some embodiments, the compounds disclosed herein are useful for increasing activity in the dorsomedial region of the brain without increasing activity in dorsolateral region of the brain. In certain embodiments, the compounds disclosed herein are useful for increasing activity in the ventromedial region of the brain.

In some embodiments, the GPR52-mediated disorder is a sleep-wake disorder. In certain embodiments, the sleep-wake disorder is selected from: insomnia disorder, hypersomnolence disorder, narcolepsy, a breathing-related sleeping disorder, a circadian rhythm sleep-wake disorder, a non-rapid eye movement (NREM) sleep arousal disorder, a nightmare disorder, a rapid eye movement (REM) sleep behavior disorder, restless legs syndrome, and a substance/medication-induced sleep disorder. In certain embodiments, the breathing-related sleeping disorder is selected from: obstructive sleep apnea hypopnea, central sleep apnea, and sleep-related hypoventilation. In certain embodiments, the sleep-wake disorder is hypersomnolence disorder. In some embodiments, the GPR52-mediated disorder is a parasomnia. In certain embodiments, the parasomnia is selected from: a non-rapid eye movement (NREM) sleep arousal disorder and a rapid eye movement (REM) sleep behavior disorder.

In some embodiments, the disorders disclosed herein are defined as described in the Diagnostic and Statistical Manual of Mental Disorders (DSM), including but not limited to disorders classified in accordance with the fifth edition of the DSM (DSM-5) [American Psychiatric Association, The Diagnostic and Statistical Manual of Mental Disorders, Fifth Edition (2013), the disclosure of which is herein incorporated by reference in its entirety], or as described in the International Statistical Classification of Diseases and Related Health Problems (ICD), including but not limited to disorders classified in accordance with the tenth edition of the ICD [World Health Organization, International Statistical Classification of Diseases and Related Health Problems, Tenth Edition (1992), the disclosure of which is herein incorporated by reference in its entirety].

Polymorphs and Pseudopolymorphs

Polymorphism is the ability of a substance to exist as two or more crystalline phases that have different arrangements and/or conformations of the molecules in the crystal lattice. Polymorphs show the same properties in the liquid or gaseous state but they behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

By way of example, Stahly published a polymorph screen of 245 compounds consisting of a "wide variety of structural types" that revealed about 90% of them exhibited multiple solid forms. Overall, approximately half of the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026).

Isotopes

The present disclosure includes all isotopes of atoms occurring in the compounds provided herein. Isotopes include those atoms having the same atomic number but different mass numbers. It is appreciated that certain features of the invention(s) include every combination of one or more atoms in the compounds provided herein that is replaced with an atom having the same atomic number but a different mass number. One such example is the replacement of an atom that is the most naturally abundant isotope, such as $^1H$ or $^{12}C$, found in one of the compounds provided herein with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being isotopically-labeled. Isotopic-labeling of the present compounds can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Also provided are compositions, such as, those prepared during synthesis, preformulation, and the like, and pharmaceutical compositions, such as, those prepared with the intent of using in a mammal for the treatment of one or more of the disorders described herein, comprising one or more of the present compounds, wherein the naturally occurring distribution of the isotopes in the composition is perturbed. Also provided herein are compositions and pharmaceutical compositions comprising compounds of the invention as described herein, wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

One challenge in drug development is improving absorption, distribution, metabolism, excretion, and toxicity (ADMET) properties while maintaining a desired pharmacological profile. Structural changes to improve ADMET properties often alter the pharmacology of a lead compound. While the effects of deuterium substitution on ADMET properties are unpredictable, in select cases deuterium can improve a compound's ADMET properties with minimal perturbation of its pharmacology. Two examples where deuterium has enabled improvements in therapeutic entities are: CTP-347 and CTP-354. CTP-347 is a deuterated version of paroxetine with a reduced liability for mechanismbased inactivation of CYP2D6 that is observed clinically with paroxetine. CTP-354 is a deuterated version of a promising preclinical gamma-aminobutyric acid A receptor (GABAA) modulator (L-838417) that was not developed due to poor pharmacokinetic (PK) properties. In both cases, deuterium substitution resulted in improved ADMET profiles that provide the potential for improved safety, efficacy, and/or tolerability without significantly altering the biochemical potency and selectivity versus the all-hydrogen compounds. Provided are deuterium substituted compounds of the present invention with improved ADMET profiles and substantially similar biochemical potency and selectivity versus the corresponding all-hydrogen compounds.

Other Utilities

Another object of the present invention relates to radio-labeled compounds of the present invention that would be useful not only in radio-imaging but also in assays, both in vitro and in vivo, for localizing and quantitating GPR52 receptors in tissue samples, including human and for identifying GPR52 receptor ligands by inhibition binding of a radio-labeled compound. It is a further object of this invention to develop novel GPR52 receptor assays of which comprise such radio-labeled compounds.

The present disclosure includes all isotopes of atoms occurring in the present compounds, intermediates, salts and crystalline forms thereof. Isotopes include those atoms having the same atomic number but different mass numbers. One aspect of the present invention includes every combination of one or more atoms in the present compounds, intermediates, salts, and crystalline forms thereof that is replaced with an atom having the same atomic number but a different mass number. One such example is the replacement of an atom that is the most naturally abundant isotope, such as $^1H$ or $^{12}C$, found in one the present compounds, intermediates, salts, and crystalline forms thereof, with a different atom that is not the most naturally abundant isotope, such as $^2H$ or $^3H$ (replacing $^1H$), or $^{11}C$, $^{13}C$, or $^{14}C$ (replacing $^{12}C$). A compound wherein such a replacement has taken place is commonly referred to as being an isotopically-labeled compound. Isotopic-labeling of the present compounds, intermediates, salts, and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2H$ (deuterium) and $^3H$ (tritium). Isotopes of carbon include $^{11}C$, $^{13}C$, and $^{14}C$. Isotopes of nitrogen include $^{13}N$ and $^{15}N$. Isotopes of oxygen include $^{15}O$, $^{17}O$, and $^{18}O$. An isotope of fluorine includes $^{18}F$. An isotope of sulfur includes $^{35}S$. An isotope of chlorine includes $^{36}Cl$. Isotopes of bromine include $^{75}Br$, $^{76}Br$, $^{77}Br$, and $^{82}Br$. Isotopes of iodine include $^{123}I$, $^{124}I$, $^{125}I$, and $^{131}I$. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present compounds, intermediates, salts, and crystalline forms thereof, wherein the naturally occurring distribution of the isotopes in the composition is perturbed. Another aspect of the present invention includes compositions and pharmaceutical compositions comprising compounds as described herein wherein the compound is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Certain isotopically-labeled compounds of the present invention are useful in compound and/or substrate tissue distribution assays. In some embodiments the radionuclide $^3H$ and/or $^{14}C$ isotopes are useful in these studies. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the present invention can generally be prepared by following procedures analogous to those disclosed in the Drawings and Examples infra, by substituting an isotopically labeled reagent for a non-isotopically labeled reagent. Other synthetic methods that are useful are discussed infra. Moreover, it should be understood that all of the atoms represented in the compounds of the invention can be either the most commonly occurring isotope of such atoms or the scarcer radio-isotope or nonradioactive isotope.

Synthetic methods for incorporating radio-isotopes into organic compounds are applicable to compounds of the invention and are well known in the art. These synthetic methods, for example, incorporating activity levels of tritium into target molecules, are as follows:

A. Catalytic Reduction with Tritium Gas: This procedure normally yields high specific activity products and requires halogenated or unsaturated precursors.

B. Reduction with Sodium Borohydride [$^3H$]: This procedure is rather inexpensive and requires precursors containing reducible functional groups such as aldehydes, ketones, lactones, esters and the like.

C. Reduction with Lithium Aluminum Hydride [$^3H$]: This procedure offers products at almost theoretical specific activities. It also requires precursors containing reducible functional groups such as aldehydes, ketones, lactones, esters and the like.

D. Tritium Gas Exposure Labeling: This procedure involves exposing precursors containing exchangeable protons to tritium gas in the presence of a suitable catalyst.

E. N-Methylation using Methyl Iodide [$^3H$]: This procedure is usually employed to prepare O-methyl or N-methyl ($^3H$) products by treating appropriate precursors with high specific activity methyl iodide ($^3H$). This method in general allows for higher specific activity, such as for example, about 70-90 Ci/mmol.

Synthetic methods for incorporating activity levels of $^{125}I$ into target molecules include:

A. Sandmeyer and like reactions: This procedure transforms an aryl amine or a heteroaryl amine into a diazonium salt, such as a diazonium tetrafluoroborate salt and subsequently to $^{125}I$ labeled compound using Na$^{125}I$. A represented procedure was reported by Zhu, G-D. and co-workers in *J. Org. Chem.*, 2002, 67, 943-948.

B. Ortho $^{125}$Iodination of phenols: This procedure allows for the incorporation of $^{125}I$ at the ortho position of a phenol as reported by Collier, T. L. and co-workers in *J. Labelled Compd. Radiopharm.*, 1999, 42, S264-S266.

C. Aryl and heteroaryl bromide exchange with $^{125}I$: This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., $(CH_3)_3SnSn(CH_3)_3$]. A representative procedure was reported by Le Bas, M.-D. and co-workers in *J. Labelled Compd. Radiopharm.* 2001, 44, S280-S282.

A radiolabeled GPR52 receptor compound of Formula (Ia) can be used in a screening assay to identify/evaluate compounds. In general terms, a newly synthesized or identified compound (i.e., test compound) can be evaluated for its ability to reduce binding of the "radiolabeled compound of Formula (Ia)" to a GPR52 receptor. Accordingly, the ability of a test compound to compete with the "radiolabeled compound of Formula (Ia)" for the binding to a GPR52 receptor directly correlates to its binding affinity.

Certain labeled compounds of the present invention bind to certain GPR52 receptors. In one embodiment the labeled compound has an $EC_{50}$ less than about 500 µM, in another embodiment the labeled compound has an $EC_{50}$ less than about 100 µM, in yet another embodiment the labeled compound has an $EC_{50}$ less than about 10 µM, in yet another embodiment the labeled compound has an $EC_{50}$ less than about 1 µM and in still yet another embodiment the labeled compound has an $EC_{50}$ less than about 0.1 µM.

Compositions and Formulations

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound provided herein in a suitable liquid vehicle and filter sterilizing the solution before filling and sealing an appropriate vial or ampule. These are just a few examples of the many appropriate methods well known in the art for preparing dosage forms.

A compound of the present invention as provided herein can be formulated into pharmaceutical compositions using techniques well known to those in the art. Suitable pharmaceutically-acceptable carriers, outside those mentioned herein, are known in the art; for example, see Remington, The Science and Practice of Pharmacy, 20th Edition, 2000, Lippincott Williams & Wilkins, (Editors: Gennaro et al.).

While it is possible that, for use in the prophylaxis or treatment, a compound provided herein may, in an alternative use, be administered as a raw or pure chemical, it is preferable however to present the compound or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds provided herein, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds provided herein or a solvate, hydrate or physiologically functional derivative thereof can be used as active ingredients in pharmaceutical compositions, specifically as GPR52 receptor modulators. The term "active ingredient", defined in the context of a "pharmaceutical composition"," refers to a component of a pharmaceutical composition that provides the primary pharmacological effect, as opposed to an "inactive ingredient" which would generally be recognized as providing no pharmaceutical benefit.

The dose when using the compounds provided herein can vary within wide limits and as is customary and is known to the physician or other clinician, it is to be tailored to the individual conditions in each individual case. It depends, for example, on the nature and severity of the illness to be treated, on the condition of the patient, on the compound employed or on whether an acute or chronic disease state is treated, or prophylaxis conducted, or on whether further active compounds are administered in addition to the compounds provided herein. Representative doses include, but are not limited to, about 0.001 mg to about 5000 mg, about 0.001 mg to about 2500 mg, about 0.001 mg to about 1000 mg, about 0.001 mg to about 500 mg, about 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3, or 4 doses. Depending on the individual and as deemed appropriate from the healthcare provider it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated, or prophylaxis conducted, or on whether further active compounds are administered in addition to the compounds provided herein and as part of a drug combination. The dosage regimen for treating a disease condition with the compounds and/or compositions provided herein is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods provided herein.

The desired dose may conveniently be presented in a single dose or as divided doses administered at appropriate intervals, for example, as two, three, four, or more sub-doses per day. The sub-dose itself may be further divided, e.g., into a number of discrete loosely spaced administrations. The daily dose can be divided, especially when relatively large amounts are administered as deemed appropriate, into several, for example two, three, or four-part administrations. If appropriate, depending on individual behavior, it may be necessary to deviate upward or downward from the daily dose indicated.

The compounds provided herein can be administered in a wide variety of oral and parenteral dosage forms. It will be obvious to those skilled in the art that the dosage forms may comprise, as the active component, either a compound provided herein or a pharmaceutically acceptable salt, hydrate, or solvate of a compound provided herein.

For preparing pharmaceutical compositions from the compounds provided herein, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethyl cellulose, a low melting wax, cocoa butter and the like. The term "preparation" refers to the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams, or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds provided herein may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethyl cellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds provided herein may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds provided herein or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds provided herein as an aerosol can be prepared by processes well known to the person skilled in the art. For their preparation, for example, solutions or dispersions of the compounds provided herein in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The compounds provided herein may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like. Certain compounds provided herein which contain a carboxylic acid functional group may optionally exist as pharmaceutically acceptable salts containing non-toxic, pharmaceutically acceptable metal cations and cations derived from organic bases. Representative metals include, but are not limited to, aluminium, calcium, lithium, magnesium, potassium, sodium, zinc and the like. In some embodiments the pharmaceutically acceptable metal is sodium. Representative organic bases include, but are not limited to, benzathine ($N^1$,$N^2$-dibenzylethane-1,2-diamine), chloroprocaine (2-(diethylamino)ethyl 4-(chloroamino)benzoate), choline, diethanolamine, ethylenediamine, meglumine ((2R,3R,4R, 5S)-6-(methylamino)hexane-1,2,3,4,5-pentaol), procaine (2-(diethylamino)ethyl 4-aminobenzoate), and the like. Certain pharmaceutically acceptable salts are listed in Berge, et. al., Journal of Pharmaceutical Sciences, 66:1-19 (1977).

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds provided herein may form solvates with standard low molecular weight solvents using methods known to the skilled artisan.

Compounds provided herein can be converted to "pro-drugs." The term "pro-drugs" refers to compounds that have been modified with specific chemical groups known in the art and when administered into an individual these groups undergo biotransformation to give the parent compound. Pro-drugs can thus be viewed as compounds provided herein containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in Bioreversible Carriers in Drug Design, ed. Edward B. Roche, American Pharmaceutical Association and Pergamon Press, 1987.

Some embodiments include a method of producing a pharmaceutical composition for "combination-therapy"

comprising admixing at least one compound according to any of the compound embodiments disclosed herein, together with at least one known pharmaceutical agent as described herein and a pharmaceutically acceptable carrier.

It is noted that when the GPR52 receptor modulators are utilized as active ingredients in pharmaceutical compositions, these are not intended for use in humans only, but in non-human mammals as well. Recent advances in the area of animal health-care mandate that consideration be given for the use of active agents, such as GPR52 receptor modulators, for the treatment of a GPR52 receptor-associated disease or disorder in companionship animals (e.g., cats, dogs, etc.) and in livestock animals (e.g., horses, cows, etc.) Those of ordinary skill in the art are readily credited with understanding the utility of such compounds in such settings.

Other uses of the disclosed receptors and methods will become apparent to those skilled in the art based upon, inter alia, a review of this disclosure.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Syntheses of Compounds of the Present Invention

Illustrated syntheses for compounds of the present invention are shown in FIG. 1 to FIG. 14 wherein the variables (e.g., Y, Ring A, $R^1$, $R^2$, $R^3$, $R^4$, and $R^5$) have the same definitions as used throughout this disclosure.

The compounds disclosed herein and their syntheses are further illustrated by the following examples. Additional illustrated syntheses for compounds of the present invention are shown in FIGS. 1 to 14 where the symbols have the same definitions as used throughout this disclosure. The following examples are provided to further define the invention without, however, limiting the invention to the particulars of these examples. The compounds described herein, supra and infra, are named according to the AutoNom version 2.2, CS ChemDraw Ultra Version 9.0.7, or ChemBioDraw Ultra 12.0.2.1076. In certain instances common names are used and it is understood that these common names would be recognized by those skilled in the art.

Chemistry: Proton nuclear magnetic resonance ($^1$H NMR) spectra were recorded on a Bruker Avance III-400 equipped with a 5 mm BBFO probe. Chemical shifts are given in parts per million (ppm) with the residual solvent signal used as reference. NMR abbreviations are used as follows: s=singlet, d=doublet, dd=doublet of doublets, t=triplet, q=quartet, m=multiplet, bs=broad singlet, sxt=sextet. Microwave irradiations were carried out using an Initiator+™ (Biotage®). Thin-layer chromatography (TLC) was performed on silica gel 60 $F_{254}$ (Merck), preparatory thin-layer chromatography (prep TLC) was performed on PK6F silica gel 60 Å 1 mm plates (Whatman) and column chromatography was carried out on a silica gel column using Kieselgel 60, 0.063-0.200 mm (Merck). Evaporation was done under reduced pressure on a Büchi rotary evaporator. Celite® 545 was used for filtration of palladium. Reactions were conducted with stirring unless specifically stated otherwise.

LCMS spec: HPLC-Agilent 1200; pumps: G1312A; DAD:G1315B; Autosampler: G1367B; Mass spectrometer-Agilent G1956A; ionization source: ESI; Drying Gas Flow: 10 L/min; Nebulizer Pressure: 40 psig; Drying Gas Temperature: 350° C.; Capillary Voltage: 2500 V) Software: Agilent Chemstation Rev.B.04.03.

Example 1.1: Preparation of (S)-3-Amino-2-fluoropropan-1-ol

Step A: Preparation of (R)-Methyl 2-Amino-3-hydroxypropanoate

To a solution of (R)-2-amino-3-hydroxypropanoic acid (3 g, 28.55 mmol) in MeOH (40 mL) was slowly added thionyl chloride (2.082 mL, 28.55 mmol) at 0° C. The mixture was heated under reflux at 70° C. for 2 hours, cooled to room temperature, and concentrated to furnish crude (R)-methyl 2-amino-3-hydroxypropanoate which was taken to Step B without further purification. LCMS m/z=120.2 [M+1]$^+$.

Step B: Preparation of (R)-Methyl 2-(Dibenzylamino)-3-hydroxypropanoate

To crude (R)-methyl 2-amino-3-hydroxypropanoate suspended in THF (40 mL) and DMSO (10 mL) was added sodium bicarbonate (23.98 g, 285.5 mmol) and benzyl bromide (16.98 mL, 142.7 mmol). The mixture was heated to reflux (85° C.) for 3 hours. After cooling to room temperature, the solids were filtered off and the solution was concentrated. The residue was then dissolved in ethyl acetate, washed with water and brine, dried over $Na_2SO_4$, and concentrated to furnish crude (R)-methyl 2-(dibenzylamino)-3-hydroxypropanoate, which was taken to Step C without further purification. LCMS m/z=300.4 [M+1]$^+$.

Step C: Preparation of (S)-Methyl 3-(Dibenzylamino)-2-fluoropropanoate

To a solution of crude (R)-methyl 2-(dibenzylamino)-3-hydroxypropanoate in THF (40 mL) was added DAST (4.149 mL, 31.40 mmol). The mixture was stirred at room temperature for 20 minutes, quenched with ice, washed with saturated aqueous $NaHCO_3$ (30 mL), and extracted with ethyl acetate (2×20 mL). The combined organics were concentrated to furnish crude (S)-methyl 3-(dibenzylamino)-2-fluoropropanoate, which was taken to Step D without further purification. LCMS m/z=302.4 [M+1]$^+$.

Step D: Preparation of (S)-3-(Dibenzylamino)-2-fluoropropan-1-ol

To a solution of crude (S)-methyl 3-(dibenzylamino)-2-fluoropropanoate in THF (40 mL) was added a 2.0 M solution of $LiBH_4$ (17.84 mL, 35.68 mmol) at −78° C. The mixture was then stirred for 30 minutes at 0° C. and then cautiously quenched with saturated aqueous $NH_4Cl$ (30 mL), extracted with EtOAc (2×20 mL), and concentrated. The crude residue was dissolved in 2 M HCl (30 mL) and washed with MTBE (2×20 mL). The aqueous phase was then basified with 80% ammonium hydroxide, brine (5 mL) was added, and then extracted with EtOAc (2×20 mL). Dried over sodium sulfate, filtered, and concentrated in vacuo. Purified by column chromatography to furnish pure (S)-3-(dibenzylamino)-2-fluoropropan-1-ol (3.03 g, 11.08 mmol, 38.8% from Step A to Step D) which was taken to Step E. LCMS m/z=274.4 [M+1]$^+$.

Step E: Preparation of (S)-3-Amino-2-fluoropropan-1-ol

To a solution of (S)-3-(dibenzylamino)-2-fluoropropan-1-ol (3.03 g, 11.08 mmol) in EtOH (30 mL) was added 20% wt Pd(OH)$_2$/C (2.5 g, 3.56 mmol). The resulting mixture was placed on a Parr shaker, charged with H$_2$ to 85 psi, and the reaction was allowed to proceed overnight. The mixture was filtered through Celite®, concentrated, and Pd(OH)$_2$/C (2.5 g, 3.56 mmol) was added. The resulting mixture was placed on a Parr shaker charged with H$_2$ overnight. The mixture was filtered through Celite® and concentrated to furnish (S)-3-amino-2-fluoropropan-1-ol (923.3 mg, 9.917 mmol, 89.5%). $^1$H NMR (400 MHz, CDCl$_3$): δ ppm 1.81 (brs, 3H), 2.97-3.14 (m, 2H), 3.79-3.93 (m, 2H), 4.46-4.63 (dp, J=9.04 Hz, 47.89 Hz, 1H).

Example 1.2: Preparation of (R)-3-Amino-2-fluoropropan-1-ol (R)-3-Amino-2-fluoropropan-1-ol was prepared from (S)-2-amino-3-hydroxypropanoic acid using the above method (Example 1.1). $^1$H NMR (400 MHz, CDCl$_3$): δ ppm 1.88 (brs, 3H), 2.97-3.13 (m, 2H), 3.80-3.88 (m, 2H), 4.47-4.62 (dp, J=9.04 Hz, 47.89 Hz, 1H).

Example 1.3: Preparation of (R)-1-Amino-3-fluoropropan-2-ol

Step A: Preparation of (R)-2-(Fluoromethyl)oxirane

A solution of (S,S)—N,N-bis(3,5-di-tert-butylsalicylidene)-1,2-cyclohexanediaminocobalt(II) (39.68 mg, 65.73 μmol) in toluene (1 mL) was treated with acetic acid (40 μl, 0.699 mmol), stirred at room temperature for 15 minutes, and then concentrated. To the mixture was then added (±)-2-(fluoromethyl)oxirane (1 g, 13.15 mmol). After stirring for 5 minutes at room temperature, the mixture was then cooled to 0° C. Water (130 μl, 7.216 mmol) was added and the reaction mixture was allowed to stir for 16 hours. Vacuum transfer of the reaction mixture into a cooled (−78° C.) flask furnished (R)-2-(fluoromethyl)oxirane (381 mg, 5.009 mmol, 38.1%). $^1$H NMR (400 MHz, DMSO-d$_6$): δ ppm 2.63-2.65 (m, 1H), 2.81-2.84 (q, J=4.2 Hz, 1H), 3.25-3.32 (m, 1H), 4.12-4.28 (ddd, J=6.60 Hz, 10.88 Hz, 47.60 Hz, 1H), 4.69-4.84 (ddd, J=2.18 Hz, 10.92 Hz, 47.75 Hz, 1H).

Step B: Preparation of (R)-1-Amino-3-fluoropropan-2-ol (R)-2-(Fluoromethyl)oxirane (381 mg, 5.009 mmol) was dissolved in a 7.0 M solution of ammonia in MeOH (37.56 mL, 262.9 mmol) and allowed to stir for 16 hours at room temperature. The mixture was then concentrated to furnish (R)-1-amino-3-fluoropropan-2-ol (358.1 mg, 3.846 mmol, 77.8%). $^1$H NMR (400 MHz, DMSO-d$_6$): δ ppm 2.47-2.59 (m, 2H), 3.51-3.61 (m, 1H), 4.20-4.45 (m, 2H).

Example 1.4: Preparation of (S)-1-Amino-3-fluoropropan-2-ol (S)-3-Amino-2-fluoropropan-1-ol was also prepared from (±)-2-(fluoromethyl)oxirane by using the above method (Example 1.3) with (R,R)—N,N-bis(3,5-di-tert-butylsalicylidene)-1,2-cyclohexanediaminocobalt(II) acid instead of (S,S)—N,N-bis(3,5-di-tert-butylsalicylidene)-1,2-cyclohexanediaminocobalt(II). $^1$H NMR (400 MHz, DMSO-d$_6$): δ ppm 2.48-2.60 (m, 2H), 3.52-3.62 (m, 1H), 4.21-4.44 (m, 2H).

Example 1.5: Preparation of Methyl 1-(4-(Hydroxymethyl)pyridin-2-yl)indoline-4-carboxylate

Step A: Preparation of 2-Bromo-4-((tert-butyldimethylsilyloxy)methyl)pyridine (Method F)

To a solution of (2-bromopyridin-4-yl)methanol (3.05 g, 16.22 mmol) and 1H-imidazole (1.28 g, 18.80 mmol) in 60 mL CH$_2$Cl$_2$, tert-butylchlorodimethylsilane (2.7 g, 17.91 mmol) was added. After stirring at RT for 1 h, solution was extracted with 1 M NaOH and CH$_2$Cl$_2$. Organic phases were dried over MgSO$_4$, filtered, and concentrated. The residue was purified by Biotage® chromatography (SiO$_2$, hexane/AcOEt gradient) to give 2-bromo-4-((tert-butyldimethylsilyloxy)methyl)pyridine (4.27 g, 87.1%) as a colorless oil. LCMS m/z=302.2 [M+1]$^+$. $^1$H NMR (400 MHz, CDCl$_3$): δ ppm 0.12 (s, 6H), 0.95 (s, 9H), 4.71, s, 2H), 7.19 (m, 1H), 7.46 (s, 1H), 8.30 (d, J=5.1 Hz, 1H).

Step B: Preparation of Methyl 1-(4-((tert-Butyldimethylsilyloxy)methyl)pyridin-2-yl)indoline-4-carboxylate A mixture of 2-bromo-4-((tert-butyldimethylsilyloxy)methyl)pyridine (2.02 g, 6.682 mmol), methyl indoline-4-carboxylate (1.18 g, 6.659 mmol), 1,1'-bis(di-tert-butylphosphino)ferrocene (327 mg, 0.692 mmol), diacetoxypalladium (80 mg, 0.356 mmol), and cesium carbonate (5.4 g, 16.57 mmol) in 40 mL dioxane was stirred at 120° C. (oil bath) for 18 h. The reaction mixture was filtered, concentrated and the resulting residue was purified by Biotage® chromatography (SiO$_2$, hexane/AcOEt) to give methyl 1-(4-((tert-butyldimethylsilyloxy)methyl)pyridin-2-yl)indoline-4-carboxylate (2.1 g, 79.1%) as a colorless oil. LCMS m/z=399.0 [M+1]$^+$. $^1$H NMR (400 MHz, CDCl$_3$): δ ppm 0.13 (s, 6H), 0.97 (s, 9H), 3.59 (t, J=8.6 Hz, 2H), 3.90 (s, 3H), 4.07 (t, J=8.3 Hz, 2H), 4.74 (s, 2H), 6.72 (d, J=5.0 Hz, 1H), 6.80 (s, 1H), 7.22-7.26 (m, 1H), 7.50 (d, J=7.9 Hz, 1H), 8.27 (d, J=5.0 Hz, 1H), 8.51 (d, J=7.9 Hz, 1H).

Step C: Preparation Methyl 1-(4-(Hydroxymethyl)pyridin-2-yl)indoline-4-carboxylate To a solution of methyl 1-(4-((tert-butyldimethylsilyloxy)methyl)pyridin-2-yl)indoline-4-carboxylate (2.1 g, 5.269 mmol) in 100 mL THF, 1 M tetrabutylammonium fluoride (TBAF) in THF (6 mL, 6.000 mmol) was added. After stirring at RT overnight, solution was concentrated. The residue was purified by Biotage® chromatography (SiO$_2$, hexane/AcOEt gradient) to give methyl 1-(4-(hydroxymethyl)pyridin-2-yl)indoline-4-carboxylate (1.45 g, 96.8%) as a white solid. LCMS m/z=285.0 [M+1]$^+$. $^1$H NMR (400 MHz, DMSO-d$_6$): δ ppm 3.51 (t, J=8.6 Hz, 2H), 3.87 (s, 3H), 4.07 (t, J=8.6 Hz, 2H), 4.57 (d, J=6.0 Hz, 2H), 5.42 (t, J=6.0 Hz, 1H), 6.85-6.87 (m, 2H), 7.27-7.31 (m, 1H), 7.41 (dd, J$_1$=7.8 Hz, J$_2$=1.1 Hz, 1H), 8.26 (d, J=5.3 Hz, 1H), 8.60-8.62 (m, 1H).

Example 1.6: Preparation of N-(2-Hydroxyethyl)-1-(4-(3-(trifluoromethyl)benzyl)pyridin-2-yl)indoline-4-carboxamide (Compound 13). (Method A)

Step A: Preparation of 2-Chloro-4-(3-(trifluoromethyl)benzyl)pyridine

To 4-bromo-2-chloropyridine (0.769 mL, 6.236 mmol) and POPd2 (63.89 mg, 93.54 μmol) was added 0.5 M (3-(trifluoromethyl) benzyl)zinc(II) chloride (12.47 mL, 6.236 mmol) in THF. The reaction was heated at 100° C. for 70 min in microwave. An additional 5 mL of (3-(trifluoromethyl)benzyl)zinc(II) chloride (2.5 mmol, 0.5 M in THF) was added into the reaction mixture and heated at 100° C. for 30 minutes with conventional heating. The mixture was concentrated and the resulting residue was purified by column chromatography (0-60% EtOAc/Hex, eluted at 32% EtOAc) to give the title compound (1.733 g, 6.124 mmol, 98.2%) as a yellow oil. LCMS m/z=272.0 [M+1]$^+$; $^1$H NMR (400 MHz, DMSO-d$_6$): δ ppm 4.11 (s, 2H), 7.31 (d, J=4.28 Hz, 1H), 7.47 (s, 1H), 7.54-7.61 (m, 3H), 7.71 (s, 1H), 8.31 (d, J=5.08 Hz, 1H).

Step B: Preparation of Methyl 1-(4-(3-(Trifluoromethyl)benzyl)pyridin-2-yl)indoline-4-carboxylate To a mixture of methyl indoline-4-carboxylate (0.626 g, 3.534 mmol), 2-chloro-4-(3-(trifluoromethyl)benzyl)pyridine (1.00 g, 3.534 mmol) and 1,1'-bis(di-tert-butylphosphino)ferrocene (0.185 g, 0.389 mmol) in dioxane (10 mL) were added palladium (II) acetate (39.67 mg, 0.177 mmol), and cesium carbonate (1.727 g, 5.301 mmol). The reaction was heated under microwave irradiation at 135° C. for 2 h. Additional palladium (II) acetate (20 mg, 0.089 mmol) and 1,1'-bis(di-tert-butylphosphino)-ferrocene (92 mg, 0.193 mmol) were added into the reaction mixture and heated at 135° C. for another 3 hours followed by heating at 135° C. overnight with conventional heating. The mixture was concentrated. The residue was dissolved in DCM and extracted with water. The organic phase was concentrated. The residue was purified by column chromatography (20-80% EtOAc/Hex, and then 20%-40% EtOAc/Hex) to give the title compound (351 mg, 0.851 mmol, 24.1%) as a yellow solid. LCMS m/z=413.3 [M+1]$^+$; $^1$H NMR (400 MHz, CDCl$_3$): δ ppm 3.57 (t, J=8.73 Hz, 2H), 3.90 (s, 3H), 3.88-4.04 (m, 4H), 6.53 (s, 1H), 6.62 (dd, J=1.14, 5.10 Hz, 1H), 7.23 (t, J=8.01 Hz, 1H), 7.33-7.53 (m, 5H), 8.26 (d, J=5.04 Hz, 1H), 8.48 (d, J=7.89 Hz, 1H).

Step C: Preparation of 1-(4-(3-(Trifluoromethyl)benzyl)pyridin-2-yl)indoline-4-carboxylic Acid The mixture of methyl 1-(4-(3-(trifluoromethyl)benzyl)pyridin-2-yl)indoline-4-carboxylate (351 mg, 0.851 mmol) and sodium hydroxide (0.204 g, 5.107 mmol) in MeOH (15 mL)/water (6 mL)/THF (5 mL) was stirred at 65° C. overnight. The solvent was evaporated, the resulting residue acidified with 2M HCl, diluted with water, and then extracted with EtOAc. The organic layer was dried with Na$_2$SO$_4$ and concentrated to give the title compound (342 mg, 0.858 mmol, 100.9%) as a pale-orange solid. LCMS m/z=399.2 [M+1]$^+$; $^1$H NMR (400 MHz, CDCl$_3$): δ ppm 3.61 (t, J=8.62 Hz, 2H), 4.03 (s, 2H), 4.08 (t, J=8.24 Hz, 2H), 6.59 (s, 1H), 6.65 (d, J=5.04 Hz, 1H), 7.27 (t, J=7.96 Hz, 1H), 7.38-7.54 (m, 4H), 7.61 (d, J=7.60 Hz, 1H), 8.28 (d, J=5.16 Hz, 1H), 8.45 (sb, 1H).

Step D: Preparation of N-(2-Hydroxyethyl)-1-(4-(3-(trifluoromethyl)benzyl)pyridin-2-yl)indoline-4-carboxamide To the mixture of 1-(4-(3-(trifluoromethyl)benzyl)pyridin-2-yl)indoline-4-carboxylic acid (100 mg, 0.251 mmol), HATU (0.191 g, 0.502 mmol) and triethylamine (76.97 μl, 0.552 mmol) in DMF (1.5 mL) was added 2-aminoethanol (65.65 μl, 1.130 mmol). The reaction was stirred at RT for 20 minutes. Water was added and the solid was collected by filtration and washed with water/acetonitrile (95/5) and dried in a vacuum oven to give the title compound (100.5 mg, 0.228 mmol, 90.7%) as a white solid. LCMS m/z=442.4 [M+1]$^+$; $^1$H NMR (400 MHz, DMSO-d$_6$): δ ppm 3.31 (t, J=9.06 Hz, 2H), 3.38 (t, J=8.66 Hz, 2H), 3.51 (q, J=6.04 Hz, 2H), 3.99 (t, J=8.70 Hz, 2H), 4.07 (s, 2H), 4.68 (t, J=5.62 Hz, 1H), 6.75 (d, J=4.08 Hz, 1H), 6.83 (s, 1H), 7.10 (dd, J=1.04, 7.89 Hz, 1H), 7.18 (t, J=7.83 Hz, 1H), 7.53-7.64 (m, 3H), 7.70 (s, 1H), 8.15 (t, J=5.54 Hz, 1H), 8.20 (d, J=5.12 Hz, 1H), 8.38 (dd, J=0.92, 8.08 Hz, 1H).

Example 1.7: Preparation of N-(2-Hydroxyethyl)-1-(2-(3-(trifluoromethyl)benzyl)pyridin-4-yl)indoline-4-carboxamide (Compound 184). (Method B)

Step A: Preparation of 4-Chloro-2-(3-(trifluoromethyl)benzyl)pyridine

2-Bromo-4-chloropyridine (2.00 g, 10.39 mmol) and POPd2 (106 mg, 0.156 mmol) were placed in a heavy-walled 20 mL microwave vial. 0.5M (3-(trifluoromethyl)benzyl)zinc(II) chloride in THF (20.79 mL, 10.39 mmol) was added. The vial was sealed, purged with nitrogen, and heated conventionally at 100° C. for 2 hours. The reaction mixture was concentrated to dryness and the residue was purified via column chromatography (0-40-60% EtOAc/Hex) to yield the title compound (2.28 g, 8.396 mmol, 80.8%) as a yellow oil. LCMS m/z=272 [M+1, $^{35}$Cl]$^+$, 274 [M+1, $^{37}$Cl]$^+$. $^1$H NMR (400 MHz, CDCl$_3$): δ ppm 4.18 (s, 2H), 7.12-7.14 (m, 1H), 7.17 (dd, J=5.34, 1.98 Hz, 1H), 7.42-7.45 (m, 2H), 7.50-7.53 (m, 2H), 8.46 (d, J=5.36 Hz, 1H).

Step B: Preparation of Methyl 1-(2-(3-(Trifluoromethyl)benzyl)pyridin-4-yl)indoline-4-carboxylate Methyl indoline-4-carboxylate (0.273 g, 1.542 mmol), 1,1'-bis(di-tert-butylphosphino)ferrocene (0.147 g, 0.308 mmol), palladium (II) acetate (34.63 mg, 0.154 mmol), cesium carbonate (0.754 g, 2.314 mmol) and 4-chloro-2-(3-(trifluoromethyl)benzyl)pyridine (0.419 g, 1.542 mmol) were taken up in dioxane (10.000 mL). The reaction was heated at 130° C. for 3 hours (in a heavy-walled sealed flask). The mixture was cooled to room temperature, filtered, and concentrated to dryness. The crude residue was purified by column chromatography (0-50-80% EtOAc/Hex) to yield the title compound (0.4984 g, 1.209 mmol, 62.7%) as a yellow solid. LCMS m/z=413.2 [M+1]$^+$. $^1$H NMR (400 MHz, CDCl$_3$): δ ppm 3.51 (t, J=8.45 Hz, 2H), 3.90 (s, 3H), 3.99 (t, J=8.46 Hz, 2H), 4.18 (s, 2H), 6.94-6.96 (m, 1H), 6.92 (dd, J=5.86, 2.38 Hz, 1H), 7.18 (t, J=7.95 Hz, 1H), 7.32-7.36 (m, 1H), 7.40-7.46 (m, 1H), 7.47-7.53 (m, 3H), 7.57 (s, 1H), 8.38 (d, J=5.84 Hz, 1H).

Step C: Preparation of 1-(2-(3-(Trifluoromethyl)benzyl)pyridin-4-yl)indoline-4-carboxylic Acid Methyl 1-(2-(3-(trifluoromethyl)benzyl)pyridin-4-yl)indoline-4-carboxylate (0.485 g, 1.176 mmol) was taken up in THF (6.00 mL)/MeOH (2.00 mL)/H$_2$O (2.00 mL). Solid sodium hydroxide (0.214 g, 5.340 mmol) was added. The reaction mixture was heated to 50° C. and stirred for 2 hours. The reaction mixture was cooled to 0° C. and acidified with 1M HCl to pH-5 to precipitate out the product. The solid was collected by filtration, washed with ice-cold water, and dried in a vacuum oven to give the title compound (0.425 g, 1.067 mmol, 90.7%) as a white solid. LCMS m/z=399.4 [M+1]⁺. ¹H NMR (400 MHz, DMSO-d₆): δ ppm 3.51 (t, J=8.07 Hz, 2H), 4.20 (t, J=8.13 Hz, 2H), 4.40 (s, 2H), 7.37-7.43 (m, 2H), 7.55-7.58 (m, 1H), 7.59-7.63 (m, 1H), 7.65-7.69 (m, 2H), 7.75-7.83 (m, 2H), 7.91 (s, 1H), 8.38 (d, J=7.13 Hz, 1H).

Step D: Preparation of N-(2-Hydroxyethyl)-1-(2-(3-(trifluoromethyl)benzyl)pyridin-4-yl)indoline-4-carboxamide 1-(2-(3-(Trifluoromethyl)benzyl)pyridin-4-yl)indoline-4-carboxylic acid (0.050 g, 0.126 mmol), HATU (59.65 mg, 0.157 mmol) and DIEA (65.58 µl, 0.377 mmol) were taken up in DMF (2.000 mL). The resulting mixture was stirred at room temperature for 10 minutes followed by the addition of 2-aminoethanol (38.33 mg, 0.628 mmol). The reaction mixture was stirred at room temperature for 3 hours. The residue was purified by preparative HPLC. The fractions containing the desired product were combined, neutralized with NaHCO₃, extracted with EtOAc, dried, filtered and concentrated to dryness to yield the title compound (43.3 mg, 98.09 µmol, 78.2%) as an off-white solid. LCMS m/z=442.4 [M+1]⁺. ¹H NMR (400 MHz, DMSO-d₆): δ ppm 3.27-3.34 (m, 4H), 3.51 (q, J=6.04 Hz, 2H), 3.97 (t, J=8.45 Hz, 2H), 4.14 (s, 2H), 4.69 (t, J=5.62 Hz, 1H), 7.00 (dd, J=5.80, 2.40 Hz, 1H), 7.10-7.15 (m, 2H), 7.17-7.22 (m, 1H), 7.36-7.42 (m, 1H), 7.50-7.59 (m, 2H), 7.61-7.65 (m, 1H), 7.71 (s, 1H), 8.19 (t, J=5.62 Hz, 1H), 8.28 (d, J=5.80 Hz, 1H).

Example 1.8: Preparation of 1-(6-(3-(Trifluoromethyl)benzyl)pyridin-2-yl)indoline-4-carboxamide (Compound 1). (Method C)

Step A: Preparation of 2-Chloro-6-(3-(trifluoromethyl)benzyl)pyridine

To 2,6-dichloropyridine (450 mg, 3.041 mmol) and POPd2 (61.95 mg, 91.22 µmol) was added 0.5 M (3-(trifluoromethyl)benzyl)zinc(II) chloride (6.081 mL, 3.041 mmol) in THF. The reaction was heated at 100° C. for 15 h. The reaction mixture was left standing for several weeks. The mixture was concentrated. The residue was purified by column chromatography to give the title compound. LCMS m/z=272.0 [M+1]⁺; ¹H NMR (400 MHz, CDCl₃): δ ppm 4.16 (s, 2H), 7.00 (d, J=8 HZ, 1H), 7.19 (d, J=8 Hz, 1H), 7.40-7.59 (m, 5H).

Step B: Preparation of Methyl 1-(6-(3-(Trifluoromethyl)benzyl)pyridin-2-yl)indoline-4-carboxylate To a mixture of methyl indoline-4-carboxylate (19.57 mg, 0.110 mmol), 2-chloro-6-(3-(trifluoromethyl)benzyl)pyridine (30 mg, 0.110 mmol), and 1,1'-bis(di-tert-butylphosphino)ferrocene (5.787 mg, 12.15 µmol) in dioxane (0.6 mL) were added palladium (II) acetate (1.240 mg, 5.5 µmol) and cesium carbonate (53.97 mg, 0.166 mmol). The reaction was heated under microwave irradiation at 135° C. for 2 h. The mixture was concentrated. The residue was dissolved in DCM and extracted with water. The organic phase was concentrated. The residue was purified by column chromatography to give the title compound. LCMS m/z=413.4 [M+1]⁺; ¹H NMR (400 MHz, CDCl₃): δ ppm 3.56 (t, J=8 Hz, 2H), 3.90 (s, 3H), 4.02 (t, J=8 Hz, 2H), 4.16 (s, 2H), 6.54 (d, J=8 HZ, 1H), 6.68 (d, J=8 Hz, 1H), 7.11 (t, J=8 Hz, 1H), 7.40-7.58 (m, 5H), 7.63 (s, 1H), 8.30 (d, J=8 Hz, 1H).

Step C: Preparation of 1-(6-(3-(Trifluoromethyl)benzyl)pyridin-2-yl)indoline-4-carboxylic Acid To a solution of methyl 1-(6-(3-(trifluoromethyl)benzyl)pyridin-2-yl)indoline-4-carboxylate (30 mg, 72.74 µmol) in MeOH (0.6 mL) was added sodium hydroxide (29.10 µL, 0.145 mmol). The reaction was heated at 65° C. for 15 h. The mixture was concentrated. The residue was treated with 4M dioxane solution of hydrogen chloride (36.37 µl, 0.145 mmol). The mixture was concentrated to give the title compound. LCMS m/z=399.2 [M+1]⁺.

Step D: Preparation of 1-(6-(3-(Trifluoromethyl)benzyl)pyridin-2-yl)indoline-4-carboxamide To a solution of 1-(6-(3-(trifluoromethyl)benzyl)pyridin-2-yl)indoline-4-carboxylic acid (14 mg, 35.14 µmol), 7M ammonia in methanol (75.31 µl, 0.527 mmol), and triethylamine (12.25 µl, 87.86 µmol) in DMF (0.1 mL) was added HATU (16.70 mg, 43.93 µmol). The reaction was stirred at 23° C. for 1 h. The reaction was diluted with ACN (0.2 mL) and 2M HCl (0.2 mL). The precipitate was collected by filtration. The solid was washed with MTBE and dried to give the title compound. LCMS m/z=398.2 [M+1]⁺; ¹H NMR (400 MHz, CDCl₃): δ ppm 3.53 (t, J=8 Hz, 2H), 4.01 (t, J=10 Hz, 2H), 4.16 (s, 2H), 5.56 (bs, 1H), 5.92 (bs, 1H), 6.53 (d, J=6 Hz, 1H), 6.67 (d, J=8 Hz, 1H), 7.03 (d, J=8 Hz, 1H), 7.10 (t, J=8 Hz, 1H), 7.40-7.57 (m, 4H), 7.64 (s, 1H), 8.24 (d, J=8 Hz, 1H).

Example 1.9: Preparation of 1-(5-(3-(Trifluoromethyl)benzyl)pyridin-3-yl)indoline-4-carboxamide (Compound 8). (Method D)

Step A: Preparation of 3-Chloro-5-(3-(trifluoromethyl)benzyl)pyridine

To 3,5-dichloropyridine (1.2 g, 8.109 mmol) and POPd2 (0.110 g, 0.162 mmol) was added 0.5 M (3-(trifluoromethyl)benzyl)zinc(II) chloride (16.22 mL, 8.109 mmol) in THF. The reaction was heated at 100° C. for 15 h. The mixture was concentrated. The residue was purified by column chromatography to give the title compound. LCMS m/z=272.2 [M+1]⁺; ¹H NMR (400 MHz, CDCl₃): δ ppm 4.03 (s, 2H), 7.35 (d, J=8 Hz, 1H), 7.42-7.48 (m, 3H), 7.53 (d, J=8 Hz, 1H), 8.38 (d, J=2 Hz, 1H), 8.46 (d, J=2 Hz, 1H).

Step B: Preparation of Methyl 1-(5-(3-(Trifluoromethyl)benzyl)pyridin-3-yl)indoline-4-carboxylate To a mixture of methyl indoline-4-carboxylate (0.130 g, 0.736 mmol), 3-chloro-5-(3-(trifluoromethyl)benzyl)pyridine (200 mg, 0.736 mmol), and 1,1'-bis(di-tert-butylphosphino)ferrocene (38.58 mg, 80.98 µmol) in dioxane (3 mL) were added palladium (II) acetate (8.264 mg, 36.81 µmol), and cesium carbonate (0.360 g, 1.104 mmol). The reaction was heated under microwave irradiation at 135° C. for 2 h. The mixture was concentrated. The residue was purified by column chromatography to give the title compound. LCMS m/z=413.4 [M+1]⁺.

Step C: Preparation of 1-(5-(3-(Trifluoromethyl)benzyl)pyridin-3-yl)indoline-4-carboxylic Acid To a solution of methyl 1-(5-(3-(trifluoromethyl)benzyl)pyridin-3-yl)indoline-4-carboxylate (131 mg, 0.318 mmol) in MeOH (1.2 mL) was added sodium hydroxide (0.127 mL, 0.635 mmol). The reaction was heated at 65° C. for 3 h. The mixture was concentrated. The residue was treated with 4M dioxane solution of hydrogen chloride (0.159 mL, 0.635 mmol). The mixture was concentrated to give the title compound. LCMS m/z=399.2 [M+1]$^+$.

Step D: Preparation of 1-(5-(3-(Trifluoromethyl)benzyl)pyridin-3-yl)indoline-4-carboxamide To a solution of 1-(5-(3-(trifluoromethyl)benzyl)pyridin-3-yl)indoline-4-carboxylic acid (20 mg, 50.20 µmol), 7 M ammonia in methanol (0.108 mL, 0.753 mmol), and triethylamine (17.49 µl, 0.126 mmol) in DMF (0.1 mL) was added HATU (23.86 mg, 62.75 µmol). The reaction was stirred at 23° C. for 1 h. The reaction was diluted with ACN (0.2 mL) and 2M HCl (0.3 mL). The mixture was purified by HPLC to give the title compound. LCMS m/z=398.2 [M+1]$^+$; $^1$H NMR (400 MHz, CDCl$_3$): δ ppm 3.57 (t, J=8 Hz, 2H), 4.05 (t, J=8 Hz, 2H), 4.19 (s, 2H), 6.15 (bs, 2H), 7.14-7.18 (m, 1H), 7.22-7.28 (m, 1H), 7.41 (d, J=8 Hz, 1H), 7.48-7.56 (m, 2H), 7.61 (d, J=8 Hz, 1H), 7.69 (s, 1H), 8.17 (s, 1H), 8.66 (s, 1H).

Example 1.10: Preparation of 1-(4-(3-Fluoro-5-(trifluoromethyl)benzyl)pyridin-2-yl)-N-(2-hydroxyethyl)indoline-4-carboxamide (Compound 28). (Method E)

Step A: Preparation of 2-Chloro-4-(3-fluoro-5-(trifluoromethyl)benzyl)pyridine The mixture of 1-(bromomethyl)-3-fluoro-5-(trifluoromethyl)benzene (1.307 g, 5.084 mmol), (2-chloropyridin-4-yl)boronic acid (2.00 g, 12.71 mmol), Pd(dppf)$_2$ DCM (0.627 g, 0.763 mmol) and potassium carbonate (1.405 g, 10.17 mmol) in dioxane (15 mL) was heated to 120° C. for 2 hours in a 20 mL heavy walled sealed tube under microwave radiation. The reaction mixture was quenched with water and extracted with EtOAc. The organic layer was dried with Na$_2$SO$_4$ and purified by Biotage® chromatography (eluting with 15% EtOAc/Hex). The appropriate fractions were concentrated to give the title compound (432.6 mg, 1.493 mmol, 29.4%) as an oil. LCMS m/z=290.0 [M+1]$^+$; $^1$H NMR (400 MHz, CDCl$_3$): δ ppm 4.03 (s, 2H), 7.04 (d, J=4.80 Hz, 1H), 7.08 (d, J=8.81 Hz, 1H), 7.16 (s, 1H), 7.28 (d, J=6.02 Hz, 2H), 8.35 (d, J=5.22 Hz, 1H).

Step B: Preparation of Methyl 1-(4-(3-Fluoro-5-(trifluoromethyl)benzyl)pyridin-2-yl)indoline-4-carboxylate To a mixture of methyl indoline-4-carboxylate (0.264 g, 1.491 mmol), 2-chloro-4-(3-fluoro-5-(trifluoromethyl)benzyl)pyridine (432 mg, 1.491 mmol) and 1,1'-bis(di-tert-butylphosphino)ferrocene (0.117 g, 0.246 mmol) in dioxane (15 mL) were added palladium (II) acetate (33.48 mg, 0.149 mmol), and cesium carbonate (0.972 g, 2.983 mmol). The reaction was heated under microwave irradiation at 150° C. for 3 h. The crude reaction mixture was filtered and concentrated. The resulting residue was purified by Biotage® chromatography (20%-40% EtOAc/Hex) to give the title compound (21 mg, 48.79 µmol, 3.3%) as a yellow solid. LCMS m/z=431.2 [M+1]$^+$; $^1$H NMR (400 MHz, CDCl$_3$): δ ppm 3.58 (t, J=8.60 Hz, 2H), 3.90 (s, 3H), 3.99 (s, 2H), 4.03 (t, J=8.60 Hz, 2H), 6.52 (s, 1H), 6.61 (dd, J=1.20, 5.20 Hz, 1H), 7.09 (d, J=9.20 Hz, 1H), 7.21-7.29 (m, 3H), 7.52 (dd, J=1.20, 8.00 Hz, 1H), 8.28 (d, J=5.60 Hz, 1H), 8.51 (dd, J=0.8, 8.40 Hz, 1H).

Step C: Preparation of 1-(4-(3-Fluoro-5-(trifluoromethyl)benzyl)pyridin-2-yl)indoline-4-carboxylic Acid The mixture of methyl 1-(4-(3-fluoro-5-(trifluoromethyl)benzyl)pyridin-2-yl)indoline-4-carboxylate (21 mg, 48.79 µmol) and sodium hydroxide (23.42 mg, 0.586 mmol) in MeOH (1.5 mL)/THF (0.5 mL)/water (0.5 mL) was stirred at 65° C. for 3.5 h. The solvent was concentrated, acidified with 2M HCl, diluted with water and then extracted with EtOAc. The organic layer was dried with Na$_2$SO$_4$ and concentrated in reduced pressure to give the title compound (22.1 mg, 53.08 µmol) as an orange solid. LCMS m/z=417.4 [M+1]$^+$.

Step D: Preparation of 1-(4-(3-fluoro-5-(trifluoromethyl)benzyl)pyridin-2-yl)-N-(2-hydroxyethyl)indoline-4-carboxamide To the mixture of 1-(4-(3-fluoro-5-(trifluoromethyl)benzyl)pyridin-2-yl)indoline-4-carboxylic acid (22.1 mg, 53.08 µmol), HATU (30.27 mg, 79.62 µmol) and triethylamine (16.28 µl, 0.117 mmol) in DMF (1.5 mL) was added 2-aminoethanol (13.88 µl, 0.239 mmol). The reaction mixture was stirred at RT for 5 mins. The crude product was purified by HPLC (CH$_3$CN/H$_2$O gradient+0.1% TFA). The appropriate fractions were treated with sat. NaHCO$_3$, extracted with EtOAc, dried with Na$_2$SO$_4$, and concentrated to give the title compound (22 mg, 47.88 µmol, 90.2%) as a white solid. LCMS m/z=460.2 [M+1]$^+$; $^1$H NMR (400 MHz, CDCl$_3$): δ ppm 3.54 (t, J=8.80 Hz, 2H), 3.64 (t, J=5.00 Hz, 2H), 3.82-3.87 (m, 2H), 4.00 (s, 2H), 4.01-4.05 (m, 2H), 6.47 (bs, 1H), 6.53 (s, 1H), 6.61 (dd, J=1.20, 5.20 Hz, 1H), 7.04 (d, J=7.20 Hz, 1H), 7.09 (d, J=8.80 Hz, 1H), 7.21-7.24 (m, 2H), 7.27-7.29 (m, 1H), 8.28 (d, J=5.20 Hz, 1H), 8.43 (d, J=8.00 Hz, 1H).

Example 1.11: Preparation of 1-(4-(3-Fluoro-4-methoxybenzyl)pyridin-2-yl)indoline-4-carboxamide (Compound 54). (Method FA)

Step A: Preparation of 1-(4-(Hydroxymethyl)pyridin-2-yl)indoline-4-carboxylic Acid To a suspension of methyl 1-(4-(hydroxymethyl)pyridin-2-yl)indoline-4-carboxylate (2.00 g, 7.035 mmol, see Example 1.5 for preparation) in MeOH/THF/H$_2$O=3:1:1 (30 mL) was added sodium hydroxide (0.647 g, 16.18 mmol). The reaction mixture was stirred at 50° C. for 16 h. The slurry was cooled to 0° C. and acidified with 2M HCl, pH~4. The solid was filtered off cold and washed with cold water (3×10 mL), dried in vacuum to give the title compound (1.66 g, 6.142 mmol, 87.3%) as a light yellow solid. LCMS m/z=271.2 [M+1]$^+$; $^1$H NMR (400 MHz, DMSO-d$_6$): δ ppm 3.50 (t, J=8.71 Hz, 2H), 4.04 (t, J=8.73 Hz, 2H), 4.54 (d, J=3.44 Hz, 2H), 5.39 (t, J=5.58 Hz, 1H), 6.80-6.84 (m, 2H), 7.24 (t, J=7.95 Hz, 1H), 7.39 (dd, J=2.91 Hz, 1H), 8.24 (d, J=5.72 Hz, 1H), 8.56 (dd, J=2.98 Hz, 1H), 12.82 (s, 1H).

Step B: Preparation of 1-(4-(Hydroxymethyl)pyridin-2-yl)indoline-4-carboxamide To a suspension of 1-(4-(hydroxymethyl)pyridin-2-yl)indoline-4-carboxylic acid (1.60 g, 5.920 mmol), potassium carbonate (1.800 g, 13.02 mmol) and ammonia (7M in MeOH) (1.860 mL, 13.02 mmol) in DMA (20.00 mL) was added HATU (2.476 g, 6.512 mmol) and the reaction mixture was stirred at 23° C. for 16 h. Reaction only about 50% complete by LC/MS. Reaction was filtered and solids were washed with 20% IPA:CHCl$_3$ (3×25 mL). The filtrate was washed with water and the aqueous layer was back extracted with 20% IPA:CHCl$_3$ (3×50 mL). Some solids that did not dissolve in the organic layer or the aqueous layer were filtered off and dried in a vacuum oven to give 1-(4-(hydroxymethyl)pyridin-2-yl)indoline-4-carboxamide (0.3786 g, 1.406 mmol, 23.7%) as an off-white solid. The organic layer was dried Na$_2$SO$_4$, filtered, and the solvent was removed under reduced pressure. The solid was triturated with MeCN. The resulting precipitate was collected by vacuum filtration, washed with MeCN (3×5 mL), and dried (vacuum oven) to give 1-(4-(hydroxymethyl)pyridin-2-yl)indoline-4-carboxamide (0.2118 g, 0.786 mmol, 13.3%) as an off white solid. The filtrate was concentrated one more time and the solid was triturated with MeCN. The resulting precipitate was collected by vacuum filtration and washed with MeCN (3×5 mL), dried (vacuum oven) to give 1-(4-(hydroxymethyl)pyridin-2-yl)indoline-4-carboxamide (0.1923 g, 0.714 mmol, 12.1%) as a slight yellow solid. All 3 batches were combined to give the title compound (0.783 g, 2.908 mmol, 49.1%) as an off white solid. LCMS m/z=270.4 [M+1]$^+$, $^1$H NMR (400 MHz, DMSO-d$_6$): δ ppm 3.42 (t, J=8.67 Hz, 2H), 4.00 (t, J=8.71 Hz, 2H), 4.53 (d, J=5.76 Hz, 2H), 5.38 (t, J=5.78 Hz, 1H), 6.80-6.84 (m, 2H), 7.12-7.21 (m, 2H), 7.27 (bs, 1H), 7.72 (bs, 1H), 8.23 (d, J=5.68 Hz, 1H), 8.43 (dd, J=2.94 Hz, 1H).

Step C: Preparation of 1-(4-(Bromomethyl)pyridin-2-yl)indoline-4-carboxamide

To a suspension of 1-(4-(hydroxymethyl)pyridin-2-yl)indoline-4-carboxamide (1.95 g, 7.241 mmol) in THF (20.00 mL) at RT was added slowly tribromophosphine (1.390 mL, 14.84 mmol), slightly exothermic. The mixture was heated to 60° C. for 2 h. Reaction mixture was cooled to 0° C., quenched with ice water and made basic using sat. NaHCO$_3$. The aqueous layer was diluted with DCM, some solids were filtered off and washed with water and DCM. The solids were dried in the vacuum oven to give 1.024 g of a tan solid which contained product. The organic layer was separated and the aqueous layer was extracted with DCM (2×100 mL). The organic layers were combined and dried over Na$_2$SO$_4$, filtered and concentrated to give a wet solid. The wet solid was triturated with MTBE. The resulting precipitate was collected by vacuum filtration to give 0.3787 g of a tan solid. Both precipitates were combined and had to be purified by preparative HPLC (5%-50% MeCN/H$_2$O). The like fractions were combined and freeze dried (lyophilizer) to give the title compound (0.548 g, 1.650 mmol, 22.8%) as a light yellow solid. LCMS m/z=332.2, 334.2 [M+1]$^+$, $^1$H NMR (400 MHz, DMSO-d$_6$): δ ppm 3.43 (t, J=8.67 Hz, 2H), 4.01 (t, J=8.65 Hz, 2H), 4.65 (s, 2H), 6.91-6.95 (m, 2H), 7.15-7.23 (m, 2H), 7.27 (bs, 1H), 7.73 (bs, 1H), 8.29 (d, J=5.04 Hz, 1H), 8.43 (dd, J=1.64, 7.37 Hz, 1H).

Step D: Preparation of 1-(4-(3-Fluoro-4-methoxybenzyl)pyridin-2-yl)indoline-4-carboxamide A suspension of 1-(4-(bromomethyl)pyridin-2-yl)indoline-4-carboxamide (50.0 mg, 0.151 mmol), (3-fluoro-4-methoxyphenyl)boronic acid (30.70 mg, 0.181 mmol), sodium carbonate (35.10 mg, 0.331 mmol) in dioxane (0.50 mL) and H$_2$O (0.10 mL) was allowed to stir for 5 minutes under a nitrogen atmosphere. Pd(dppf)$_2$, DCM (12.38 mg, 15.05 µmol) was added and the reaction was heated to 90° C. for 4 h in a sealed tube. The reaction mixture was filtered by vacuum filtration through Celite® and washed with DMSO (3×1 mL). The filtrate was acidified with 1M HCl and purified by semi-preparative HPLC (5%-95% MeCN/H$_2$O). The like fractions were combined, neutralized with sat. NaHCO3 and the volatile solvent was removed under reduced pressure. The resulting precipitate was collected by vacuum filtration, washed with H$_2$O (3×10 mL), dried (vacuum oven) to give the title compound as an off-white solid. LCMS m/z=378.4 [M+1]$^+$; $^1$H NMR (400 MHz, DMSO-d$_6$): δ ppm 3.41 (t, J=8.57 Hz, 2H), 3.80 (s, 3H), 3.88 (s, 2H), 3.98 (t, J=8.55 Hz, 2H), 6.71 (d, J=4.96 Hz, 1H), 6.76 (s, 1H), 7.05-7.21 (m, 5H), 7.26 (s, 1H), 7.72 (s, 1H), 8.18 (d, J=4.92 Hz, 1H), 8.41 (d, J=7.09 Hz, 1H).

Example 1.12: Preparation of N-(2-Hydroxyethyl)-1-(4-(3,4,5-trifluorobenzyl)pyridin-2-yl)indoline-4-carboxamide (Compound 92). (Method FB)

Step A: Preparation of 1-(4-(Hydroxymethyl)pyridin-2-yl)indoline-4-carboxylic Acid To a suspension of methyl 1-(4-(hydroxymethyl)pyridin-2-yl)indoline-4-carboxylate (3.0 g, 10.55 mmol, see Example 1.5 for preparation) in THF/MeOH/H$_2$O=3:1:1 (25 mL) was added sodium hydroxide (0.971 g, 24.27 mmol). The reaction mixture was stirred at 50° C. for 2 h. The slurry was cooled to 0° C. and acidified with 1M HCl to ~pH4. The solid was filtered off and washed with ice cold water (3×5 mL), dried in a vacuum oven to give the title compound (2.7863 g, 10.31 mmol, 97.7%) as a light yellow solid. LCMS m/z=271.1 [M+1]$^+$; $^1$H NMR (400 MHz, CD$_3$OD): δ ppm 3.53 (t, J=8.62 Hz, 2H), 4.06 (t, J=8.64 Hz, 2H), 4.64 (s, 2H), 6.82 (d, J=5.64 Hz, 1H), 6.93 (s, 1H), 7.18 (t, J=7.92 Hz, 1H), 7.42 (dd, J=0.92, 7.80 Hz, 1H), 8.21 (d, J=5.12 Hz, 1H), 8.31 (dd, J=0.70, 7.98 Hz, 1H).

Step B: Preparation of 1-(4-(Chloromethyl)pyridin-2-yl)indoline-4-carboxylic Acid To 1-(4-(hydroxymethyl)pyridin-2-yl)indoline-4-carboxylic acid (1.786 g, 6.608 mmol) in CH$_2$Cl$_2$ (20 mL) was added thionyl chloride (1.928 mL, 26.43 mmol) at rt. The resulting solution was stirred at rt for 18 h. The reaction was quenched with ice-H$_2$O. The resulting solid was filtered, washed with ice cold water (3×10 mL), and dried in a vacuum oven to give the title compound (1.794 g, 6.213 mmol, 94.0%) as a yellow solid. LCMS m/z=289.2 [M+1]$^+$; $^1$H NMR (400 MHz, DMSO-d$_6$): δ ppm 3.51 (t, J=8.68 Hz, 2H), 4.06 (t, J=8.72 Hz, 2H), 4.77 (s, 2H), 6.93-6.96 (m, 2H), 7.26 (t, J=7.94 Hz, 1H), 7.41 (dd, J=0.98, 7.78 Hz, 1H), 8.32 (d, J=5.40 Hz, 1H), 8.55 (dd, J=0.66, 8.03 Hz, 1H).

Step C: Preparation of 1-(4-(3,4,5-Trifluorobenzyl)pyridin-2-yl)indoline-4-carboxylic Acid To a solution of 1-(4-(chloromethyl)pyridin-2-yl)indoline-4-carboxylic acid (300 mg, 1.039 mmol) in dioxane (5 mL) was added Pd(dppf)$_2$ DCM (85.48 mg, 0.104 mmol), and the mixture stirred at rt for 10 minutes. Sodium carbonate (0.242 g, 2.286 mmol), (3,4,5-trifluorophenyl)boronic acid (0.311 g, 1.766 mmol) and H$_2$O (1.000 mL) were added into the reaction mixture which was then heated at 100° C. for 4 h. The resulting mixture was cooled to RT, filtered, and washed with DMSO. The filtrate was purified by prep-preparative HPLC, concentrated, and dried in a vacuum oven to give the title compound (241 mg, 0.627 mmol, 60.3%) as a brown solid. LCMS m/z=385.4 [M+1]$^+$; $^1$H NMR (400 MHz, DMSO-d$_6$): δ ppm 3.49 (t, J=8.68 Hz, 2H), 3.95 (s, 2H), 4.04 (t, J=8.70 Hz, 2H), 6.79 (dd, J=1.04, 5.20 Hz, 1H), 6.86 (s, 1H), 7.24 (t, J=7.96 Hz, 1H), 7.30-7.35 (m, 2H), 7.40 (dd, J=1.00, 7.80 Hz, 1H), 8.21 (d, J=5.12 Hz, 1H), 8.50 (dd, J=0.83, 8.07 Hz, 1H).

Step D: Preparation of N-(2-Hydroxyethyl)-1-(4-(3,4,5-trifluorobenzyl)pyridin-2-yl)indoline-4-carboxamide To the mixture of 1-(4-(3,4,5-trifluorobenzyl)pyridin-2-yl)indoline-4-carboxylic acid (95 mg, 0.148 mmol), potassium carbonate (26.64 mg, 0.193 mmol) and HATU (73.31 mg, 0.193 mmol) in DMA (1.5 mL) was added 2-aminoethanol (13.59 mg, 0.222 mmol). The reaction was stirred at 21° C. for 1 h. The crude mixture was purified by semi-preparative HPLC, appropriate fractions were treated with sat. NaHCO$_3$, acetonitrile was removed under reduced pressure, and the resulting solid was filtered, washed with water, and then dried in vacuum oven to give the title compound (23.3 mg, 54.51 mol, 36.8%) as a solid. LCMS m/z=428.4 [M+1]$^+$; $^1$H NMR (400 MHz, DMSO-d$_6$): δ ppm 3.28-3.33 (m, 2H), 3.38 (t, J=8.61 Hz, 2H), 3.51 (q, J=6.07 Hz, 2H), 3.94 (s, 2H), 4.00 (t, J=8.73 Hz, 2H), 4.69 (t, J=5.62 Hz, 1H), 6.76 (dd, J=1.03, 5.08 Hz, 1H), 6.81 (s, 1H), 7.10 (dd, J=0.95, 7.73 Hz, 1H), 7.18 (t, J=7.88 Hz, 1H), 7.29-7.35 (m, 2H), 8.16 (t, J=5.68 Hz, 1H), 8.21 (d, J=5.04 Hz, 1H), 8.41 (dd, J=0.83, 8.05 Hz, 1H).

Example 1.13: Preparation of 1-(4-(Benzofuran-5-ylmethyl)pyridin-2-yl)-N-(2-hydroxyethyl)indoline-4-carboxamide (Compound 174). (Method FC)

Step A: Preparation of Methyl 1-(4-(Chloromethyl)pyridin-2-yl)indoline-4-carboxylate To a solution of methyl 1-(4-(hydroxymethyl)pyridin-2-yl)indoline-4-carboxylate (1.90 g, 6.683 mmol) in CH$_2$Cl$_2$ (15 mL) was added thionyl chloride (1.950 mL, 26.73 mmol) at rt. The resulting solution was stirred at RT for 1.5 h. The mixture was quenched with ice-H$_2$O and extracted with DCM (3×50 mL). The organic phase was dried over Na$_2$SO$_4$, filtered, concentrated, and then dried (vacuum oven) to give the title compound (2.02 g, 6.678 mmol, 99%) as a yellow solid. LCMS m/z=303.2, 305.0 [M+1]$^+$. $^1$H NMR (400 MHz, CDCl$_3$): δ ppm 3.60 (t, J=8.64 Hz, 2H), 3.91 (s, 3H), 4.12 (t, J=8.62 Hz, 2H), 4.54 (s, 2H), 6.81 (bs, 1H), 6.82 (d, J=5.20 Hz, 1H), 7.27 (t, J=7.98 Hz, 1H), 7.55 (dd, J=0.82, 7.86 Hz, 1H), 8.33 (d, J=5.64 Hz, 1H), 8.48 (d, J=7.80 Hz, 1H).

Step B: Preparation of Methyl 1-(4-(Benzofuran-5-ylmethyl)pyridin-2-yl)indoline-4-carboxylate A suspension of methyl 1-(4-(chloromethyl)pyridin-2-yl)indoline-4-carboxylate (1.00 g, 3.303 mmol), benzofuran-5-ylboronic acid (0.642 g, 3.964 mmol), sodium carbonate (0.770 g, 7.267 mmol) in dioxane (10.00 mL) and H$_2$O (2.000 mL) was allowed to stir for 5 minutes under a nitrogen atmosphere. Pd(dppf)$_2$, DCM (0.272 g, 0.330 mmol) was added and the reaction was heated to 90° C. for 16 h in a sealed tube. The reaction mixture was filtered by vacuum filtration through Celite® and washed with EtOAc (3×40 mL). The organic layer was washed with brine (1×100 mL), dried over MgSO4, filtered and concentrated. The residue was purified via Biotage® column chromatography (5%-10% EtOAc/hexanes, silica; 50 g ultra snap column) to give methyl 1-(4-(benzofuran-5-ylmethyl)pyridin-2-yl)indoline-4-carboxylate (0.7826 g, 2.036 mmol, 61.6%) as an off-white solid. LCMS m/z=385.4 [M+1]$^+$. $^1$H NMR (400 MHz, DMSO-d$_6$): δ ppm 3.47 (t, J=8.69 Hz, 2H), 3.84 (s, 3H), 3.98-4.07 (m, 4H), 6.76 (dd, J=2.05 Hz, 1H), 6.80 (s, 1H), 6.91 (dd, J=1.03 Hz, 1H), 7.22-7.27 (m, 2H), 7.38 (dd, J=2.94 Hz, 1H), 7.52 (d, J=8.49 Hz, 1H), 7.56 (d, J=1.36 Hz, 1H), 7.95 (d, J=2.20 Hz, 1H), 8.19 (d, J=5.12 Hz, 1H), 8.56 (dd, J=2.99 Hz, 1H).

Step C: Preparation of 1-(4-(Benzofuran-5-ylmethyl)pyridin-2-yl)indoline-4-carboxylic Acid To a suspension of methyl 1-(4-(benzofuran-5-ylmethyl)pyridin-2-yl)indoline-4-carboxylate (0.783 g, 2.037 mmol) in THF/MeOH/H$_2$O=3:1:1 (10.00 mL) was added sodium hydroxide (0.187 g, 4.685 mmol). The reaction mixture was stirred at 50° C. for 1.5 h, at which time the reaction was not complete. An additional amount of sodium hydroxide (0.187 g, 4.685 mmol) added and the reaction mixture was allowed to continue for 1 hr. The reaction was determined to be complete by LC/MS. The crude mixture was cooled down to 0° C. and acidified to ph~4 using 1M HCl (aq). The resulting precipitate was collected by vacuum filtration, washed with H$_2$O (3×20 mL), and dried (vacuum oven) at 40° C. to give 1-(4-(benzofuran-5-ylmethyl)pyridin-2-yl)indoline-4-carboxylic acid (0.691 g, 1.866 mmol, 91.6%) as an off-white solid. LCMS m/z=371.2 [M+1]$^+$. $^1$H NMR (400 MHz, DMSO-d$_6$): δ ppm 3.47 (t, J=8.69 Hz, 3H), 3.97 (t, J=8.69 Hz, 2H), 4.04 (s, 2H), 6.72 (d, J=6.00 Hz, 1H), 6.78 (s, 1H), 6.91 (q, J=1.04 Hz, 1H), 7.12 (t, J=7.91 Hz, 1H), 7.24 (dd, J=3.42 Hz, 1H), 7.33 (dd, J=2.88 Hz, 1H), 7.52 (dd, J=8.45 Hz, 1H), 7.56 (d, J=1.36 Hz, 1H), 7.95 (d, J=2.16 Hz, 1H), 8.17 (d, J=5.12 Hz, 1H), 8.39 (d, J=7.89 Hz, 1H).

Step D: preparation of 1-(4-(Benzofuran-5-ylmethyl)pyridin-2-yl)-N-(2-hydroxyethyl)indoline-4-carboxamide To a suspension of 1-(4-(benzofuran-5-ylmethyl)pyridin-2-yl)indoline-4-carboxylic acid (50.0 mg, 0.121 mmol), 2-aminoethanol (11.13 mg, 0.182 mmol) and Potassium carbonate (21.83 mg, 0.158 mmol) in DMA (1.00 mL) was added HATU (60.05 mg, 0.158 mmol). The reaction was stirred at 23° C. for 16 h. The reaction was then diluted with 1 mL of DMSO, acidified with 1M HCl (aq), filtered by vacuum filtration through Celite®, and the Celite® was washed with DMSO (3×1 mL). The product was purified by semi-preparative HPLC (5%-50% MeCN/H$_2$O). The appropriate fractions were combined, neutralized with sat. NaHCO$_3$, and the volatile solvent was removed under reduced pressure. The resulting precipitate was collected by vacuum filtration, washed with H$_2$O (3×5 mL) dried (vacuum oven) at 50° C. to give 1-(4-(benzofuran-5-ylmethyl)pyridin-2-yl)-N-(2-hydroxyethyl)indoline-4-carboxamide (32.4 mg, 78.36 μmol, 64.5%) as an off-white solid. LCMS m/z=414.4 [M+1]$^+$. $^1$H NMR (400 MHz, DMSO-d$_6$): δ ppm 3.31 (q, J=6.06 Hz, 2H), 3.37 (t, J=8.65 Hz, 2H), 3.51 (t, J=6.29 Hz, 2H), 3.98 (t, J=8.69 Hz, 2H), 4.04 (s, 2H), 6.74 (dd, J=1.99 Hz, 1H), 6.81 (s, 1H), 6.91 (q, J=1.03 Hz, 1H), 7.10 (dd, J=2.84 Hz, 1H), 7.17 (t, J=7.89 Hz, 1H), 7.24 (dd, J=3.39 Hz, 1H), 7.52 (d, J=8.45 Hz, 1H), 7.56 (d, J=1.28 Hz, 1H), 7.95 (d, J=2.16 Hz, 1H), 8.12-8.21 (m, 2H), 8.38 (d, J=7.53 Hz, 1H).

Example 1.14: Preparation of 1-(4-(3-Fluoro-5-(trifluoromethyl)phenoxy)pyridin-2-yl)-N-(2-hydroxyethyl)indoline-4-carboxamide and 1-(4-(3-Fluoro-5-(trifluoromethyl)phenoxy)pyridin-2-yl)indoline-4-carboxamide (Compound 23). (Method G)

Step A: Preparation of 2-Bromo-4-(3-fluoro-5-(trifluoromethyl)phenoxy)pyridine A mixture of 2-bromo-4-chloropyridine (354 mg, 1.840 mmol), 3-fluoro-5-(trifluoromethyl)phenol (330 mg, 1.832 mmol), and cesium carbonate (630 mg, 1.934 mmol) in 10 mL DMF was stirred at 60° C. over the weekend. The mixture was diluted with water and extracted with water and $CH_2Cl_2$. The organic phases were concentrated and the residue was purified by HPLC ($CH_3CN/H_2O$ gradient+0.1% TFA). The fractions containing product were partly concentrated and residue was extracted with 1 M NaOH and $CH_2Cl_2$. The organic phases were dried over $MgSO_4$, filtered, and concentrated to give 2-bromo-4-(3-fluoro-5-(trifluoromethyl)phenoxy)pyridine (196 mg, 31.8%) as a colorless oil. LCMS m/z=336.2 [M+1]$^+$.]$^+$. $^1$H NMR (400 MHz, $CDCl_3$): δ ppm 6.87 (dd, $J_1$=5.7 Hz, $J_2$=2.3 Hz, 1H), 7.00-7.04 (m, 1H), 7.07 (d, J=2.3 Hz, 1H), 7.17-7.19 (m, 1H), 7.25-7.28 (m, 1H), 8.31 (d, J=5.6 Hz, 1H).

Step B: Preparation of methyl 1-(4-(3-Fluoro-5-(trifluoromethyl)phenoxy)pyridin-2-yl)indoline-4-carboxylate A mixture of 2-bromo-4-(3-fluoro-5-(trifluoromethyl)phenoxy)pyridine (99.6 mg, 0.296 mmol), methyl indoline-4-carboxylate (58 mg, 0.327 mmol), diacetoxypalladium (7.6 mg, 33.85 mol), 1,1'-bis(di-tert-butylphosphino)ferrocene (327 mg, 0.692 mmol) (14.6 mg, 30.91 µmol), and cesium carbonate (260 mg, 0.798 mmol) in 3 mL dioxane was stirred at 120° C. (oil bath) overnight. The mixture was purified by HPLC ($CH_3CN/H_2O$ gradient+0.1% TFA). Fractions containing product were partly concentrated and residue was extracted with 1 M $NaHCO_3$ and $CH_2Cl_2$. Organic phases were dried over $MgSO_4$, filtered, and concentrated to give methyl 1-(4-(3-fluoro-5-(trifluoromethyl)phenoxy)pyridin-2-yl)indoline-4-carboxylate (64.7 mg, 45.7%) as a solid. LCMS m/z=433.2 [M+1]$^+$. $^1$H NMR (400 MHz, $CDCl_3$): δ ppm 3.59 (t, J=8.5 Hz, 2H), 3.91 (s, 3H), 3.99 (t, J=8.5 Hz, 2H), 6.33 (d, J=2.0 Hz, 1H), 6.42 (dd, $J_1$=5.6 Hz, $J_2$=2.0 Hz, 1H), 6.99-7.03 (m, 1H), 7.17-7.20 (m, 2H), 7.24-7.28 (m, 1H), 7.54 (dd, $J_1$=7.7 Hz, $J_2$=1.0 Hz, 1H), 8.29 (d, J=5.7 Hz, 1H), 8.54 (dd, $J_1$=8.1 Hz, $J_2$=0.7 Hz, 1H).

Step C: Preparation of Lithium 1-(4-(3-Fluoro-5-(trifluoromethyl)phenoxy)pyridin-2-yl)indoline-4-carboxylate A mixture of methyl 1-(4-(3-fluoro-5-(trifluoromethyl)phenoxy)pyridin-2-yl)indoline-4-carboxylate (60.9 mg, 0.141 mmol) and lithium hydroxide hydrate (20 mg, 0.477 mmol) in 1.5 mL (THF/MeOH/$H_2O$ 3:1:1) was stirred at 60° C. (oil bath) for 2 h. The mixture was concentrated and dried under high vacuum to give lithium 1-(4-(3-fluoro-5-(trifluoromethyl)phenoxy)pyridin-2-yl)indoline-4-carboxylate (80% pure, 75 mg, 100%) as a white solid. The crude product was used in the next step without further purification.

Step D: Preparation of 1-(4-(3-Fluoro-5-(trifluoromethyl)phenoxy)pyridin-2-yl)-N-(2-hydroxyethyl)indoline-4-carboxamide To a solution of lithium 1-(4-(3-fluoro-5-(trifluoromethyl)phenoxy)pyridin-2-yl)indoline-4-carboxylate (80% pure, 30 mg, 56.57 µmol) and 2-aminoethanol (50 µl, 0.841 mmol) in 1 mL DMF, HATU (60 mg, 0.158 mmol) was added. After stirring at RT for 1 h, the mixture was purified by HPLC ($CH_3CN/H_2O$ gradient+0.1% TFA). Fractions containing product were partly concentrated and the residue was extracted with 1 M NaOH and $CH_2Cl_2$. The organic phases were dried over $MgSO_4$, filtered, and concentrated to give 1-(4-(3-fluoro-5-(trifluoromethyl)phenoxy)pyridin-2-yl)-N-(2-hydroxyethyl)indoline-4-carboxamide (14.7 mg, 56.3%) as a white solid. LCMS m/z=462.2 [M+1]$^+$. $^1$H NMR (400 MHz, $CDCl_3$): δ ppm 2.51 (s, 1H), 3.53 (t, J=8.6 Hz, 2H), 3.60-3.64 (m, 2H), 3.83-3.86 (m, 2H), 3.98 (t, J=8.5 Hz, 2H), 6.34 (d, J=2.1 Hz, 1H), 6.42 (dd, $J_1$=5.7 Hz, $J_2$=1.9 Hz, 1H), 6.47-6.52 (m, 1H), 6.99-7.03 (m, 1H), 7.06-7.08 (m, 1H), 7.17-7.25 (m, 3H), 8.29 (d, J=5.8 Hz, 1H), 8.44-8.47 (m, 1H).

Example 1.15: Preparation of 3-(4-Carbamoylindolin-1-yl)-5-(3-(trifluoromethyl)benzyl)pyridine 1-Oxide (Compound 12). (Method H)

To a mixture of 1-(5-(3-(trifluoromethyl)benzyl)pyridin-3-yl)indoline-4-carboxamide (8.2 mg, 20.63 µmol) in $CHCl_3$ (0.1 mL) was added 3-chlorobenzoperoxoic acid (9.249 mg, 41.27 µmol). The reaction was heated under microwave irradiation at 75° C. for 2 h. The reaction was diluted with DCM and washed with 1M NaOH. The organic layer was concentrated and the residue purified by HPLC to give the title compound. LCMS m/z=414.2 [M+1]$^+$.

Example 1.16: Preparation of N-(2-Hydroxyethyl)-1-(6-(3-(trifluoromethyl)benzyl)pyrazin-2-yl)indoline-4-carboxamide (Compound 38)

The title compound was prepared in a manner similar to that described in Method A. LCMS m/z=443.4 [M+1]$^+$; $^1$H NMR (400 MHz, $CDCl_3$): δ ppm 3.58 (t, J=8.80 Hz, 2H), 3.63 (t, J=4.80 Hz, 2H), 3.85 (t, J=4.60 Hz, 2H), 4.10 (t, J=8.60 Hz, 2H), 4.16 (s, 2H), 6.46 (bs, 1H), 7.07 (d, J=7.60 Hz, 1H), 7.14 (t, J=7.60 Hz, 1H), 7.43-7.47 (m, 1H), 7.49-7.54 (m, 2H), 7.66 (s, 1H), 8.02 (d, J=10.4 Hz, 2H), 8.18 (d, J=8.00 Hz, 1H).

Example 1.17: Preparation of 1-(4-(3-Chloro-5-fluorobenzyl)pyridin-2-yl)-N-(2-hydroxyethyl)indoline-4-carboxamide (Compound 43)

The title compound was prepared in a manner similar to that described in Method FC. LCMS m/z=426.4 [M+1]$^+$; $^1$H NMR (400 MHz, DMSO-$d_6$): δ ppm 3.28-3.33 (m, 2H), 3.38 (t, J=8.78 Hz, 2H), 3.51 (q, J=5.43 Hz, 2H), 3.97 (s, 2H), 4.00 (t, J=8.85 Hz, 2H), 4.69 (t, J=5.12 Hz, 1H), 6.76 (dd, J=1.04, 5.12 Hz, 1H), 6.83 (s, 1H), 7.10 (dd, J=0.96, 7.78 Hz, 1H), 7.18 (t, J=7.74 Hz, 1H), 7.19-7.28 (m, 2H), 7.28 (d, J=1.76 Hz, 1H), 8.15 (t, J=5.56 Hz, 1H), 8.21 (d, J=7.96 Hz, 1H), 8.41 (dd, J=0.79, 7.96 Hz, 1H).

Example 1.18: Preparation of 1-(4-(3-Fluoro-4-methoxybenzyl)pyridin-2-yl)-N-(2-hydroxyethyl)indoline-4-carboxamide (Compound 69)

The title compound was prepared in a manner similar to that described in Method FB. LCMS m/z=422.2 [M+1]$^+$; $^1$H NMR (400 MHz, DMSO-d$_6$): δ ppm 3.25-3.33 (m, 2H), 3.38 (t, J=8.69 Hz, 2H), 3.51 (q, J=6.02 Hz, 2H), 3.80 (s, 3H), 3.88 (s, 2H), 3.98 (t, J=8.66 Hz, 2H), 4.69 (t, J=5.64 Hz, 1H), 6.72 (dd, J=1.06, 5.10 Hz, 1H), 6.76 (s, 1H), 7.05-7.12 (m, 3H), 7.14-7.20 (m, 2H), 8.15 (t, J=5.61 Hz, 1H), 8.18 (d, J=5.12 Hz, 1H), 8.40 (dd, J=0.99, 8.04 Hz, 1H).

Example 1.19: Preparation of 1-(4-(3-Chloro-4-fluorobenzyl)pyridin-2-yl)-N-(2-hydroxyethyl)indoline-4-carboxamide (Compound 70)

The title compound was prepared in a manner similar to that described in Method FB. LCMS m/z=426.2 [M+1]$^+$; $^1$H NMR (400 MHz, DMSO-d$_6$): δ ppm 3.25-3.33 (m, 2H), 3.38 (t, J=8.76 Hz, 2H), 3.51 (q, J=6.02 Hz, 2H), 3.95 (s, 2H), 3.99 (t, J=8.70 Hz, 2H), 4.69 (t, J=5.54 Hz, 1H), 6.74 (d, J=5.12 Hz, 1H), 6.80 (s, 1H), 7.10 (dd, J=0.84, 7.74 Hz, 1H), 7.18 (t, J=7.84 Hz, 1H), 7.30-7.37 (m, 2H), 7.55 (dd, J=1.62, 7.52 Hz, 1H), 8.16 (t, J=5.62 Hz, 1H), 8.20 (d, J=5.12 Hz, 1H), 8.40 (d, J=8.00 Hz, 1H).

Example 1.20: Preparation of 1-(4-((2,3-Dihydrobenzofuran-5-yl)methyl)pyridin-2-yl)-N-(2-hydroxyethyl)indoline-4-carboxamide (Compound 76)

The title compound was prepared in a manner similar to that described in Method FB. LCMS m/z=416.2 [M+1]$^+$; $^1$H NMR (400 MHz, DMSO-d$_6$): δ ppm 3.13 (t, J=8.70 Hz, 2H), 3.26-3.33 (m, 2H), 3.37 (t, J=8.66 Hz, 2H), 3.51 (q, J=6.07 Hz, 2H), 3.85 (s, 2H), 3.98 (t, J=8.68 Hz, 2H), 4.47 (t, J=8.70 Hz, 2H), 4.69 (t, J=5.60 Hz, 1H), 6.68 (d, J=8.16 Hz, 1H), 6.70 (d, J=5.16 Hz, 1H), 6.75 (s, 1H), 7.00 (dd, J=1.64, 8.12 Hz, 1H), 7.09 (dd, J=0.90, 7.72 Hz, 1H), 7.13 (s, 1H), 7.18 (t, J=7.85 Hz, 1H), 8.15 (t, J=5.80 Hz, 1H), 8.17 (d, J=5.04 Hz, 1H), 8.39 (d, J=8.00 Hz, 1H).

Example 1.21: Preparation of 1-(4-(3-Chloro-5-fluorobenzyl)pyridin-2-yl)-N-(1-(2-hydroxyethyl)piperidin-4-yl)indoline-4-carboxamide (Compound 90)

The title compound was prepared in a manner similar to that described in Method FB. LCMS m/z=509.4 [M+1]$^+$; $^1$H NMR (400 MHz, DMSO-d$_6$): δ ppm 1.86-2.08 (m, 4H), 3.05-3.19 (m, 4H), 3.37 (t, J=8.50 Hz, 2H), 3.52-3.58 (m, 2H), 3.78 (t, J=5.17 Hz, 2H), 3.99 (s, 2H), 4.03 (t, J=8.63 Hz, 2H), 3.90-4.07 (bs, 2H), 6.80 (d, J=5.16 Hz, 1H), 6.90 (s, 1H), 7.13 (d, J=7.37 Hz, 1H), 7.16-7.25 (m, 2H), 7.26-7.30 (m, 1H), 7.29 (d, J=1.73 Hz, 1H), 8.21 (d, J=5.20 Hz, 1H), 8.35 (d, J=8.18 Hz, 1H), 8.39 (d, J=7.44 Hz, 1H).

Example 1.22: Preparation of (R)—N-(2-Hydroxy-3-methoxypropyl)-1-(4-(3,4,5-trifluorobenzyl)pyridin-2-yl)indoline-4-carboxamide (Compound 137)

Step A: Preparation of (R)-1-amino-3-methoxypropan-2-ol

The mixture of (R)-2-(methoxymethyl)oxirane (2.00 g, 22.70 mmol) in 7M ammonia in MeOH (64.86 mL, 454.0 mmol) was stirred at RT for 18 h. Solvent was removed under reduced pressure, and the resulting yellow oil was dried (vacuum oven) to give (R)-1-amino-3-methoxypropan-2-ol (2.0055 g, 19.08 mmol, 84.0%) as yellow oil. LCMS m/z=106.2 [M+1]$^+$; $^1$H NMR (400 MHz, CDCl$_3$): δ ppm 2.67-2.73 (m, 1H), 2.81 (dd, J=4.04, 12.86 Hz, 1H), 3.33-3.44 (m, 3H), 3.38 (s, 3H), 3.69-3.75 (m, 1H).

Step B: Preparation of (R)—N-(2-Hydroxy-3-methoxypropyl)-1-(4-(3,4,5-trifluorobenzyl)pyridin-2-yl)indoline-4-carboxamide To the mixture of 1-(4-(3,4,5-trifluorobenzyl)pyridin-2-yl)indoline-4-carboxylic acid (50 mg, 0.130 mmol), potassium carbonate (23.37 mg, 0.169 mmol) and HATU (64.30 mg, 0.169 mmol) in DMA (1.5 mL) was added (R)-1-amino-3-methoxypropan-2-ol (17.78 mg, 0.169 mmol). The reaction was stirred at 21° C. for 30 min. The crude product was purified by semi-preparative HPLC, appropriate fractions were treated with sat. NaHCO$_3$, acetonitrile was removed under reduced pressure, and the resulting solid was filtered, washed with water, and then dried to give the title compound (32.5 mg, 68.93 μmol, 53.0%) as a white solid. LCMS m/z=472.6 [M+1]; $^1$H NMR (400 MHz, DMSO-d$_6$): δ ppm 3.14-3.21 (m, 1H), 3.28 (s, 3H), 3.25-3.35 (m, 3H), 3.38 (t, J=8.64 Hz, 2H), 3.78 (q, J=5.25 Hz, 1H), 3.94 (s, 2H), 4.00 (t, J=8.70 Hz, 2H), 4.94 (d, J=5.08 Hz, 1H), 6.76 (dd, J=1.04, 5.04 Hz, 1H), 6.81 (s, 1H), 7.10 (dd, J=0.92, 7.74 Hz, 1H), 7.19 (t, J=7.89 Hz, 1H), 7.27-7.35 (m, 2H), 8.13 (t, J=5.72 Hz, 1H), 8.20 (d, J=5.12 Hz, 1H), 8.41 (dd, J=0.81, 7.96 Hz, 1H).

Example 1.23: Preparation of (S)—N-(2-Hydroxy-3-methoxypropyl)-1-(4-(3,4,5-trifluorobenzyl)pyridin-2-yl)indoline-4-carboxamide (Compound 138)

Step A: Preparation of (S)-1-Amino-3-methoxypropan-2-ol

The mixture of (S)-2-(methoxymethyl)oxirane (2.00 g, 22.70 mmol) in 7M ammonia in MeOH (64.86 mL, 454.0 mmol) was stirred at RT for 18 h. Solvent was removed under reduced pressure, and the resulting oil was dried in vacuum oven to give the title compound (1.8796 g, 17.88 mmol, 78.8%) as a pale yellow oil. LCMS m/z=106.2 [M+1]$^+$; $^1$H NMR (400 MHz, CDCl$_3$): δ ppm 2.64-2.74 (m, 1H), 2.81 (dd, J=4.06, 12.89 Hz, 1H), 3.33-3.45 (m, 3H), 3.37 (s, 3H), 3.69-3.75 (m, 1H).

Step B: Preparation of (S)—N-(2-Hydroxy-3-methoxypropyl)-1-(4-(3,4,5-trifluorobenzyl)pyridin-2-yl)indoline-4-carboxamide The title compound was prepared in a manner similar to that described in Method FB using (S)-1-amino-3-methoxypropan-2-ol.
LC/MS m/z=472.6 [M+1]$^+$; $^1$H NMR (400 MHz, DMSO-d$_6$): δ ppm 3.14-3.21 (m, 1H), 3.28 (s, 3H), 3.26-3.35 (m, 3H), 3.38 (t, J=8.78 Hz, 2H), 3.78 (qun, J=5.77 Hz, 1H), 3.94 (s, 2H), 4.01 (t, J=8.72 Hz, 2H), 4.95 (bs, 1H), 6.76 (dd, J=1.06, 5.10 Hz, 1H), 6.81 (s, 1H), 7.10 (dd, J=0.94, 7.68 Hz, 1H), 7.19 (t, J=7.88 Hz, 1H), 7.28-7.35 (m, 2H), 8.12 (t, J=5.64 Hz, 1H), 8.20 (d, J=5.08 Hz, 1H), 8.41 (dd, J=0.82, 8.05 Hz, 1H).

Example 1.24: Preparation of (R)—N-(2-Fluoro-3-hydroxypropyl)-1-(4-(3,4,5-trifluorobenzyl)pyridin-2-yl)indoline-4-carboxamide (Compound 166)

The title compound was prepared in a manner similar to that described in Method FB. LCMS m/z=460.2 [M+1]$^+$; $^1$H NMR (400 MHz, DMSO-d₆): δ ppm 3.38 (t, J=8.56 Hz, 2H), 3.44-3.69 (m, 4H), 3.94 (s, 2H), 4.01 (t, J=8.54 Hz, 2H), 4.54-4.71 (m, 1H), 4.97 (t, J=5.74 Hz, 1H), 6.77 (d, J=4.84 Hz, 1H), 6.81 (s, 1H), 7.10 (d, J=7.61 Hz, 1H), 7.20 (t, J=7.85 Hz, 1H), 7.32 (t, J=7.74 Hz, 2H), 8.21 (d, J=4.96 Hz, 1H), 8.42 (d, J=8.04 Hz, 2H).

Example 1.25: Preparation of (S)-1-(4-(Benzofuran-5-ylmethyl)pyridin-2-yl)-N-(2-fluoro-3-hydroxypropyl)indoline-4-carboxamide (Compound 182)

The title compound was prepared in a manner similar to that described in Method FC. LCMS m/z=446.6 [M+1]⁺; ¹H NMR (400 MHz, DMSO-d₆): δ ppm 3.37 (t, J=8.68 Hz, 2H), 3.45 (t, J=5.80 Hz, 1H), 3.48-3.69 (m, 3H), 3.99 (t, J=8.68 Hz, 2H), 4.04 (s, 2H), 4.55-4.72 (m, 1H), 4.96 (t, J=5.78 Hz, 1H), 6.74 (dd, J=0.95, 5.08 Hz, 1H), 6.80 (s, 1H), 6.91 (dd, J=0.95, 2.24 Hz, 1H), 7.09 (dd, J=0.92, 7.79 Hz, 1H), 7.18 (t, J=7.88 Hz, 1H), 7.24 (dd, J=1.76, 8.48 Hz, 1H), 7.52 (d, J=8.44 Hz, 1H), 7.56 (d, J=1.40 Hz, 1H), 7.95 (d, J=2.20 Hz, 1H), 8.18 (d, J=5.08 Hz, 1H), 8.39-8.43 (m, 2H).

Example 1.26: Preparation of (R)—N-(3-Fluoro-2-hydroxypropyl)-1-(4-(3,4,5-trifluorobenzyl)pyridin-2-yl)indoline-4-carboxamide (Compound 201)

The title compound was prepared in a manner similar to that described in Method FB. LCMS m/z=460.2 [M+1]⁺; ¹H NMR (400 MHz, DMSO-d₆): δ ppm 3.24-3.35 (m, 2H), 3.38 (t, J=8.62 Hz, 2H), 3.81-3.92 (m, 1H), 3.94 (s, 2H), 4.01 (t, J=8.72 Hz, 2H), 4.25-4.49 (m, 2H), 5.26 (d, J=5.28 Hz, 1H), 6.76 (dd, J=1.05, 5.08 Hz, 1H), 6.81 (s, 1H), 7.11 (dd, J=0.94, 7.72 Hz, 1H), 7.19 (t, J=7.89 Hz, 1H), 7.28-7.36 (m, 2H), 8.20 (d, J=5.20 Hz, 1H), 8.25 (t, J=5.78 Hz, 1H), 8.42 (dd, J=0.80, 8.00 Hz, 1H).

Example 1.27: Preparation of 5-Fluoro-N-(2-hydroxyethyl)-1-(4-(3-(trifluoromethyl)benzyl)pyridin-2-yl)indoline-4-carboxamide (Compound 108)

Step A: Preparation of 5-Fluoro-1-(triisopropylsilyl)-1H-indole 5-fluoro-1H-indole (2.5 g, 18.50 mmol) and chlorotriisopropylsilane (4.355 mL, 20.35 mmol) were dissolved in THF (74.00 mL) and cooled to −78° C. To the mixture was added butyl lithium (10.17 mL, 20.35 mmol) drop wise and allowed to stir at −78° C. for 1 hour. The resulting mixture was poured into water and extracted with DCM, dried over MgSO₄, and concentrated. The crude product was purified by column chromatography to furnish 5-fluoro-1-(triisopropylsilyl)-1H-indole (4.43 g, 15.20 mmol, 82.2%). LCMS m/z=292.4 [M+1]⁺; ¹H NMR (400 MHz, CDCl₃): δ ppm 1.13-1.15 (d, J=7.53 Hz, 18H), 1.62-1.73 (m, 3H), 6.57-6.58 (dd, J=0.78, 3.12 Hz, 1H), 6.85-6.90 (td, J=2.63, 9.06 Hz, 1H), 7.23-7.26 (dd, J=2.83, 9.39 Hz, 1H), 7.27-7.28 (d, J=3.10 Hz, 1H), 7.38-7.42 (dd, J=4.36, 9.02 Hz, 1H).

Step B: Preparation of 5-Fluoro-1-(triisopropylsilyl)-1H-indole-4-carboxylic Acid To a solution of butyllithium (10.43 mL, 26.07 mmol) in THF at −78° C. was added 2,2,6,6-tetramethylpiperidine (4.437 mL, 26.07 mmol), then potassium 2-methylpropan-2-olate (2.926 g, 26.07 mmol), and then 5-fluoro-1-(triisopropylsilyl)-1H-indole (3.8 g, 13.04 mmol). After stirring for 2 hours at −78° C., the reaction was poured over a beaker of freshly crushed dry ice and allowed to stir for 45 minutes, quenched with 40 mL water and then extracted with ethyl acetate (3×25 mL), dried over sodium sulfate, and concentrated. The residue was purified by column chromatography to yield 5-fluoro-1-(triisopropylsilyl)-1H-indole-4-carboxylic acid (3.69 g, 11.00 mmol, 84.4%). LCMS m/z=336.4 [M+1]⁺; ¹H NMR (400 MHz, DMSO-d₆): δ ppm 1.07-1.09 (d, J=7.49 Hz, 1H), 1.71-1.79 (m, 1H), 6.99-7.04 (m, 2H), 7.55-7.56 (d, J=3.20 Hz, 1H), 7.70-7.73 (dd, J=3.87 Hz, 9.03 Hz, 1H), 12.95 (brs, 1H).

Step C: Preparation of Methyl 5-Fluoroindoline-4-carboxylate

To 5-fluoro-1-(triisopropylsilyl)-1H-indole-4-carboxylic acid (594 mg, 1.771 mmol) in DCM (17.71 mL) was added N-ethyl-N-isopropylpropan-2-amine (0.339 mL, 1.948 mmol) and then trimethyloxonium tetrafluoroborate (0.288 g, 1.948 mmol). After stirring at room temperature for 10 minutes the mixture was quenched with saturated aqueous NH₄Cl solution, extracted with DCM (3×10 mL), dried over sodium sulfate, and concentrated to yield crude methyl 5-fluoro-1-(triisopropylsilyl)-1H-indole-4-carboxylate. Crude methyl 5-fluoro-1-(triisopropylsilyl)-1H-indole-4-carboxylate was then immediately dissolved in triethylsilane (2 mL, 12.52 mmol) and TFA (4 mL, 52.23 mmol), and stirred overnight at room temperature. The mixture was then poured into saturated aqueous NaHCO₃ solution until a basic pH was achieved, and was extracted with ethyl acetate (3×20 mL). The combined organics were dried over sodium sulfate, concentrated, and purified by column chromatography to yield methyl 5-fluoroindoline-4-carboxylate (265 mg, 1.358 mmol, 76.7%). LCMS m/z=196.0 [M+1]⁺; ¹H NMR (400 MHz, DMSO-d₆): δ ppm 3.09-3.13 (t, J=8.70 Hz, 2H), 3.43-3.47 (t, J=8.69 Hz, 2H), 3.81 (s, 3H), 6.64-6.67 (dd, J=4.00 Hz, 8.50 Hz, 1H), 6.84-6.89 (t, J=8.54 Hz, 11.21 Hz 1H).

Step D: Preparation of 5-Fluoro-N-(2-hydroxyethyl)-1-(4-(3-(trifluoromethyl)benzyl)pyridin-2-yl)indoline-4-carboxamide The title compound was prepared in a manner similar to that described in Method A using methyl 5-fluoroindoline-4-carboxylate using: LCMS m/z=460.4 [M+1]⁺; ¹H NMR (400 MHz, DMSO-d₆): δ ppm 3.20-3.24 (t, J=8.63 Hz, 2H), 3.29-3.33 (q, J=6.12 Hz, 2H), 3.49-3.52 (t, J=6.33 Hz, 2H), 3.99-4.04 (t, J=8.71 Hz, 2H), 4.06 (s, 2H), 6.73-6.75 (dd, J=1.06 Hz, 5.14 Hz, 1H), 6.80 (s, 1H), 6.97-7.01 (dd, J=9.12 Hz, 9.89 Hz, 1H), 7.53-7.63 (m, 3H), 7.69 (s, 1H), 8.18-8.19 (d, J=5.16 Hz, 1H), 8.29-8.34 (m, 2H).

Example 1.28: Preparation of 5-Fluoro-N-(2-hydroxyethyl)-1-(4-(3,4,5-trifluorobenzyl)pyridin-2-yl)indoline-4-carboxamide (Compound 140)

The title compound was prepared in a manner similar to that described in Method FC using methyl 5-fluoroindoline-4-carboxylate using: LCMS m/z=446.2 [M+1]⁺; ¹H NMR (400 MHz, DMSO-d₆): δ ppm 3.20-3.24 (t, J=8.65 Hz, 2H), 3.30-3.34 (t, J=6.04 Hz, 2H), 3.48-3.51 (q, J=5.72 Hz, 2H), 3.93 (s, 2H), 4.00-4.05 (t, J=8.71 Hz, 2H), 4.67-4.70 (t, J=5.50 Hz, 1H), 6.74-6.75 (d, J=5.08 Hz, 1H), 6.77 (s, 1H), 6.97-7.02 (t, J=9.49 Hz, 1H), 7.29-7.33 (dd, J=6.82 Hz, 8.92 Hz, 2H), 8.18-8.19 (d, J=5.12 Hz, 1H), 8.29-8.35 (m, 2H).

Example 1.29: Preparation of (R)—N-(2-Fluoro-3-hydroxypropyl)-1-(4-(3-fluoro-4-methoxybenzyl)pyridin-2-yl)indoline-4-carboxamide (Compound 202)

The title compound was prepared in a manner similar to that described in Method FC: LCMS m/z=454.4 [M+1]$^+$; $^1$H NMR (400 MHz, DMSO-d$_6$): δ ppm 3.35-3.40 (t, J=9.48 Hz, 2H), 3.44-3.66 (m, 4H), 3.80 (s, 3H), 3.88 (s, 2H), 3.97-4.02 (t, J=8.61 Hz, 2H), 4.54-4.72 (m, 1H), 4.95-4.98 (t, J=5.67 Hz, 1H), 6.71-6.73 (m, 1H), 6.77 (s, 1H), 7.05-7.21 (m, 5H), 8.18-8.19 (d, J=5.14 Hz, 1H), 8.40-8.42 (m, 2H).

Example 1.30: Preparation of N-(2-Hydroxyethyl)-1-(4-((3-(trifluoromethyl)phenyl)thio)-pyridin-2-yl)indoline-4-carboxamide and 1-(4-((3-(trifluoromethyl)phenyl)thio)pyridin-2-yl)indoline-4-carboxamide (Compound 29)

The title compound was prepared in a manner similar to that described in Method G starting with 3-(trifluoromethyl)benzenethiol. LCMS m/z=460.2 [M+1]$^+$. $^1$H NMR (400 MHz, CDCl$_3$): δ ppm 2.46 (t, J=5.2 Hz, 1H), 3.49 (t, J=8.3 Hz, 2H), 3.60-3.64 (m, 2H), 3.82-3.86 (m, 2H), 3.93 (t, J=8.7 Hz, 2H), 6.44-6.53 (m, 3H), 7.03 (d, J=7.7 Hz, 1H), 7.16-7.20 (m, 1H), 7.53-7.57 (m, 1H), 7.66-7.73 (m, 2H), 7.82 (s, 1H), 8.16 (d, J=5.3 Hz, 1H), 8.30 (d, J=8.1 Hz, 1H).

Example 1.31: Preparation of N-(2-Fluoroethyl)-1-(2-(3,4,5-trifluorobenzyl)pyridin-4-yl)indoline-4-carboxamide (Compound 190)

The title compound was prepared in a manner similar to that described in Method B. LCMS m/z=430.4 [M+1]$^+$. $^1$H NMR (400 MHz, DMSO-d$_6$): δ ppm 3.33 (t, J=8.25 Hz, 2H), 3.54 (dq, J=26.95, 5.31 Hz, 2H), 3.99 (t, J=8.47 Hz, 2H), 4.03 (s, 2H), 4.54 (dt, J=47.30, 5.15 Hz, 2H), 7.04 (dd, J=5.84, 2.40 Hz, 1H), 7.13-7.18 (m, 2H), 7.21-7.32 (m, 3H), 7.46 (d, J=7.69 Hz, 2H), 8.28 (d, J=5.84 Hz, 1H), 8.50 (t, J=5.52 Hz, 1H).

Example 1.32: Preparation of 1-(4-(3-Chloro-4-fluorobenzyl)pyridin-2-yl)indoline-4-carboxamide (Compound 58)

The title compound was prepared in a manner similar to that described in Method FA. LCMS m/z=382.4, 384.4 [M+1]$^+$, $^1$H NMR (400 MHz, DMSO-d$_6$): δ ppm 3.41 (t, J=8.65 Hz, 2H), 3.93-4.02 (m, 4H), 6.74 (dd, J=2.00 Hz, 1H), 6.80 (s, 1H), 7.13-7.20 (m, 2H), 7.26 (s, 1H), 7.31-7.38 (m, 2H), 7.55 (dd, J=2.95 Hz, 1H), 7.72 (s, 1H), 8.20 (d, J=5.08 Hz, 1H), 8.41 (dd, J=3.02 Hz, 1H).

Example 1.33: Preparation of 1-(4-(3,4,5-Trifluorobenzyl)pyridin-2-yl)indoline-4-carboxamide (Compound 65)

The title compound was prepared in a manner similar to that described in Method FA. LCMS m/z=384.4 [M+1]$^+$, $^1$H NMR (400 MHz, DMSO-d$_6$): δ ppm 3.41 (t, J=8.63 Hz, 2H), 3.94 (s, 2H), 4.00 (t, J=8.77 Hz, 2H), 6.76 (d, J=5.04 Hz, 1H), 6.81 (s, 1H), 7.13-7.20 (m, 2H), 7.26 (s, 1H), 7.29-7.36 (m, 2H), 7.72 (s, 1H), 8.20 (d, J=5.04 Hz, 1H), 8.42 (dd, J=3.00 Hz, 1H).

Example 1.34: Preparation of 1-(4-((2,3-Dihydrobenzofuran-5-yl)methyl)pyridin-2-yl)indoline-4-carboxamide (Compound 66)

The title compound was prepared in a manner similar to that described in Method FA. LCMS m/z=372.2 [M+1]$^+$, $^1$H NMR (400 MHz, DMSO-d$_6$): δ ppm 3.13 (t, J=8.71 Hz, 2H), 3.40 (t, J=8.65 Hz, 2H), 3.85 (s, 2H), 3.98 (t, J=8.69 Hz, 2H), 4.47 (t, J=8.69 Hz, 2H), 6.69 (t, J=7.57 Hz, 2H), 6.75 (s, 1H), 7.00 (d, J=8.49 Hz, 1H), 7.11-7.20 (m, 3H), 7.26 (s, 1H), 7.71 (s, 1H), 8.17 (d, J=5.08 Hz, 1H), 8.40 (dd, J=2.91 Hz, 1H).

Example 1.35: Preparation of 1-(4-(3-Acetylbenzyl)pyridin-2-yl)indoline-4-carboxamide (Compound 78)

The title compound was prepared in a manner similar to that described in Method FA. LCMS m/z=372.0 [M+1]$^+$; $^1$H NMR (400 MHz, DMSO-d$_6$): δ ppm 2.57 (s, 3H), 3.41 (t, J=8.65 Hz, 2H), 3.98 (t, J=8.69 Hz, 2H), 4.04 (s, 2H), 6.74 (d, J=5.12 Hz, 1H), 6.81 (s, 1H), 7.12-7.20 (m, 2H), 7.27 (s, 1H), 7.47 (t, J=7.65 Hz, 1H), 7.58 (d, J=7.65 Hz, 1H), 7.72 (s, 1H), 7.83 (d, J=2.10 Hz, 1H), 7.89 (s, 1H), 8.19 (d, J=5.08 Hz, 1H), 8.40 (dd, J=3.00 Hz, 1H).

Example 1.36: Preparation of 1-(4-(Benzofuran-5-ylmethyl)pyridin-2-yl)indoline-4-carboxamide (Compound 106)

The title compound was prepared in a manner similar to that described in Method FA. LCMS m/z=370.2 [M+1]$^+$; $^1$H NMR (400 MHz, DMSO-d$_6$): δ ppm 3.40 (t, J=8.67 Hz, 2H), 3.98 (t, J=8.69 Hz, 2H), 4.04 (s, 2H), 6.74 (dd, J=2.03 Hz, 1H), 6.79 (s, 1H), 6.91 (q, J=1.03 Hz, 1H), 7.11-7.19 (m, 2H), 7.22-7.28 (m, 2H), 7.52 (dd, J=8.45 Hz, 1H), 7.56 (d, J=1.36 Hz, 1H), 7.71 (s, 1H), 7.95 (d, J=2.16 Hz, 1H), 8.18 (d, J=5.08 Hz, 1H), 8.40 (dd, J=3.02 Hz, 1H).

Example 1.37: Preparation of (R)-1-(4-(Benzofuran-5-ylmethyl)pyridin-2-yl)-N-(2-fluoro-3-hydroxypropyl)indoline-4-carboxamide (Compound 176)

The title compound was prepared in a manner similar to that described in Method FC. LCMS m/z=446.4 [M+1]$^+$; $^1$H NMR (400 MHz, DMSO-d$_6$): δ ppm 3.37 (t, J=8.68 Hz, 2H), 3.43-3.71 (m, J=8.31 Hz, 4H), 3.99 (t, J=8.70 Hz, 2H), 4.04 (s, 2H), 4.53-4.73 (m, J=6.34 Hz, 1H), 4.96 (s, 1H), 6.74 (dd, J=2.01 Hz, 1H), 6.80 (s, 1H), 6.91 (q, J=1.04 Hz, 1H), 7.09 (dd, J=2.84 Hz, 1H), 7.19 (t, J=7.88 Hz, 1H), 7.24 (dd, J=3.40 Hz, 1H), 7.52 (d, J=8.44 Hz, 1H), 7.56 (d, J=1.36 Hz, 1H), 7.95 (d, J=2.20 Hz, 1H), 8.18 (d, J=5.08 Hz, 1H), 8.38-8.45 (m, 2H).

Example 1.38: Preparation of 1-(4-(Benzofuran-5-ylmethyl)pyridin-2-yl)-N-(3-fluoro-2-hydroxypropyl)indoline-4-carboxamide (Compound 177)

The title compound was prepared in a manner similar to that described in Method FC. LCMS m/z=446.2 [M+1]$^+$; $^1$H NMR (400 MHz, DMSO-d$_6$): δ ppm 3.21-3.29 (m, 2H), 3.32-3.42 (m, 2H), 3.80-3.93 (m, 1H), 3.99 (t, J=8.71 Hz, 2H), 4.04 (s, 2H), 4.25-4.50 (m, 2H), 5.26 (d, J=5.28 Hz, 1H), 6.74 (d, J=5.96 Hz, 1H), 6.80 (s, 1H), 6.91 (q, J=1.03 Hz, 1H), 7.10 (dd, J=2.86 Hz, 1H), 7.18 (t, J=7.91 Hz, 1H), 7.24 (dd, J=3.40 Hz, 1H), 7.52 (d, J=8.49 Hz, 1H), 7.56 (d, J=1.32 Hz, 1H), 7.95 (d, J=2.20 Hz, 1H), 8.18 (d, J=5.12 Hz, 1H), 8.25 (t, J=5.70 Hz, 1H), 8.40 (dd, J=2.90 Hz, 1H).

Example 1.39: Preparation of (R)—N-(2-Hydroxypropyl)-1-(4-(3,4,5-trifluorobenzyl)pyridin-2-yl) indoline-4-carboxamide (Compound 179)

The title compound was prepared in a manner similar to that described in Method FC. LCMS m/z=442.2 [M+1]$^+$; $^1$H NMR (400 MHz, DMSO-d$_6$): δ ppm 1.08 (d, J=6.24 Hz, 3H), 3.19 (t, J=6.00 Hz, 2H), 3.38 (t, J=8.72 Hz, 2H), 3.78 (q, J=6.07 Hz, 1H), 3.94 (s, 2H), 4.00 (t, J=8.70 Hz, 2H), 4.71 (s, 1H), 6.76 (d, J=5.08 Hz, 1H), 6.81 (s, 1H), 7.11 (d, J=6.92 Hz, 1H), 7.19 (t, J=7.88 Hz, 1H), 7.28-7.36 (m, 2H), 8.13 (t, J=5.72 Hz, 1H), 8.20 (d, J=5.08 Hz, 1H), 8.41 (d, J=7.44 Hz, 1H).

Example 1.40: Preparation of (S)-1-(4-(Benzofuran-5-ylmethyl)pyridin-2-yl)-N-(3-fluoro-2-hydroxypropyl)indoline-4-carboxamide (Compound 199)

The title compound was prepared in a manner similar to that described in Method FC. LCMS m/z=446.2 [M+1]$^+$; $^1$H NMR (400 MHz, DMSO-d$_6$): δ ppm 3.21-3.33 (m, 2H), 3.34-3.41 (m, 2H), 3.81-3.93 (m, 1H), 3.99 (t, J=8.70 Hz, 2H), 4.04 (s, 2H), 4.24-4.49 (m, 2H), 5.26 (d, J=5.28 Hz, 1H), 6.74 (dd, J=2.05 Hz, 1H), 6.80 (s, 1H), 6.91 (q, J=1.04 Hz, 1H), 7.10 (dd, J=2.89 Hz, 1H), 7.18 (t, J=7.88 Hz, 1H), 7.24 (dd, J=3.41 Hz, 1H), 7.52 (d, J=8.44 Hz, 1H), 7.56 (d, J=1.36 Hz, 1H), 7.95 (d, J=2.20 Hz, 1H), 8.18 (d, J=5.08 Hz, 1H), 8.24 (t, J=5.76 Hz, 1H), 8.40 (dd, J=2.93 Hz, 1H).

Example 1.41: Preparation of (R)—N-(2-Fluoro-3-hydroxypropyl)-1-(4-(3-fluoro-4-methoxybenzyl) pyridin-2-yl)indoline-4-carboxamide (Compound 202)

The title compound was prepared in a manner similar to that described in Method FC: LCMS m/z=454.4 [M+1]$^+$; $^1$H NMR (400 MHz, DMSO-d$_6$): δ ppm 3.35-3.40 (t, J=9.48 Hz, 2H), 3.44-3.66 (m, 4H), 3.80 (s, 3H), 3.88 (s, 2H), 3.97-4.02 (t, J=8.61 Hz, 2H), 4.54-4.72 (m, 1H), 4.95-4.98 (t, J=5.67 Hz, 1H), 6.71-6.73 (m, 1H), 6.77 (s, 1H), 7.05-7.21 (m, 5H), 8.18-8.19 (d, J=5.14 Hz, 1H), 8.40-8.42 (m, 2H).

Example 2: Analytical Data and Methods of Preparing Additional Compounds of the Present Invention Compounds of the present invention were prepared in a similar manner as described herein. The general synthetic methods and analytical data for these compounds are shown below.

The following compounds were prepared in a manner similar to that described in Method A, the MS m/z [M+1]$^+$ data for each compound is shown directly after each compound:

Cmpd No. 4, 468.2 [M+1]$^+$; Cmpd No. 5, 398.2 [M+1]$^+$; Cmpd No. 13, 442.4 [M+1]$^+$; Cmpd No. 14, 410.4 [M+1]$^+$; Cmpd No. 15, 366.2 [M+1]$^+$; Cmpd No. 16, 380.4 [M+1]$^+$; Cmpd No. 17, 412.4 [M+1]$^+$; Cmpd No. 18, 426.2 [M+1]$^+$; Cmpd No. 19, 436.2 [M+1]$^+$; Cmpd No. 20, 451.2 [M+1]$^+$; Cmpd No. 21, 472.2 [M+1]$^+$; Cmpd No. 22, 472.2 [M+1]$^+$; Cmpd No. 25, 456 [M+1]$^+$; Cmpd No. 26, 456.2 [M+1]$^+$; Cmpd No. 27, 437 [M+1]$^+$; Cmpd No. 36, 469.4 [M+1]$^+$; Cmpd No. 37, 472.2 [M+1]$^+$; Cmpd No. 38, 443.4 [M+1]$^+$; Cmpd No. 39, 399.2 [M+1]$^+$; Cmpd No. 53, 495.6 [M+1]$^+$; Cmpd No. 108, 460.4 [M+1]$^+$; Cmpd No. 109, 543.6 [M+1]$^+$; and Cmpd No. 122, 416.2 [M+1]$^+$.

The following compounds were prepared in a manner similar to that described in Method B, the MS m/z [M+1]$^+$ data for each compound is shown directly after each compound number:

Cmpd No. 3, 468.2 [M+1]$^+$; Cmpd No. 6, 398.2 [M+1]$^+$; Cmpd No. 184, 442.4 [M+1]$^+$; Cmpd No. 186, 428.2 [M+1]$^+$; Cmpd No. 189, 472.4 [M+1]$^+$; Cmpd No. 190, 430.4 [M+1]$^+$; Cmpd No. 191, 472.2 [M+1]$^+$; Cmpd No. 192, 460.4 [M+1]$^+$; Cmpd No. 193, 460.4 [M+1]$^+$; Cmpd No. 194, 467.4 [M+1]$^+$; Cmpd No. 195, 442.4 [M+1]$^+$; and Cmpd No. 196, 442.4 [M+1]$^+$.

The following compounds were prepared in a manner similar to that described in Method C, the MS m/z [M+1]$^+$ data for each compound is shown directly after each compound number:

Cmpd No. 1, 398.2 [M+1]$^+$ and Cmpd No. 2, 468.2 [M+1]$^+$.

The following compounds were prepared in a manner similar to that described in Method D, the MS m/z [M+1]$^+$ data for each compound is shown directly after each compound number:

Cmpd No. 7, 468.4 [M+1]$^+$; Cmpd No. 8, 398.2 [M+1]$^+$; Cmpd No. 9, 412.4 [M+1]$^+$; and Cmpd No. 10, 442.4 [M+1]$^+$.

The following compounds were prepared in a manner similar to that described in Method D and Method H, the MS m/z [M+1]$^+$ data is shown directly after each compound number:

Cmpd No. 11, 484.2 [M+1]$^+$ and Cmpd No. 12, 414.2 [M+1]$^+$.

The following compounds were prepared in a manner similar to that described in Method E, the MS m/z [M+1]$^+$ data for each compound is shown directly after each compound number:

Cmpd No. 28, 460.2 [M+1]$^+$; Cmpd No. 31, 490.4 [M+1]$^+$; Cmpd No. 32, 490.4 [M+1]$^+$; Cmpd No. 33, 416.2 [M+1]$^+$; Cmpd No. 34, 487.4 [M+1]$^+$; Cmpd No. 35, 490.4 [M+1]$^+$; Cmpd No. 40, 443.4 [M+1]$^+$; and Cmpd No. 41, 399.2 [M+1]$^+$.

The following compounds were prepared in a manner similar to that described in Method FA, the MS m/z [M+1]$^+$ data for each compound is shown directly after each compound number:

Cmpd No. 46, 365.4 [M+1]$^+$; Cmpd No. 47, 399.2 [M+1]$^+$; Cmpd No. 49, 367.4 [M+1]$^+$; Cmpd No. 50, 363.4 [M+1]$^+$; Cmpd No. 51, 399.4 [M+1]$^+$; Cmpd No. 52, 383.4 [M+1]$^+$; Cmpd No. 54, 378.4 [M+1]$^+$; Cmpd No. 55, 372.2 [M+1]$^+$; Cmpd No. 56, 428.2 [M+1]$^+$; Cmpd No. 57, 382.2 [M+1]$^+$; Cmpd No. 58, 382.4 [M+1]$^+$; Cmpd No. 59, 405.4 [M+1]$^+$; Cmpd No. 60, 373.4 [M+1]$^+$; Cmpd No. 61, 416.4 [M+1]$^+$; Cmpd No. 62, 390.4 [M+1]$^+$; Cmpd No. 63, 378.4 [M+1]$^+$; Cmpd No. 64, 414.4 [M+1]$^+$; Cmpd No. 65, 384.4 [M+1]$^+$; Cmpd No. 66, 372.2 [M+1]$^+$; Cmpd No. 67, 378.4 [M+1]$^+$; Cmpd No. 68, 373.2 [M+1]$^+$; Cmpd No. 71, 378.4 [M+1]$^+$; Cmpd No. 72, 362.6 [M+1]$^+$; Cmpd No. 73, 366.2 [M+1]$^+$; Cmpd No. 78, 372 [M+1]$^+$; Cmpd No. 81, 387.2 [M+1]$^+$; Cmpd No. 82, 390.2 [M+1]$^+$; Cmpd No. 83, 379.4 [M+1]$^+$; Cmpd No. 84, 395.4 [M+1]$^+$; Cmpd No. 85, 361.4 [M+1]$^+$; Cmpd No. 86, 356.2 [M+1]$^+$; Cmpd No. 87, 378.4 [M+1]$^+$; Cmpd No. 88, 373.4 [M+1]$^+$; Cmpd No. 96, 402.2 [M+1]$^+$; Cmpd No. 97, 364.4 [M+1]$^+$; Cmpd No. 98, 360.4 [M+1]$^+$; Cmpd No. 99, 374.4 [M+1]$^+$; Cmpd No. 100, 394.4 [M+1]$^+$; Cmpd No. 101, 374.2 [M+1]$^+$; Cmpd No. 102, 388.4 [M+1]$^+$; Cmpd No. 103, 320.2 [M+1]$^+$; Cmpd No.

104, 349.4 [M+1]⁺; Cmpd No. 105, 320.2 [M+1]⁺; Cmpd No. 106, 370.2 [M+1]⁺; Cmpd No. 107, 394.4 [M+1]⁺; Cmpd No. 110, 392.2 [M+1]⁺; Cmpd No. 111, 381.4 [M+1]⁺; Cmpd No. 112, 381.2 [M+1]⁺; Cmpd No. 114, 364.4 [M+1]⁺; Cmpd No. 115, 394.4 [M+1]⁺; Cmpd No. 116, 366.2 [M+1]⁺; Cmpd No. 119, 370.2 [M+1]⁺; Cmpd No. 120, 369.2 [M+1]⁺; and Cmpd No. 121, 396.2 [M+1]⁺.

The following compounds were prepared in a manner similar to that described in Method FB, the MS m/z [M+1]⁺ data for each compound is shown directly after each compound number:

Cmpd No. 48, 443.6 [M+1]⁺; Cmpd No. 69, 422.2 [M+1]⁺; Cmpd No. 70, 426.2 [M+1]⁺; Cmpd No. 74, 422.2 [M+1]⁺; Cmpd No. 75, 460.4 [M+1]⁺; Cmpd No. 76, 416.2 [M+1]⁺; Cmpd No. 77, 434.4 [M+1]⁺; Cmpd No. 79, 499.8 [M+1]⁺; Cmpd No. 80, 517.6 [M+1]⁺; Cmpd No. 89, 525.4 [M+1]⁺; Cmpd No. 90, 509.4 [M+1]⁺; Cmpd No. 91, 505.4 [M+1]⁺; Cmpd No. 92, 428.4 [M+1]⁺; Cmpd No. 93, 511.4 [M+1]⁺; Cmpd No. 94, 511.4 [M+1]⁺; Cmpd No. 95, 495.6 [M+1]⁺; Cmpd No. 113, 458.4 [M+1]⁺; Cmpd No. 117, 464.4 [M+1]⁺; Cmpd No. 118, 494.6 [M+1]⁺; Cmpd No. 123, 458.2 [M+1]⁺; Cmpd No. 124, 458.2 [M+1]⁺; Cmpd No. 125, 505.4 [M+1]⁺; Cmpd No. 126, 505.4 [M+1]⁺; Cmpd No. 127, 505.4 [M+1]⁺; Cmpd No. 128, 481.4 [M+1]⁺; Cmpd No. 129, 469.6 [M+1]⁺; Cmpd No. 130, 472.2 [M+1]⁺; Cmpd No. 131, 486.4 [M+1]⁺; Cmpd No. 132, 495.5 [M+1]⁺; Cmpd No. 133, 496.6 [M+1]⁺; Cmpd No. 134, 472.6 [M+1]⁺; Cmpd No. 135, 468.4 [M+1]⁺; Cmpd No. 136, 468.4 [M+1]⁺; Cmpd No. 137, 472.6 [M+1]⁺; Cmpd No. 138, 472.6 [M+1]⁺; Cmpd No. 139, 478.4 [M+1]⁺; Cmpd No. 148, 505.4 [M+1]⁺; Cmpd No. 149, 505.4 [M+1]⁺; Cmpd No. 151, 467.2 [M+1]⁺; Cmpd No. 152, 467.4 [M+1]⁺; Cmpd No. 153, 478.4 [M+1]⁺; Cmpd No. 154, 484.4 [M+1]⁺; Cmpd No. 156, 466.4 [M+1]⁺; Cmpd No. 157, 461.4 [M+1]⁺; Cmpd No. 158, 485.4 [M+1]⁺; Cmpd No. 159, 442.4 [M+1]⁺; Cmpd No. 160, 496.4 [M+1]⁺; Cmpd No. 161, 430.2 [M+1]⁺; Cmpd No. 165, 460.2 [M+1]⁺; Cmpd No. 166, 460.2 [M+1]⁺; Cmpd No. 172, 469.4 [M+1]⁺; Cmpd No. 181, 460.4 [M+1]⁺; Cmpd No. 183, 460.4 [M+1]⁺; and Cmpd No. 201, 460.2 [M+1]⁺.

The following compounds were prepared in a manner similar to that described in Method FC, the MS m/z [M+1]⁺ data for each compound is shown directly after each compound number:

Cmpd No. 42, 382.4 [M+1]⁺; Cmpd No. 43, 426.4 [M+1]⁺; Cmpd No. 44, 453.2 [M+1]⁺; Cmpd No. 45, 459.2 [M+1]⁺; Cmpd No. 140, 446.2 [M+1]⁺; Cmpd No. 141, 476 [M+1]⁺; Cmpd No. 142, 476.2 [M+1]⁺; Cmpd No. 143, 523.4 [M+1]⁺; Cmpd No. 144, 490.4 [M+1]⁺; Cmpd No. 145, 487.1 [M+1]⁺; Cmpd No. 146, 485.4 [M+1]⁺; Cmpd No. 147, 485.4 [M+1]⁺; Cmpd No. 150, 490.4 [M+1]⁺; Cmpd No. 155, 502.2 [M+1]⁺; Cmpd No. 162, 440.4 [M+1]⁺; Cmpd No. 163, 442.4 [M+1]⁺; Cmpd No. 164, 481.2 [M+1]⁺; Cmpd No. 167, 472.2 [M+1]⁺; Cmpd No. 168, 470.4 [M+1]⁺; Cmpd No. 169, 456.4 [M+1]⁺; Cmpd No. 170, 458.2 [M+1]⁺; Cmpd No. 171, 465.2 [M+1]⁺; Cmpd No. 173, 458.2 [M+1]⁺; Cmpd No. 174, 414.4 [M+1]⁺; Cmpd No. 175, 453 [M+1]⁺; Cmpd No. 176, 446.4 [M+1]⁺; Cmpd No. 177, 446.2 [M+1]⁺; Cmpd No. 178, 458.4 [M+1]⁺; Cmpd No. 179, 442.2 [M+1]⁺; Cmpd No. 180, 442.4 [M+1]⁺; Cmpd No. 182, 446.6 [M+1]⁺; Cmpd No. 185, 416.6 [M+1]⁺; Cmpd No. 187, 426.2 and 428.2 [M+1]⁺; Cmpd No. 188, 460.2 [M+1]⁺; Cmpd No. 197, 454.4 [M+1]⁺; Cmpd No. 198, 454.4 [M+1]⁺; Cmpd No. 199, 446.2 [M+1]⁺; Cmpd No. 200, 446.4 [M+1]⁺; Cmpd No. 202, 454.4 [M+1]⁺; Cmpd No. 203, 424.2 [M+1]⁺; Cmpd No. 204, 478.4 [M+1]⁺; Cmpd No. 205, 466.4 [M+1]⁺; Cmpd No. 206, 472.2 [M+1]⁺; Cmpd No. 207, 458.2 [M+1]⁺; and Cmpd No. 208, 416.4 [M+1]⁺.

The following compounds were prepared in a manner similar to that described in Method G, the MS m/z [M+1]⁺ data for each compound is shown directly after each compound number:

Cmpd No. 23, 462.2 [M+1]⁺; Cmpd No. 24, 418.2 [M+1]⁺; Cmpd No. 29, 460.2 [M+1]⁺; and Cmpd No. 30, 416.2 [M+1]⁺.

Compounds of the present invention were additionally subjected to LCMS analysis. MS m/z [M+1]⁺ data and retention times are shown in the following table:

| Cmpd No. | Chemical Structure | Synthetic Method | MS | Retention time (min) |
|---|---|---|---|---|
| 1 | 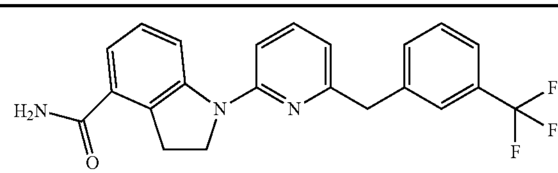 | C | 398.2 | 4.14 |
| 2 | 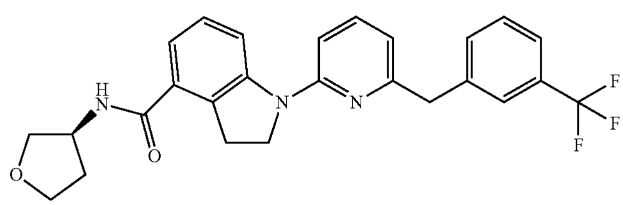 [SMILES: O=C(N[C@H]1CCOC1)c1cccc2c1CCN2c1cccc(Cc2cccc(C(F)(F)F)c2)n1] | C | 468.2 | 4.18 |
| 3 | 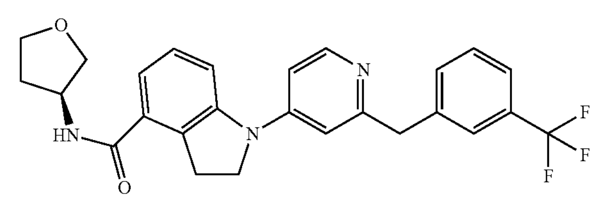 [SMILES: O=C(N[C@H]1CCOC1)c1cccc2c1CCN2c1ccnc(Cc2cccc(C(F)(F)F)c2)c1] | B | 468.2 | 2.79 |

-continued

| Cmpd No. | Chemical Structure | Synthetic Method | MS | Retention time (min) |
|---|---|---|---|---|
| 4 | 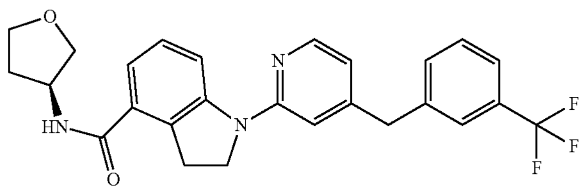 [SMILES: O=C(N[C@H]1CCOC1)c1cccc2c1CCN2c1cc(Cc2cccc(C(F)(F)F)c2)ccn1] | A | 468.2 | 3.05 |
| 5 | 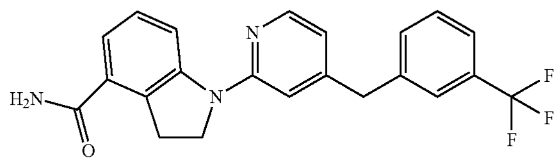 | A | 398.2 | 2.95 |
| 6 | 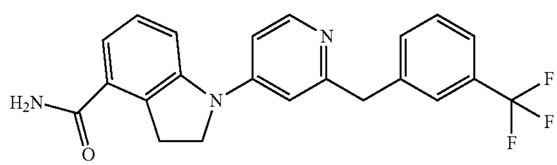 [SMILES: NC(=O)c1cccc2c1CCN2c1ccnc(Cc2cccc(C(F)(F)F)c2)c1] | B | 398.2 | 2.57 |
| 7 | 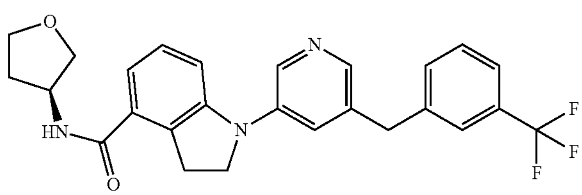 [SMILES: O=C(N[C@H]1CCOC1)c1cccc2c1CCN2c1cncc(Cc2cccc(C(F)(F)F)c2)c1] | D | 468.4 | 2.79 |
| 8 | 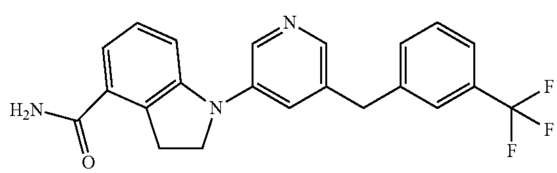 [SMILES: NC(=O)c1cccc2c1CCN2c1cncc(Cc2cccc(C(F)(F)F)c2)c1] | D | 398.2 | 2.68 |
| 9 | 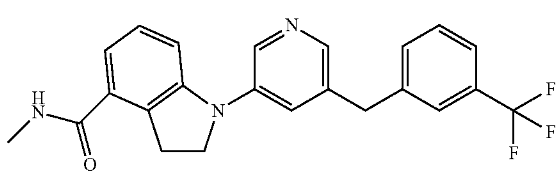 [SMILES: CNC(=O)c1cccc2c1CCN2c1cncc(Cc2cccc(C(F)(F)F)c2)c1] | D | 412.4 | 2.76 |
| 10 | 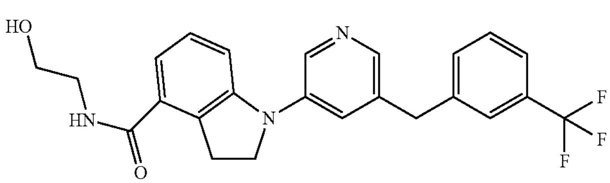 [SMILES: O=C(NCCO)c1cccc2c1CCN2c1cncc(Cc2cccc(C(F)(F)F)c2)c1] | D | 442.4 | 2.56 |
| 11 | 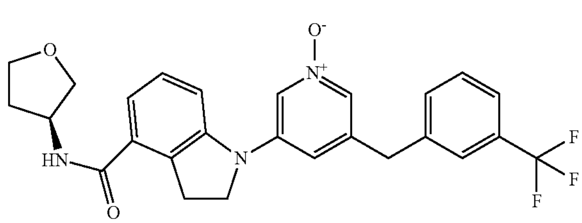 [SMILES: O=C(N[C@H]1CCOC1)c1cccc2c1CCN2c1cc(Cc2cccc(C(F)(F)F)c2)c[n+]([O-])c1] | D, H | 484.2 | 3.62 |

| Cmpd No. | Chemical Structure | Synthetic Method | MS | Retention time (min) |
|---|---|---|---|---|
| 12 | 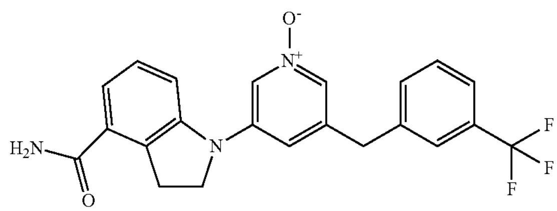 [SMILES: NC(=O)c1cccc2c1CCN2c1cc(Cc2cccc(C(F)(F)F)c2)c[n+]([O-])c1] | D, H | 414.2 | 3.54 |
| 13 | 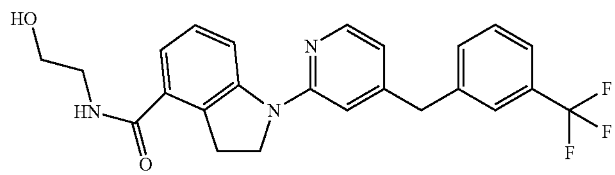 [SMILES: O=C(NCCO)c1cccc2c1CCN2c1cc(Cc2cccc(C(F)(F)F)c2)ccn1] | A | 442.4 | 2.83 |
| 14 | 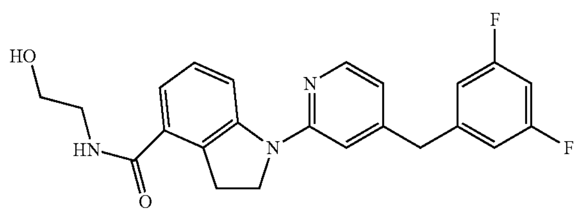 [SMILES: O=C(NCCO)c1cccc2c1CCN2c1cc(Cc2cc(F)cc(F)c2)ccn1] | A | 410.4 | 2.62 |
| 15 | 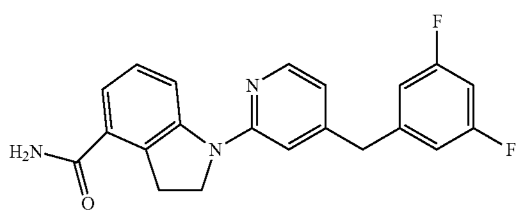 | A | 366.2 | 2.83 |
| 16 | 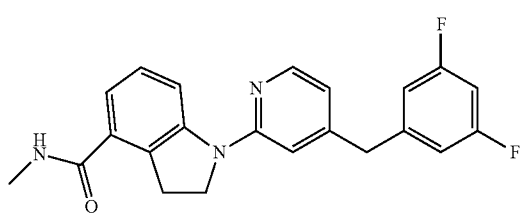 [SMILES: CNC(=O)c1cccc2c1CCN2c1cc(Cc2cc(F)cc(F)c2)ccn1] | A | 380.4 | 2.90 |
| 17 | 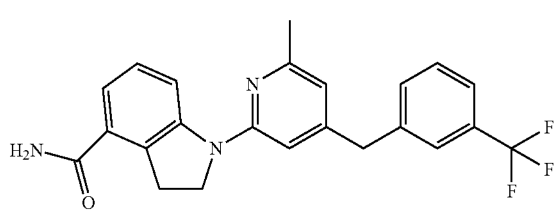 [SMILES: Cc1cc(Cc2cccc(C(F)(F)F)c2)cc(N2CCc3c(C(N)=O)cccc32)n1] | A | 412.4 | 3.05 |
| 18 | 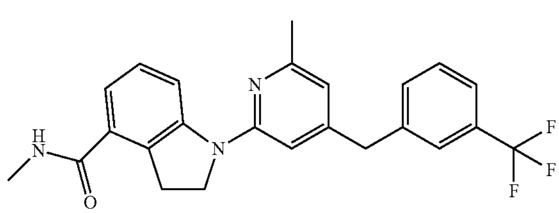 [SMILES: CNC(=O)c1cccc2c1CCN2c1cc(Cc2cccc(C(F)(F)F)c2)cc(C)n1] | A | 426.2 | 3.12 |

-continued

| Cmpd No. | Chemical Structure | Synthetic Method | MS | Retention time (min) |
|---|---|---|---|---|
| 19 | 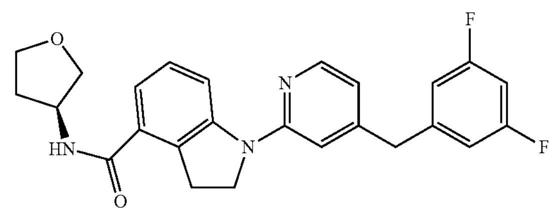 [SMILES: O=C(N[C@H]1CCOC1)c1cccc2c1CCN2c1cc(Cc2cc(F)cc(F)c2)ccn1] | A | 436.2 | 2.92 |
| 20 | 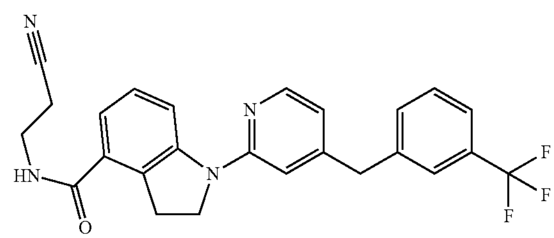 [SMILES: N#CCCNC(=O)c1cccc2c1CCN2c1cc(Cc2cccc(C(F)(F)F)c2)ccn1] | A | 451.2 | 3.18 |
| 21 | 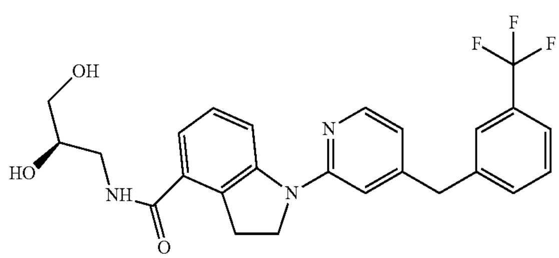 [SMILES: O=C(NC[C@@H](O)CO)c1cccc2c1CCN2c1cc(Cc2cccc(C(F)(F)F)c2)ccn1] | A | 472.2 | 2.73 |
| 22 | 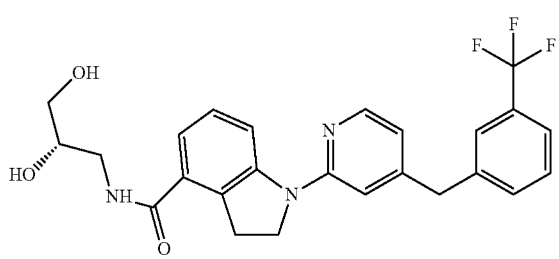 [SMILES: O=C(NC[C@H](O)CO)c1cccc2c1CCN2c1cc(Cc2cccc(C(F)(F)F)c2)ccn1] | A | 472.2 | 2.70 |
| 23 | 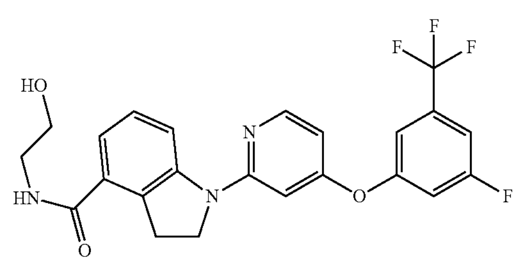 | G | 462.2 | 3.15 |
| 24 | 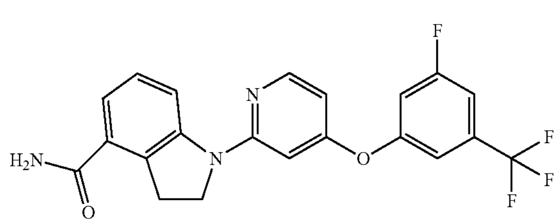 [SMILES: NC(=O)c1cccc2c1CCN2c1cc(Oc2cc(F)cc(C(F)(F)F)c2)ccn1] | G | 418.2 | 3.44 |

-continued
| Cmpd No. | Chemical Structure | Synthetic Method | MS | Retention time (min) |
|---|---|---|---|---|
| 25 | 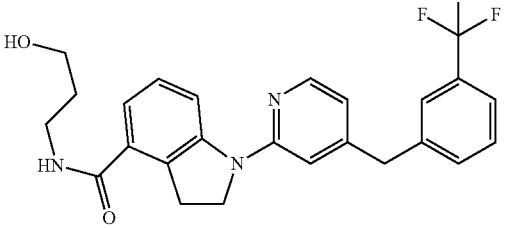 | A | 456.0 | 2.78 |
| 26 | 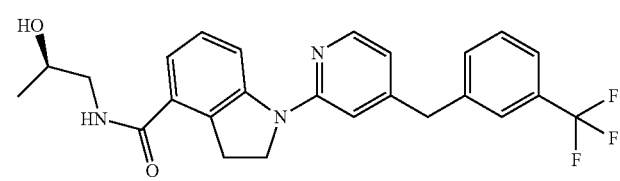 [SMILES: C[C@@H](O)CNC(=O)c1cccc2c1CCN2c1cc(Cc2cccc(C(F)(F)F)c2)ccn1] | A | 456.2 | 2.83 |
| 27 | 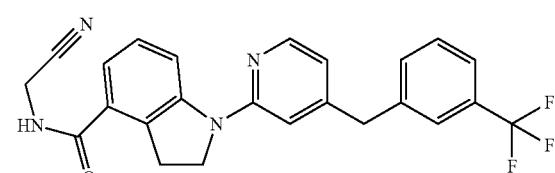 | A | 437.0 | 3.09 |
| 28 | 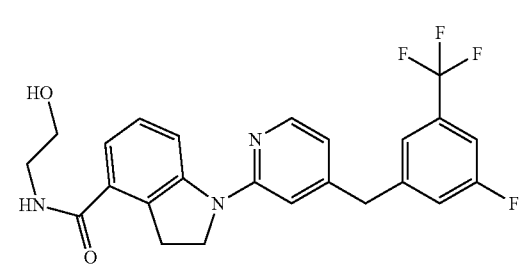 [SMILES: O=C(NCCO)c1cccc2c1CCN2c1cc(Cc2cc(F)cc(C(F)(F)F)c2)ccn1] | E | 460.2 | 2.84 |
| 29 | 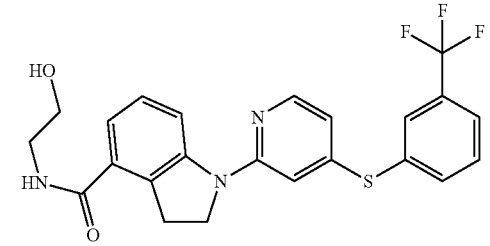 [SMILES: O=C(NCCO)c1cccc2c1CCN2c1cc(Sc2cccc(C(F)(F)F)c2)ccn1] | G | 460.2 | 3.12 |
| 30 | 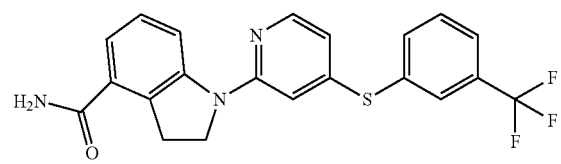 [SMILES: NC(=O)c1cccc2c1CCN2c1cc(Sc2cccc(C(F)(F)F)c2)ccn1] | G | 416.2 | 3.37 |
| 31 | 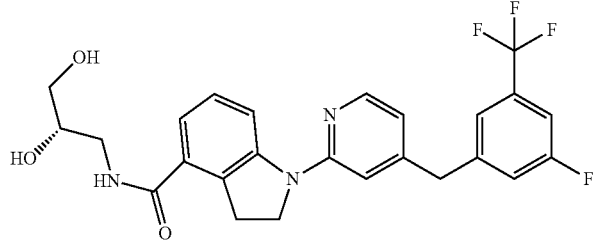 [SMILES: O=C(NC[C@H](O)CO)c1cccc2c1CCN2c1cc(Cc2cc(F)cc(C(F)(F)F)c2)ccn1] | E | 490.4 | 2.80 |

-continued

| Cmpd No. | Chemical Structure | Synthetic Method | MS | Retention time (min) |
|---|---|---|---|---|
| 32 | 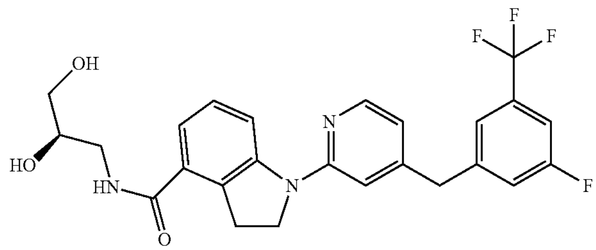 [SMILES: O=C(NC[C@@H](O)CO)c1cccc2c1CCN2c1cc(Cc2cc(F)cc(C(F)(F)F)c2)ccn1] | E | 490.4 | 2.80 |
| 33 | 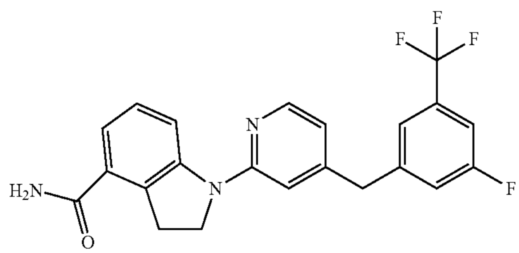 [SMILES: NC(=O)c1cccc2c1CCN2c1cc(Cc2cc(F)cc(C(F)(F)F)c2)ccn1] | E | 416.2 | 3.16 |
| 34 | 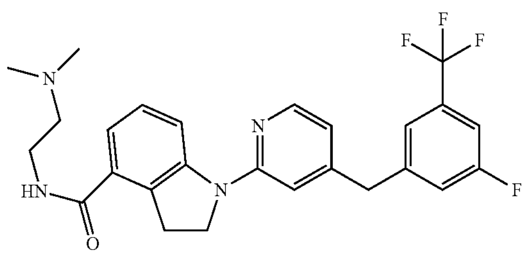 [SMILES: CN(C)CCNC(=O)c1cccc2c1CCN2c1cc(Cc2cc(F)cc(C(F)(F)F)c2)ccn1] | E | 487.4 | 2.91 |
| 35 | 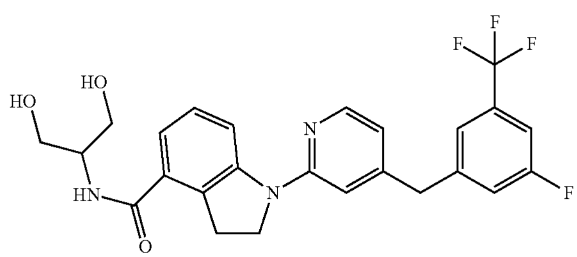 [SMILES: O=C(NC(CO)CO)c1cccc2c1CCN2c1cc(Cc2cc(F)cc(C(F)(F)F)c2)ccn1] | E | 490.4 | 2.78 |
| 36 | 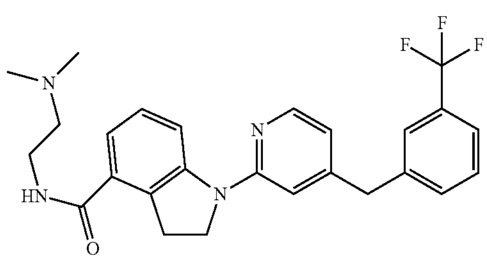 [SMILES: CN(C)CCNC(=O)c1cccc2c1CCN2c1cc(Cc2cccc(C(F)(F)F)c2)ccn1] | A | 469.4 | 2.76 |
| 37 | 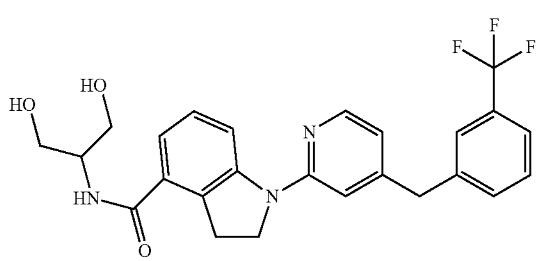 [SMILES: O=C(NC(CO)CO)c1cccc2c1CCN2c1cc(Cc2cccc(C(F)(F)F)c2)ccn1] | A | 472.2 | 2.67 |

-continued

| Cmpd No. | Chemical Structure | Synthetic Method | MS | Retention time (min) |
|---|---|---|---|---|
| 38 | 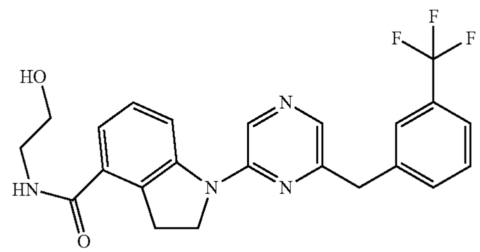 [SMILES: O=C(NCCO)c1cccc2c1CCN2c1cncc(Cc2cccc(C(F)(F)F)c2)n1] | A | 443.4 | 3.59 |
| 39 | 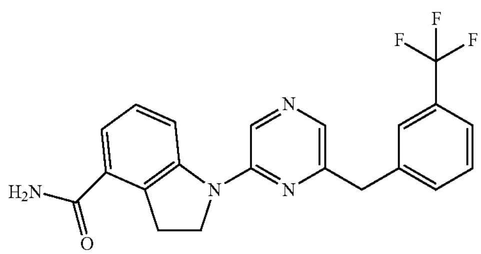 [SMILES: NC(=O)c1cccc2c1CCN2c1cncc(Cc2cccc(C(F)(F)F)c2)n1] | A | 399.2 | 3.88 |
| 40 | 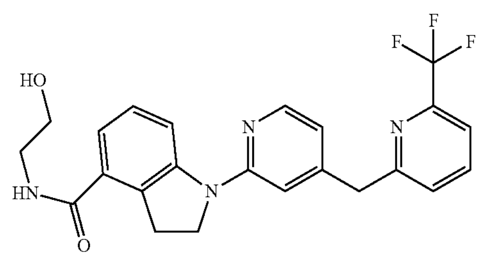 [SMILES: O=C(NCCO)c1cccc2c1CCN2c1cc(Cc2cccc(C(F)(F)F)n2)ccn1] | E | 443.4 | 2.47 |
| 41 | 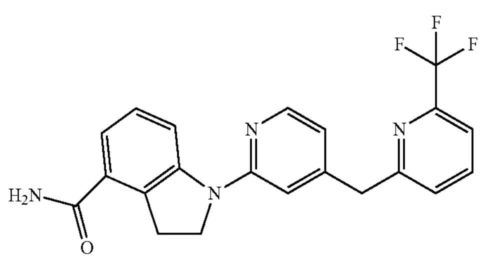 [SMILES: NC(=O)c1cccc2c1CCN2c1cc(Cc2cccc(C(F)(F)F)n2)ccn1] | E | 399.2 | 2.64 |
| 42 | 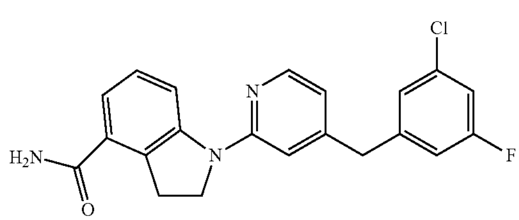 [SMILES: NC(=O)c1cccc2c1CCN2c1cc(Cc2cc(F)cc(Cl)c2)ccn1] | FC | 382.4 | 2.74 |
| 43 | 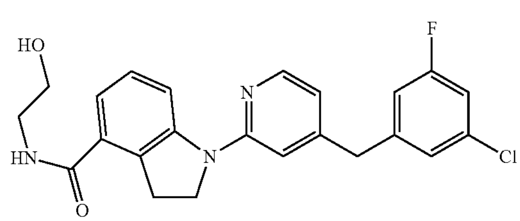 [SMILES: O=C(NCCO)c1cccc2c1CCN2c1cc(Cc2cc(F)cc(Cl)c2)ccn1] | FC | 426.4 | 2.61 |

-continued

| Cmpd No. | Chemical Structure | Synthetic Method | MS | Retention time (min) |
|---|---|---|---|---|
| 44 | (structure) | FC | 453.2 | 2.58 |
| 45 | (structure) | FC | 459.2 | 3.54 |
| 46 | (structure) | FA | 365.4 | 2.29 |
| 47 | (structure) | FA | 399.2 | 2.45 |
| 48 | (structure) | FB | 443.6 | 2.27 |
| 49 | (structure) | FA | 367.4 | 2.31 |
| 50 | (structure) | FA | 363.4 | 2.28 |

| Cmpd No. | Chemical Structure | Synthetic Method | MS | Retention time (min) |
|---|---|---|---|---|
| 51 | 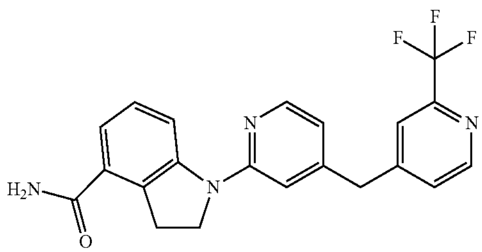 [SMILES: NC(=O)c1cccc2c1CCN2c1cc(Cc2ccnc(C(F)(F)F)c2)ccn1] | FA | 399.4 | 2.43 |
| 52 | 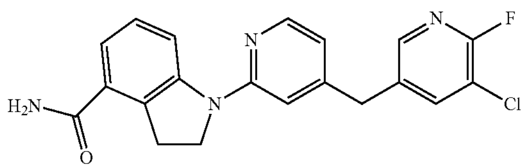 [SMILES: NC(=O)c1cccc2c1CCN2c1cc(Cc2cnc(F)c(Cl)c2)ccn1] | FA | 383.4 | 2.52 |
| 53 | 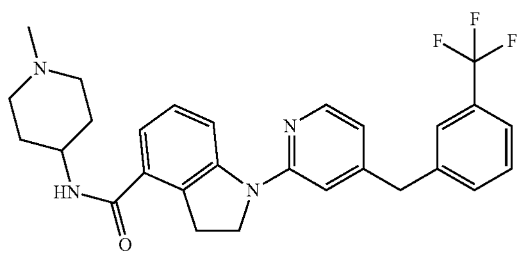 [SMILES: CN1CCC(NC(=O)c2cccc3c2CCN3c2cc(Cc3cccc(C(F)(F)F)c3)ccn2)CC1] | A | 495.6 | 2.63 |
| 54 | 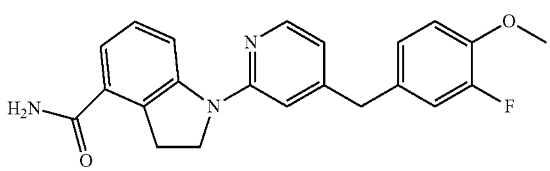 [SMILES: COc1ccc(Cc2ccnc(N3CCc4c(C(N)=O)cccc43)c2)cc1F] | FA | 378.4 | 2.87 |
| 55 | 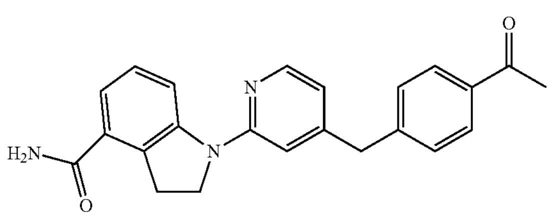 [SMILES: CC(=O)c1ccc(Cc2ccnc(N3CCc4c(C(N)=O)cccc43)c2)cc1] | FA | 372.2 | 2.35 |
| 56 | 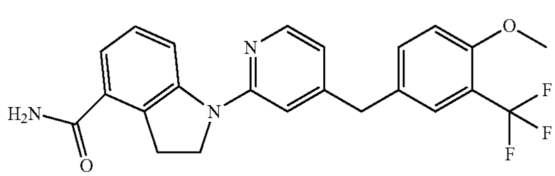 [SMILES: COc1ccc(Cc2ccnc(N3CCc4c(C(N)=O)cccc43)c2)cc1C(F)(F)F] | FA | 428.2 | 2.90 |
| 57 | 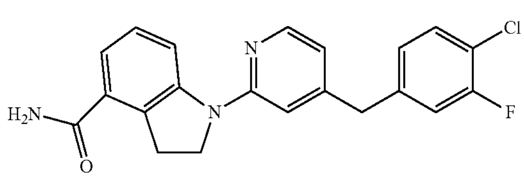 [SMILES: NC(=O)c1cccc2c1CCN2c1cc(Cc2ccc(Cl)c(F)c2)ccn1] | FA | 382.2 | 2.92 |

-continued

| Cmpd No. | Chemical Structure | Synthetic Method | MS | Retention time (min) |
|---|---|---|---|---|
| 58 | 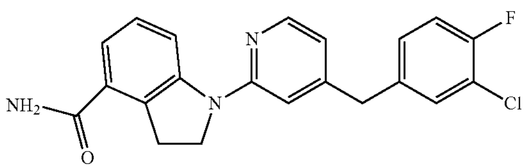 [SMILES: NC(=O)c1cccc2c1CCN2c1cc(Cc2ccc(F)c(Cl)c2)ccn1] | FA | 382.4 | 2.89 |
| 59 | 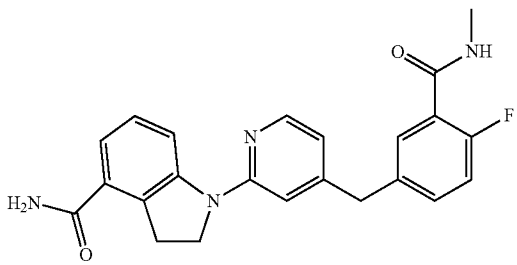 [SMILES: CNC(=O)c1cc(Cc2ccnc(N3CCc4c(C(N)=O)cccc43)c2)ccc1F] | FA | 405.4 | 2.01 |
| 60 | 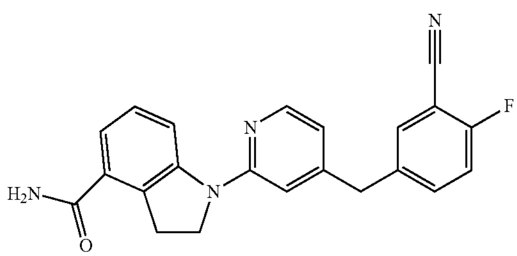 [SMILES: N#Cc1cc(Cc2ccnc(N3CCc4c(C(N)=O)cccc43)c2)ccc1F] | FA | 373.4 | 2.65 |
| 61 | 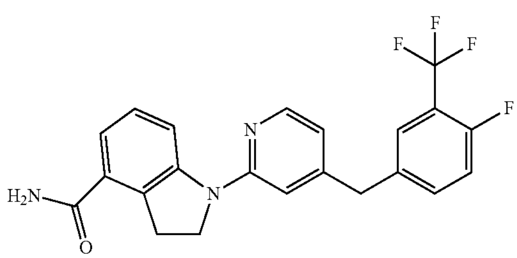 [SMILES: NC(=O)c1cccc2c1CCN2c1cc(Cc2ccc(F)c(C(F)(F)F)c2)ccn1] | FA | 416.4 | 3.10 |
| 62 | 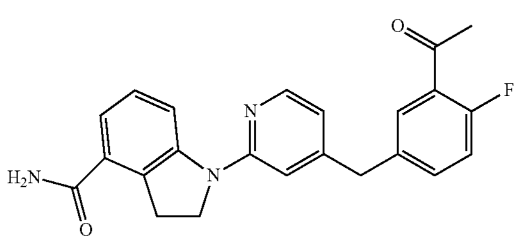 [SMILES: CC(=O)c1cc(Cc2ccnc(N3CCc4c(C(N)=O)cccc43)c2)ccc1F] | FA | 390.4 | 2.49 |
| 63 | 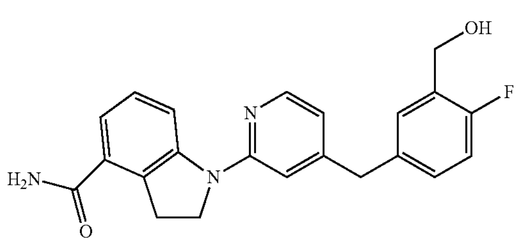 [SMILES: NC(=O)c1cccc2c1CCN2c1cc(Cc2ccc(F)c(CO)c2)ccn1] | FA | 378.4 | 2.11 |

-continued
| Cmpd No. | Chemical Structure | Synthetic Method | MS | Retention time (min) |
|---|---|---|---|---|
| 64 | 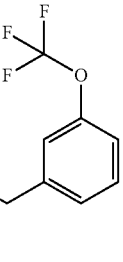 | FA | 414.4 | 3.00 |
| 65 | 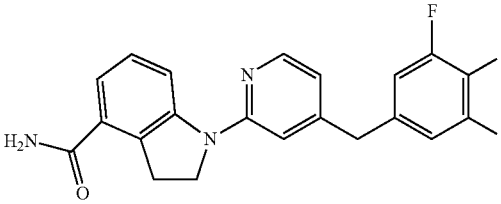 | FA | 384.4 | 2.88 |
| 66 | 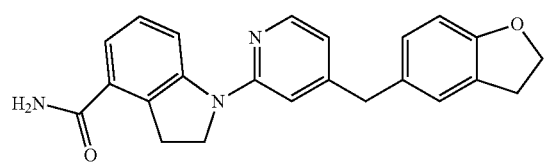 [SMILES: NC(=O)c1cccc2c1CCN2c1cc(Cc2ccc3c(c2)CCO3)ccn1] | FA | 372.2 | 2.46 |
| 67 | 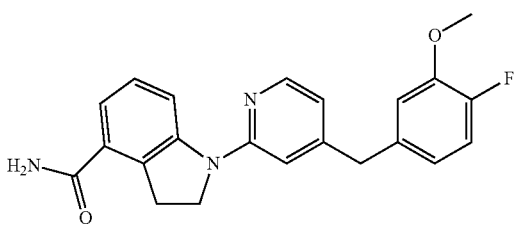 [SMILES: COc1cc(Cc2ccnc(N3CCc4c(C(N)=O)cccc43)c2)ccc1F] | FA | 378.4 | 2.56 |
| 68 | 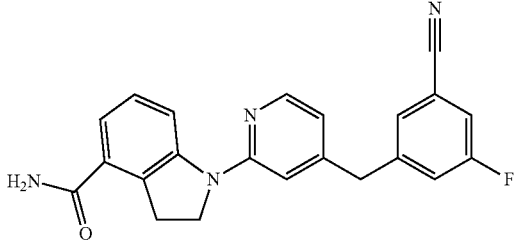 [SMILES: N#Cc1cc(F)cc(Cc2ccnc(N3CCc4c(C(N)=O)cccc43)c2)c1] | FA | 373.2 | 2.82 |
| 69 | 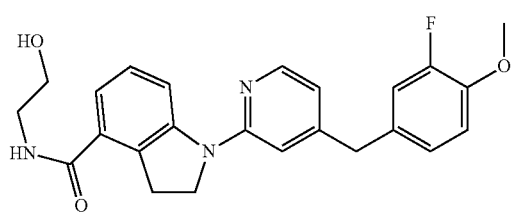 [SMILES: COc1ccc(Cc2ccnc(N3CCc4c(C(=O)NCCO)cccc43)c2)cc1F] | FB | 422.2 | 2.82 |
| 70 | 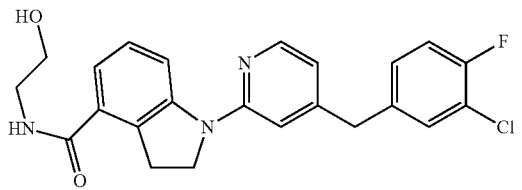 [SMILES: O=C(NCCO)c1cccc2c1CCN2c1cc(Cc2ccc(F)c(Cl)c2)ccn1] | FB | 426.2 | 3.08 |

-continued

| Cmpd No. | Chemical Structure | Synthetic Method | MS | Retention time (min) |
|---|---|---|---|---|
| 71 | 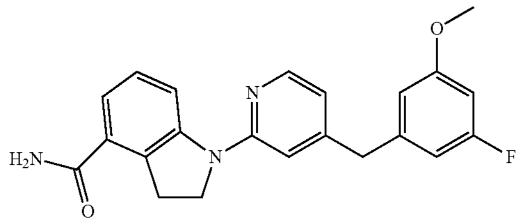 [SMILES: COc1cc(F)cc(Cc2ccnc(N3CCc4c(C(N)=O)cccc43)c2)c1] | FA | 378.4 | 2.69 |
| 72 | 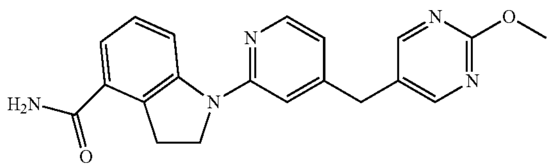 [SMILES: COc1ncc(Cc2ccnc(N3CCc4c(C(N)=O)cccc43)c2)cn1] | FA | 362.6 | 1.89 |
| 73 | 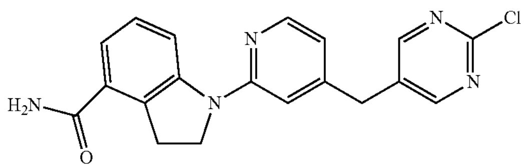 [SMILES: NC(=O)c1cccc2c1CCN2c1cc(Cc2cnc(Cl)nc2)ccn1] | FA | 366.2 | 2.05 |
| 74 | 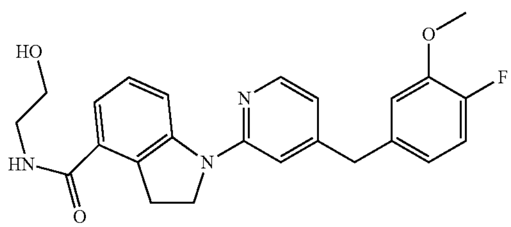 [SMILES: COc1cc(Cc2ccnc(N3CCc4c(C(=O)NCCO)cccc43)c2)ccc1F] | FB | 422.2 | 2.63 |
| 75 | 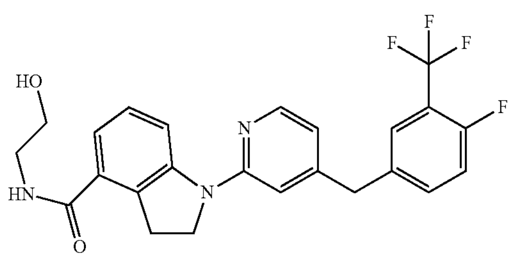 [SMILES: O=C(NCCO)c1cccc2c1CCN2c1cc(Cc2ccc(F)c(C(F)(F)F)c2)ccn1] | FB | 460.4 | 3.04 |
| 76 | 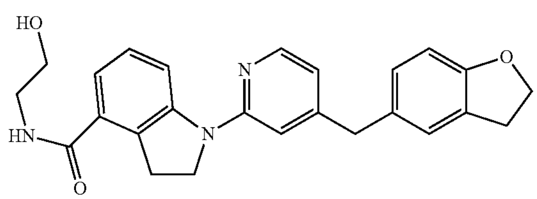 [SMILES: O=C(NCCO)c1cccc2c1CCN2c1cc(Cc2ccc3c(c2)CCO3)ccn1] | FB | 416.2 | 2.56 |
| 77 | 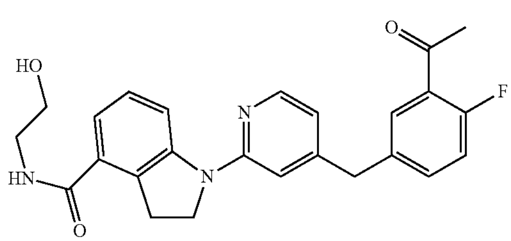 [SMILES: CC(=O)c1cc(Cc2ccnc(N3CCc4c(C(=O)NCCO)cccc43)c2)ccc1F] | FB | 434.4 | 2.56 |

-continued

| Cmpd No. | Chemical Structure | Synthetic Method | MS | Retention time (min) |
|---|---|---|---|---|
| 78 | 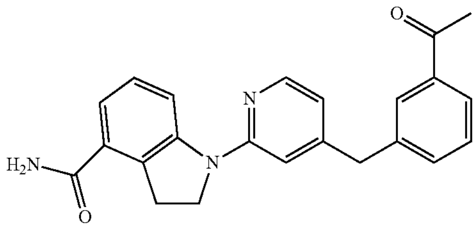 [SMILES: CC(=O)c1cccc(Cc2ccnc(N3CCc4c(C(N)=O)cccc43)c2)c1] | FA | 372.0 | 2.32 |
| 79 | 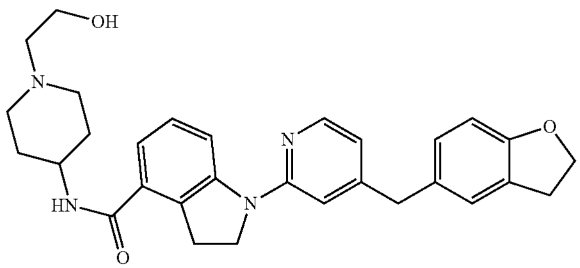 [SMILES: O=C(NC1CCN(CCO)CC1)c1cccc2c1CCN2c1cc(Cc2ccc3c(c2)CCO3)ccn1] | FB | 499.8 | 2.59 |
| 80 | 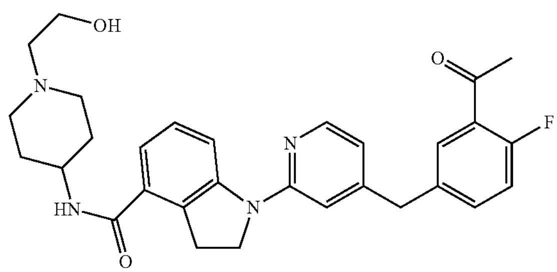 [SMILES: CC(=O)c1cc(Cc2ccnc(N3CCc4c(C(=O)NC5CCN(CCO)CC5)cccc43)c2)ccc1F] | FB | 517.6 | 2.63 |
| 81 | 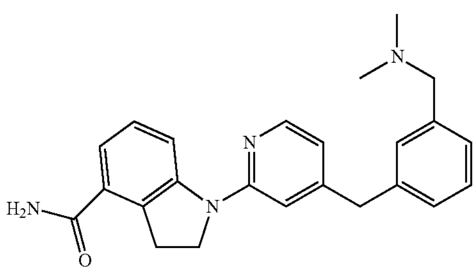 [SMILES: CN(C)Cc1cccc(Cc2ccnc(N3CCc4c(C(N)=O)cccc43)c2)c1] | FA | 387.2 | 1.66 |
| 82 | 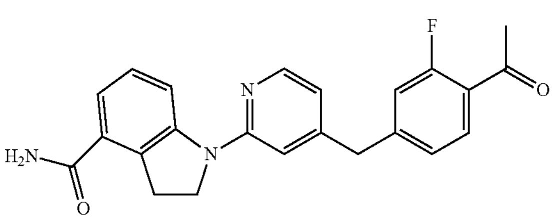 [SMILES: CC(=O)c1ccc(Cc2ccnc(N3CCc4c(C(N)=O)cccc43)c2)cc1F] | FA | 390.2 | 2.85 |
| 83 | 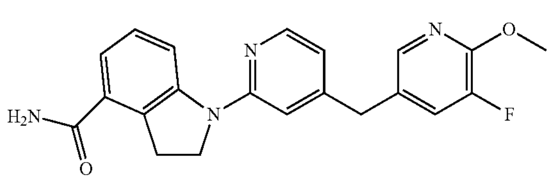 [SMILES: COc1ncc(Cc2ccnc(N3CCc4c(C(N)=O)cccc43)c2)cc1F] | FA | 379.4 | 2.43 |

| Cmpd No. | Chemical Structure | Synthetic Method | MS | Retention time (min) |
|---|---|---|---|---|
| 84 | 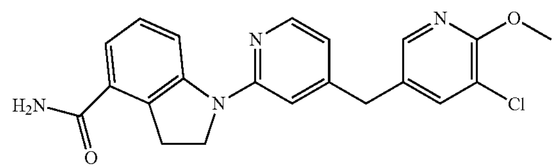 [SMILES: COc1ncc(Cc2ccnc(N3CCc4c(C(N)=O)cccc43)c2)cc1Cl] | FA | 395.4 | 2.64 |
| 85 | 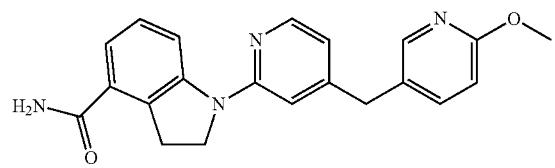 [SMILES: COc1ccc(Cc2ccnc(N3CCc4c(C(N)=O)cccc43)c2)cn1] | FA | 361.4 | 2.54 |
| 86 | 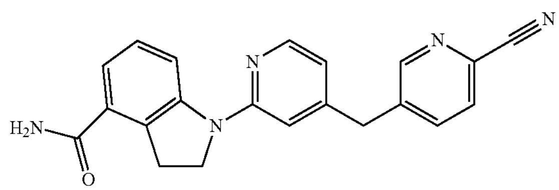 [SMILES: N#Cc1ccc(Cc2ccnc(N3CCc4c(C(N)=O)cccc43)c2)cn1] | FA | 356.2 | 2.09 |
| 87 | 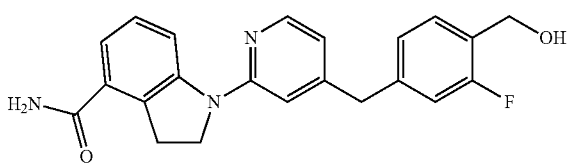 [SMILES: NC(=O)c1cccc2c1CCN2c1cc(Cc2ccc(CO)c(F)c2)ccn1] | FA | 378.4 | 2.05 |
| 88 | 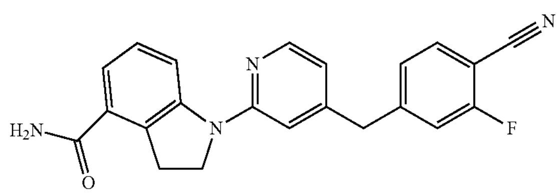 [SMILES: N#Cc1ccc(Cc2ccnc(N3CCc4c(C(N)=O)cccc43)c2)cc1F] | FA | 373.4 | 2.59 |
| 89 | 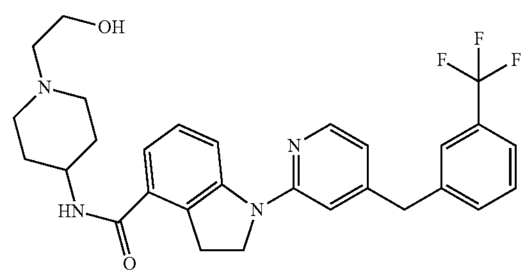 [SMILES: O=C(NC1CCN(CCO)CC1)c1cccc2c1CCN2c1cc(Cc2cccc(C(F)(F)F)c2)ccn1] | FB | 525.4 | 3.25 |
| 90 | 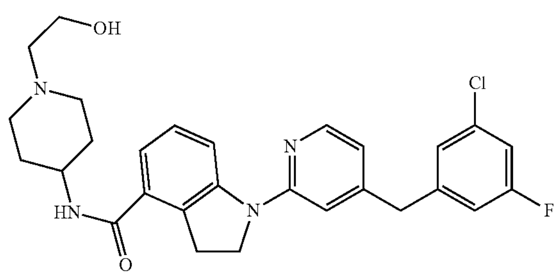 [SMILES: O=C(NC1CCN(CCO)CC1)c1cccc2c1CCN2c1cc(Cc2cc(F)cc(Cl)c2)ccn1] | FB | 509.4 | 3.22 |

-continued

| Cmpd No. | Chemical Structure | Synthetic Method | MS | Retention time (min) |
|---|---|---|---|---|
| 91 | 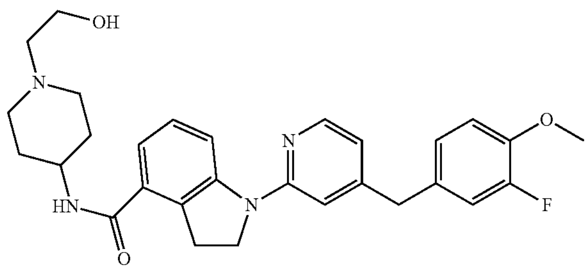 [SMILES: COc1ccc(Cc2ccnc(N3CCc4c(C(=O)NC5CCN(CCO)CC5)cccc43)c2)cc1F] | FB | 505.4 | 3.21 |
| 92 | 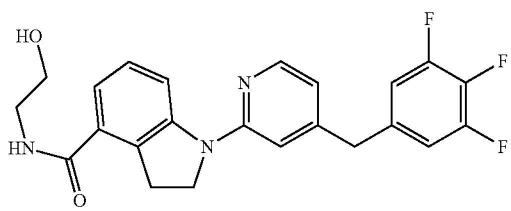 [SMILES: O=C(NCCO)c1cccc2c1CCN2c1cc(Cc2cc(F)c(F)c(F)c2)ccn1] | FB | 428.4 | 3.08 |
| 93 | 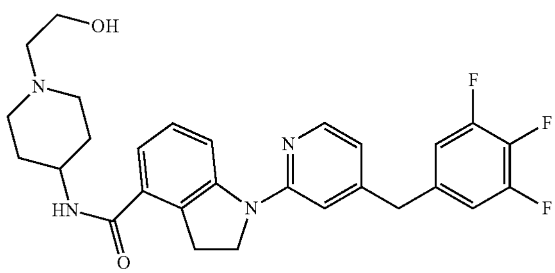 [SMILES: O=C(NC1CCN(CCO)CC1)c1cccc2c1CCN2c1cc(Cc2cc(F)c(F)c(F)c2)ccn1] | FB | 511.4 | 3.11 |
| 94 | 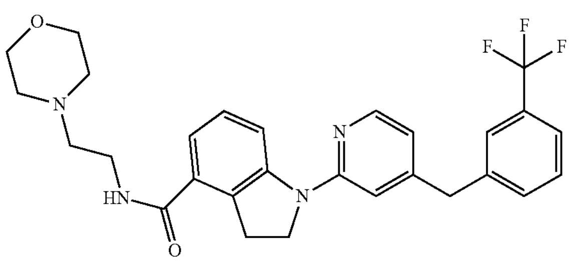 [SMILES: O=C(NCCN1CCOCC1)c1cccc2c1CCN2c1cc(Cc2cccc(C(F)(F)F)c2)ccn1] | FB | 511.4 | 2.30 |
| 95 | 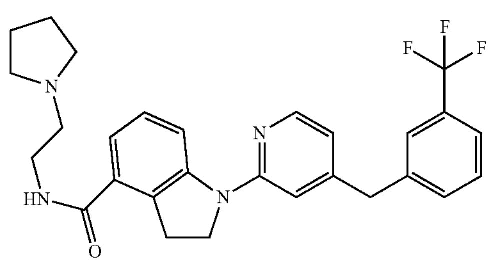 [SMILES: O=C(NCCN1CCCC1)c1cccc2c1CCN2c1cc(Cc2cccc(C(F)(F)F)c2)ccn1] | FB | 495.6 | 3.44 |
| 96 | 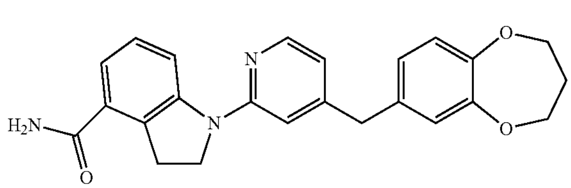 [SMILES: NC(=O)c1cccc2c1CCN2c1cc(Cc2ccc3c(c2)OCCCO3)ccn1] | FA | 402.2 | 3.18 |

-continued

| Cmpd No. | Chemical Structure | Synthetic Method | MS | Retention time (min) |
|---|---|---|---|---|
| 97 | 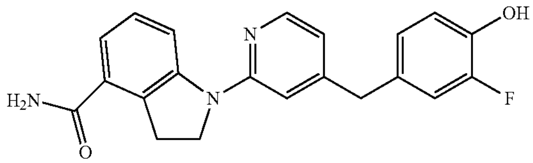 [SMILES: NC(=O)c1cccc2c1CCN2c1cc(Cc2ccc(O)c(F)c2)ccn1] | FA | 364.4 | 2.81 |
| 98 | 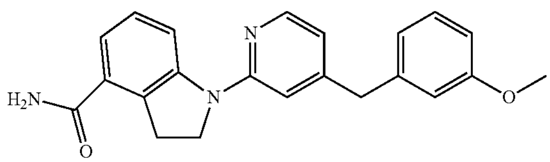 [SMILES: COc1cccc(Cc2ccnc(N3CCc4c(C(N)=O)cccc43)c2)c1] | FA | 360.4 | 2.75 |
| 99 | 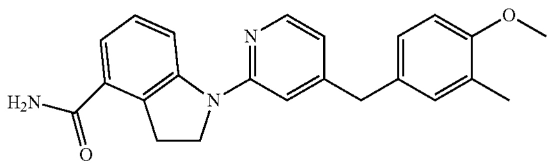 [SMILES: COc1ccc(Cc2ccnc(N3CCc4c(C(N)=O)cccc43)c2)cc1C] | FA | 374.4 | 3.04 |
| 100 | 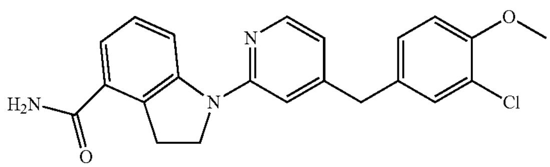 [SMILES: COc1ccc(Cc2ccnc(N3CCc4c(C(N)=O)cccc43)c2)cc1Cl] | FA | 394.4 | 2.73 |
| 101 | 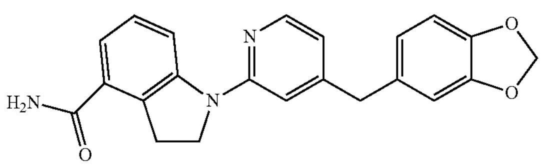 [SMILES: NC(=O)c1cccc2c1CCN2c1cc(Cc2ccc3c(c2)OCO3)ccn1] | FA | 374.2 | 2.46 |
| 102 | 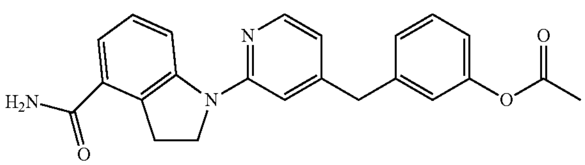 [SMILES: CC(=O)Oc1cccc(Cc2ccnc(N3CCc4c(C(N)=O)cccc43)c2)c1] | FA | 388.4 | 2.42 |
| 103 | 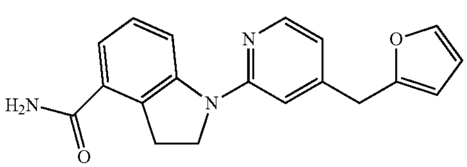 [SMILES: NC(=O)c1cccc2c1CCN2c1cc(Cc2ccco2)ccn1] | FA | 320.2 | 2.58 |
| 104 | 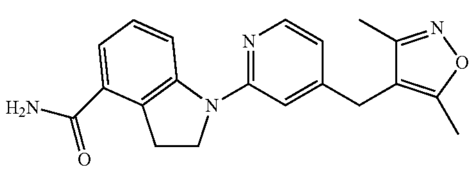 [SMILES: Cc1noc(C)c1Cc1ccnc(N2CCc3c(C(N)=O)cccc32)c1] | FA | 349.4 | 2.35 |
| 105 | 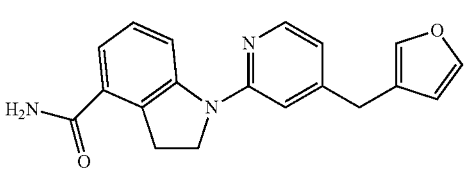 [SMILES: NC(=O)c1cccc2c1CCN2c1cc(Cc2ccoc2)ccn1] | FA | 320.2 | 2.46 |

-continued

| Cmpd No. | Chemical Structure | Synthetic Method | MS | Retention time (min) |
|---|---|---|---|---|
| 106 | 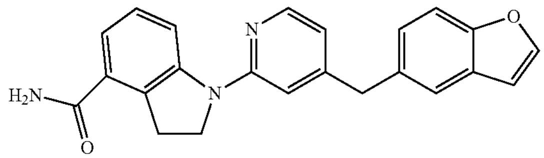 | FA | 370.2 | 2.96 |
| 107 | 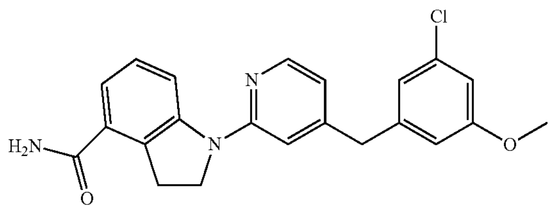 [SMILES: COc1cc(Cl)cc(Cc2ccnc(N3CCc4c(C(N)=O)cccc43)c2)c1] | FA | 394.4 | 3.18 |
| 108 | 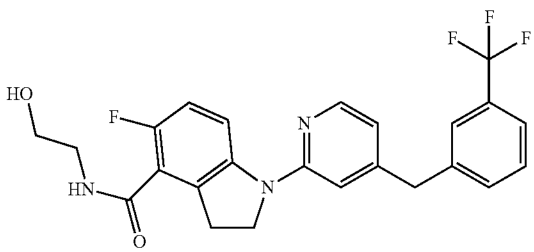 [SMILES: O=C(NCCO)c1c(F)ccc2c1CCN2c1cc(Cc2cccc(C(F)(F)F)c2)ccn1] | A | 460.4 | 3.18 |
| 109 | 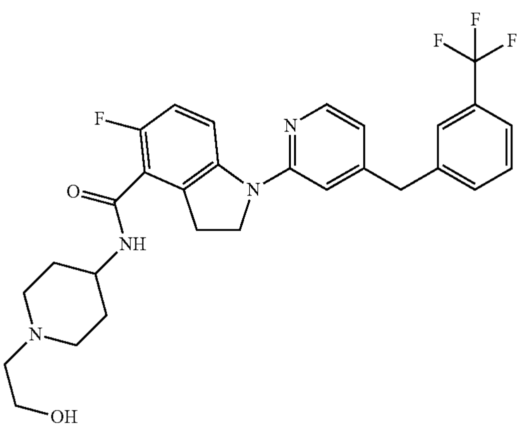 [SMILES: O=C(NC1CCN(CCO)CC1)c1c(F)ccc2c1CCN2c1cc(Cc2cccc(C(F)(F)F)c2)ccn1] | A | 543.6 | 3.42 |
| 110 | 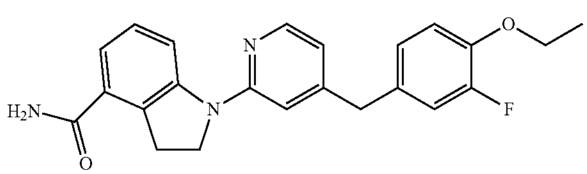 [SMILES: CCOc1ccc(Cc2ccnc(N3CCc4c(C(N)=O)cccc43)c2)cc1F] | FA | 392.2 | 3.09 |
| 111 | 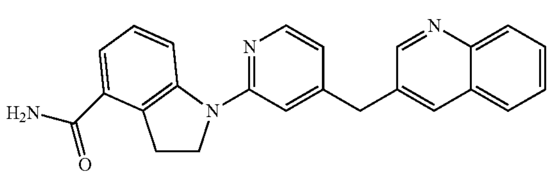 [SMILES: NC(=O)c1cccc2c1CCN2c1cc(Cc2cnc3ccccc3c2)ccn1] | FA | 381.4 | 2.27 |
| 112 | 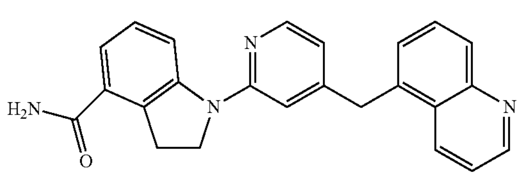 [SMILES: NC(=O)c1cccc2c1CCN2c1cc(Cc2cccc3ncccc23)ccn1] | FA | 381.2 | 2.12 |

-continued

| Cmpd No. | Chemical Structure | Synthetic Method | MS | Retention time (min) |
|---|---|---|---|---|
| 113 | 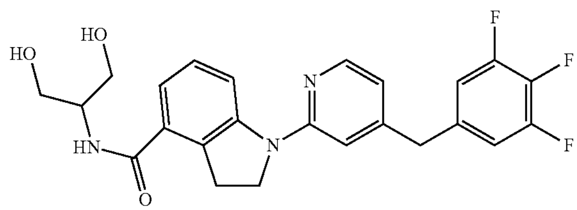 [SMILES: O=C(NC(CO)CO)c1cccc2c1CCN2c1cc(Cc2cc(F)c(F)c(F)c2)ccn1] | FB | 458.4 | 3.23 |
| 114 | 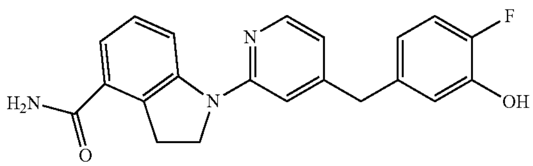 [SMILES: NC(=O)c1cccc2c1CCN2c1cc(Cc2ccc(F)c(O)c2)ccn1] | FA | 364.4 | 2.16 |
| 115 | 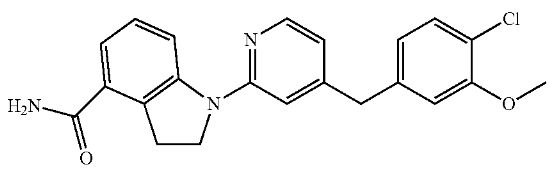 [SMILES: COc1cc(Cc2ccnc(N3CCc4c(C(N)=O)cccc43)c2)ccc1Cl] | FA | 394.4 | 2.74 |
| 116 | 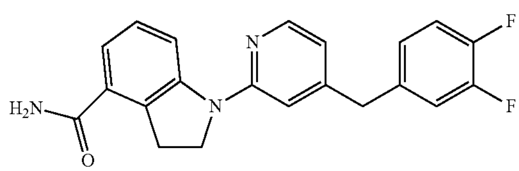 [SMILES: NC(=O)c1cccc2c1CCN2c1cc(Cc2ccc(F)c(F)c2)ccn1] | FA | 366.2 | 2.69 |
| 117 | 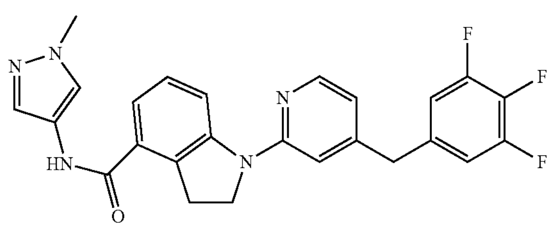 [SMILES: Cn1cc(NC(=O)c2cccc3c2CCN3c2cc(Cc3cc(F)c(F)c(F)c3)ccn2)cn1] | FB | 464.4 | 3.80 |
| 118 | 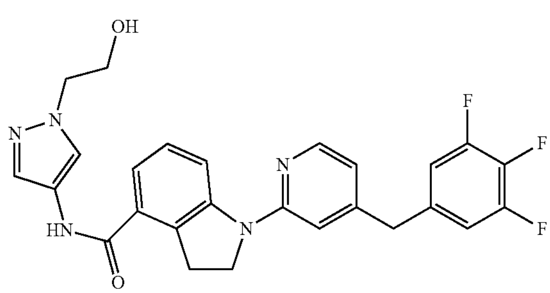 [SMILES: O=C(Nc1cnn(CCO)c1)c1cccc2c1CCN2c1cc(Cc2cc(F)c(F)c(F)c2)ccn1] | FB | 494.6 | 2.87 |
| 119 | 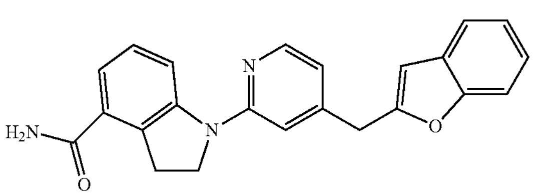 [SMILES: NC(=O)c1cccc2c1CCN2c1cc(Cc2cc3ccccc3o2)ccn1] | FA | 370.2 | 2.89 |

| Cmpd No. | Chemical Structure | Synthetic Method | MS | Retention time (min) |
|---|---|---|---|---|
| 120 | 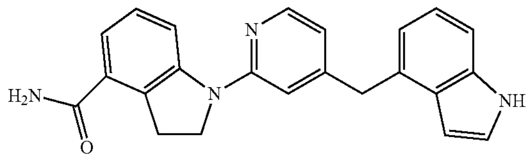 [SMILES: NC(=O)c1cccc2c1CCN2c1cc(Cc2cccc3[nH]ccc23)ccn1] | FA | 369.2 | 2.36 |
| 121 | 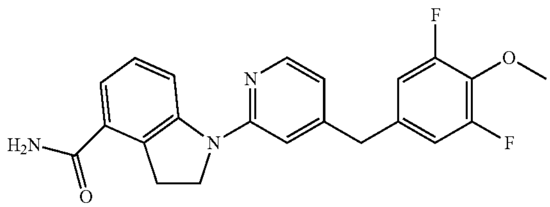 [SMILES: COc1c(F)cc(Cc2ccnc(N3CCc4c(C(N)=O)cccc43)c2)cc1F] | FA | 396.2 | 3.04 |
| 122 | 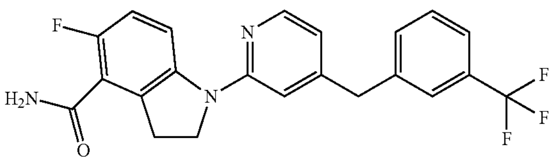 [SMILES: NC(=O)c1c(F)ccc2c1CCN2c1cc(Cc2cccc(C(F)(F)F)c2)ccn1] | A | 416.2 | 3.39 |
| 123 | 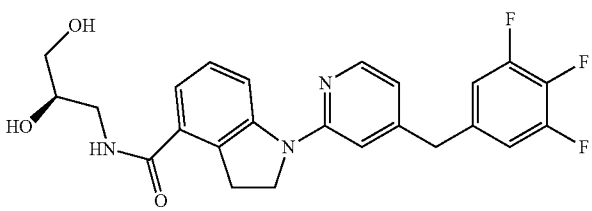 [SMILES: O=C(NC[C@@H](O)CO)c1cccc2c1CCN2c1cc(Cc2cc(F)c(F)c(F)c2)ccn1] | FB | 458.2 | 3.24 |
| 124 | 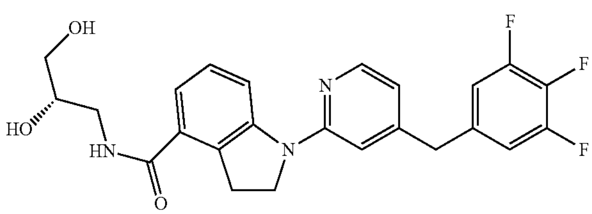 [SMILES: O=C(NC[C@H](O)CO)c1cccc2c1CCN2c1cc(Cc2cc(F)c(F)c(F)c2)ccn1] | FB | 458.2 | 3.22 |
| 125 | 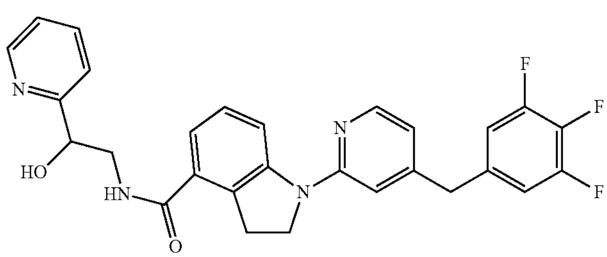 [SMILES: O=C(NCC(O)c1ccccn1)c1cccc2c1CCN2c1cc(Cc2cc(F)c(F)c(F)c2)ccn1] | FB | 505.4 | 2.50 |
| 126 | 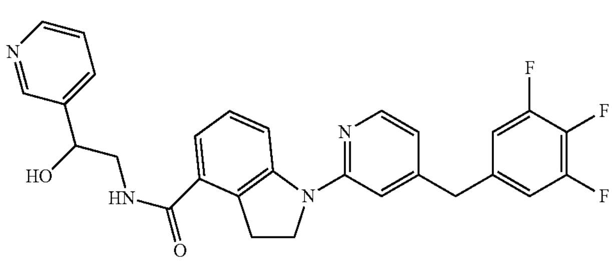 [SMILES: O=C(NCC(O)c1cccnc1)c1cccc2c1CCN2c1cc(Cc2cc(F)c(F)c(F)c2)ccn1] | FB | 505.4 | 3.23 |

-continued

| Cmpd No. | Chemical Structure | Synthetic Method | MS | Retention time (min) |
|---|---|---|---|---|
| 127 | 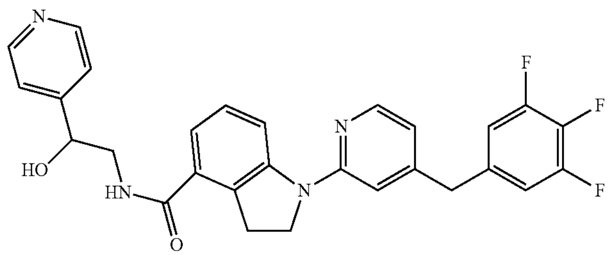 [SMILES: O=C(NCC(O)c1ccncc1)c1cccc2c1CCN2c1cc(Cc2cc(F)c(F)c(F)c2)ccn1] | FB | 505.4 | 3.22 |
| 128 | 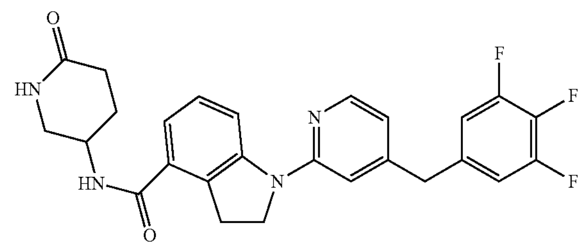 [SMILES: O=C1CCC(NC(=O)c2cccc3c2CCN3c2cc(Cc3cc(F)c(F)c(F)c3)ccn2)CN1] | FB | 481.4 | 3.60 |
| 129 | 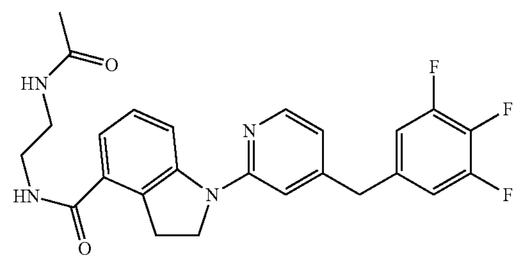 [SMILES: CC(=O)NCCNC(=O)c1cccc2c1CCN2c1cc(Cc2cc(F)c(F)c(F)c2)ccn1] | FB | 469.6 | 3.17 |
| 130 | 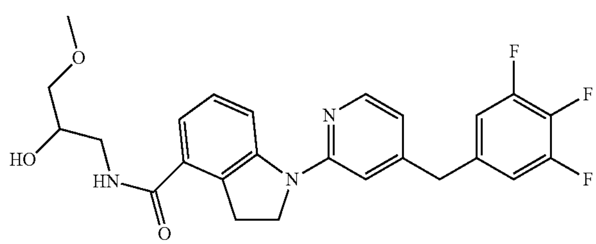 [SMILES: COCC(O)CNC(=O)c1cccc2c1CCN2c1cc(Cc2cc(F)c(F)c(F)c2)ccn1] | FB | 472.2 | 3.07 |
| 131 | 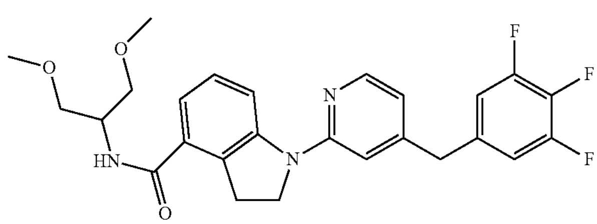 [SMILES: COCC(COC)NC(=O)c1cccc2c1CCN2c1cc(Cc2cc(F)c(F)c(F)c2)ccn1] | FB | 486.4 | 3.08 |
| 132 | 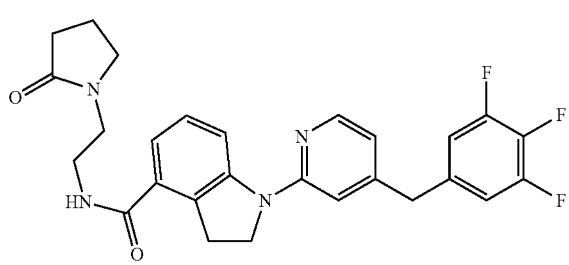 [SMILES: O=C(NCCN1CCCC1=O)c1cccc2c1CCN2c1cc(Cc2cc(F)c(F)c(F)c2)ccn1] | FB | 495.5 | 2.94 |

-continued

| Cmpd No. | Chemical Structure | Synthetic Method | MS | Retention time (min) |
|---|---|---|---|---|
| 133 | 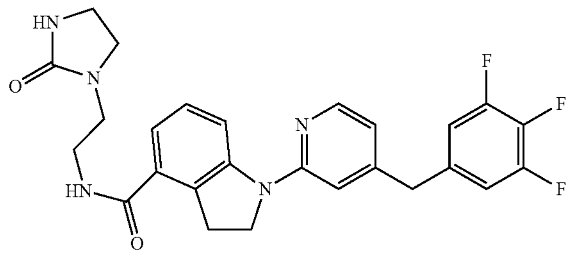 [SMILES: O=C(NCCN1CCNC1=O)c1cccc2c1CCN2c1cc(Cc2cc(F)c(F)c(F)c2)ccn1] | FB | 496.6 | 2.87 |
| 134 | 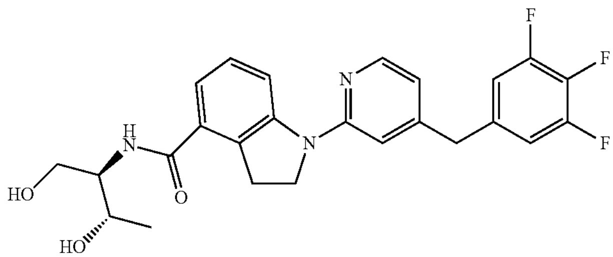 [SMILES: C[C@H](O)[C@@H](CO)NC(=O)c1cccc2c1CCN2c1cc(Cc2cc(F)c(F)c(F)c2)ccn1] | FB | 472.6 | 2.62 |
| 135 | 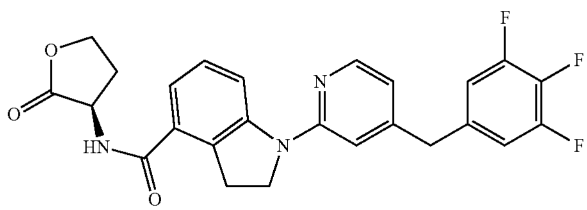 [SMILES: O=C(N[C@@H]1CCOC1=O)c1cccc2c1CCN2c1cc(Cc2cc(F)c(F)c(F)c2)ccn1] | FB | 468.4 | 3.70 |
| 136 | 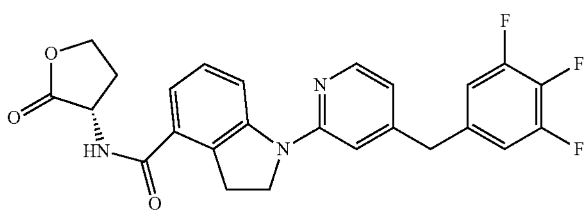 [SMILES: O=C(N[C@H]1CCOC1=O)c1cccc2c1CCN2c1cc(Cc2cc(F)c(F)c(F)c2)ccn1] | FB | 468.4 | 3.30 |
| 137 | 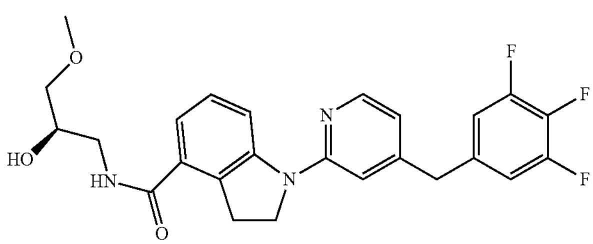 [SMILES: COC[C@H](O)CNC(=O)c1cccc2c1CCN2c1cc(Cc2cc(F)c(F)c(F)c2)ccn1] | FB | 472.6 | 3.60 |
| 138 | 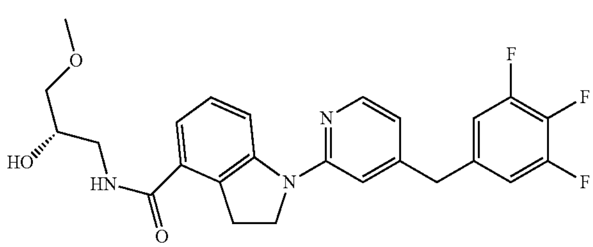 | FB | 472.6 | 2.81 |

-continued

| Cmpd No. | Chemical Structure | Synthetic Method | MS | Retention time (min) |
|---|---|---|---|---|
| 139 | 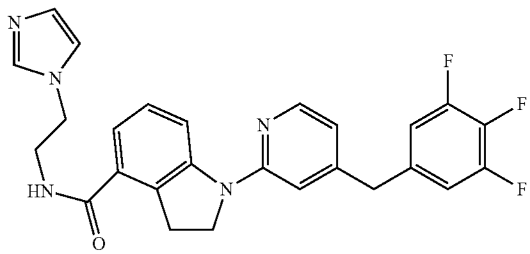 [SMILES: O=C(NCCn1ccnc1)c1cccc2c1CCN2c1cc(Cc2cc(F)c(F)c(F)c2)ccn1] | FB | 478.4 | 3.52 |
| 140 | 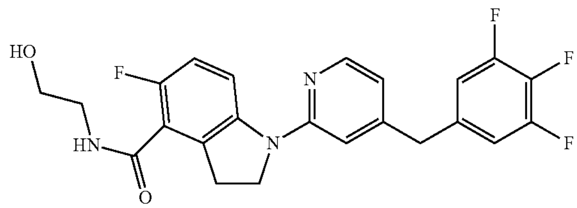 [SMILES: O=C(NCCO)c1c(F)ccc2c1CCN2c1cc(Cc2cc(F)c(F)c(F)c2)ccn1] | FC | 446.2 | 3.15 |
| 141 | 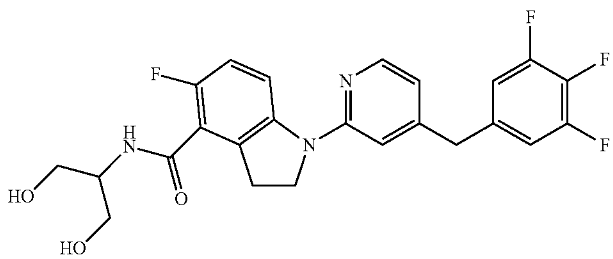 [SMILES: O=C(NC(CO)CO)c1c(F)ccc2c1CCN2c1cc(Cc2cc(F)c(F)c(F)c2)ccn1] | FC | 476.0 | 2.94 |
| 142 | 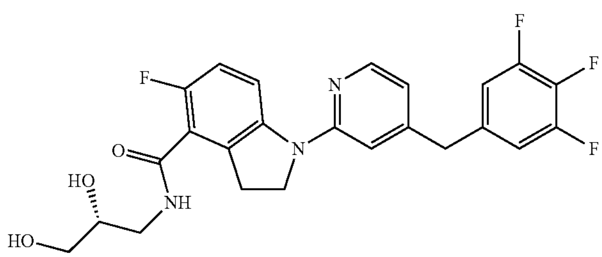 [SMILES: O=C(NC[C@@H](O)CO)c1c(F)ccc2c1CCN2c1cc(Cc2cc(F)c(F)c(F)c2)ccn1] | FC | 476.2 | 2.96 |
| 143 | 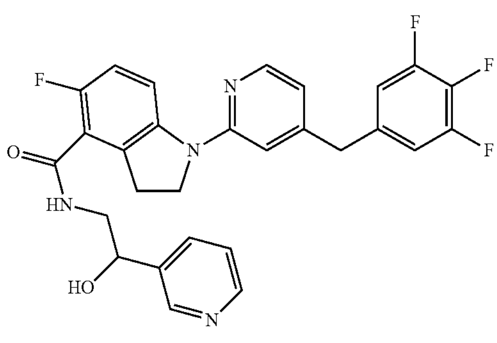 [SMILES: O=C(NCC(O)c1cccnc1)c1c(F)ccc2c1CCN2c1cc(Cc2cc(F)c(F)c(F)c2)ccn1] | FC | 523.4 | 3.43 |
| 144 | 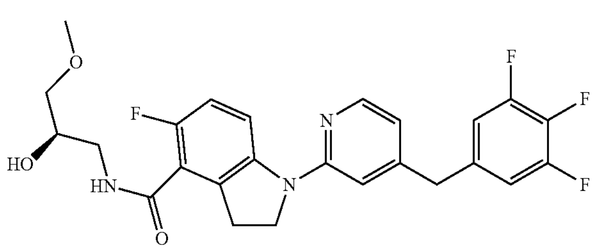 [SMILES: COC[C@H](O)CNC(=O)c1c(F)ccc2c1CCN2c1cc(Cc2cc(F)c(F)c(F)c2)ccn1] | FC | 490.4 | 3.24 |

-continued

| Cmpd No. | Chemical Structure | Synthetic Method | MS | Retention time (min) |
|---|---|---|---|---|
| 145 | 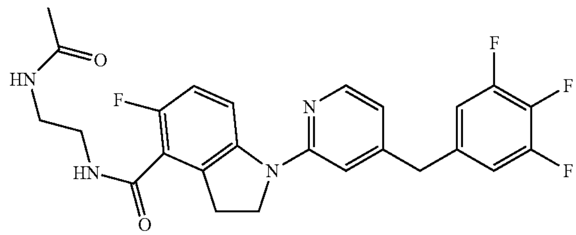 [SMILES: CC(=O)NCCNC(=O)c1c(F)ccc2c1CCN2c1cc(Cc2cc(F)c(F)c(F)c2)ccn1] | FC | 487.1 | 2.95 |
| 146 | 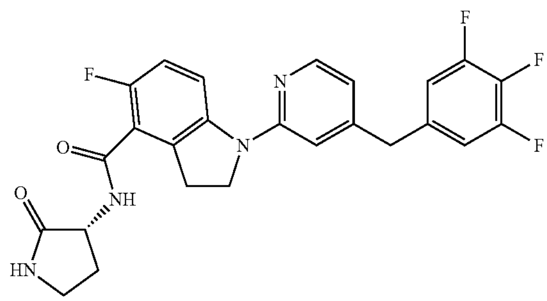 [SMILES: O=C(N[C@@H]1CCNC1=O)c1c(F)ccc2c1CCN2c1cc(Cc2cc(F)c(F)c(F)c2)ccn1] | FC | 485.4 | 2.93 |
| 147 | 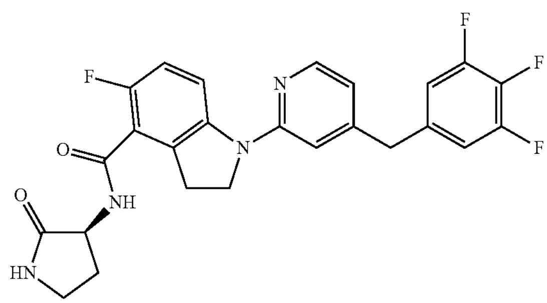 [SMILES: O=C(N[C@H]1CCNC1=O)c1c(F)ccc2c1CCN2c1cc(Cc2cc(F)c(F)c(F)c2)ccn1] | FC | 485.4 | 2.93 |
| 148 | 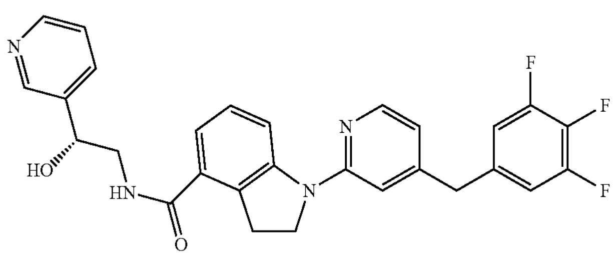 [SMILES: O=C(NC[C@H](O)c1cccnc1)c1cccc2c1CCN2c1cc(Cc2cc(F)c(F)c(F)c2)ccn1] | FB | 505.4 | 2.61 |
| 149 | 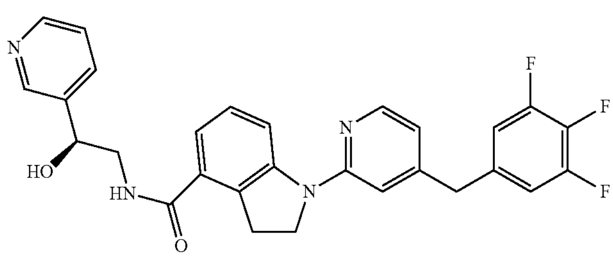 [SMILES: O=C(NC[C@@H](O)c1cccnc1)c1cccc2c1CCN2c1cc(Cc2cc(F)c(F)c(F)c2)ccn1] | FB | 505.4 | 2.62 |
| 150 | 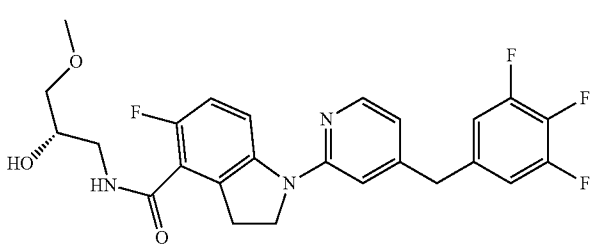 [SMILES: COC[C@@H](O)CNC(=O)c1c(F)ccc2c1CCN2c1cc(Cc2cc(F)c(F)c(F)c2)ccn1] | FC | 490.4 | 2.97 |

| Cmpd No. | Chemical Structure | Synthetic Method | MS | Retention time (min) |
|---|---|---|---|---|
| 151 | 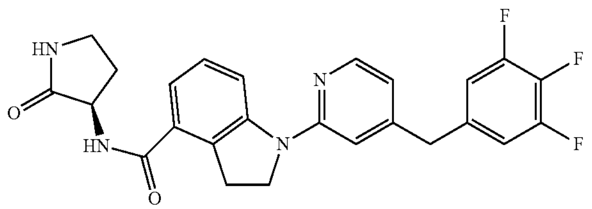 [SMILES: O=C(N[C@@H]1CCNC1=O)c1cccc2c1CCN2c1cc(Cc2cc(F)c(F)c(F)c2)ccn1] | FB | 467.2 | 3.59 |
| 152 | 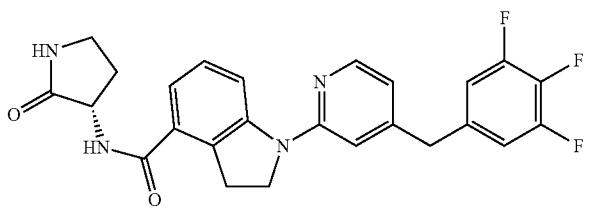 [SMILES: O=C(N[C@H]1CCNC1=O)c1cccc2c1CCN2c1cc(Cc2cc(F)c(F)c(F)c2)ccn1] | FB | 467.4 | 3.60 |
| 153 | 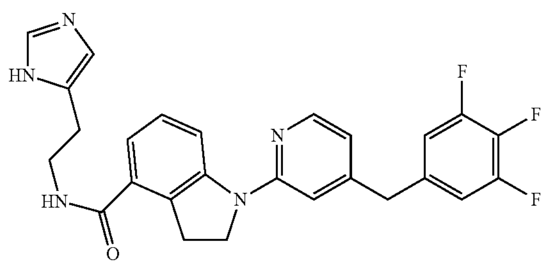 [SMILES: O=C(NCCc1cnc[nH]1)c1cccc2c1CCN2c1cc(Cc2cc(F)c(F)c(F)c2)ccn1] | FB | 478.4 | 3.55 |
| 154 | 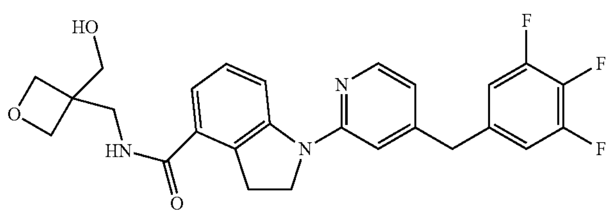 [SMILES: O=C(NCC1(CO)COC1)c1cccc2c1CCN2c1cc(Cc2cc(F)c(F)c(F)c2)ccn1] | FB | 484.4 | 3.64 |
| 155 | 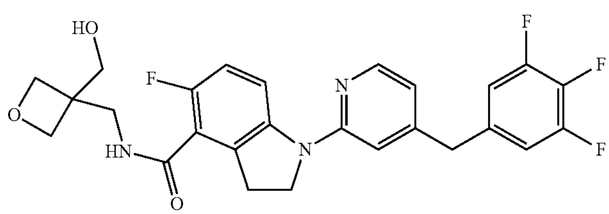 [SMILES: O=C(NCC1(CO)COC1)c1c(F)ccc2c1CCN2c1cc(Cc2cc(F)c(F)c(F)c2)ccn1] | FC | 502.2 | 3.72 |
| 156 | 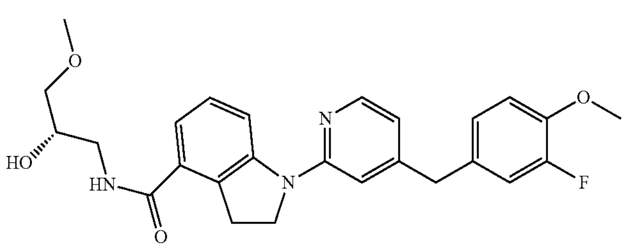 [SMILES: COC[C@@H](O)CNC(=O)c1cccc2c1CCN2c1cc(Cc2ccc(OC)c(F)c2)ccn1] | FB | 466.4 | 3.03 |
| 157 | 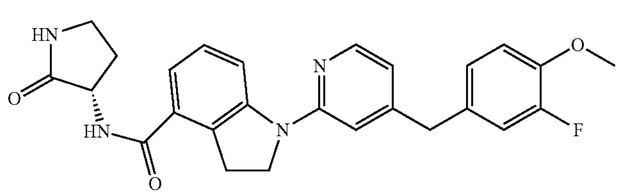 [SMILES: COc1ccc(Cc2ccnc(N3CCc4c(C(=O)N[C@H]5CCNC5=O)cccc43)c2)cc1F] | FB | 461.4 | 2.42 |

-continued

| Cmpd No. | Chemical Structure | Synthetic Method | MS | Retention time (min) |
|---|---|---|---|---|
| 158 | 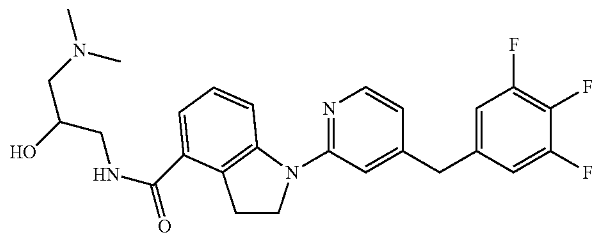 [SMILES: CN(C)CC(O)CNC(=O)c1cccc2c1CCN2c1cc(Cc2cc(F)c(F)c(F)c2)ccn1] | FB | 485.4 | 2.46 |
| 159 | 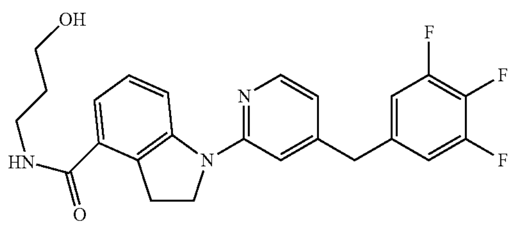 [SMILES: O=C(NCCCO)c1cccc2c1CCN2c1cc(Cc2cc(F)c(F)c(F)c2)ccn1] | FB | 442.4 | 2.70 |
| 160 | 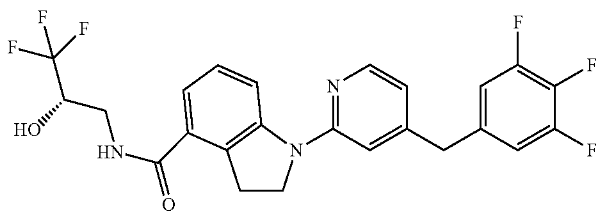 [SMILES: O=C(NC[C@H](O)C(F)(F)F)c1cccc2c1CCN2c1cc(Cc2cc(F)c(F)c(F)c2)ccn1] | FB | 496.4 | 3.02 |
| 161 | 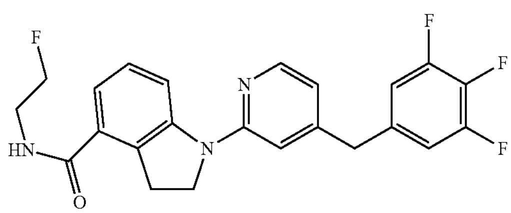 [SMILES: O=C(NCCF)c1cccc2c1CCN2c1cc(Cc2cc(F)c(F)c(F)c2)ccn1] | FB | 430.2 | 2.95 |
| 162 | 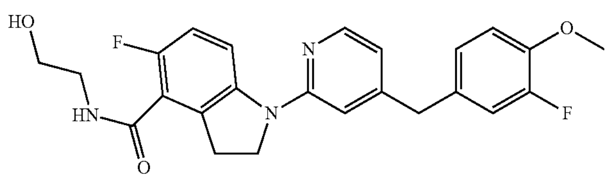 [SMILES: COc1ccc(Cc2ccnc(N3CCc4c3ccc(F)c4C(=O)NCCO)c2)cc1F] | FC | 440.4 | 2.53 |
| 163 | 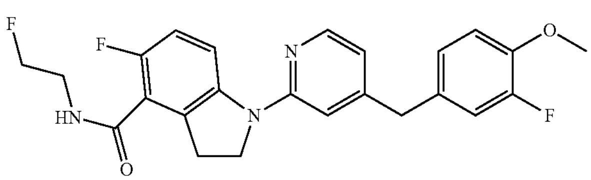 [SMILES: COc1ccc(Cc2ccnc(N3CCc4c3ccc(F)c4C(=O)NCCF)c2)cc1F] | FC | 442.4 | 2.88 |
| 164 | 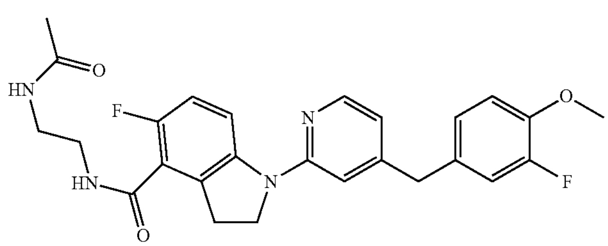 [SMILES: COc1ccc(Cc2ccnc(N3CCc4c3ccc(F)c4C(=O)NCCNC(C)=O)c2)cc1F] | FC | 481.2 | 2.59 |

-continued

| Cmpd No. | Chemical Structure | Synthetic Method | MS | Retention time (min) |
|---|---|---|---|---|
| 165 | 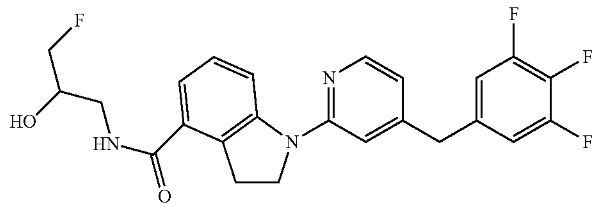 | FB | 460.2 | 2.71 |
| 166 | 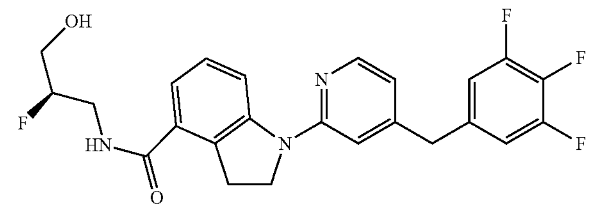 [SMILES: O=C(NC[C@@H](F)CO)c1cccc2c1CCN2c1cc(Cc2cc(F)c(F)c(F)c2)ccn1] | FB | 460.2 | 2.70 |
| 167 | 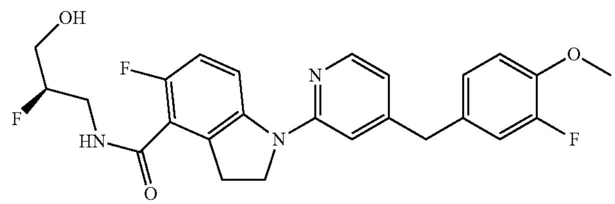 [SMILES: COc1ccc(Cc2ccnc(N3CCc4c3ccc(F)c4C(=O)NC[C@@H](F)CO)c2)cc1F] | FC | 472.2 | 3.06 |
| 168 | 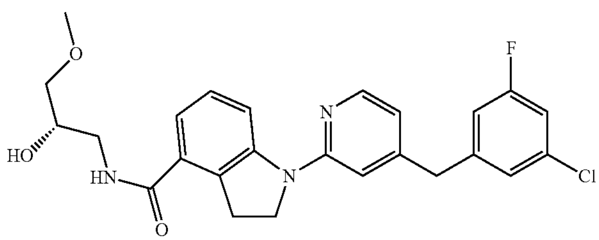 [SMILES: COC[C@@H](O)CNC(=O)c1cccc2c1CCN2c1cc(Cc2cc(F)cc(Cl)c2)ccn1] | FC | 470.4 | 2.83 |
| 169 | 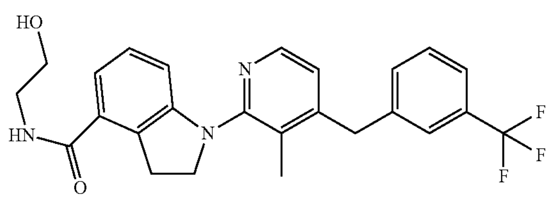 [SMILES: Cc1c(Cc2cccc(C(F)(F)F)c2)ccnc1N1CCc2c(C(=O)NCCO)cccc21] | FC | 456.4 | 3.30 |
| 170 | 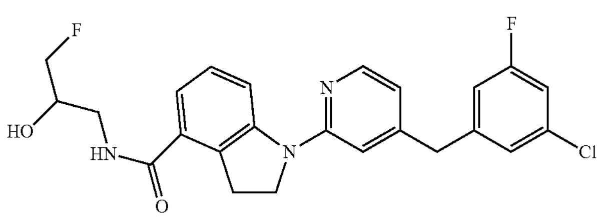 [SMILES: O=C(NCC(O)CF)c1cccc2c1CCN2c1cc(Cc2cc(F)cc(Cl)c2)ccn1] | FC | 458.2 | 2.77 |
| 171 | 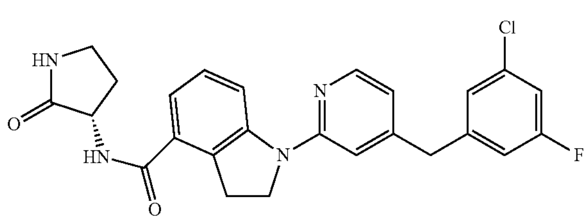 [SMILES: O=C(N[C@H]1CCNC1=O)c1cccc2c1CCN2c1cc(Cc2cc(F)cc(Cl)c2)ccn1] | FC | 465.2 | 3.28 |

-continued

| Cmpd No. | Chemical Structure | Synthetic Method | MS | Retention time (min) |
|---|---|---|---|---|
| 172 | 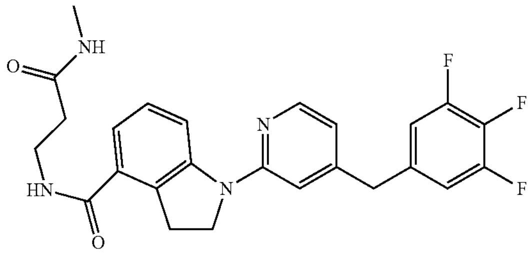 [SMILES: CNC(=O)CCNC(=O)c1cccc2c1CCN2c1cc(Cc2cc(F)c(F)c(F)c2)ccn1] | FB | 469.4 | 2.77 |
| 173 | 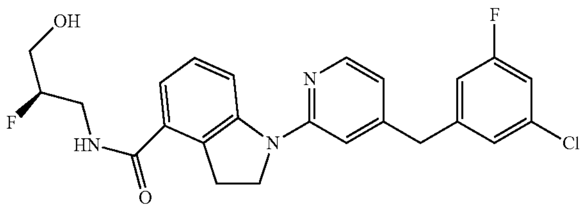 [SMILES: O=C(NC[C@@H](F)CO)c1cccc2c1CCN2c1cc(Cc2cc(F)cc(Cl)c2)ccn1] | FC | 458.2 | 2.77 |
| 174 | 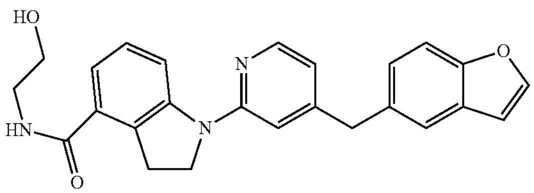 [SMILES: O=C(NCCO)c1cccc2c1CCN2c1cc(Cc2ccc3occc3c2)ccn1] | FC | 414.4 | 2.53 |
| 175 | 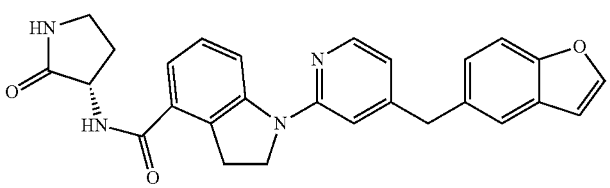 [SMILES: O=C(N[C@H]1CCNC1=O)c1cccc2c1CCN2c1cc(Cc2ccc3occc3c2)ccn1] | FC | 453.0 | 2.58 |
| 176 | 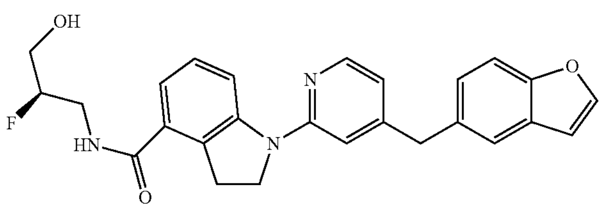 [SMILES: O=C(NC[C@@H](F)CO)c1cccc2c1CCN2c1cc(Cc2ccc3occc3c2)ccn1] | FC | 446.4 | 2.60 |
| 177 | 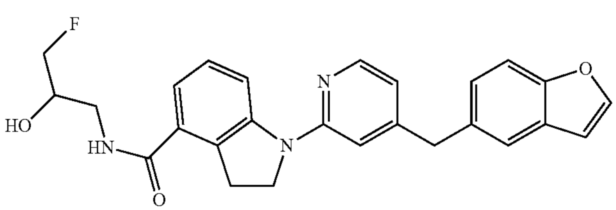 [SMILES: O=C(NCC(O)CF)c1cccc2c1CCN2c1cc(Cc2ccc3occc3c2)ccn1] | FC | 446.2 | 3.28 |
| 178 | 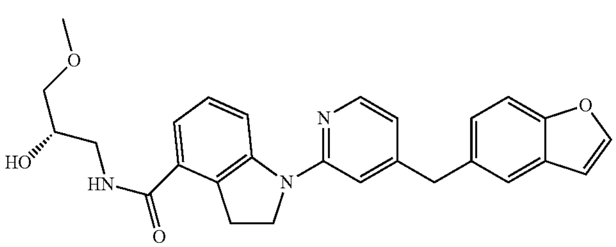 [SMILES: COC[C@@H](O)CNC(=O)c1cccc2c1CCN2c1cc(Cc2ccc3occc3c2)ccn1] | FC | 458.4 | 2.57 |

-continued

| Cmpd No. | Chemical Structure | Synthetic Method | MS | Retention time (min) |
|---|---|---|---|---|
| 179 | 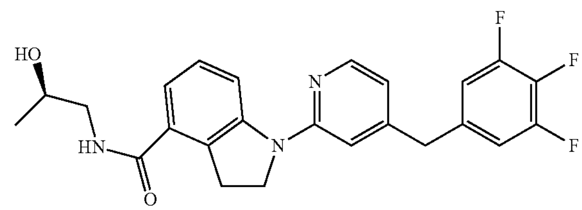 [SMILES: C[C@@H](O)CNC(=O)c1cccc2c1CCN2c1cc(Cc2cc(F)c(F)c(F)c2)ccn1] | FC | 442.2 | 2.78 |
| 180 | 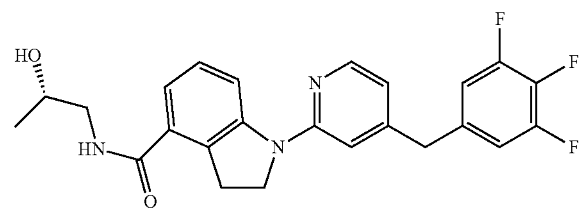 [SMILES: C[C@H](O)CNC(=O)c1cccc2c1CCN2c1cc(Cc2cc(F)c(F)c(F)c2)ccn1] | FC | 442.4 | 2.77 |
| 181 | 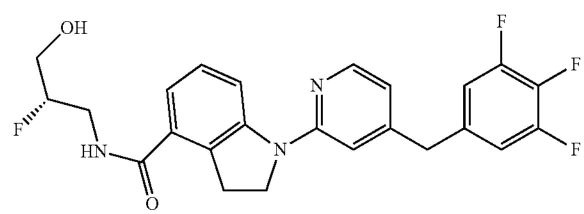 [SMILES: O=C(NC[C@H](F)CO)c1cccc2c1CCN2c1cc(Cc2cc(F)c(F)c(F)c2)ccn1] | FB | 460.4 | 2.68 |
| 182 | 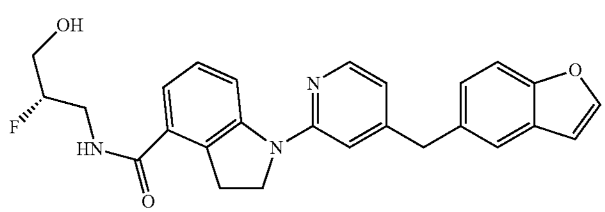 [SMILES: O=C(NC[C@H](F)CO)c1cccc2c1CCN2c1cc(Cc2ccc3occc3c2)ccn1] | FC | 446.6 | 2.53 |
| 183 | 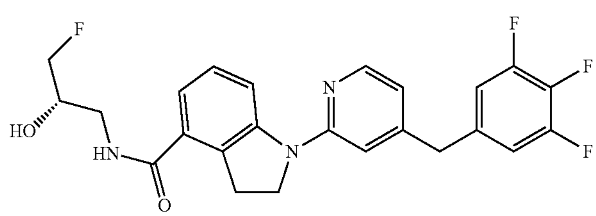 [SMILES: O=C(NC[C@H](O)CF)c1cccc2c1CCN2c1cc(Cc2cc(F)c(F)c(F)c2)ccn1] | FB | 460.4 | 2.69 |
| 184 | 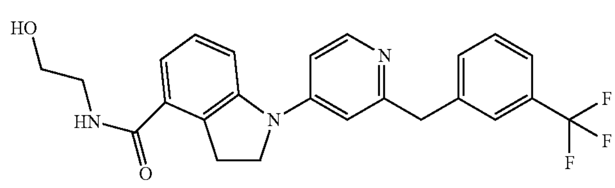 [SMILES: O=C(NCCO)c1cccc2c1CCN2c1ccnc(Cc2cccc(C(F)(F)F)c2)c1] | B | 442.4 | 2.43 |
| 185 | 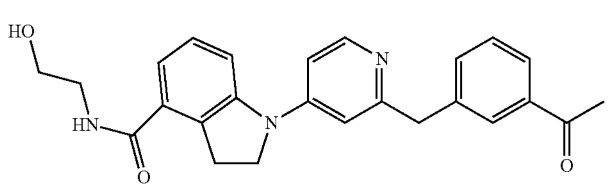 [SMILES: CC(=O)c1cccc(Cc2cc(N3CCc4c(C(=O)NCCO)cccc43)ccn2)c1] | FC | 416.6 | 2.02 |

-continued

| Cmpd No. | Chemical Structure | Synthetic Method | MS | Retention time (min) |
|---|---|---|---|---|
| 186 | 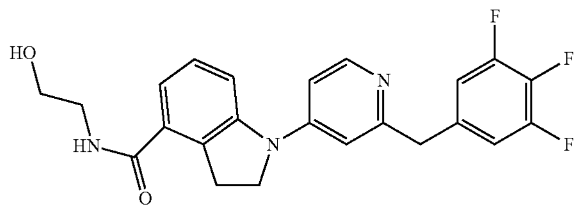 [SMILES: O=C(NCCO)c1cccc2c1CCN2c1ccnc(Cc2cc(F)c(F)c(F)c2)c1] | B | 428.2 | 2.35 |
| 187 | 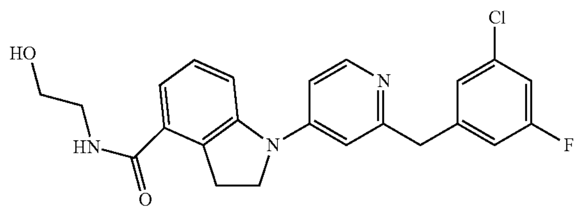 [SMILES: O=C(NCCO)c1cccc2c1CCN2c1ccnc(Cc2cc(F)cc(Cl)c2)c1] | FC | 426.2 & 428.2 | 2.39 |
| 188 | 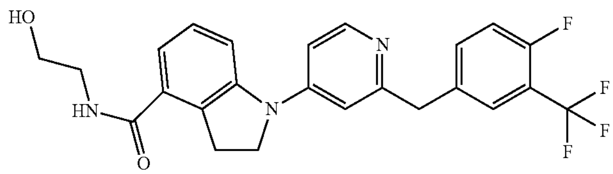 [SMILES: O=C(NCCO)c1cccc2c1CCN2c1ccnc(Cc2ccc(F)c(C(F)(F)F)c2)c1] | FC | 460.2 | 2.55 |
| 189 | 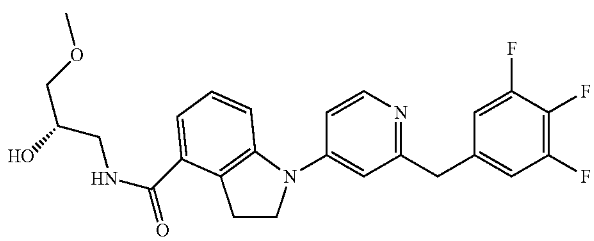 [SMILES: COC[C@@H](O)CNC(=O)c1cccc2c1CCN2c1ccnc(Cc2cc(F)c(F)c(F)c2)c1] | B | 472.4 | 2.45 |
| 190 | 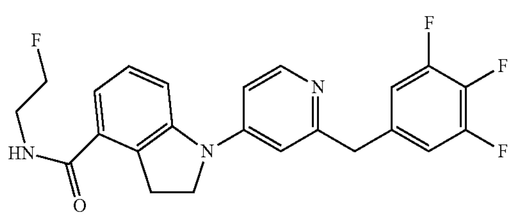 [SMILES: O=C(NCCF)c1cccc2c1CCN2c1ccnc(Cc2cc(F)c(F)c(F)c2)c1] | B | 430.4 | 3.38 |
| 191 | 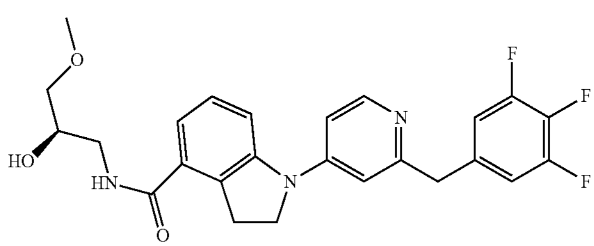 [SMILES: COC[C@H](O)CNC(=O)c1cccc2c1CCN2c1ccnc(Cc2cc(F)c(F)c(F)c2)c1] | B | 472.2 | 3.06 |
| 192 | 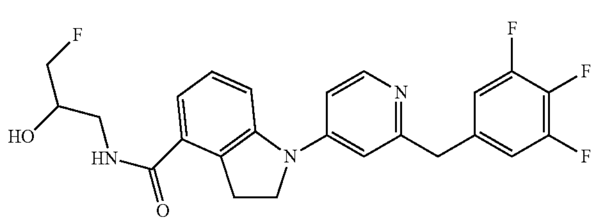 [SMILES: O=C(NCC(O)CF)c1cccc2c1CCN2c1ccnc(Cc2cc(F)c(F)c(F)c2)c1] | B | 460.4 | 3.14 |

-continued
| Cmpd No. | Chemical Structure | Synthetic Method | MS | Retention time (min) |
|---|---|---|---|---|
| 193 | 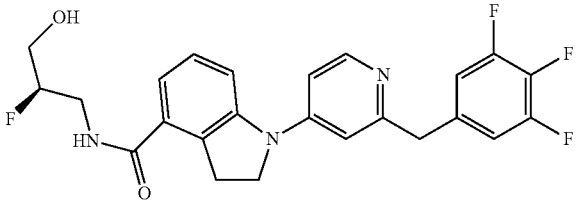 [SMILES: O=C(NC[C@@H](F)CO)c1cccc2c1CCN2c1ccnc(Cc2cc(F)c(F)c(F)c2)c1] | B | 460.4 | 3.11 |
| 194 | 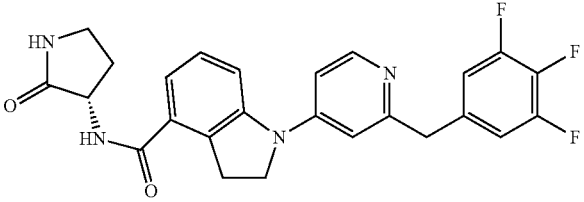 [SMILES: O=C(N[C@H]1CCNC1=O)c1cccc2c1CCN2c1ccnc(Cc2cc(F)c(F)c(F)c2)c1] | B | 467.4 | 3.05 |
| 195 | 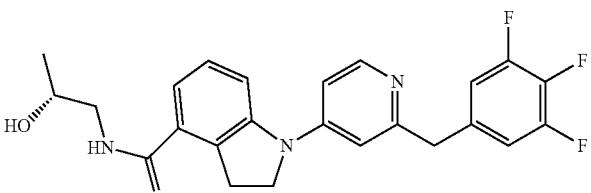 | B | 442.4 | 2.43 |
| 196 | 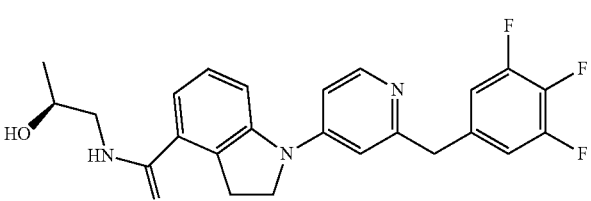 | B | 442.4 | 2.44 |
| 197 | 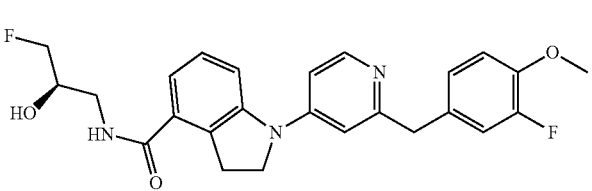 [SMILES: COc1ccc(Cc2cc(N3CCc4c(C(=O)NC[C@@H](O)CF)cccc43)ccn2)cc1F] | FC | 454.4 | 3.24 |
| 198 | 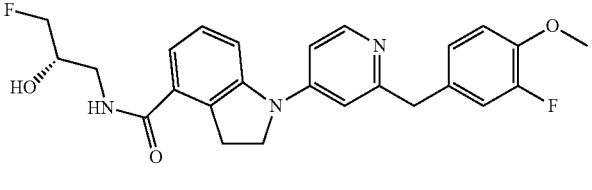 [SMILES: COc1ccc(Cc2cc(N3CCc4c(C(=O)NC[C@H](O)CF)cccc43)ccn2)cc1F] | FC | 454.4 | 3.16 |
| 199 | 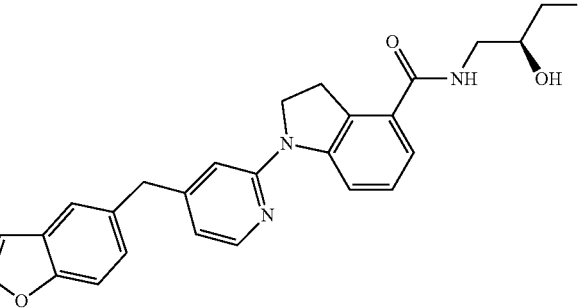 | FC | 446.2 | 3.30 |

-continued

| Cmpd No. | Chemical Structure | Synthetic Method | MS | Retention time (min) |
|---|---|---|---|---|
| 200 | 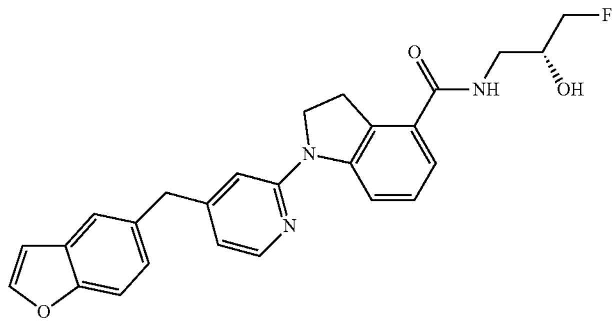 [SMILES: O=C(NC[C@@H](O)CF)c1cccc2c1CCN2c1cc(Cc2ccc3occc3c2)ccn1] | FC | 446.4 | 2.60 |
| 201 | 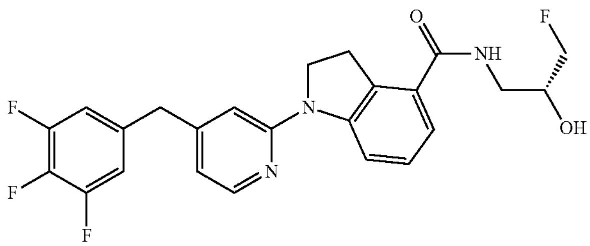 [SMILES: O=C(NC[C@@H](O)CF)c1cccc2c1CCN2c1cc(Cc2cc(F)c(F)c(F)c2)ccn1] | FB | 460.2 | 2.78 |
| 202 | 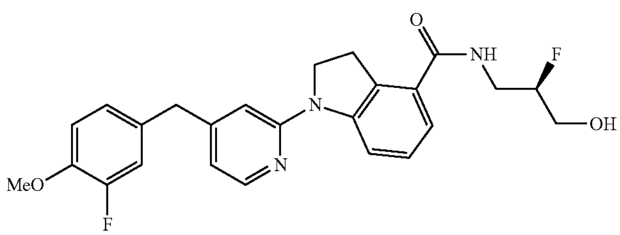 [SMILES: COc1ccc(Cc2ccnc(N3CCc4c(C(=O)NC[C@@H](F)CO)cccc43)c2)cc1F] | FC | 454.4 | 3.15 |
| 203 | 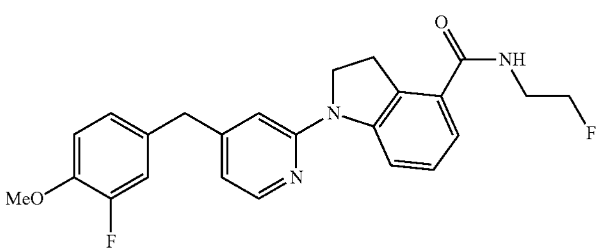 [SMILES: COc1ccc(Cc2ccnc(N3CCc4c(C(=O)NCCF)cccc43)c2)cc1F] | FC | 424.2 | 3.45 |
| 204 | 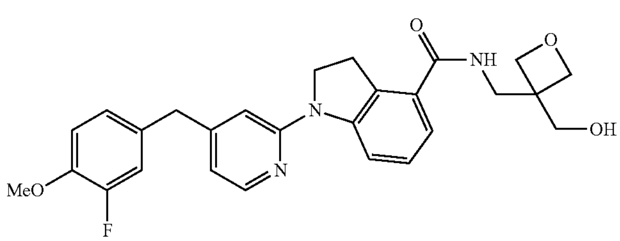 [SMILES: COc1ccc(Cc2ccnc(N3CCc4c(C(=O)NCC5(CO)COC5)cccc43)c2)cc1F] | FC | 478.4 | 3.13 |
| 205 | 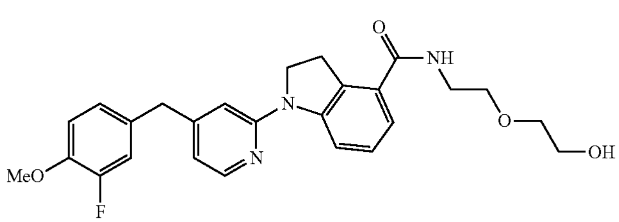 [SMILES: COc1ccc(Cc2ccnc(N3CCc4c(C(=O)NCCOCCO)cccc43)c2)cc1F] | FC | 466.4 | 3.18 |

-continued

| Cmpd No. | Chemical Structure | Synthetic Method | MS | Retention time (min) |
|---|---|---|---|---|
| 206 | 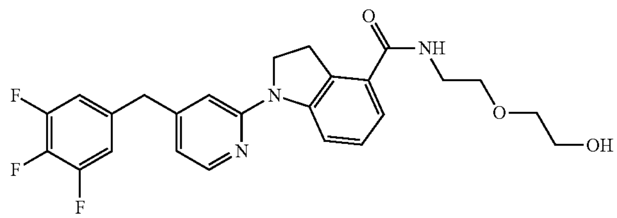 [SMILES: O=C(NCCOCCO)c1cccc2c1CCN2c1cc(Cc2cc(F)c(F)c(F)c2)ccn1] | FC | 472.2 | 3.46 |
| 207 | 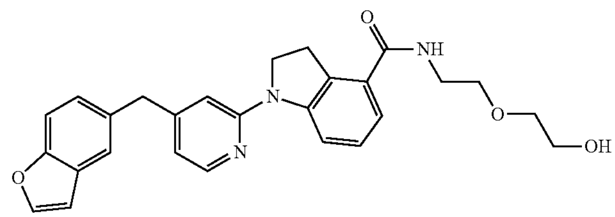 [SMILES: O=C(NCCOCCO)c1cccc2c1CCN2c1cc(Cc2ccc3occc3c2)ccn1] | FC | 458.2 | 2.48 |
| 208 | 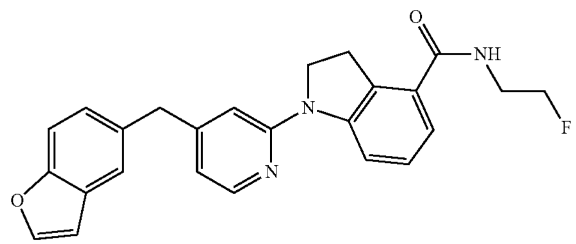 [SMILES: O=C(NCCF)c1cccc2c1CCN2c1cc(Cc2ccc3occc3c2)ccn1] | FC | 416.4 | 2.72 |

LCMS Devices Information:
Integrated System Shimadzu Controller SCL10Avp, ROM Version 5.40
Pump Shimadzu LC10ADvp, ROM Version 5.27
AutoSampler CTC PAL, Vendor Driver Ver 1.3.0.40, Device FW Ver 2.3.6
UV Detector Shimadzu SPD10Avp, ROM Version 5.23
Mass Spectrometer API 150 EX, Single Quadrupole Mass Spectrometer
Manufacturer AB Sciex Instruments
LCMS Column Information:
Brand of Column GRACE Prevail
Phase C18
Particle size 5 μm
I.D.×length 4.6 mm×50 mm
LC Method Parameters:
1). Detector
Model: SPD-10Avp
Run Time: 6.00
Acquisition Delay: 0.00
Sampling Frequency: 10 Hz
Wavelength (Ch1): 214 nm
Wavelength (Ch2): 254 nm
Lamp: D2
Polarity: Positive
2). Pumps
Pump A Model: LC-10ADvp
Pump B Model: LC-10ADvp
Binary Gradient Total Flow: 2.0 mL/min or 3.5 mL/min
Pump B Percent: 5.0
Pressure Range: 100-3000 psi
3). Gradient
Mobile phase A (pump A): 0.05% TFA in H2O Mobile phase B (pump B): 0.05% TFA in Acetonitrile
Start gradient: 5% pump B at 0 min
End gradient: 95% pump B at 5.00 min
4). CTC PAL Autosampler properties
Loop Volume1 (μl): 100
Loop Volume2 (μl): 100
Injection Volume (μl): 10.000
API 150 EX Mass Spectrometer parameters:
Scan Type: Q1 MS (Q1)
Polarity: Positive
Scan Mode: Profile
Ion Source: Turbo Spray
Data Analysis Software Version:
Analyst 1.4.1

Example 3: Homogeneous Time-Resolved Fluorescence (HTRF®) Assay for Direct cAMP Measurement HTRF cAMP assays were performed using commercially available assay kits according to the manufacturer's instructions (cAMP Dynamic 2 Assay Kit; #62AM4PEJ, Cisbio Bioassays, Bedford, Mass.). CHO-K1 or HEK293 cells stably expressing recombinant GPR52 were harvested and resuspended in assay buffer (PBS containing 0.5 mM IBMX and 0.1% BSA) at a density of $1.2 \times 10^6$ cells per mL. This cell suspension was dispensed into 384-well assay plates (ProxiPlate #6008280, PerkinElmer, Waltham, Mass.) at 5 μL per well. Columns 23 and 24 on the plates did not receive cells and were reserved for a cAMP standard curve. Test compounds were solubilized and serially diluted in DMSO using 5-fold dilutions to generate 10-point dose response curves. These serially diluted samples were then further diluted in PBS to achieve a 2× stock. The diluted compounds were transferred to triplicate assay plates (5 μL per well to achieve the 1× final assay concentration). A positive control was included in each assay run. After one-hour incubation at room temperature, 5 μL of cAMP D2 reagent diluted in lysis buffer was added to each well, followed by 5 μL of cryptate reagent. Plates were then incubated at room temperature for one hour prior to reading. Time-resolved fluorescence measurements were collected on an HTRF-capable plate reader (e.g., EnVision® (PerkinElmer, Waltham, Mass.) or PHERAstar (BMG LABTECH, Cary, N.C.)). Counts from the plate reader were fit to the cAMP standard curve included on each plate to determine the amount of cAMP in each test well. Dose-response curves were generated from the cAMP data and analyzed using a nonlinear least squares curve-fitting program to obtain $EC_{50}$ values. Mean $EC_{50}$ values were calculated from the mean log $EC_{50}$ value and are provided in Table B.

TABLE B

| Cmpd No. | $EC_{50}$ |
|---|---|
| 2 | 106 nM |
| 3 | 10.3 nM |
| 4 | 12.3 nM |
| 7 | 5.21 nM |
| 9 | 7.45 nM |
| 13 | 12.6 nM |
| 17 | 80.4 nM |
| 20 | 36.3 nM |
| 23 | 98.4 nM |
| 30 | 428 nM |
| 31 | 72 nM |
| 38 | 601 nM |
| 43 | 9.76 nM |
| 49 | 61.6 nM |
| 50 | 17.4 nM |
| 54 | 5.57 nM |
| 55 | 16 nM |
| 59 | 223 nM |
| 60 | 11.7 nM |
| 63 | 36.5 nM |
| 64 | 23.1 nM |
| 69 | 3.11 nM |
| 77 | 10.7 nM |
| 78 | 11.2 nM |
| 81 | 3.75 uM |
| 91 | 1.06 nM |
| 92 | 8.87 nM |
| 96 | 212 nM |
| 97 | 35.9 nM |
| 102 | 21.4 nM |
| 111 | 61 nM |
| 117 | 23.6 nM |
| 118 | 9.74 nM |
| 119 | 38.7 nM |
| 131 | 307 nM |
| 133 | 18.3 nM |
| 135 | 142 nM |
| 140 | 30.1 nM |
| 148 | 37 nM |
| 155 | 55.9 nM |
| 158 | 6.76 nM |
| 160 | 292 nM |
| 164 | 10.9 nM |
| 166 | 12.2 nM |
| 167 | 18.2 nM |
| 168 | 31.6 nM |
| 172 | 18 nM |
| 187 | 12.9 nM |
| 189 | 21.9 nM |
| 203 | 5.54 nM |
| 205 | 8.56 nM |

Each of the compounds in Table A was observed to have a GPR52 $EC_{50}$ value in the range of about 1.1 nM to about 6.1 μM.

Example 4: GPR52 Expression in Rodent and Human Tissues a) Rodent Tissue Preparation.

Brains were collected from male Sprague-Dawley rats (Harlan, Livermore, Calif.), and male C57BL/6J mice (Jackson Laboratories, Sacramento, Calif.), immediately frozen by immersion in 2-methylbutane (Sigma-Aldrich, St. Louis, Mo.), and stored in a plastic bag at −80° C. before sectioning. Brains were sectioned on a cryostat (−20° C., 14-20 micron thick) along the coronal plane according to the rat and mouse brain atlas (G. Paxinos and C. Watson, *The Rat Brain in Stereotaxic Coordinates*, 6th ed., 2007, Academic Press; G. Paxinos and K. B. J. Franklin, *The Mouse Brain in Stereotaxic Coordinates*, 2nd ed. 2001, Academic Press), and 1:10 equal series were generated in duplicate from the anterior olfactory nucleus to the cervical region of the spinal cord. Sections were collected on Superfrost™ Plus Slides (VWR, West Chester, Pa.) and stored at −80° C. until used.

b) Human Tissue Preparation.

Three whole human brains from individuals with no known disease history (two male, one female) were collected at post-mortem intervals not exceeding 24 hours (Asterand Bioscience, Detroit, Mich.). The brains were collected and immediately submerged in ice cold transport medium (Dulbecco's modified Eagle medium, phosphate buffered saline (PBS), or histidine-tryptophan-ketoglutarate or University of Wisconsin buffers) in a sealed plastic bag and shipped on wet ice. Upon arrival, the brains were removed from the bag and hand sliced through the coronal plane using a dissecting knife and a custom made slicing guide board with intervals ranging from 1-3 cm. Coronal brain slabs were sealed in a plastic bag and immediately frozen by immersion in 2-methylbutane cooled at −30° C. with dry ice. Coronal brain slabs were then further dissected into pieces according to the Atlas of the Human Brain (J. K. Mai, J. Assheuer and G. Paxinos, *Atlas of the Human Brain*, 2nd ed., 2004, Academic Press) to fit on a standard microscopic slide (25×60 mm) using a rotary saw or copper saw. Twenty-micrometer-thick sections were generated by sectioning each brain slab piece on a cryostat, and stored at −80° C. until further processing.

c) Rodent Radioactive In Situ Hybridization Histochemistry.

To create GPR52 cRNA probes, a PCR fragment of the entire coding region of rat GPR52 or mouse GPR52 was generated and inserted into a pBlueScript DNA expression vector (Agilent Technologies, Santa Clara, Calif.). PCR fragments were sequenced to verify orientation. Plasmids were linearized with appropriate enzymes, purified, and subsequently used for in vitro transcription. Sense and antisense $^{33}$P radiolabeled probes were generated using in vitro transcription by incubating linearized plasmids in transcription buffer containing RNasin (40 units), DTT (2 mM), ATP, CTP, and GTP (0.33 mM), [alpha-$^{33}$P]-UTP (50 mCi, NEG307 H001MC, PerkinElmer, Waltham, Mass.) and the appropriate polymerase (T7, Sp6 50 units or T3, 20 units). Probes were DNase treated, purified by ethanol precipitation and resuspended in 2× hybridization mix (8×SET, 2×Denhardt's, 0.4% SDS, 200 mM dithiothreitol (DTT), 500 ug/mL tRNA, 50 mg/mL polyA, and 50 mg/mL polyC).

Tissue sections were removed from the freezer and allowed to air dry for 30 minutes. Sections were subsequently fixed in 4% paraformaldehyde in phosphate buffer (0.1 M, pH 7.4) for 30 minutes at room temperature, rinsed 3 times in 1×PBS, and acetylated in 0.1M triethanolamine, pH 8.0 (TEA, Sigma-Aldrich, St-Louis, Mo.) for 2 minutes, then briefly in the same buffer containing 0.25% acetic anhydride. Slides were then rinsed for 5 minutes in 1×PBS and dehydrated through graded alcohol concentrations and air dried. Radiolabeled probes were diluted in 2× hybridization buffer to yield an approximate concentration of 8-10×10$^6$ cpm per slide. Dextran sulfate/formamide (20%) was added to give a 1:1 ratio with 2× hybridization buffer. Diluted probes were placed on slides, coverslipped and incubated at 55° C. for 16-18 hours in plastic trays humidified with 1×PBS. Coverslips were floated off with 1 mM DTT/4×SSC (600 mM sodium chloride and 60 mM sodium citrate, pH 7.2) and sections were subsequently washed once in 4×SSC for 10 minutes, incubated in ribonuclease A (200 μg/mL) for 60 minutes at 37° C. on a rocker, then rinsed in 2×, 1×, and 0.5×SSC for five minutes each. Sections were washed to a final stringency of 0.1×SSC at 65° C. for 1 hour, then washed twice in 0.1×SSC to cool to room temperature. Slides were then dehydrated through graded alcohols (70% and 95%) containing 300 mM ammonium acetate and then 100% ethanol, exposed to X-ray sensitive film (Kodak BioMax®, Eastman Kodak Co., Rochester, N.Y.) for 2-7 days and dipped in photographic emulsion (IB1654433, Kodak), dried, and stored in slide boxes with desiccant at 4° C. for 2-4 weeks (depending on the level of expression). After development of dipped slides following manufacturer recommendations (Kodak D19), sections were washed extensively in water, thionin stained, dehydrated in alcohol, and mounted in a xylene-based mounting medium for microscopic examination.

d) Rodent and Human Non-Radioactive In Situ Hybridization Histochemistry.

Sections were processed to detect mRNA at the cellular level by in situ hybridization using RNAscope® 2-plex (Advanced Cell Diagnostics, Inc., Hayward, Calif.) or ViewRNA® ISH tissue 2-plex assay (Affymetrix Panomics Solutions, Santa Clara, Calif.) branched DNA detection technology (See, e.g., Wang F, Flanagan J, Su N, Wang L-C, Bui S, Nielson A, Wu x, Vo H-T, Ma X-J and Luo Y. *RNAscope®: a Novel In situ RNA analysis Platform for formalin-fixed paraffin—Embedded Tissues. J. Mol. Diagnostics,* 2012, 14:22-2). Brain sections were fixed in 4% paraformaldehyde in PBS, dehydrated, treated with proteinase, and hybridized with a cocktail of oligonucleotides probes (see Table C). Probes were designed and manufactured by Advanced Cell Diagnostics, Inc. and Affymetrix, and visualized by chromogenic detection with multiple steps of amplification. Slides were then counterstained with Gill's II hematoxylin (American MasterTech Scientific, Lodi, Calif.), dried, and mounted with EcoMount (Biocare Medical, Concord, Calif.) or Ultramount (Dako, Carpinteria, Calif.) mounting medium before microscopic examination.

TABLE C

Oligonucleotide Probes for GPR52 Co-Expression Studies

| Probe Name | Probe Abbreviation | Probe NCBI Code |
|---|---|---|
| Mouse GPR52 | mGPR52 | NM_001146330 |
| Mouse dopamine receptor 1 | mDRD1 | NM_010076 |
| Mouse dopamine receptor 2 | mDRD2 | NM_010077 |
| Rat GPR52 | rGPR52 | NM_001289935 |
| Rat dopamine receptor 1 | rDRD1 | NM_012546 |
| Rat dopamine receptor 2 | rDRD2 | NM_012547 |
| Rat glutamate decarboxylase 1 | rGAD | NM_017007.1 |
| Rat vesicular glutamate transporter 1 | rGlut1 | NM_053859.2 |
| Human GPR52 | hGPR52 | NM_005684 |
| Human dopamine receptor 1 | hDRD1 | NM_000794 |
| Human dopamine receptor 2 | hDRD2 | NM_000795 |
| Human glutamate decarboxylase 1 | hGAD | NM_000817 |
| Human vesicular glutamate transporter 1 | hGlut1 | NM_020309 | e) Microscopic Evaluation of Single-Labeled Cells

Microscopic examinations were made on an Olympus BX51 connected to a digital camera CX9000 (MBF Biosciences, Williston, Vt.) controlled by Stereo Investigator software (v 11.05, MBF Biosciences, Williston, Vt.). Pictures were acquired under 10× and 40× objectives and anatomical maps were generated using the 40× objective under simultaneous brightfield and lateral darkfield illumination using a Darklite Illuminator (Micro Video Instruments, Inc., Avon, Mass.). Rodent brain cells were counted as positive for GPR52 mRNA (radioactive in situ hybridization) when the number of silver grains accumulated over the cell body was at least five times above the background (the area devoid of cells such as the corpus callosum). Brain structures and nuclei were visualized under brightfield illumination and identified according to the rat and mouse brain atlas (G. Paxinos and C. Watson, *The Rat Brain in Stereotaxic Coordinates,* 6th ed., 2007, Academic Press; G. Paxinos and K. B. J. Franklin, *The Mouse Brain in Stereotaxic Coordinates,* 2nd ed. 2001, Academic Press).

Rodent and human brain chromogenic single-labeled cells were quantified under 20× or 40× magnification when the signal over the cell body (identified by hematoxylin staining) consisted of at least 3 dots per cell. Cells were counted only if they displayed a clear cellular morphology and their size was within the range of average size of cell bodies within the area. When a cluster of cells was encountered, only cells with clearly visualized nuclei were scored. Regions of interest were delineated at low magnification using a tracing probe with the Stereo Investigator software (MBF Biosciences, Williston, Vt.) and single-labeled cells were quantified within these boundaries. For a specific region of interest, the number of single-labeled cells was calculated as a percentage of the total number of cells quantified. The region of interest (ROI) quantified for the human ventral and dorsal striatum consisted of 500 μm$^2$× 500 μm$^2$ squares. For the human cortex, layers I to VI were identified and ROI was drawn within each layer to determine the number of single-labeled cells.

A summary of the distribution and relative expression levels of GPR52 in the rat brain is provided in FIG. 15. A comparison of GPR52 expression levels in the rat and mouse brain is provided in FIG. 16. A summary of relative expression levels of GPR52 in select structures in the human brain is provided in FIG. 17. Expression levels in the rat and mouse brain were very similar. The highest expression levels in the human brain were found in the striatum. Lower but significant expression levels were found in several other structures in the human brain, including the cortex.

Example 5: GPR52 Co-Expression in Rat and Human Tissues

Rat and human tissue samples were prepared for non-radioactive in situ hybridization histochemistry as described in Example 4.

Microscopic Evaluation of Double-Labeled Cells

Microscopic examinations were made on an Olympus BX51 connected to a digital camera CX9000 (MBF Biosciences, Williston, Vt.) controlled by Stereo Investigator software (v 11.05, MBF Biosciences, Williston, Vt.). Pictures were acquired under 10× and 40× objectives and anatomical maps were generated using the 20× or 40× objective under brightfield illumination.

Rat and human brain chromogenic double-labeled cells were quantified under 20× or 40× magnification when the signal over the cell body (identified by hematoxylin staining) consisted of at least 3 dots per cell. Cells were counted only if they displayed a clear cellular morphology and their size was within the range of average size of cell bodies within the area. When a cluster of cells was encountered, only cells with clearly visualized nuclei were scored. Regions of interest were delineated at low magnification using a tracing probe with the Stereo Investigator software (MBF Biosciences, Williston, Vt.) and double-labeled cells were quantified within these boundaries. For a specific region of interest, the number of double-labeled cells was calculated as a percentage of the total number of cells quantified. The ROI quantified for the human ventral and dorsal striatum consisted of 500 $\mu m^2 \times 500$ $\mu m^2$ squares. For the human cortex, layers I to VI were identified and ROI was drawn within each layer to determine the number of double-labeled cells.

GPR52 exhibited strong co-expression with D2 in the rat striatum, and with D1 and vGlut1 in the rat cortex. GPR52 exhibited strong co-expression with D2 in the human striatum, and moderate co-expression with D1 in human cortex. GPR52 also exhibited strong co-expression with vGlut1 in the human cortex, and low levels of co-expression with D2 and GAD1 (see FIG. 18).

Example 6: Intracellular Events

Mouse Studies

To demonstrate that intracellular signaling was activated following acute and subchronic GPR52 agonist administration, C57BL/6J mice were dosed for nine days per os (P.O.) with vehicle or 5, 10, or 20 mg/kg Compound 13. On day 10, the mice previously dosed with vehicle were dosed P.O. with 5, 10, or 20 mg/kg Compound 13 ("acute" administration) or vehicle. The mice that received Compound 13 during the first nine days continued to receive the same dosages of Compound 13 on day 10 ("subchronic" administration). Tissue was collected two hours post-dose on day 10 and analyzed by qPCR, Western blot, or ELISA.

Nine week old male C57BL/6J mice from Jackson Laboratories (Sacramento, Calif.) were dosed for nine days per os (P.O., oral administration) with Compound 13 (5, 10, or 20 mg/kg, n=10 each) or vehicle (0.5% methylcellulose, n=40). On day 10, the mice previously dosed with vehicle were dosed P.O. with Compound 13 (5, 10, or 20 mg/kg P.O., n=10 each) ("acute" administration) or vehicle (0.5% methylcellulose, n=10). Mice that received Compound 13 during the first nine days continued to receive the same dosages of Compound 13 on day 10 ("subchronic" administration). Mice were sacrificed two hours post-dose on day 10, and the cortex and striatum were dissected using a mouse brain matrix. Tissues were placed in lysing matrix D tubes (MP Biomedicals, Santa Ana, Calif.) and flash frozen in liquid nitrogen. Samples were placed at −70° C. in preparation for subsequent RNA isolation.

RNA was isolated from cortex and striatal samples by homogenization in 1 mL of TRIzol® reagent (Cat. No. 15596018; Life Technologies, Carlsbad, Calif.) using a MP FastPrep® homogenizing machine (speed 4, 30 second homogenization). Ultrapure phenol:chloroform:isoamyl alcohol (200 µL; Cat. No. 15593-031; Life Technologies, Carlsbad, Calif.) was immediately added, and the samples were incubated at room temperature for 10 minutes before centrifugation at 15,000 rpm (15 minutes at 4° C.). The upper clear phase was removed and placed in a new tube containing 500 µL isopropanol. Tubes were incubated for 10 minutes at room temperature and then centrifuged at 10,000 rpm for 10 minutes. The RNA pellet was then washed twice in ice cold 70% ethanol and centrifuged at 10,000 rpm for 10 minutes. The RNA pellet was then dissolved in sterile RNase/DNase-free water and quantitated using a Nano-Drop™ Lite (Thermo Scientific, Waltham, Mass.). Striatal and cortical RNA samples were then treated with DNase (DNase I; Cat No. 18068-015, Life Technologies, Carlsbad, Calif.) and reverse transcribed using qScript™ cDNA synthesis kit (Quanta Biosciences Inc., Gaithersburg, Md.) according to the manufacturer's instructions for quantitative PCR (qPCR). Quantitative PCR was performed in triplicate using mouse Fos (Mm00487425_m1; Life Technologies, Carlsbad, Calif.), mouse neurotensin (Mm00481140_m1; Life Technologies, Carlsbad, Calif.), and mouse Zif268 (EGR1; Mm00656724_m1; Life Technologies, Carlsbad, Calif.) primer/probe sets, and normalized within the same well using a mouse beta-actin primer/probe set. iTaq™ Universal Supermix (Cat. No. 172-5132; Bio-Rad Laboratories, Inc., Philadelphia, Pa.) and samples were run on the QuantStudio™ 6 Flex Real-Time PCR System (Life Technologies, Carlsbad, Calif.). QuantStudio™ 6 and 7 Flex software was used to analyze the data.

Total protein was isolated from cortex and striatal samples in 500 µL of RIPA Lysis and Extraction Buffer (Cat. No. 89901; Pierce Biotechnology, Rockford, Ill.) containing sodium orthovanadate (Cat. No. S6508; Sigma-Aldrich, St. Louis, Mo.), protease (Cat. No. 87785; Life Technologies, Carlsbad, Calif.), and phosphatase (Cat. No. 78420; Life Technologies, Carlsbad, Calif.) inhibitor cocktails. A handheld pestle homogenizer was used to disrupt the tissue. All steps were carried out at 4° C. to minimize protein degradation. After two hours of mixing at 4° C., the homogenate was centrifuged at 12,000 rpm for 20 minutes at 4° C. The pellet was discarded and the supernatant was aliquoted and quantitated for protein using a Pierce Microplate BCA Protein Assay Kit (Cat. No. 23252; Life Technologies, Carlsbad, Calif.). Protein samples (20 µg) were denatured in LDS sample buffer (NP0007; Life Technologies, Carlsbad, Calif.) and reducing agent (Cat. No. NP0009; Life Technologies Corporation) and placed at 70° C. for 10 minutes. Samples were run on 4-12% Bis-Tris Gels (Cat. No. NP0322; Life Technologies, Carlsbad, Calif.) in MES SDS buffer (Cat. No. NP0002; Life Technologies, Carlsbad, Calif.) containing antioxidant (Cat. No. NP0005; Life Technologies, Carlsbad, Calif.) at 200V for 30 minutes. Separated protein was then transferred onto a pre-cut PVDF blotting membrane (LC2002; Life Technologies, Carlsbad, Calif.) in transfer buffer (NP006; Life Technologies, Carlsbad, Calif.) using a x-cell SureLock® Blot Module (Life Technologies, Carlsbad, Calif.) at 30V for one hour. Membranes were blocked in 5% milk (Cat. No. 170-6404EDU;

Bio-Rad Laboratories, Inc., Philadelphia, Pa.) for one hour prior to incubation with primary antibodies against DARPP-32 (LS-C150127; LifeSpan BioSciences Inc., Seattle, Wash.), phosphorylated DARPP-32 (Thr34) (sc-21601; Santa Cruz Biotechnology, Dallas, Tex.), or Actin (sc-130656; Santa Cruz Biotechnology, Dallas, Tex.) in 5% Bovine Serum Albumin (Cat. No. 05470; Sigma-Aldrich, St. Louis, Mo.) overnight at 4° C. Membranes were incubated with secondary antibodies goat anti-rabbit HRP (AP187P; EMD Millipore, Billerica, Mass.) or rabbit anti-goat HRP (R21459; Life Technologies, Carlsbad, Calif.) in 5% milk for one hour. Membranes were incubated in ECL substrate (Cat No. 32106; Life Technologies, Carlsbad, Calif.) and developed on BioMax® Light-1 Film (Eastman Kodak Co., Rochester, N.Y.) using a AFP Mini-Med 90 automatic film processor (AFP Imaging Corporation, Mount Kisco, N.Y.). Densitometry was performed using UVP VisionWorks® LS Software (UVP, LLC, Upland, Calif.), where total DARPP and phosphorylated DARPP-32 (Thr34) levels were normalized against Actin prior to calculating phosphorylated DARPP-32 (Thr34) versus total DARPP levels. Protein kinase A (Cat. No. ab139435; abcam, Cambridge, Mass.) and phosphorylated Creb (pS133; Cat No. ab176659; abcam, Cambridge, Mass.) were determined on cortical and striatal protein samples via enzyme linked immunosorbent assay (ELISA).

a) PKA, PP2A, DARPP-32, and CREB.

PKA was activated in the striatum and cortex, and protein phosphatase 2A (PP2A) was phosphorylated in the striatum. Further, DARPP-32 (which has been shown to be activated by antipsychotics and is known to regulate striatal function) was activated in the striatum. In addition, cAMP response element-binding protein (CREB) is a nuclear transcription factor that binds to cAMP response elements (CRE) involved in the formation of spatial memory. CREB was phosphorylated in the striatum and cortex following acute administration (see FIG. 19).

b) IEGs and Neurotensin.

Immediate early genes (IEGs) c-fos and zif268 were upregulated in the striatum and cortex. These immediate early genes are induced by antipsychotics, and are involved in functional plasticity in striatal neurons. Increased neurotensin (a neuropeptide implicated in the pathophysiology of schizophrenia and downregulated in the CSF of individuals with schizophrenia, which can be restored by the administration of antipsychotics) was also observed in the striatum (see FIG. 19).

Rat Studies

Forty male Sprague-Dawley rats (250-350 g, Harlan, Livermore, Calif.) were handled for one week and dosed with water (2.5 ml, per os) for three days before the study. Rats were dosed with either 20% (2-hydroxypropyl)-β-cyclodextrin (HPCD) or compound 13 (5, 10, or 20 mg/kg PO) and returned to their home cages. Sixty minutes later, they were euthanized with $CO_2$ inhalation and their brains were collected, immediately frozen by immersion in 2-Methylbutane (Sigma-Aldrich, St-Louis, Mo.) cooled at −30° C. and stored at −80° C. Brains were sectioned on a cryostat (−20° C., 20 micrometers thick) along the coronal plane according to the rat brain atlas (G. Paxinos and C. Watson, *The Rat Brain in Stereotaxic Coordinates*, 6th ed., 2007, Academic Press) and 1:10 equal series were generated from the anterior olfactory nucleus to the cervical region of the spinal cord. Sections were collected on Superfrost™ Plus Slides (VWR, West Chester, Pa.) and stored at −80° C. until used.

A rat c-fos cRNA probe was generated by inserting a PCR fragment including 77 bp of the 3' untranslated region and 770 bp of the 3' coding region in a pBlueScript expression vector (Agilent Technologies, Santa Clara, Calif.). PCR fragments were sequenced to verify orientation. Sense and antisense $^{35}$S labelled probes were synthesized in vitro by incubating linearized plasmids in transcription buffer containing dithiothreitol (8 mM), RNase Inhibitor (40 Units), ATP and GTP (0.4 mM), T7 or T3 Polymerase (40 Units) and [alpha-$^{35}$S]-CTP and [alpha-$^{35}$S]-UTP (120 µCi, PerkinElmer, Waltham, Mass.) for 90 minutes at 37° C. Probes were then DNase treated, cleaned up using a ProbeQuant™ G-50 Microcolumn (#2890 3408, GE Healthcare, Little Chalfont, UK) and resuspended in 2× hybridization mix (8×SET, 2×Denhardt's, 0.4% SDS, 200 mM dithiothreitol (DTT), 500 µg/ml tRNA, 50 mg/ml polyA, and 50 mg/ml polyC). In situ hybridization histochemistry was carried out as described in Example 4 herein.

Dry slides were exposed to X-ray sensitive film (Kodak BioMax®, Eastman Kodak Co., Rochester, N.Y.) for 5-10 days and optical density was determined to evaluate transcript levels. One section per animal for all groups (n=8-10) was matched anatomically according to the Paxinos and Watson atlas (Bregma: 2.04 mm) and processed simultaneously to allow for direct comparisons in the same region. Semiquantitative analyses were performed using Scion Image software based on NIH Image (Scion Corporation, Frederick, Md.). Digital images were captured in the linear range of the gray levels from X-ray films illuminated by a Northern Light Desktop Illuminator (Imaging Research Inc, St Catherine, Canada) with a CCD camera (CCD72, DAGE MTI, Michigan City, Ind.) fitted with a Nikkor 55 mm lens. Signal pixels of a region of interest were defined as having a gray value of 3.5 standard deviations above the mean gray value of white matter (corpus callosum) set as the background. The number of pixels and the average gray values above the set background for each region of interest were multiplied to generate the relative integrated optical density. The accumbens nuclei (core and shell) and the dorsomedial and dorsolateral striatum from each side were analyzed and averaged for each animal.

Figure 21:
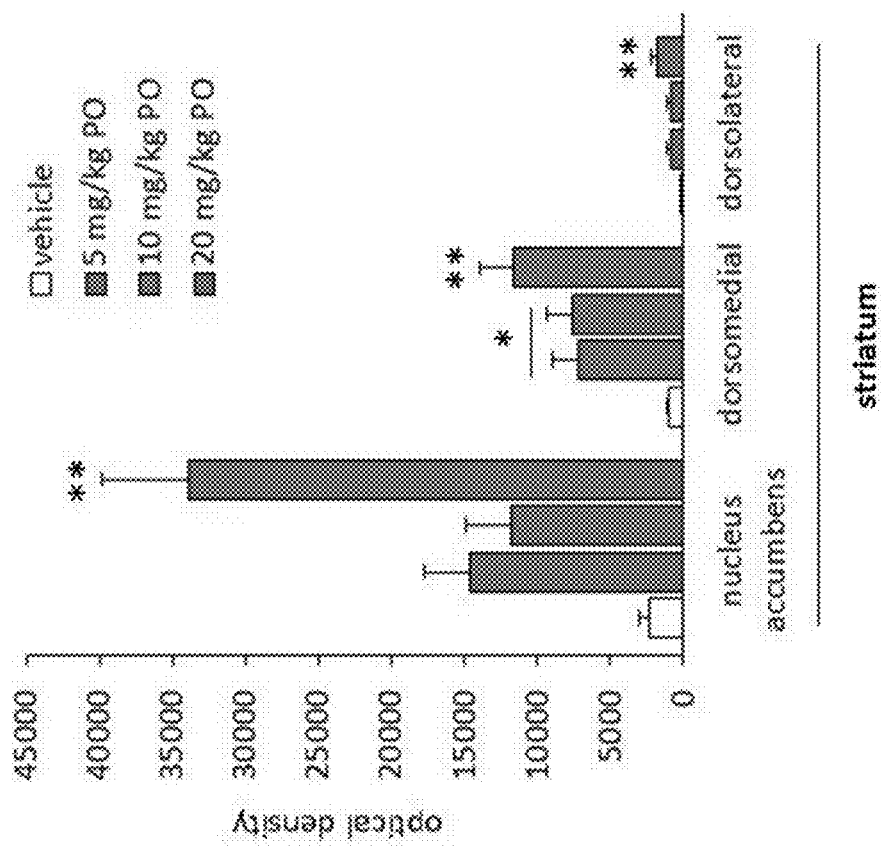
FIG. 21 shows the activation of immediate early genes in the rat brain following the administration of Compound 13.

Medial regions of the brain have been associated with the efficacy of existing antipsychotics, while lateral regions have been associated with side effects. IEGs were found to be activated in the dorsomedial region of the rat brain (see FIG. 21), demonstrating that a region of the striatum associated with the efficacy of existing antipsychotics is also affected by the administration of a GPR52 agonist.

Figure 20:
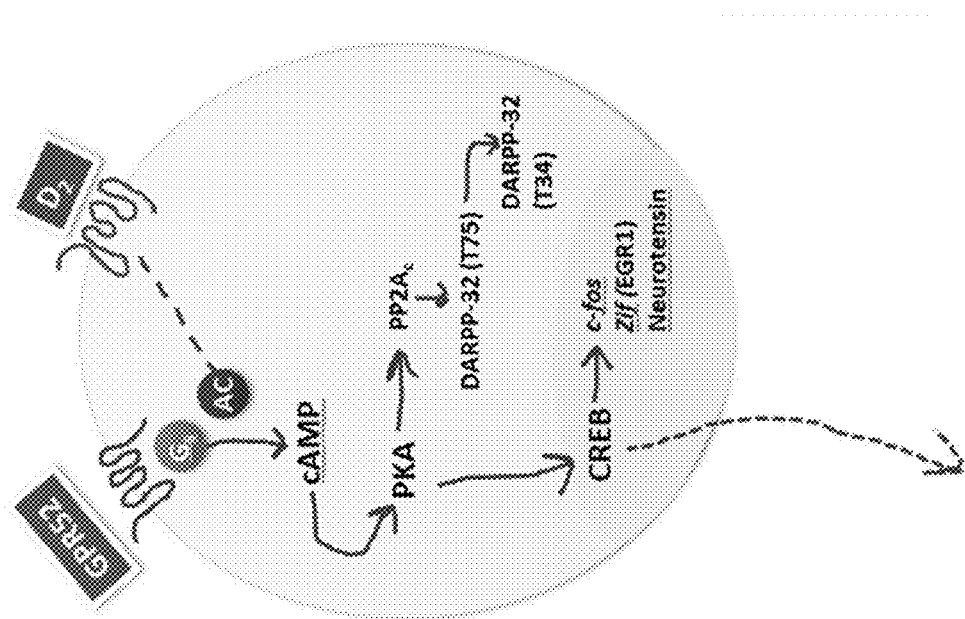
FIG. 20 depicts the theoretical signaling cascade following the administration of Compound 13 to mice.

GPR52 agonist administration caused measurable changes in intracellular signaling markers in mice neurons, and the activation of immediate early genes in mice and rat neurons. A depiction of the theoretical signaling cascade is provided in FIG. 20.

Example 7: GPR52 Knockout Mice

GPR52 knock-out (KO) mice were generated using a targeted strategy for constitutive knock-out of the Gpr52 allele (Jackson Labs, Sacramento, Calif.). A targeting vector was generated using clones from the C57BL/6J RPCIB-731 BAC library. Gpr52 exon 1 contains the complete open reading frame (ORF). Exon 1 and approximately 1.5 kb of the proximal promoter region were replaced with a F3-flanked positive selection cassette (puromycin resistance) expressed under the control of a eukaryotic promoter and containing a polyadenylation signal. Homologous recombinant clones were isolated using positive (puromycin resistance) and negative (thymidine kinase) selection. Replacement of the proximal promoter and exon 1 with the positive selection cassette, and Flp-mediated removal of the positive selection cassette, resulted in deletion of the complete ORF. The targeting vector was then electroporated into the TaconicArtemis C57BL/6N Tac ES cell line. Correctly targeted ES cells were microinjected into blastocysts and transferred to surrogate C57BL/6 females. Male chimeras were bred to C57BL/6J females to generate F1 mice with germline transmission of the KO allele, which were then bred with littermates to generate homozygous KO mice.

Figure 22:
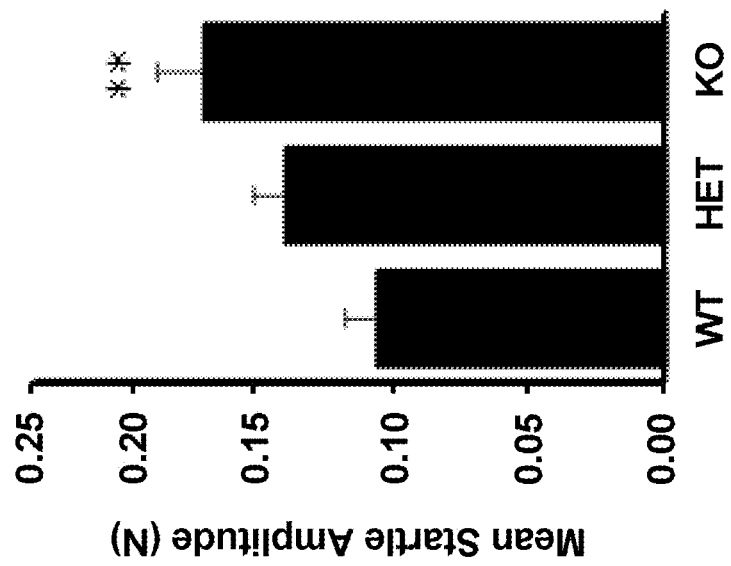
FIG. 22 shows the mean startle response in GPR52 WT, HET, and KO knockout mice.

The GPR52 KO mice exhibited a mild increase in locomotor activity, including increased rearing and increased nose-poking in modified open field. The KO mice also exhibited an increased startle response (see FIG. 22), enhanced acquisition of an operant task, an increased preference for sweetened solutions, and a late-onset decrease in body weight.

Example 8: Locomotor Activity

Locomotor activity was assessed in a photocell monitoring caging system (Kinder Scientific MotorMonitor System, Kinder Scientific, Poway, Calif.). Each cage consisted of a standard plastic rodent cage (24×45.5 cm) placed inside a stainless steel frame. Infrared photocell beams were located across the long axis of the frame. Interruption of a photocell beam due to movement of the animal in front of a beam was recorded and used as a measure of ambulatory activity. Photocell beam interruptions were automatically recorded by a computer system. Perforated cage tops were placed on top of the test enclosures during testing.

To measure basal locomotor activity, male C57/BL6 mice (8-16 weeks) (Jackson Laboratories, Sacramento, Calif.) were transferred in home cages to the testing room approximately 60 minutes prior to testing. Approximately 15 minutes after arrival in the testing room, a dark cycle commenced, with lights turning off and infrared lights turning on for experimenter visibility. Thirty minutes after the lights were turned off, animals were individually weighed and administered either vehicle (20% hydroxypropyl-β-cyclodextrin) Compound 13 (1, 2, 5, 10, or 20 mg/kg P.O.), or another GPR52 agonist (10 mg/kg P.O.) and returned to home cages. Fifteen minutes later, mice were placed into locomotor cages and activity was recorded for 60 minutes. The $ED_{50}$ value for Compound 13 is provided in Table D.

TABLE D

| Cmpd. No. | $ED_{50}$ (% Inhibition in Mouse Basal Locomotor Activity)[1] |
|---|---|
| 13 | 2.7 mg/kg |

[1]P.O.

The percent inhibition values in mouse basal locomotor activity for the compounds are provided in Table E.

TABLE E

| Cmpd. No. | % Inhibition in Mouse Basal Locomotor Activity[1] |
|---|---|
| 13 | 70 |
| 43 | 79 |
| 54 | 66 |
| 61 | 61 |
| 78 | 72 |
| 92 | 65 |

TABLE E-continued

| Cmpd. No. | % Inhibition in Mouse Basal Locomotor Activity[1] |
|---|---|
| 106 | 81 |
| 138 | 72 |
| 140 | 68 |
| 166 | 70 |
| 167 | 62 |
| 179 | 68 |
| 202 | 67 |

[1]10 mg/kg P.O.

Genotype-Dependent Locomotor Activity

Figures 23A, 23B:
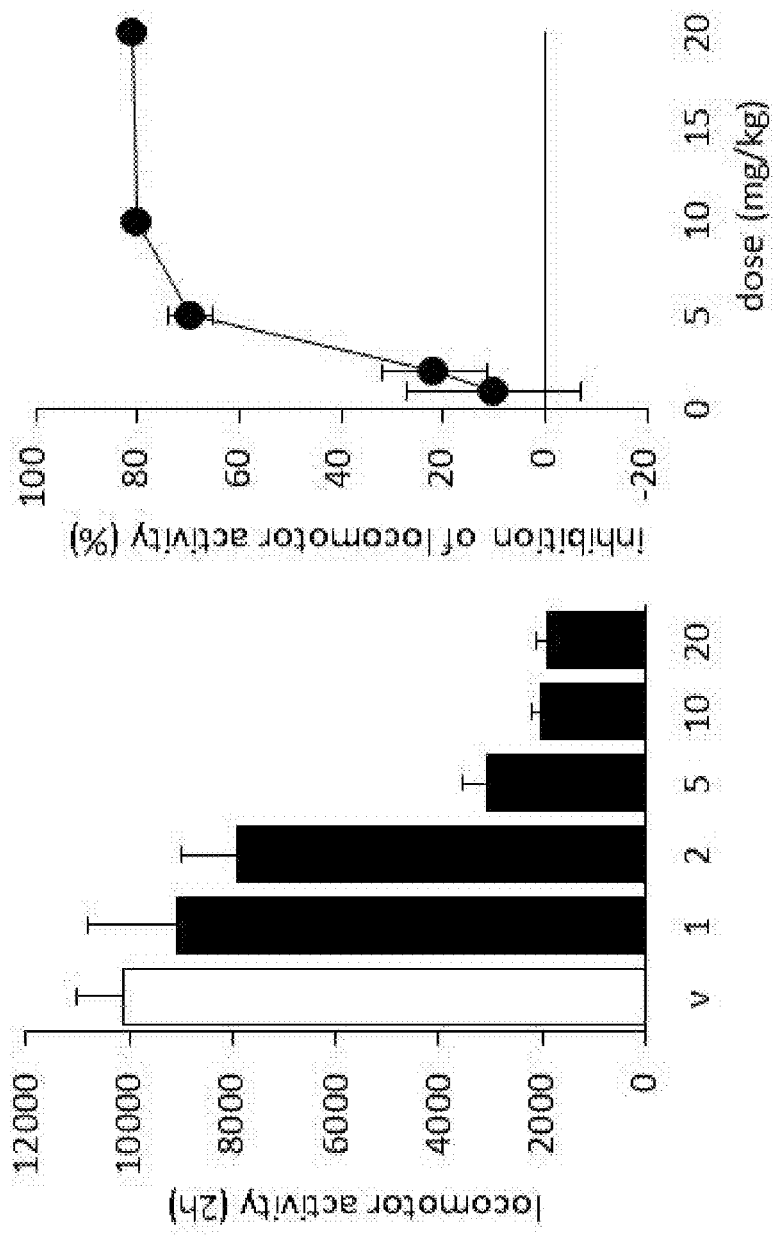
FIGS. 23A-B show genotype-dependent locomotor activity in GPR52 WT, HET, and KO mice following the administration of Compound 13.
Figure 23C:
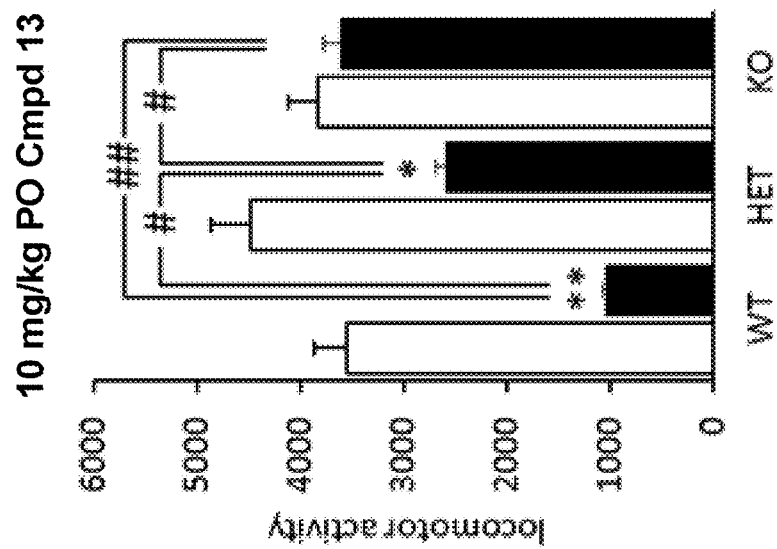
FIG. 23C shows genotype-dependent locomotor activity in GPR52 WT, HET, and KO mice following the administration of Compound 13.

The same experiment was then performed to measure locomotor activity in wild type (WT), GPR52 heterozygous (HET), and GPR52 knockout (KO) mice. Data is expressed both as the total locomotor activity counts for each group, and as a percentage of vehicle scores (% inhibition=[((vehicle-treatment)/treatment)*100]) (see FIGS. 23A-C). A genotype-dependent loss of locomotor activity was observed (see FIG. 23C), indicating that the hypoactivity associated with Compound 13 is GPR52-mediated, and confirming that there is a motor component to GPR52 function.

Amphetamine-Stimulated Locomotor Activity

To measure basal locomotor activity, male Sprague-Dawley rats (250-380 g) were injected with Compound 13 in home cages (0.5, 1, 2, 5, 10, and 20 mg/kg P.O. in volume of 3 mL/kg) and placed into locomotor activity test cages 30 minutes later. Activity was then measured for the following 30 minutes. Animals were naïve to the testing apparatus prior to performing the test. Activity is expressed as the total number of ambulations over the 30 minutes of locomotor testing (i.e., 30-60 minutes post-injection).

To examine the effect of Compound 13 on amphetamine-induced locomotion, rats were placed into locomotor activity test cages for a 60-minute period of habituation, at which point they were injected with Compound 13 (0.5, 1, 2, 5, 10, and 20 mg/kg P.O. in volume of 3 mL/kg). Fifteen minutes later, rats were injected with amphetamine (0.5 mg/kg SC in volume of 1 mL/kg). Activity was then measured for 90 minutes. Activity is expressed both as the total number of ambulations from minutes 15-45 of the locomotor testing (i.e., 30-60 minutes post-Compound 13 administration and 15-45 minutes post-amphetamine administration), and as a percentage of vehicle scores (% inhibition=[((vehicle-treatment)/treatment)*100]).

Figure 24:
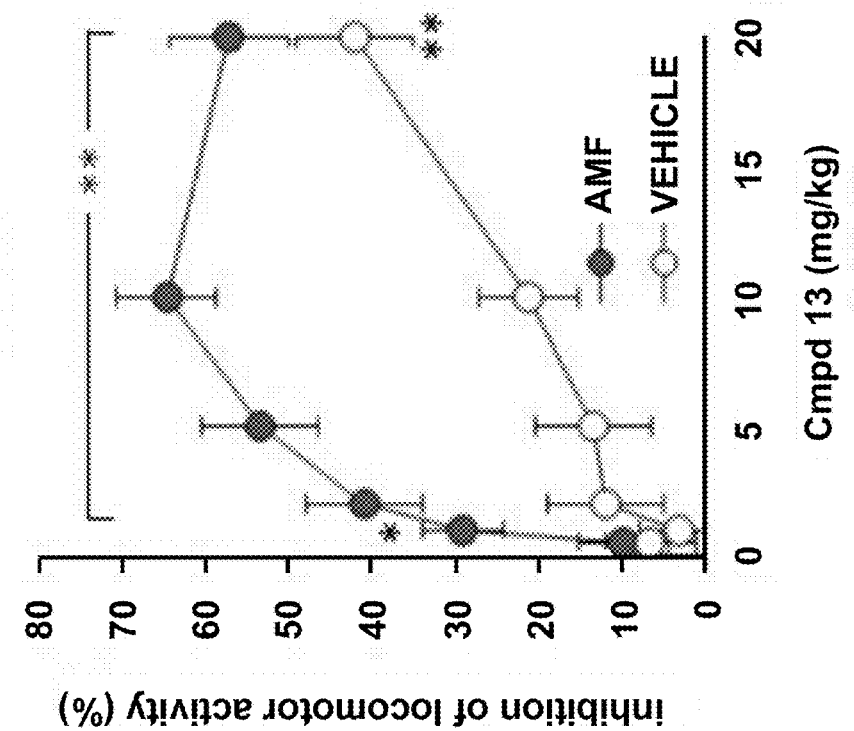
FIG. 24 shows the effect of Compound 13 on amphetamine-stimulated locomotion in rats.

Amphetamine-stimulated activity represents a hyperdopaminergic state (e.g., as found in psychosis), while blockade of basal activity represents a potential side effect. Compound 13 blocked amphetamine-stimulated locomotion at several doses (see FIG. 24). In contrast, a significant reduction in basal locomotor activity was only seen at the highest dose of Compound 13.

Example 9: Prepulse Inhibition

Prepulse inhibition of the startle response (PPI) was tested to evaluate interactions with and similarities to antipsychotics. PPI measures the pre-conscious ability to filter sensory information, and is cross-modal and cross-species. PPI is disrupted in certain clinical populations, including in populations of schizophrenia, OCD, and Tourette's syndrome patients. Further, PPI has been shown to be pharmacologically disrupted by psychotomimetics (e.g., NMDA receptor antagonists and dopamine receptor agonists) and improved by antipsychotics.

Prepulse inhibition testing was conducted in enclosed startle chambers (Kinder Scientific StartleMonitor System, Kinder Scientific, Poway, Calif.) in which animals were placed into restrainers secured onto startle-sensing plates. A constant background white noise of 65 dB was audible in the chambers throughout testing. Test sessions consisted of a 5-minute acclimation period, followed by 10 (mouse) or 20 (rat) habituation trials to the startle stimulus (120 dB), followed by 35 trials of the following presented in pseudo-random order: 120 dB startle stimulus (6 trials), 120 dB startle stimulus preceded by a prepulse 4 dB above background (6 trials), 120 dB startle stimulus preceded by a prepulse 8 dB above background (6 trials), 120 dB startle stimulus preceded by a prepulse 12 dB above background (6 trials), 120 dB startle stimulus preceded by a prepulse 16 dB above background (6 trials), and no stimulus (5 trials). Inter-trial intervals throughout the test session ranged from 5-15 seconds and were presented in pseudorandom order.

For each animal, mean startle amplitude for each trial type during the 35-trial block was calculated, and percent pre-pulse inhibition (% PPI) for each prepulse intensity was calculated as the percent decrease in the mean startle amplitude in response to a given prepulse and 120 dB startle stimulus relative to the mean startle amplitude in response to the 120 dB startle stimulus alone. The % PPI was then calculated for each animal as the mean % PPI across all four prepulse intensities.

A baseline test session was conducted, and animals were sorted into groups of 'good performers' and 'poor performers' with relatively high or low baseline % PPI, respectively. Mice or rats exhibiting a low mean startle (<0.2N) during the baseline test were not used for further studies.

Mouse Studies

For studies examining the effects of compounds in male 129Sv/Ev mice (20-26 g) with relatively low PPI, compounds or combinations (Compound 13 10 mg/kg P.O. in a volume of 10 mL/kg, haloperidol 3 mg/kg P.O. in a volume of 10 mL/kg, clozapine 10 mg/kg P.O. in a volume of 10 mL/kg, or the combination of Compound 13 and haloperidol injected as a cocktail P.O. in volume of 10 mL/kg) were administered, and the mice were immediately returned to home cages. Thirty minutes later, the mice were placed into startle chambers and testing commenced.

MK-801 is an NMDA receptor antagonist that has been used to mimic psychosis. For studies examining the effects of compounds on MK-801-induced disruption of PPI in mice with relatively high PPI, compounds or combinations (vehicle, Compound 13 10 mg/kg P.O. in a volume of 10 mL/kg, haloperidol 3 mg/kg P.O. in a volume of 10 mL/kg, and the combination of Compound 13 and haloperidol injected as a cocktail P.O. in volume of 10 mL/kg) were administered, and the mice were immediately returned to home cages. Fifteen minutes later, the mice were dosed with vehicle or MK-801 (0.3 mg/kg IP in volume of 10 mL/kg) and again returned to home cages. Fifteen minutes later, mice were placed into startle chambers and testing commenced.

Rat Studies

Male Sprague-Dawley rats (250-380 g) with relatively high PPI were administered vehicle or Compound 13 (5 or 20 mg/kg P.O. in volume of 3 mL/kg) and returned to home cages. Fifteen minutes later, the rats were administered vehicle, amphetamine (0.5 mg/kg SC in volume of 1 mL/kg), or MK-801 (0.3 mg/kg SC in volume of 1 mL/kg) and again returned to home cages. Fifteen minutes later, the rats were placed into startle chambers and testing commenced.

Figures 25A, 25B:
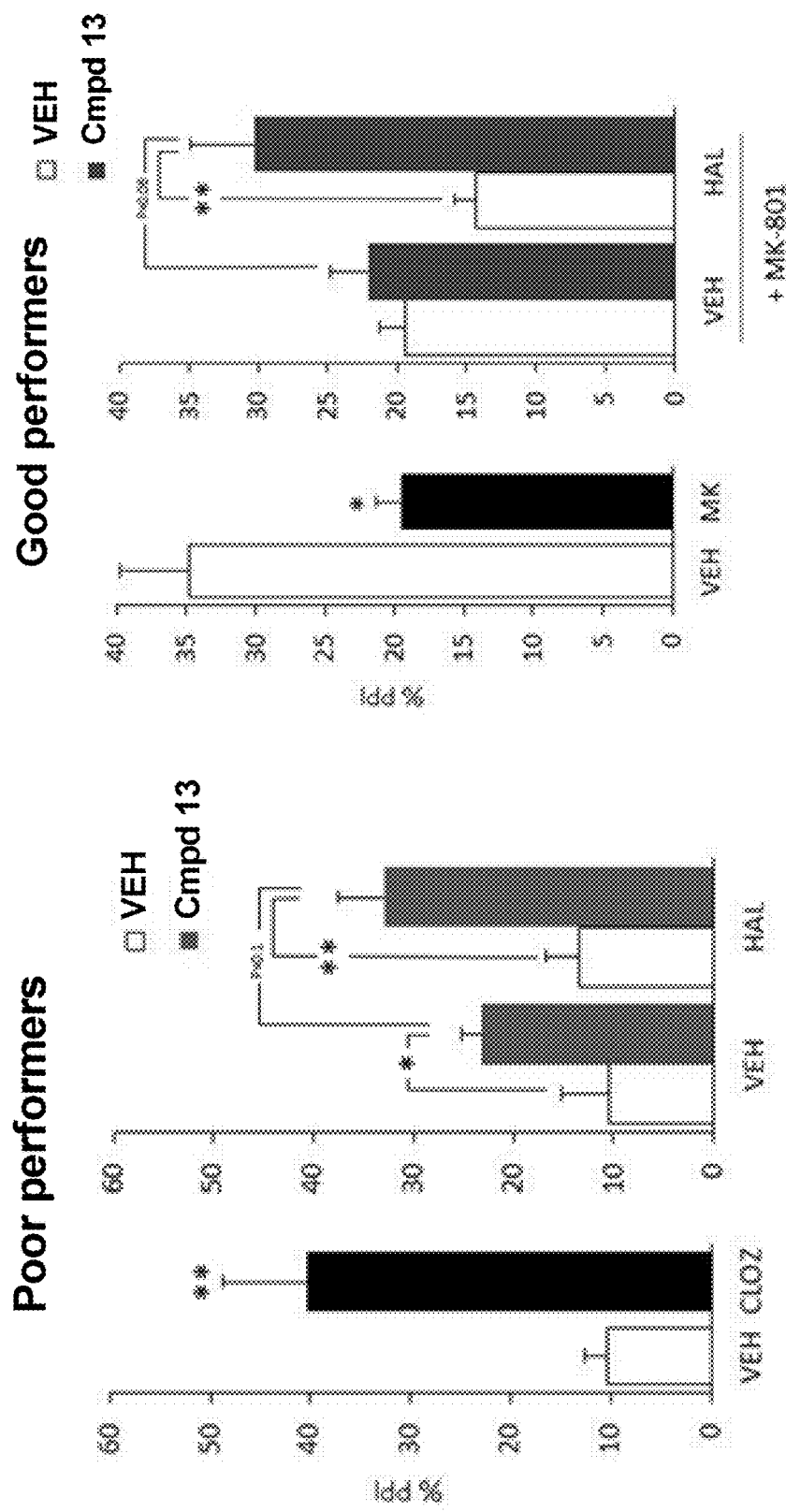
FIGS. 25A-B show prepulse inhibition in mice with relatively low (FIG. 25A) or high (FIG. 25B) prepulse inhibition following the administration of vehicle, haloperidol, MK-801, and/or Compound 13.
Figures 26A, 26B:
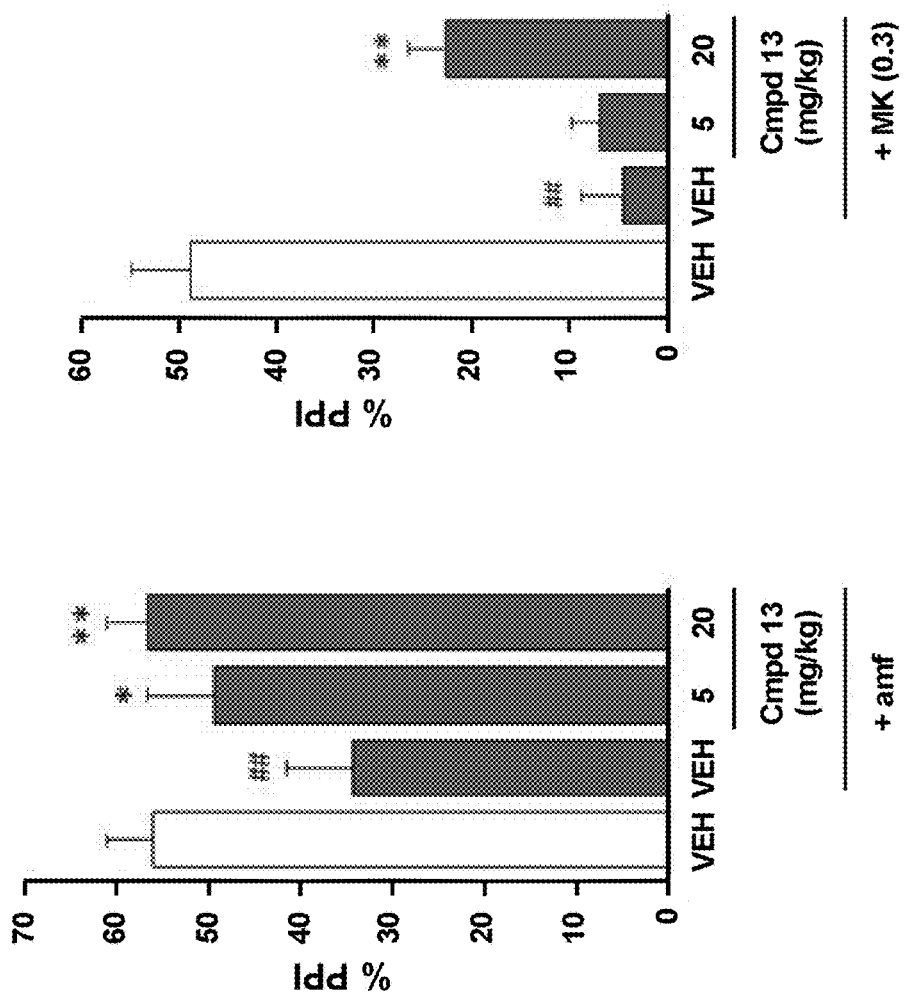
FIGS. 26A-B show prepulse inhibition in rats following the administration of vehicle, amphetamine, MK-801, and/or Compound 13.

The administration of Compound 13 in mice increased basal % PPI in 'poor performers' (see FIG. 25A), and the combination of Compound 13 and haloperidol reversed MK-801-induced disruption in % PPI in 'good performers' (see FIG. 25B). The administration of Compound 13 in rats reversed amphetamine- and MK-801-induced disruption in % PPI in 'good performers' (see FIGS. 26A-B). These findings demonstrate an improvement in the ability to filter sensory information and a reversal of effects caused by a psychotomimetic following the administration of a GPR52 agonist.

Example 10: Catalepsy

Catalepsy is used as a model for detecting extrapyramidal side effects of antipsychotic drugs. To examine catalepsy following the administration of a GPR52 agonist, male Sprague-Dawley rats (250-380 g) were administered vehicle or Compound 13 (5, 10, 20, 30, or 100 mg/kg P.O. in volume of 3 mL/kg) (see FIG. 27A), or vehicle or haloperidol (0.1, 0.3, or 1 mg/kg subcutaneous (S.C.)) (see FIG. 27B) and returned to home cages. The rats were removed from home cages 45 minutes later and placed on a vertical stainless steel grid, and the latency to move both forepaws from their starting position was measured for a maximum of 30 seconds. The test was repeated three times consecutively.

Catalepsy is expressed as the average latency to move both forepaws over the three trials. Latency increased in the rats administered haloperidol (see FIG. 27B), but was unchanged in rats administered Compound 13 (see FIG. 27A).

Example 11: Prolactin

Another unwanted side effect of certain antipsychotics is hyperprolactinemia. To examine prolactin levels following the administration of a GPR52 agonist, male Sprague Dawley rats (Harlan Laboratories, San Diego, Calif.) were single-housed, handled, and moved to a private housing room one week prior to testing. Rats were individually handled and sham dosed P.O. for four days prior to testing. For an assessment of haloperidol (0.1 and 1 mg/kg P.O.) and Compound 13 (1, 10, and 100 mg/kg P.O.) on basal prolactin release, rats were dosed with acidic 20% HP-β-cyclodextrin (HBCD) or compound at 3 mL/kg P.O. in their housing room 60 minutes prior to harvest. For interaction studies, rats were dosed with 20% HBCD or Compound 13 (10 mg/kg P.O.) 90 minutes prior to harvest, and additionally with 20% HBCD vehicle or haloperidol (0.3 and 1 mg/kg P.O.) 60 minutes prior to harvest. Rats were individually taken to the harvest room, and trunk blood was collected into 4 mL EDTA tubes following live decapitation. Samples were stored on wet ice until collection was complete, then spun in a cooling centrifuge at 2400 rpm for 20 minutes. Plasma was collected and frozen for subsequent analysis using a Rat Prolactin ELISA kit (ALPCO Diagnostics: Cat#55-PRLRT-E01).

Briefly, frozen plasma was thawed on ice and mixed prior to initiation of the ELISA. Twenty-five microliters of sample plasma along with serially diluted standards (lyophilized purified rat prolactin diluted with rat prolactin calibrator/sample diluent), and calibrator/sample diluent used as a blank were placed in a 96-well plate provided with the ELISA kit. Samples, blank, and standards were measured in duplicate. Sample buffer (50 μL) was also added to each well and the plate was incubated for two hours at room temperature on a plate shaker (Lab-Line Instruments: Model #4625, Conquer Scientific, San Diego, Calif.), shaking at greater than 900 rpm. The plate was then washed four times with 300 μL of diluted 1× wash buffer. Enzyme-labeled Rat Prolactin antibody (200 μL; horseradish peroxidase-labeled polyclonal anti-rat prolactin antibody) was then added to all wells and the plate was incubated for one hour on a plate shaker at greater than 900 rpm. The plate was then washed four times with 300 μL of 1× wash buffer before adding 200 μL of liquid TMB-Substrate Solution (3, 3',5, 5'-Tetra-Methyl-Benzidine in buffered peroxide solution, Life Technologies, Carlsbad, Calif.) to all the wells. The plate was then incubated in the dark for 30 minutes at room temperature. Fifty microliters of stop solution (2M hydrochloric acid) was added to the wells prior to reading on a 96-well plate reader (SpectraMax® 340PC; Molecular Devices, Sunnyvale, Calif.) at 450 nM. The quantity of prolactin in each sample was calculated using a standard curve.

Figures 28A, 28B:
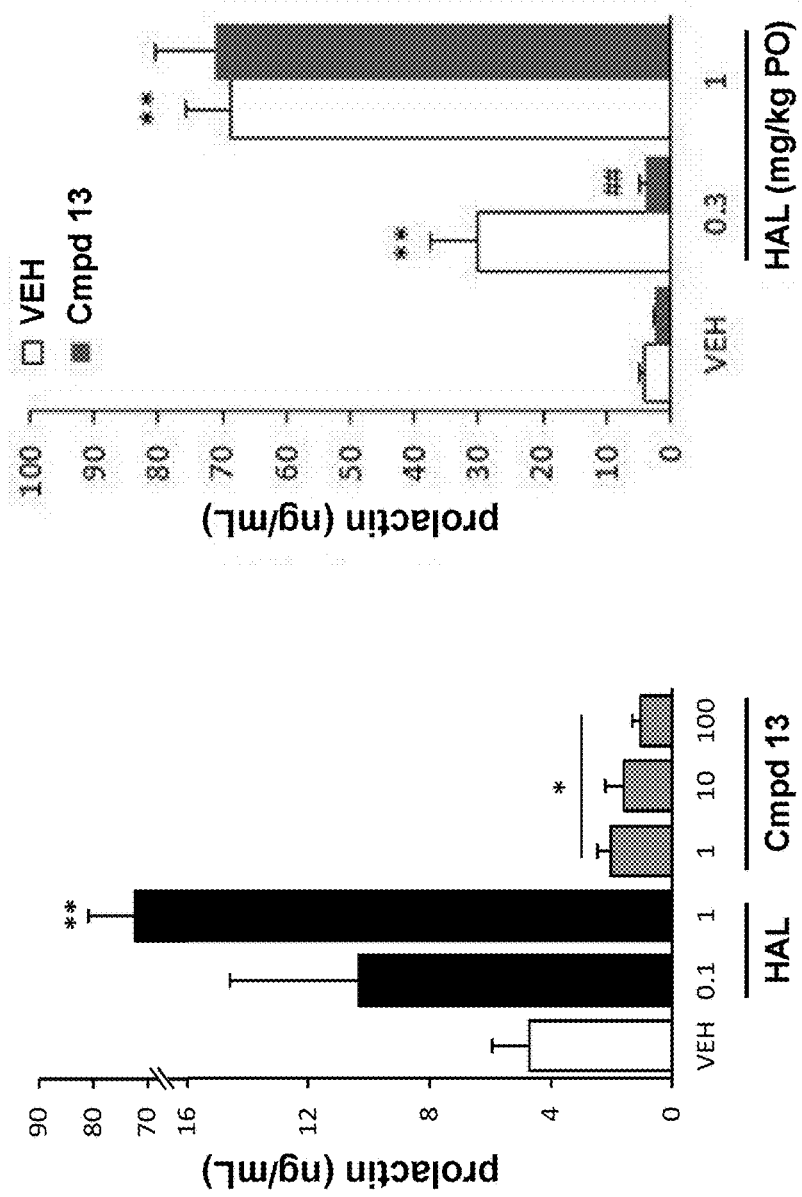
FIGS. 28A-B show prolactin levels in rats following the administration of vehicle, haloperidol, and/or Compound 13.

Prolactin levels increased following the administration of haloperidol. In contrast, prolactin levels decreased following the administration of Compound 13 (see FIG. 28A). Further, Compound 13 reversed a haloperidol-induced increase in prolactin levels at a low dose of haloperidol (see FIG. 28B).

Example 12: Brain Penetration

Plasma and brain exposure were evaluated to determine the brain penetration of compounds described herein. Male C57BL6 mice were administered a single per oral (PO) dose of compound at 3 or 10 mg/kg (as a free base) formulated in 20% HPCD in 0.9% NaCl. Blood and brain samples were collected 60 minutes post-dose (n=3-6 animals). Blood was collected via cardiac puncture and stored on ice prior to the separation of plasma by centrifugation. Brains were extracted from the cranium and frozen on dry ice. Tissue samples were stored at approximately −80° C. prior to bioanalytical analysis.

Analyte plasma and brain concentrations were determined by LC/MS/MS. The mean ratio of brain concentration to plasma concentration for each compound is provided in Table F.

TABLE F

| Compound No. | PO Dose (mg/kg) | Brain/Plasma Ratio[1] |
|---|---|---|
| 5 | 3 | 4.49 |
| 13 | 3 | 3.51 |
| 42 | 10 | 12.40 |
| 43 | 10 | 5.45 |
| 47 | 10 | 4.67 |
| 54 | 10 | 6.32 |
| 58 | 10 | 7.76 |
| 69 | 10 | 0.87 |
| 78 | 10 | 1.36 |
| 79 | 10 | 0.16 |
| 92 | 10 | 3.00 |
| 108 | 10 | 1.67 |
| 166 | 10 | 2.85 |

[1] 60 minute time point

Example 13: Plasma and Brain Concentrations

Plasma and brain concentration profiles were evaluated for 8 hours following the administration of a single 5 mg/kg per oral (PO) dose of Compound 13 in male CD-1 mice. The samples from each time point were collected, prepared, and analyzed using a similar protocol as described in Example 12.

Figure 29:
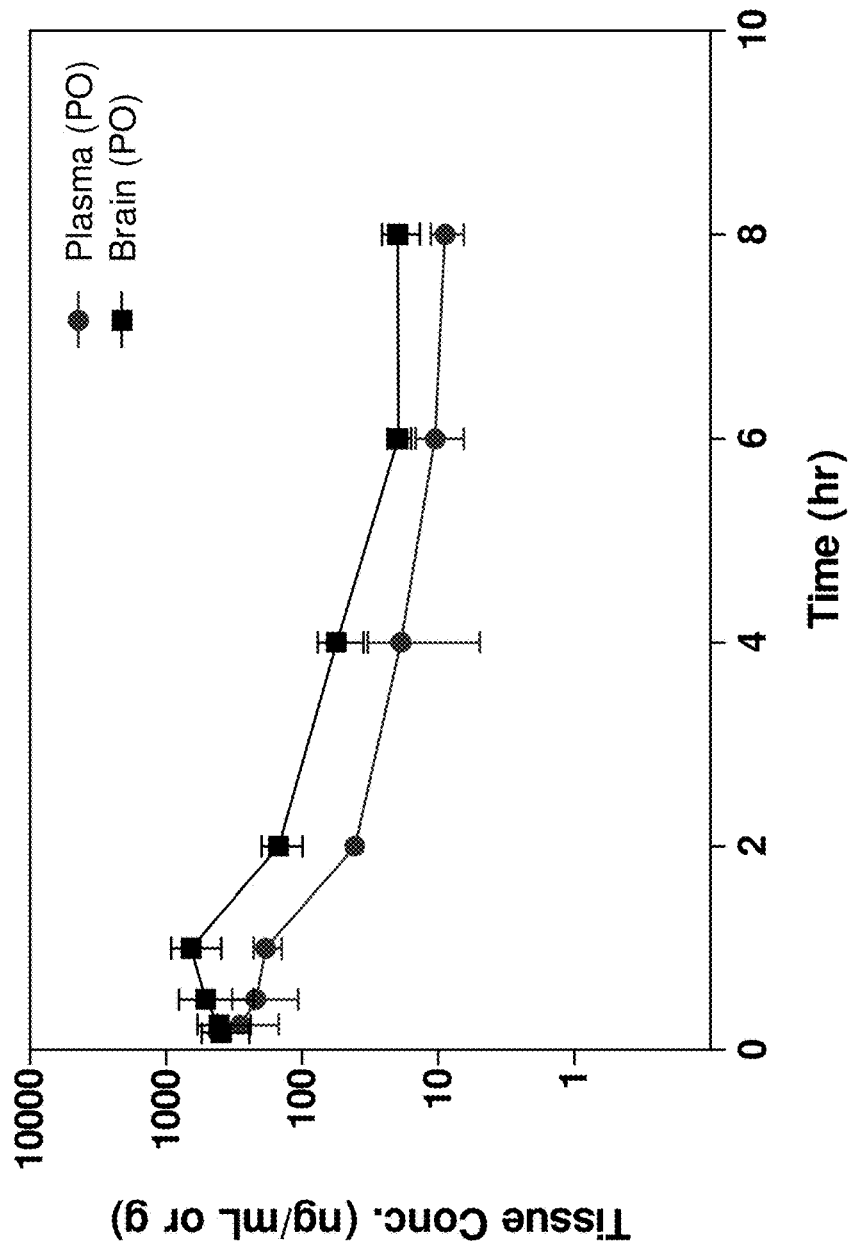
FIG. 29 shows plasma and brain concentration profiles in male CD-1 mice over an 8 hour period following administration of a single 5 mg/kg per oral (PO) dose of Compound 13.

The plasma and brain concentration profiles for Compound 13 are shown in FIG. 29.

The effect of the GPR52 agonists of the present invention can also be determined by the following methods.

MEA Neurochips.

To investigate the effect of a GPR52 agonist on patterns of electrical activity in primary cortical cultures, the compound can be tested in neurochips and compared to the "fingerprints" and phenotypic effects of several marketed drugs, such as e.g. haloperidol, (NeuroProof GmbH, Rostock, Germany).

The following steps are performed. Frontal cortex tissue from embryonic day 15-16 NRMI mice is grown on 5×5 cm$^2$ glass neurochips (Center for Network Neuroscience, University of North Texas, Denton, Tex.). Each neurochip contains a multi-electrode array (MEA) with a dual recording matrix (with 32 passive electrodes per matrix) and indium tin oxide conductors. After establishing a stable activity pattern for four weeks, MEA neurochips are placed into sterilized constant-bath recording chambers and tested for native activity. The MEA neurochips are then treated with increasing concentrations of test compound(s) and comparative compound(s) (1 pM-1 mM) and recorded to generate concentration/response profiles.

The MEA neurochips allow for extracellular recording of action potentials ("spikes") from up to 128 neurons simultaneously. Spikes are recorded in spike trains and clustered in "bursts" (defined by the beginning and end of short spikes). Bursts are quantitatively characterized via direct spike train analysis using the NeuroEXplorer (Plexon Inc., Dallas, Tex.) and NPWaveX (NeuroProof GmbH, Rostock, Germany) programs. Several parameters can be tested, including general activity (e.g., spike rate, burst rate, burst period, and event rate); burst structure (e.g., burst duration, burst area, burst spike number, and maximal spike rate in bursts); oscillatory behavior (e.g., standard deviation of spike rate, standard deviation of percentage of spikes within bursts, standard deviation of distance between bursts, and maximum amplitude); and synchronicity (e.g., CVnet of spike rate, CVnet of burst area, average distance of bursts in a population, and average number of units involved in a population burst). A total of 200 activity-describing spike train parameters are analyzed per data set, and classified against a database of marketed drugs. Data is subjected to cross validation, similarity analysis, and characterized by parameter.

Object Recognition.

Male C57BL/6J mice are habituated to an open field (51 cm×38 cm×25 cm) for five minutes on two consecutive days. On the training day (day 3), two identical objects are placed in adjacent corners of the open field, and subjects are allowed to explore freely for 10 minutes. Immediately after training, mice are injected with vehicle (20% hydroxypropyl-β-cyclodextrin), the test compound (e.g. 2, 5, or 10 mg/kg IP), or a comparative compound (e.g. 20 mg/kg IP), and returned to their home cages. Testing occurs 24 hours later, when mice are placed in the presence of both a familiar (previously explored) and a novel object, and allowed to explore the objects and the arena for five minutes. Exploration of the objects is recorded by video camera and subsequently scored, and the difference in time spent exploring each object during the test session is used to indicate recognition of the previously explored object. The difference is expressed as a proportion of total time spent exploring both objects (d(N−F/N+F), where N is the novel and F is the familiar object).

Finally, one aspect of the present invention relates to the following preferred embodiments:

i) A compound selected from compounds of Formula (Ia) and pharmaceutically acceptable salts, solvates, hydrates, and N-oxides thereof:

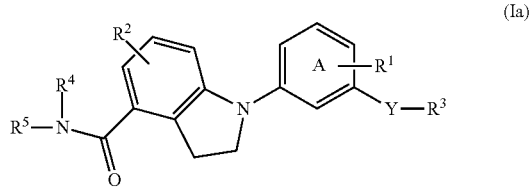

(Ia)

wherein:
Y is selected from: —CH$_2$—, —O—, and —S—;
Ring A is pyridinediyl or pyrazine-2,6-diyl;
R$^1$ is H or C$_1$-C$_6$ alkyl;
R$^2$ is H or halogen;
R$^3$ is aryl or heteroaryl, wherein each ring is optionally substituted with one or more groups selected independently from: C$_1$-C$_6$ acyl, C$_1$-C$_6$ acyloxy, C$_1$-C$_6$ alkoxy, C$_1$-C$_6$ alkylcarboxamide, C$_1$-C$_6$ alkyl, cyano, C$_1$-C$_6$ haloalkoxy, C$_1$-C$_6$ haloalkyl, halogen, hydroxyl, and hydroxy-C$_1$-C$_6$-alkyl; and said C$_1$-C$_6$ alkyl is optionally substituted with one or more groups selected independently from: C$_1$-C$_6$ alkylamino, C$_2$-C$_6$ dialkylamino, and oxo;
R$^4$ is H; and
R$^5$ is selected from: H, C$_1$-C$_6$ alkyl, heteroaryl, heteroaryl-C$_1$-C$_6$ alkyl, heterocyclyl, heterocyclyl-C$_1$-C$_6$ alkyl, and hydroxy-C$_1$-C$_6$-alkyl; and each group is optionally substituted with one or more groups selected independently from: C$_1$-C$_6$ alkoxy, C$_1$-C$_6$ alkylcarboxamide, C$_1$-C$_6$ alkyl, cyano, C$_1$-C$_6$ alkylamino, C$_2$-C$_6$ dialkylamino, C$_1$-C$_6$ haloalkyl, halogen, hydroxyl, hydroxy-C$_1$-C$_6$-alkoxy, hydroxy-C$_1$-C$_6$-alkyl, and oxo.

ii) The compound according to i), wherein Y is —CH$_2$—.
iii) The compound according to i), wherein Y is —O—.
iv) The compound according to i), wherein Y is —S—.
v) The compound according to any one of i)-iv), wherein Ring A is pyridinediyl.
vi) The compound according to any one of i)-iv), wherein Ring A is:

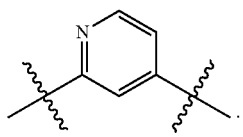 [SMILES: *c1ccnc(*)c1]

vii) The compound according to any one of i)-iv), wherein Ring A is:

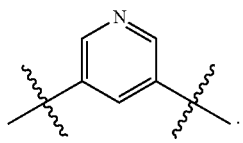 [SMILES: *c1cncc(*)c1]

viii) The compound according to any one of i)-iv), wherein Ring A is:

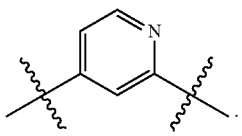

ix) The compound according to any one of i)-iv), wherein Ring A is:

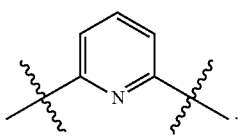 [SMILES: *c1cccc(*)n1]

x) The compound according to any one of i)-iv), wherein Ring A is pyrazine-2,6-diyl of the formula:

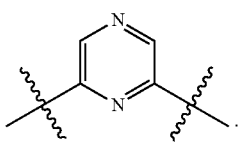

xi) The compound according to any one of i)-x), wherein R$^1$ is H or methyl.
xii) The compound according to any one of i)-x), wherein R$^1$ is H.
xiii) The compound according to any one of i)-x), wherein R$^1$ is C$_1$-C$_6$ alkyl.
xiv) The compound according to any one of i)-x), wherein R$^1$ is methyl.
xv) The compound according to any one of i)-xiv), wherein R$^2$ is H or fluoro.
xvi) The compound according to any one of i)-xiv), wherein R$^2$ is H.
xvii) The compound according to any one of i)-xiv), wherein R$^2$ is halogen.
xviii) The compound according to any one of i)-xiv), wherein R$^2$ is fluoro.
xix) The compound according to any one of i)-xviii), wherein R$^3$ is aryl or heteroaryl, wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.
xx) The compound according to any one of i)-xviii), wherein R$^3$ is aryl optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.
xxi) The compound according to any one of i)-xviii), wherein R$^3$ is heteroaryl optionally substituted with one or more groups selected independently from: chloro, cyano, fluoro, methoxy, methyl, and trifluoromethyl.
xxii) The compound according to any one of i)-xviii), wherein R$^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein said $C_1$-$C_6$ alkyl is optionally substituted with one or more groups selected independently from: $C_1$-$C_6$ alkylamino, $C_2$-$C_6$ dialkylamino, and oxo.

xxiii) The compound according to any one of i)-xviii), wherein $R^3$ is phenyl optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein said $C_1$-$C_6$ alkyl is optionally substituted with one or more groups selected independently from: $C_1$-$C_6$ alkylamino, $C_2$-$C_6$ dialkylamino, and oxo.

xxiv) The compound according to any one of i)-xviii), wherein $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ alkoxy, $C_1$-$C_6$ alkyl, cyano, $C_1$-$C_6$ haloalkyl, and halogen.

xxv) The compound according to any one of i)-xviii), wherein $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

xxvi) The compound according to any one of i)-xviii), wherein $R^3$ is phenyl optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

xxvii) The compound according to any one of i)-xviii), wherein $R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: chloro, cyano, fluoro, methoxy, methyl, and trifluoromethyl.

xxviii) The compound according to any one of i)-xviii), wherein $R^3$ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl.

xxix) The compound according to any one of i)-xviii), wherein $R^3$ is selected from: 3-((dimethylamino)methyl)phenyl, 3-(trifluoromethoxy)phenyl, 3-(trifluoromethyl)phenyl, 3,4,5-trifluorophenyl, 3,4-difluorophenyl, 3,5-difluoro-4-methoxyphenyl, 3,5-difluorophenyl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, and 4-methoxy-3-methylphenyl.

xxx) The compound according to any one of i)-xviii), wherein $R^3$ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3,4-dihydro-2H-benzo[b][1,4]dioxepin-7-yl, 3,5-dimethylisoxazol-4-yl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl.

xxxi) The compound according to any one of i)-xxx), wherein $R^5$ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

xxxii) The compound according to any one of i)-xxx), wherein $R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

xxxiii) The compound according to any one of i)-xxx), wherein $R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

xxxiv) The compound according to any one of i)-xxx), wherein $R^5$ is selected from: H, (3-(hydroxymethyl)oxetan-3-yl)methyl, (dimethylamino)ethyl, 1-(2-hydroxyethyl)-1H-pyrazol-4-yl, 1-(2-hydroxyethyl)piperidin-4-yl, 1,3-dihydroxybutan-2-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2,3-dihydroxypropyl, 2-acetamidoethyl, 2-cyanoethyl, 2-fluoro-3-hydroxypropyl, 2-fluoroethyl, 2-hydroxy-2-(pyridin-2-yl)ethyl, 2-hydroxy-2-(pyridin-3-yl)ethyl, 2-hydroxy-2-(pyridin-4-yl)ethyl, 2-hydroxy-3-methoxypropyl, 2-hydroxyethyl, 2-hydroxypropyl, 2-morpholinoethyl, 2-oxopyrrolidin-3-yl, 2-oxotetrahydrofuran-3-yl, 3-(dimethylamino)-2-hydroxypropyl, 3-(methylamino)-3-oxopropyl, 3,3,3-trifluoro-2-hydroxypropyl, 3-fluoro-2-hydroxypropyl, 3-hydroxypropyl, 6-oxopiperidin-3-yl, cyanomethyl, methyl, pyridin-4-yl, and tetrahydrofuran-3-yl.

xxxv) The compound according to any one of i)-xxx), wherein $R^5$ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl) ethyl, 2-(2-oxopyrrolidin-1-yl)ethyl, 2-(pyrrolidin-1-yl) ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

xxxvi) The compound according to i), selected from compounds of Formula (Im) and pharmaceutically acceptable salts, solvates, hydrates, and N-oxides thereof:

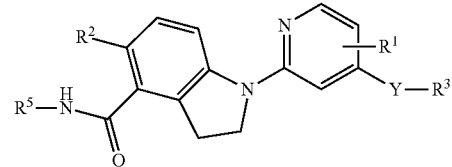

(Im)

wherein:
Y is selected from: —$CH_2$—, —O—, and —S—;
$R^1$ is H or $C_1$-$C_6$ alkyl;
$R^2$ is H or halogen;
$R^3$ is aryl or heteroaryl, wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and
$R^5$ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: 2-hydroxyethyl, acetamido, cyano, dimethylamino, fluoro, hydroxy, hydroxymethyl, methoxy, methyl, methylamino, oxo, and trifluoromethyl.

xxxvii) The compound according to i), selected from compounds of Formula (Im) and pharmaceutically acceptable salts, solvates, hydrates, and N-oxides thereof:

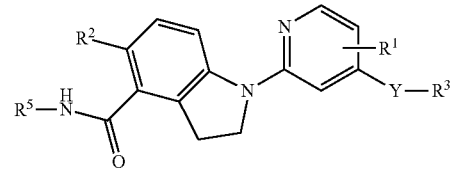

(Im)

wherein:
Y is selected from: —$CH_2$—, —O—, and —S—;
$R^1$ is H or $C_1$-$C_6$ alkyl;
$R^2$ is H or halogen;
$R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein said $C_1$-$C_6$ alkyl is optionally substituted with one or more groups selected independently from: $C_1$-$C_6$ alkylamino, $C_2$-$C_6$ dialkylamino, and oxo; and $R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

xxxviii) The compound according to i), selected from compounds of Formula (Im) and pharmaceutically acceptable salts, solvates, hydrates, and N-oxides thereof:

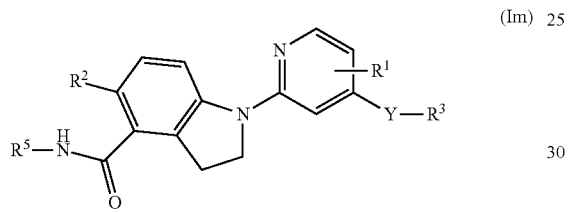

(Im)

wherein:
Y is selected from: —$CH_2$—, —O—, and —S—;
$R^1$ is H or methyl;
$R^2$ is H or fluoro;
$R^3$ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and $R^5$ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

xxxix) The compound according to i), selected from compounds of Formula (Im) and pharmaceutically acceptable salts, solvates, hydrates, and N-oxides thereof:

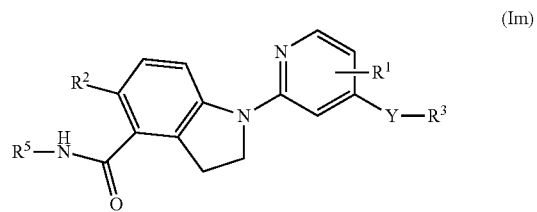

(Im)

wherein:
Y is selected from: —$CH_2$—, —O—, and —S—;
$R^1$ is H or methyl;
$R^2$ is H or fluoro;
$R^3$ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl; and $R^5$ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

xl) The compound according to i), selected from compounds of Formula (Io) and pharmaceutically acceptable salts, solvates, hydrates, and N-oxides thereof:

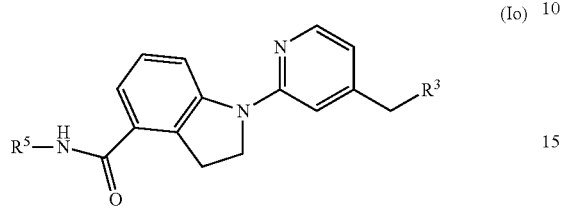

(Io)

wherein:
R³ is aryl or heteroaryl, wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and
R⁵ is selected from: H, $C_1$-$C_6$ alkyl, heteroaryl, heteroaryl-$C_1$-$C_6$ alkyl, heterocyclyl, heterocyclyl-$C_1$-$C_6$ alkyl, and hydroxy-$C_1$-$C_6$-alkyl; and each group is optionally substituted with one or more groups selected independently from: 2-hydroxyethyl, acetamido, cyano, dimethylamino, fluoro, hydroxy, hydroxymethyl, methoxy, methyl, methylamino, oxo, and trifluoromethyl.

xli) The compound according to i), selected from compounds of Formula (Io) and pharmaceutically acceptable salts, solvates, hydrates, and N-oxides thereof:

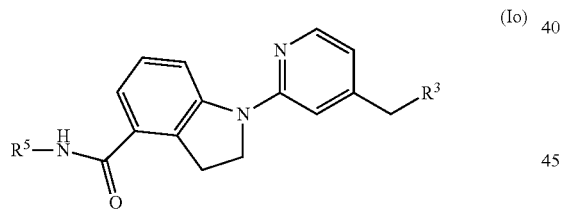

(Io)

wherein:
R³ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: $C_1$-$C_6$ acyl, $C_1$-$C_6$ acyloxy, $C_1$-$C_6$ alkoxy, $C_1$-$C_6$ alkylcarboxamide, $C_1$-$C_6$ alkyl, cyano, $C_1$-$C_6$ haloalkoxy, $C_1$-$C_6$ haloalkyl, halogen, hydroxyl, and hydroxy-$C_1$-$C_6$-alkyl; and wherein said $C_1$-$C_6$ alkyl is optionally substituted with one or more groups selected independently from: $C_1$-$C_6$ alkylamino, $C_2$-$C_6$ dialkylamino, and oxo; and
R⁵ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally with one or more groups selected independently from: $C_1$-$C_6$ alkoxy, $C_1$-$C_6$ alkylcarboxamide, $C_1$-$C_6$ alkyl, cyano, $C_1$-$C_6$ alkylamino, $C_2$-$C_6$ dialkylamino, $C_1$-$C_6$ haloalkyl, halogen, hydroxyl, hydroxy-$C_1$-$C_6$-alkoxy, hydroxy-$C_1$-$C_6$-alkyl, and oxo.

xlii) The compound according to i), selected from compounds of Formula (Io) and pharmaceutically acceptable salts, solvates, hydrates, and N-oxides thereof:

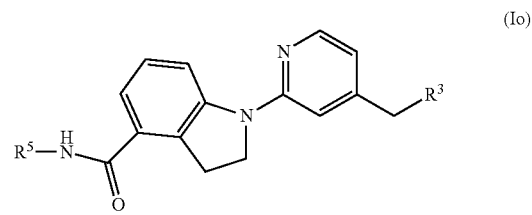

(Io)

wherein:
R³ is selected from: 1H-indol-4-yl, 2,3-dihydrobenzofuran-5-yl, 3,4-dihydro-2H-benzo[b][1,4]dioxepin-7-yl, benzo[d][1,3]dioxol-5-yl, benzofuran-2-yl, benzofuran-5-yl, furan-2-yl, furan-3-yl, isoxazol-4-yl, phenyl, pyridin-2-yl, pyridin-3-yl, pyridin-4-yl, pyrimidin-5-yl, quinolin-3-yl, and quinolin-5-yl; wherein each ring is optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl; and
R⁵ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

xliii) The compound according to i), selected from compounds of Formula (Io) and pharmaceutically acceptable salts, solvates, hydrates, and N-oxides thereof:

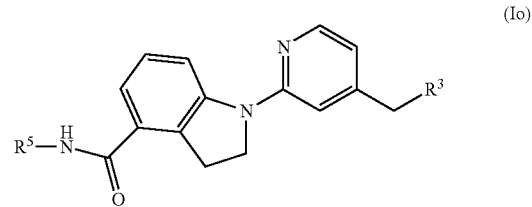

(Io)

wherein:
R³ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl; and
R⁵ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

xliv) The compound according to i), selected from compounds of Formula (Iq) and pharmaceutically acceptable salts, solvates, hydrates, and N-oxides thereof:

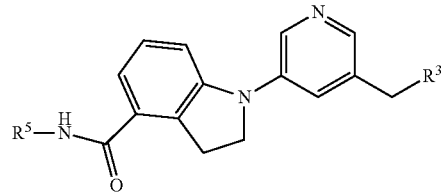

(Iq)

wherein:
R³ is aryl optionally substituted with C₁-C₆ haloalkyl; and
R⁵ is selected from: H, C₁-C₆ alkyl, and heterocyclyl; and C₁-C₆ alkyl is optionally substituted with hydroxyl.

xlv) The compound according to i), selected from compounds of Formula (Iq) and pharmaceutically acceptable salts, solvates, hydrates, and N-oxides thereof:

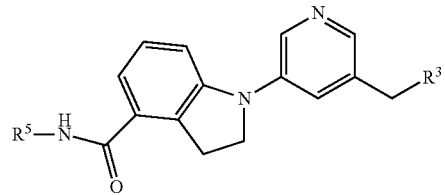

(Iq)

wherein:
R³ is phenyl optionally substituted with trifluoromethyl; and
R⁵ is selected from: H, methyl, ethyl, and tetrahydrofuranyl; and ethyl is optionally substituted with hydroxyl.

xlvi) The compound according to i), selected from compounds of Formula (Iq) and pharmaceutically acceptable salts, solvates, hydrates, and N-oxides thereof:

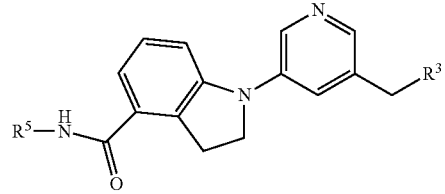

(Iq)

wherein:
R³ is 3-(trifluoromethyl)phenyl; and
R⁵ is selected from: H, methyl, 2-hydroxyethyl, and tetrahydrofuran-3-yl.

xlvii) The compound according to i), selected from compounds of Formula (Is) and pharmaceutically acceptable salts, solvates, hydrates, and N-oxides thereof:

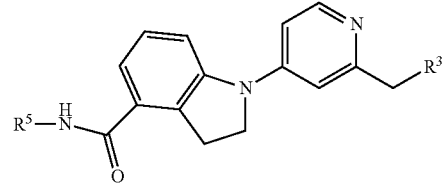

(Is)

wherein:
R³ is aryl is optionally substituted with one or more groups selected independently from: $C_1$-$C_6$ acyl, $C_1$-$C_6$ alkoxy, $C_1$-$C_6$ haloalkyl, and halogen; and
R⁵ is selected from: H, $C_1$-$C_6$ alkyl, and heterocyclyl; and $C_1$-$C_6$ alkyl and heterocyclyl are each optionally substituted with one or more groups selected independently from: $C_1$-$C_6$ alkoxy, halogen, hydroxyl, and oxo.

xlviii) The compound according to i), selected from compounds of Formula (Is) and pharmaceutically acceptable salts, solvates, hydrates, and N-oxides thereof:

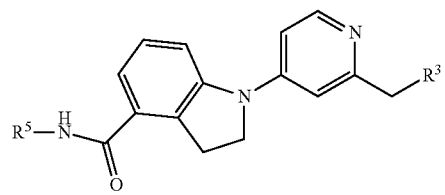

(Is)

wherein:
R³ is phenyl is optionally substituted with one or more groups selected independently from: acetyl, methoxy, trifluoromethyl, chloro, and fluoro; and
R⁵ is selected from: H, ethyl, pyrrolidinyl, and tetrahydrofuranyl; and ethyl and pyrrolidinyl are each optionally substituted with one or more groups selected independently from: methoxy, fluoro, hydroxyl, and oxo.

xlix) The compound according to i), selected from compounds of Formula (Is) and pharmaceutically acceptable salts, solvates, hydrates, and N-oxides thereof:

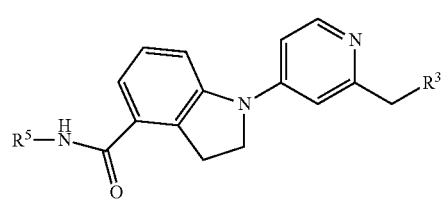

(Is)

wherein:
R³ is 3-(trifluoromethyl)phenyl, 3-acetylphenyl, 3,4,5-trifluorophenyl, 3-chloro-5-fluorophenyl, 4-fluoro-3-(trifluoromethyl)phenyl, and 3-fluoro-4-methoxyphenyl; and
R⁵ is selected from: H, 2-fluoro-3-hydroxypropyl, 2-hydroxy-3-methoxypropyl, 2-oxopyrrolidin-3-yl, 2-hydroxypropyl, 3-fluoro-2-hydroxypropyl, tetrahydrofuran-3-yl, 2-fluoroethyl, and 2-hydroxyethyl.

l) The compound according to i), selected from compounds of Formula (Iu) and pharmaceutically acceptable salts, solvates, hydrates, and N-oxides thereof:

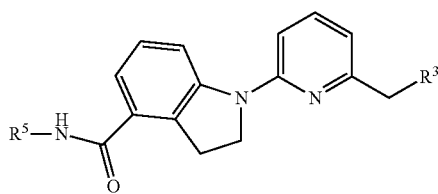

(Iu)

wherein:
R³ is aryl optionally substituted with $C_1$-$C_6$ haloalkyl; and
R⁵ is selected from: H and heterocyclyl.

li) The compound according to i), selected from compounds of Formula (Iu) and pharmaceutically acceptable salts, solvates, hydrates, and N-oxides thereof:

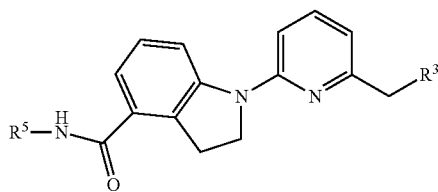

(Iu)

wherein:
R³ is phenyl optionally substituted with trifluoromethyl; and
R⁵ is selected from: H and tetrahydrofuranyl.

lii) The compound according to i), selected from compounds of Formula (Iu) and pharmaceutically acceptable salts, solvates, hydrates, and N-oxides thereof:

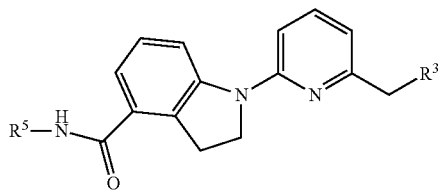

(Iu)

wherein:
R³ is 3-(trifluoromethyl)phenyl; and
R⁵ is selected from: H and tetrahydrofuran-3-yl.

liii) The compound according to i), selected from compounds of Formula (Iw) and pharmaceutically acceptable salts, solvates, hydrates, and N-oxides thereof:

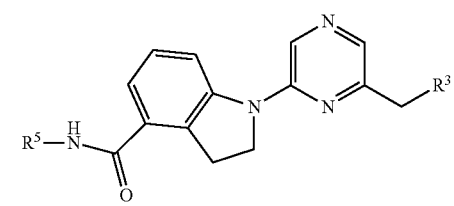

(Iw)

wherein:
R³ is aryl optionally substituted with C₁-C₆ haloalkyl; and
R⁵ is selected from: H and C₁-C₆ alkyl; and C₁-C₆ alkyl is optionally substituted with hydroxyl.

liv) The compound according to i), selected from compounds of Formula (Iw) and pharmaceutically acceptable salts, solvates, hydrates, and N-oxides thereof:

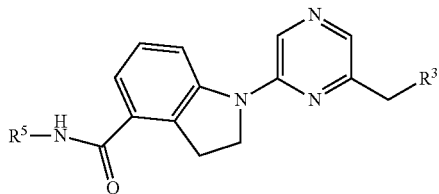

(Iw)

wherein:
R³ is phenyl optionally substituted with trifluoromethyl; and
R⁵ is selected from: H and ethyl; and ethyl is optionally substituted with hydroxyl.

lv) The compound according to i), selected from compounds of Formula (Iw) and pharmaceutically acceptable salts, solvates, hydrates, and N-oxides thereof:

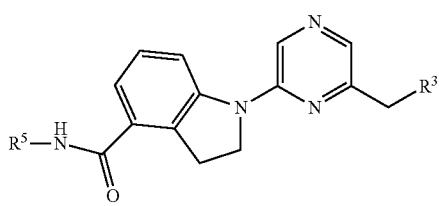

(Iw)

wherein:
R³ is 3-(trifluoromethyl)phenyl; and
R⁵ is selected from: H and 2-hydroxyethyl.

lvi) The compound according to i), selected from the following compounds and pharmaceutically acceptable salts, solvates, and hydrates thereof:
1-(6-(3-(Trifluoromethyl)benzyl)pyridin-2-yl)indoline-4-carboxamide;
(S)—N-(Tetrahydrofuran-3-yl)-1-(6-(3-(trifluoromethyl)benzyl)pyridin-2-yl)indoline-4-carboxamide;
(S)—N-(Tetrahydrofuran-3-yl)-1-(2-(3-(trifluoromethyl)benzyl)pyridin-4-yl)indoline-4-carboxamide;
(S)—N-(Tetrahydrofuran-3-yl)-1-(4-(3-(trifluoromethyl)benzyl)pyridin-2-yl)indoline-4-carboxamide;
1-(4-(3-(Trifluoromethyl)benzyl)pyridin-2-yl)indoline-4-carboxamide;
1-(2-(3-(Trifluoromethyl)benzyl)pyridin-4-yl)indoline-4-carboxamide;
(S)—N-(Tetrahydrofuran-3-yl)-1-(5-(3-(trifluoromethyl)benzyl)pyridin-3-yl)indoline-4-carboxamide;
1-(5-(3-(Trifluoromethyl)benzyl)pyridin-3-yl)indoline-4-carboxamide;
N-Methyl-1-(5-(3-(trifluoromethyl)benzyl)pyridin-3-yl)indoline-4-carboxamide;
N-(2-Hydroxyethyl)-1-(5-(3-(trifluoromethyl)benzyl)pyridin-3-yl)indoline-4-carboxamide;
(S)-3-(4-(Tetrahydrofuran-3-ylcarbamoyl)indolin-1-yl)-5-(3-(trifluoromethyl)benzyl)pyridine 1-oxide;
3-(4-Carbamoylindolin-1-yl)-5-(3-(trifluoromethyl)benzyl)pyridine 1-oxide;
N-(2-Hydroxyethyl)-1-(4-(3-(trifluoromethyl)benzyl)pyridin-2-yl)indoline-4-carboxamide;
1-(4-(3,5-Difluorobenzyl)pyridin-2-yl)-N-(2-hydroxyethyl)indoline-4-carboxamide;
1-(4-(3,5-Difluorobenzyl)pyridin-2-yl)indoline-4-carboxamide;
1-(4-(3,5-Difluorobenzyl)pyridin-2-yl)-N-methylindoline-4-carboxamide;
1-(6-Methyl-4-(3-(trifluoromethyl)benzyl)pyridin-2-yl)indoline-4-carboxamide;
N-Methyl-1-(6-methyl-4-(3-(trifluoromethyl)benzyl)pyridin-2-yl)indoline-4-carboxamide;
(S)-1-(4-(3,5-Difluorobenzyl)pyridin-2-yl)-N-(tetrahydrofuran-3-yl)indoline-4-carboxamide;
N-(2-Cyanoethyl)-1-(4-(3-(trifluoromethyl)benzyl)pyridin-2-yl)indoline-4-carboxamide;
(R)—N-(2,3-Dihydroxypropyl)-1-(4-(3-(trifluoromethyl)benzyl)pyridin-2-yl)indoline-4-carboxamide;
(S)—N-(2,3-Dihydroxypropyl)-1-(4-(3-(trifluoromethyl)benzyl)pyridin-2-yl)indoline-4-carboxamide;
1-(4-(3-Fluoro-5-(trifluoromethyl)phenoxy)pyridin-2-yl)-N-(2-hydroxyethyl)indoline-4-carboxamide;
1-(4-(3-Fluoro-5-(trifluoromethyl)phenoxy)pyridin-2-yl)indoline-4-carboxamide;
N-(3-Hydroxypropyl)-1-(4-(3-(trifluoromethyl)benzyl)pyridin-2-yl)indoline-4-carboxamide;
(R)—N-(2-Hydroxypropyl)-1-(4-(3-(trifluoromethyl)benzyl)pyridin-2-yl)indoline-4-carboxamide;
N-(Cyanomethyl)-1-(4-(3-(trifluoromethyl)benzyl)pyridin-2-yl)indoline-4-carboxamide;
1-(4-(3-Fluoro-5-(trifluoromethyl)benzyl)pyridin-2-yl)-N-(2-hydroxyethyl)indoline-4-carboxamide;
N-(2-Hydroxyethyl)-1-(4-(3-(trifluoromethyl)phenyl)pyridin-2-yl)indoline-4-carboxamide;
1-(4-(3-(Trifluoromethyl)phenylthio)pyridin-2-yl) indoline-4-carboxamide;
(S)—N-(2,3-Dihydroxypropyl)-1-(4-(3-fluoro-5-(trifluoromethyl)benzyl)pyridin-2-yl)indoline-4-carboxamide;
(R)—N-(2,3-Dihydroxypropyl)-1-(4-(3-fluoro-5-(trifluoromethyl)benzyl)pyridin-2-yl)indoline-4-carboxamide;
1-(4-(3-Fluoro-5-(trifluoromethyl)benzyl)pyridin-2-yl)indoline-4-carboxamide;
N-(2-(Dimethylamino)ethyl)-1-(4-(3-fluoro-5-(trifluoromethyl)benzyl)pyridin-2-yl)indoline-4-carboxamide;
N-(1,3-Dihydroxypropan-2-yl)-1-(4-(3-fluoro-5-(trifluoromethyl)benzyl)pyridin-2-yl)indoline-4-carboxamide;
N-(2-(Dimethylamino)ethyl)-1-(4-(3-(trifluoromethyl)benzyl)pyridin-2-yl)indoline-4-carboxamide;
N-(1,3-Dihydroxypropan-2-yl)-1-(4-(3-(trifluoromethyl)benzyl)pyridin-2-yl)indoline-4-carboxamide;
N-(2-Hydroxyethyl)-1-(6-(3-(trifluoromethyl)benzyl)pyrazin-2-yl)indoline-4-carboxamide;
1-(6-(3-(Trifluoromethyl)benzyl)pyrazin-2-yl)indoline-4-carboxamide;
N-(2-Hydroxyethyl)-1-(4-((6-(trifluoromethyl)pyridin-2-yl)methyl)pyridin-2-yl)indoline-4-carboxamide;
1-(4-((6-(Trifluoromethyl)pyridin-2-yl)methyl)pyridin-2-yl)indoline-4-carboxamide;
1-(4-(3-Chloro-5-fluorobenzyl)pyridin-2-yl)indoline-4-carboxamide;
1-(4-(3-Chloro-5-fluorobenzyl)pyridin-2-yl)-N-(2-hydroxyethyl)indoline-4-carboxamide;
1-(4-(3-Chloro-5-fluorobenzyl)pyridin-2-yl)-N-(2-(dimethylamino)ethyl)indoline-4-carboxamide;

1-(4-(3-Chloro-5-fluorobenzyl)pyridin-2-yl)-N-(pyridin-4-yl)indoline-4-carboxamide;
1-(4-((5-Chloropyridin-3-yl)methyl)pyridin-2-yl)indoline-4-carboxamide;
1-(4-((5-(Trifluoromethyl)pyridin-3-yl)methyl)pyridin-2-yl)indoline-4-carboxamide;
N-(2-Hydroxyethyl)-1-(4-((5-(trifluoromethyl)pyridin-3-yl)methyl)pyridin-2-yl)indoline-4-carboxamide;
1-(4-((5,6-Difluoropyridin-3-yl)methyl)pyridin-2-yl)indoline-4-carboxamide;
1-(4-((6-Fluoro-5-methylpyridin-3-yl)methyl)pyridin-2-yl)indoline-4-carboxamide;
1-(4-((2-(Trifluoromethyl)pyridin-4-yl)methyl)pyridin-2-yl)indoline-4-carboxamide;
1-(4-((5-Chloro-6-fluoropyridin-3-yl)methyl)pyridin-2-yl)indoline-4-carboxamide;
N-(1-Methylpiperidin-4-yl)-1-(4-(3-(trifluoromethyl)benzyl)pyridin-2-yl)indoline-4-carboxamide;
1-(4-(3-Fluoro-4-methoxybenzyl)pyridin-2-yl)indoline-4-carboxamide;
1-(4-(4-Acetylbenzyl)pyridin-2-yl)indoline-4-carboxamide;
1-(4-(4-Methoxy-3-(trifluoromethyl)benzyl)pyridin-2-yl)indoline-4-carboxamide;
1-(4-(4-Chloro-3-fluorobenzyl)pyridin-2-yl)indoline-4-carboxamide;
1-(4-(3-Chloro-4-fluorobenzyl)pyridin-2-yl) indoline-4-carboxamide;
1-(4-(4-Fluoro-3-(methylcarbamoyl)benzyl)pyridin-2-yl)indoline-4-carboxamide;
1-(4-(3-Cyano-4-fluorobenzyl)pyridin-2-yl)indoline-4-carboxamide;
1-(4-(4-Fluoro-3-(trifluoromethyl)benzyl)pyridin-2-yl)indoline-4-carboxamide;
1-(4-(3-Acetyl-4-fluorobenzyl)pyridin-2-yl) indoline-4-carboxamide;
1-(4-(4-Fluoro-3-(hydroxymethyl)benzyl)pyridin-2-yl)indoline-4-carboxamide;
1-(4-(3-(Trifluoromethoxy)benzyl)pyridin-2-yl) indoline-4-carboxamide;
1-(4-(3,4,5-Trifluorobenzyl)pyridin-2-yl)indoline-4-carboxamide;
1-(4-((2,3-Dihydrobenzofuran-5-yl)methyl)pyridin-2-yl)indoline-4-carboxamide;
1-(4-(4-Fluoro-3-methoxybenzyl)pyridin-2-yl)indoline-4-carboxamide;
1-(4-(3-Cyano-5-fluorobenzyl)pyridin-2-yl)indoline-4-carboxamide;
1-(4-(3-Fluoro-4-methoxybenzyl)pyridin-2-yl)-N-(2-hydroxyethyl)indoline-4-carboxamide;
1-(4-(3-Chloro-4-fluorobenzyl)pyridin-2-yl)-N-(2-hydroxyethyl)indoline-4-carboxamide;
1-(4-(3-Fluoro-5-methoxybenzyl)pyridin-2-yl)indoline-4-carboxamide;
1-(4-((2-Methoxypyrimidin-5-yl)methyl)pyridin-2-yl)indoline-4-carboxamide;
1-(4-((2-Chloropyrimidin-5-yl)methyl)pyridin-2-yl)indoline-4-carboxamide;
1-(4-(4-Fluoro-3-methoxybenzyl)pyridin-2-yl)-N-(2-hydroxyethyl)indoline-4-carboxamide;
1-(4-(4-Fluoro-3-(trifluoromethyl)benzyl)pyridin-2-yl)-N-(2-hydroxyethyl)indoline-4-carboxamide;
1-(4-((2,3-Dihydrobenzofuran-5-yl)methyl)pyridin-2-yl)-N-(2-hydroxyethyl)indoline-4-carboxamide;
1-(4-(3-Acetyl-4-fluorobenzyl)pyridin-2-yl)-N-(2-hydroxyethyl)indoline-4-carboxamide;
1-(4-(3-Acetylbenzyl)pyridin-2-yl)indoline-4-carboxamide;
1-(4-((2,3-Dihydrobenzofuran-5-yl)methyl)pyridin-2-yl)-N-(1-(2-hydroxyethyl)piperidin-4-yl)indoline-4-carboxamide;
1-(4-(3-Acetyl-4-fluorobenzyl)pyridin-2-yl)-N-(1-(2-hydroxyethyl)piperidin-4-yl)indoline-4-carboxamide;
1-(4-(3-((Dimethylamino)methyl)benzyl)pyridin-2-yl)indoline-4-carboxamide;
1-(4-(4-Acetyl-3-fluorobenzyl)pyridin-2-yl)indoline-4-carboxamide;
1-(4-((5-Fluoro-6-methoxypyridin-3-yl)methyl)pyridin-2-yl)indoline-4-carboxamide;
1-(4-((5-Chloro-6-methoxypyridin-3-yl)methyl)pyridin-2-yl)indoline-4-carboxamide;
1-(4-((6-Methoxypyridin-3-yl)methyl)pyridin-2-yl)indoline-4-carboxamide;
1-(4-((6-Cyanopyridin-3-yl)methyl)pyridin-2-yl)indoline-4-carboxamide;
1-(4-(3-Fluoro-4-(hydroxymethyl)benzyl)pyridin-2-yl)indoline-4-carboxamide;
1-(4-(4-Cyano-3-fluorobenzyl)pyridin-2-yl)indoline-4-carboxamide;
N-(1-(2-Hydroxyethyl)piperidin-4-yl)-1-(4-(3-(trifluoromethyl)benzyl)pyridin-2-yl)indoline-4-carboxamide;
1-(4-(3-Chloro-5-fluorobenzyl)pyridin-2-yl)-N-(1-(2-hydroxyethyl)piperidin-4-yl)indoline-4-carboxamide;
1-(4-(3-Fluoro-4-methoxybenzyl)pyridin-2-yl)-N-(1-(2-hydroxyethyl)piperidin-4-yl)indoline-4-carboxamide;
N-(2-Hydroxyethyl)-1-(4-(3,4,5-trifluorobenzyl)pyridin-2-yl)indoline-4-carboxamide;
N-(1-(2-Hydroxyethyl)piperidin-4-yl)-1-(4-(3,4,5-trifluorobenzyl)pyridin-2-yl)indoline-4-carboxamide;
N-(2-Morpholinoethyl)-1-(4-(3-(trifluoromethyl)benzyl)pyridin-2-yl)indoline-4-carboxamide;
N-(2-(Pyrrolidin-1-yl)ethyl)-1-(4-(3-(trifluoromethyl)benzyl)pyridin-2-yl)indoline-4-carboxamide;
1-(4-((3,4-Dihydro-2H-benzo[b][1,4]dioxepin-7-yl)methyl)pyridin-2-yl)indoline-4-carboxamide;
1-(4-(3-Fluoro-4-hydroxybenzyl)pyridin-2-yl) indoline-4-carboxamide;
1-(4-(3-Methoxybenzyl)pyridin-2-yl)indoline-4-carboxamide;
1-(4-(4-Methoxy-3-methylbenzyl)pyridin-2-yl)indoline-4-carboxamide;
1-(4-(3-Chloro-4-methoxybenzyl)pyridin-2-yl)indoline-4-carboxamide;
1-(4-(Benzo[d][1,3]dioxol-5-ylmethyl)pyridin-2-yl)indoline-4-carboxamide;
3-((2-(4-Carbamoylindolin-1-yl)pyridin-4-yl)methyl)phenyl acetate;
1-(4-(Furan-2-ylmethyl)pyridin-2-yl)indoline-4-carboxamide;
1-(4-((3,5-Dimethylisoxazol-4-yl)methyl)pyridin-2-yl)indoline-4-carboxamide;
1-(4-(Furan-3-ylmethyl)pyridin-2-yl) indoline-4-carboxamide;
1-(4-(Benzofuran-5-ylmethyl)pyridin-2-yl) indoline-4-carboxamide;
1-(4-(3-Chloro-5-methoxybenzyl)pyridin-2-yl)indoline-4-carboxamide;
5-Fluoro-N-(2-hydroxyethyl)-1-(4-(3-(trifluoromethyl)benzyl)pyridin-2-yl)indoline-4-carboxamide;
5-Fluoro-N-(1-(2-hydroxyethyl)piperidin-4-yl)-1-(4-(3-(trifluoromethyl)benzyl)pyridin-2-yl)indoline-4-carboxamide;
1-(4-(4-Ethoxy-3-fluorobenzyl)pyridin-2-yl)indoline-4-carboxamide;

1-(4-(Quinolin-3-ylmethyl)pyridin-2-yl)indoline-4-carboxamide;
1-(4-(Quinolin-5-ylmethyl)pyridin-2-yl)indoline-4-carboxamide;
N-(1,3-Dihydroxypropan-2-yl)-1-(4-(3,4,5-trifluorobenzyl)pyridin-2-yl)indoline-4-carboxamide;
1-(4-(4-Fluoro-3-hydroxybenzyl)pyridin-2-yl)indoline-4-carboxamide;
1-(4-(4-Chloro-3-methoxybenzyl)pyridin-2-yl)indoline-4-carboxamide;
1-(4-(3,4-Difluorobenzyl)pyridin-2-yl)indoline-4-carboxamide;
N-(1-Methyl-1H-pyrazol-4-yl)-1-(4-(3,4,5-trifluorobenzyl)pyridin-2-yl)indoline-4-carboxamide;
N-(1-(2-Hydroxyethyl)-1H-pyrazol-4-yl)-1-(4-(3,4,5-trifluorobenzyl)pyridin-2-yl)indoline-4-carboxamide;
1-(4-(Benzofuran-2-ylmethyl)pyridin-2-yl) indoline-4-carboxamide;
1-(4-((1H-Indol-4-yl)methyl)pyridin-2-yl) indoline-4-carboxamide;
1-(4-(3, 5-Difluoro-4-methoxybenzyl)pyridin-2-yl)indoline-4-carboxamide;
5-Fluoro-1-(4-(3-(trifluoromethyl)benzyl)pyridin-2-yl)indoline-4-carboxamide;
(R)—N-(2,3-Dihydroxypropyl)-1-(4-(3,4,5-trifluorobenzyl)pyridin-2-yl)indoline-4-carboxamide;
(S)—N-(2, 3-dihydroxypropyl)-1-(4-(3,4,5-trifluorobenzyl)pyridin-2-yl)indoline-4-carboxamide;
N-(2-Hydroxy-2-(pyridin-2-yl)ethyl)-1-(4-(3,4,5-trifluorobenzyl)pyridin-2-yl)indoline-4-carboxamide;
N-(2-Hydroxy-2-(pyridin-3-yl)ethyl)-1-(4-(3,4,5-trifluorobenzyl)pyridin-2-yl)indoline-4-carboxamide;
N-(2-Hydroxy-2-(pyridin-4-yl)ethyl)-1-(4-(3,4,5-trifluorobenzyl)pyridin-2-yl)indoline-4-carboxamide;
N-(6-Oxopiperidin-3-yl)-1-(4-(3,4,5-trifluorobenzyl)pyridin-2-yl)indoline-4-carboxamide;
N-(2-Acetamidoethyl)-1-(4-(3,4,5-trifluorobenzyl)pyridin-2-yl)indoline-4-carboxamide;
N-(2-Hydroxy-3-methoxypropyl)-1-(4-(3,4,5-trifluorobenzyl)pyridin-2-yl)indoline-4-carboxamide;
N-(1,3-Dimethoxypropan-2-yl)-1-(4-(3,4,5-trifluorobenzyl)pyridin-2-yl)indoline-4-carboxamide;
N-(2-(2-Oxopyrrolidin-1-yl)ethyl)-1-(4-(3,4,5-trifluorobenzyl)pyridin-2-yl)indoline-4-carboxamide;
N-(2-(2-Oxoimidazolidin-1-yl)ethyl)-1-(4-(3,4,5-trifluorobenzyl)pyridin-2-yl)indoline-4-carboxamide;
N-((2R,3S)-1,3-Dihydroxybutan-2-yl)-1-(4-(3,4,5-trifluorobenzyl)pyridin-2-yl)indoline-4-carboxamide;
(R)—N-(2-Oxotetrahydrofuran-3-yl)-1-(4-(3,4,5-trifluorobenzyl)pyridin-2-yl)indoline-4-carboxamide;
(S)—N-(2-Oxotetrahydrofuran-3-yl)-1-(4-(3,4,5-trifluorobenzyl)pyridin-2-yl)indoline-4-carboxamide;
(R)—N-(2-Hydroxy-3-methoxypropyl)-1-(4-(3,4,5-trifluorobenzyl)pyridin-2-yl)indoline-4-carboxamide;
(S)—N-(2-Hydroxy-3-methoxypropyl)-1-(4-(3,4,5-trifluorobenzyl)pyridin-2-yl)indoline-4-carboxamide;
N-(2-(1H-Imidazol-1-yl)ethyl)-1-(4-(3,4,5-trifluorobenzyl)pyridin-2-yl)indoline-4-carboxamide;
5-Fluoro-N-(2-hydroxyethyl)-1-(4-(3,4,5-trifluorobenzyl)pyridin-2-yl)indoline-4-carboxamide;
N-(1,3-Dihydroxypropan-2-yl)-5-fluoro-1-(4-(3,4,5-trifluorobenzyl)pyridin-2-yl)indoline-4-carboxamide;
(R)—N-(2,3-Dihydroxypropyl)-5-fluoro-1-(4-(3,4,5-trifluorobenzyl)pyridin-2-yl)indoline-4-carboxamide;
5-Fluoro-N-(2-hydroxy-2-(pyridin-3-yl)ethyl)-1-(4-(3,4,5-trifluorobenzyl)pyridin-2-yl)indoline-4-carboxamide;
(R)-5-Fluoro-N-(2-hydroxy-3-methoxypropyl)-1-(4-(3,4,5-trifluorobenzyl)pyridin-2-yl)indoline-4-carboxamide;
N-(2-Acetamidoethyl)-5-fluoro-1-(4-(3,4,5-trifluorobenzyl)pyridin-2-yl)indoline-4-carboxamide;
(R)-5-Fluoro-N-(2-oxopyrrolidin-3-yl)-1-(4-(3,4,5-trifluorobenzyl)pyridin-2-yl)indoline-4-carboxamide;
(S)-5-Fluoro-N-(2-oxopyrrolidin-3-yl)-1-(4-(3,4,5-trifluorobenzyl)pyridin-2-yl)indoline-4-carboxamide;
(R)—N-(2-Hydroxy-2-(pyridin-3-yl)ethyl)-1-(4-(3,4,5-trifluorobenzyl)pyridin-2-yl)indoline-4-carboxamide;
(S)—N-(2-Hydroxy-2-(pyridin-3-yl)ethyl)-1-(4-(3,4,5-trifluorobenzyl)pyridin-2-yl)indoline-4-carboxamide;
(S)-5-Fluoro-N-(2-hydroxy-3-methoxypropyl)-1-(4-(3,4,5-trifluorobenzyl)pyridin-2-yl)indoline-4-carboxamide;
(R)—N-(2-Oxopyrrolidin-3-yl)-1-(4-(3,4,5-trifluorobenzyl)pyridin-2-yl)indoline-4-carboxamide;
(S)—N-(2-Oxopyrrolidin-3-yl)-1-(4-(3,4,5-trifluorobenzyl)pyridin-2-yl)indoline-4-carboxamide;
N-(2-(1H-Imidazol-5-yl)ethyl)-1-(4-(3,4,5-trifluorobenzyl)pyridin-2-yl)indoline-4-carboxamide;
N-((3-(Hydroxymethyl)oxetan-3-yl)methyl)-1-(4-(3,4,5-trifluorobenzyl)pyridin-2-yl)indoline-4-carboxamide;
5-Fluoro-N-((3-(hydroxymethyl)oxetan-3-yl)methyl)-1-(4-(3,4,5-trifluorobenzyl)pyridin-2-yl)indoline-4-carboxamide;
(S)-1-(4-(3-Fluoro-4-methoxybenzyl)pyridin-2-yl)-N-(2-hydroxy-3-methoxypropyl)indoline-4-carboxamide;
(S)-1-(4-(3-Fluoro-4-methoxybenzyl)pyridin-2-yl)-N-(2-oxopyrrolidin-3-yl)indoline-4-carboxamide;
N-(3-(Dimethylamino)-2-hydroxypropyl)-1-(4-(3,4,5-trifluorobenzyl)pyridin-2-yl)indoline-4-carboxamide;
N-(3-Hydroxypropyl)-1-(4-(3,4,5-trifluorobenzyl)pyridin-2-yl)indoline-4-carboxamide;
(S)—N-(3,3,3-Trifluoro-2-hydroxypropyl)-1-(4-(3,4,5-trifluorobenzyl)pyridin-2-yl)indoline-4-carboxamide;
N-(2-Fluoroethyl)-1-(4-(3,4,5-trifluorobenzyl)pyridin-2-yl)indoline-4-carboxamide;
5-Fluoro-1-(4-(3-fluoro-4-methoxybenzyl)pyridin-2-yl)-N-(2-hydroxyethyl)indoline-4-carboxamide;
5-Fluoro-1-(4-(3-fluoro-4-methoxybenzyl)pyridin-2-yl)-N-(2-fluoroethyl)indoline-4-carboxamide;
N-(2-Acetamidoethyl)-5-fluoro-1-(4-(3-fluoro-4-methoxybenzyl)pyridin-2-yl)indoline-4-carboxamide;
N-(3-Fluoro-2-hydroxypropyl)-1-(4-(3,4,5-trifluorobenzyl)pyridin-2-yl)indoline-4-carboxamide;
(R)—N-(2-Fluoro-3-hydroxypropyl)-1-(4-(3,4,5-trifluorobenzyl)pyridin-2-yl)indoline-4-carboxamide;
(R)-5-Fluoro-N-(2-fluoro-3-hydroxypropyl)-1-(4-(3-fluoro-4-methoxybenzyl)pyridin-2-yl)indoline-4-carboxamide;
(S)-1-(4-(3-Chloro-5-fluorobenzyl)pyridin-2-yl)-N-(2-hydroxy-3-methoxypropyl)indoline-4-carboxamide;
N-(2-Hydroxyethyl)-1-(3-methyl-4-(3-(trifluoromethyl)benzyl)pyridin-2-yl)indoline-4-carboxamide;
1-(4-(3-Chloro-5-fluorobenzyl)pyridin-2-yl)-N-(3-fluoro-2-hydroxypropyl)indoline-4-carboxamide;
(S)-1-(4-(3-Chloro-5-fluorobenzyl)pyridin-2-yl)-N-(2-oxopyrrolidin-3-yl)indoline-4-carboxamide;
N-(3-(Methylamino)-3-oxopropyl)-1-(4-(3,4,5-trifluorobenzyl)pyridin-2-yl)indoline-4-carboxamide;
(R)-1-(4-(3-Chloro-5-fluorobenzyl)pyridin-2-yl)-N-(2-fluoro-3-hydroxypropyl)indoline-4-carboxamide;
1-(4-(Benzofuran-5-ylmethyl)pyridin-2-yl)-N-(2-hydroxyethyl)indoline-4-carboxamide;
(S)-1-(4-(Benzofuran-5-ylmethyl)pyridin-2-yl)-N-(2-oxopyrrolidin-3-yl)indoline-4-carboxamide;
(R)-1-(4-(Benzofuran-5-ylmethyl)pyridin-2-yl)-N-(2-fluoro-3-hydroxypropyl)indoline-4-carboxamide;

1-(4-(Benzofuran-5-ylmethyl)pyridin-2-yl)-N-(3-fluoro-2-hydroxypropyl)indoline-4-carboxamide;

(S)-1-(4-(Benzofuran-5-ylmethyl)pyridin-2-yl)-N-(2-hydroxy-3-methoxypropyl)indoline-4-carboxamide;

(R)—N-(2-Hydroxypropyl)-1-(4-(3,4,5-trifluorobenzyl)pyridin-2-yl)indoline-4-carboxamide;

(S)—N-(2-Hydroxypropyl)-1-(4-(3,4,5-trifluorobenzyl)pyridin-2-yl)indoline-4-carboxamide;

(S)—N-(2-Fluoro-3-hydroxypropyl)-1-(4-(3,4,5-trifluorobenzyl)pyridin-2-yl)indoline-4-carboxamide;

(S)-1-(4-(Benzofuran-5-ylmethyl)pyridin-2-yl)-N-(2-fluoro-3-hydroxypropyl)indoline-4-carboxamide;

(S)—N-(3-Fluoro-2-hydroxypropyl)-1-(4-(3,4,5-trifluorobenzyl)pyridin-2-yl)indoline-4-carboxamide;

N-(2-Hydroxyethyl)-1-(2-(3-(trifluoromethyl)benzyl)pyridin-4-yl)indoline-4-carboxamide;

1-(2-(3-Acetylbenzyl)pyridin-4-yl)-N-(2-hydroxyethyl)indoline-4-carboxamide;

N-(2-Hydroxyethyl)-1-(2-(3,4,5-trifluorobenzyl)pyridin-4-yl)indoline-4-carboxamide;

1-(2-(3-Chloro-5-fluorobenzyl)pyridin-4-yl)-N-(2-hydroxyethyl)indoline-4-carboxamide;

1-(2-(4-Fluoro-3-(trifluoromethyl)benzyl)pyridin-4-yl)-N-(2-hydroxyethyl)indoline-4-carboxamide;

(S)—N-(2-Hydroxy-3-methoxypropyl)-1-(2-(3,4,5-trifluorobenzyl)pyridin-4-yl)indoline-4-carboxamide;

N-(2-Fluoroethyl)-1-(2-(3,4,5-trifluorobenzyl)pyridin-4-yl)indoline-4-carboxamide;

(R)—N-(2-Hydroxy-3-methoxypropyl)-1-(2-(3,4,5-trifluorobenzyl)pyridin-4-yl)indoline-4-carboxamide;

N-(3-Fluoro-2-hydroxypropyl)-1-(2-(3,4,5-trifluorobenzyl)pyridin-4-yl)indoline-4-carboxamide;

(R)—N-(2-Fluoro-3-hydroxypropyl)-1-(2-(3,4,5-trifluorobenzyl)pyridin-4-yl)indoline-4-carboxamide;

(S)—N-(2-Oxopyrrolidin-3-yl)-1-(2-(3,4,5-trifluorobenzyl)pyridin-4-yl)indoline-4-carboxamide;

(R)—N-(2-Hydroxypropyl)-1-(2-(3,4,5-trifluorobenzyl)pyridin-4-yl)indoline-4-carboxamide;

(S)—N-(2-Hydroxypropyl)-1-(2-(3,4,5-trifluorobenzyl)pyridin-4-yl)indoline-4-carboxamide;

(R)—N-(3-fluoro-2-hydroxypropyl)-1-(4-(3-fluoro-4-methoxybenzyl)pyridin-2-yl)indoline-4-carboxamide;

(S)—N-(3-fluoro-2-hydroxypropyl)-1-(4-(3-fluoro-4-methoxybenzyl)pyridin-2-yl)indoline-4-carboxamide;

(S)-1-(4-(benzofuran-5-ylmethyl)pyridin-2-yl)-N-(3-fluoro-2-hydroxypropyl)indoline-4-carboxamide;

(R)-1-(4-(benzofuran-5-ylmethyl)pyridin-2-yl)-N-(3-fluoro-2-hydroxypropyl)indoline-4-carboxamide;

(R)—N-(3-fluoro-2-hydroxypropyl)-1-(4-(3,4,5-trifluorobenzyl)pyridin-2-yl)indoline-4-carboxamide;

(R)—N-(2-fluoro-3-hydroxypropyl)-1-(4-(3-fluoro-4-methoxybenzyl)pyridin-2-yl)indoline-4-carboxamide;

1-(4-(3-fluoro-4-methoxybenzyl)pyridin-2-yl)-N-(2-fluoroethyl)indoline-4-carboxamide;

1-(4-(3-fluoro-4-methoxybenzyl)pyridin-2-yl)-N-((3-(hydroxymethyl)oxetan-3-yl)methyl)indoline-4-carboxamide;

1-(4-(3-fluoro-4-methoxybenzyl)pyridin-2-yl)-N-(2-(2-hydroxyethoxy)ethyl)indoline-4-carboxamide;

N-(2-(2-hydroxyethoxy)ethyl)-1-(4-(3,4,5-trifluorobenzyl)pyridin-2-yl)indoline-4-carboxamide;

1-(4-(benzofuran-5-ylmethyl)pyridin-2-yl)-N-(2-(2-hydroxyethoxy)ethyl)indoline-4-carboxamide; and 1-(4-(benzofuran-5-ylmethyl)pyridin-2-yl)-N-(2-fluoroethyl)indoline-4-carboxamide.

lvii) A pharmaceutical product selected from: a pharmaceutical composition, a formulation, a unit dosage form, and a kit; each comprising a compound according to any one of i)-lvi).

lviii) A pharmaceutical composition comprising a compound according to any one of i)-lvi), and a pharmaceutically acceptable carrier.

lix) A method for preparing a pharmaceutical composition comprising the step of admixing a compound according to any one of i)-lvi), and a pharmaceutically acceptable carrier.

lx) A method for treating or preventing a GPR52-mediated disorder in an individual, comprising administering to said individual in need thereof, a therapeutically effective amount of a compound according to any one of i)-lvi); a pharmaceutical product according to lvii); or a pharmaceutical composition according to lviii).

lxi) A method for treating or preventing an extrapyramidal or movement disorder in an individual, comprising administering to said individual in need thereof, a therapeutically effective amount of a compound according to any one of i)-lvi); a pharmaceutical product according to lvii); or a pharmaceutical composition according to lviii).

lxii) A method for treating or preventing a psychotic disorder in an individual, comprising administering to said individual in need thereof, a therapeutically effective amount of a compound according to any one of i)-lvi); a pharmaceutical product according to lvii); or a pharmaceutical composition according to lviii).

lxiii) A method for treating or preventing a mood disorder, a depressive disorder, or a bipolar or related disorder in an individual, comprising administering to said individual in need thereof, a therapeutically effective amount of a compound according to any one of i)-lvi); a pharmaceutical product according to lvii); or a pharmaceutical composition according to lviii).

lxiv) A method for treating or preventing attention deficit disorder (ADHD), anxiety disorder, obsessive-compulsive disorder (OCD), or autism spectrum disorder in an individual, comprising administering to said individual in need thereof, a therapeutically effective amount of a compound according to any one of i)-lvi); a pharmaceutical product according to lvii); or a pharmaceutical composition according to lviii).

lxv) A method for treating or preventing a prolactin-related disorder in an individual, comprising administering to said individual in need thereof, a therapeutically effective amount of a compound according to any one of i)-lvi); a pharmaceutical product according to lvii); or a pharmaceutical composition according to lviii).

lxvi) A method for treating or preventing a neurocognitive disorder in an individual, comprising administering to said individual in need thereof, a therapeutically effective amount of a compound according to any one of i)-lvi); a pharmaceutical product according to lvii); or a pharmaceutical composition according to lviii).

lxvii) A method for treating or preventing a trauma- or stressor-related disorder; a disruptive, impulse-control, or conduct disorder; or a sleep-wake disorder in an individual, comprising administering to said individual in need thereof, a therapeutically effective amount of a compound according to any one of i)-lvi); a pharmaceutical product according to lvii); or a pharmaceutical composition according to lviii).

lxviii) A method for treating or preventing a substance-related disorder, an addictive disorder, or a behavioral disorder in an individual, comprising administering to said individual in need thereof, a therapeutically effective amount of a compound according to any one of i)-lvi); a pharmaceutical product according to lvii); or a pharmaceutical composition according to lviii).

lxix) A method for treating or preventing hypofrontality in an individual, comprising administering to said individual in need thereof, a therapeutically effective amount of a compound according to any one of i)-lvi); a pharmaceutical product according to lvii); or a pharmaceutical composition according to lviii).

lxx) A method for treating or preventing an abnormality in the tuberoinfundibular pathway, mesolimbic pathway, mesocortical pathway, or nigrostriatal pathway in an individual, comprising administering to said individual in need thereof, a therapeutically effective amount of a compound according to any one of i)-lvi); a pharmaceutical product according to lvii); or a pharmaceutical composition according to lviii).

lxxi) A method for increasing activity in the striatum in an individual, comprising administering to said individual in need thereof, a therapeutically effective amount of a compound according to any one of i)-lvi); a pharmaceutical product according to lvii); or a pharmaceutical composition according to lviii).

lxxii) A method for improving cortical function in an individual, comprising administering to said individual in need thereof, a therapeutically effective amount of a compound according to any one of i)-lvi); a pharmaceutical product according to lvii); or a pharmaceutical composition according to lviii).

lxxiii) A method for improving neurocognitive function in an individual, comprising administering to said individual in need thereof, a therapeutically effective amount of a compound according to any one of i)-lvi); a pharmaceutical product according to lvii); or a pharmaceutical composition according to lviii).

lxxiv) Use of a compound according to any one of i)-lvi) in the manufacture of a medicament for treating or preventing a GPR52-mediated disorder in an individual.

lxxv) Use of a compound according to any one of i)-lvi) in the manufacture of a medicament for treating or preventing an extrapyramidal or movement disorder in an individual.

lxxvi) Use of a compound according to any one of i)-lvi) in the manufacture of a medicament for treating or preventing a psychotic disorder in an individual.

lxxvii) Use of a compound according to any one of i)-lvi) in the manufacture of a medicament for treating or preventing a mood disorder, a depressive disorder, or a bipolar or related disorder in an individual.

lxxviii) Use of a compound according to any one of i)-lvi) in the manufacture of a medicament for treating or preventing attention deficit disorder (ADHD), anxiety disorder, obsessive-compulsive disorder (OCD), or autism spectrum disorder in an individual.

lxxix) Use of a compound according to any one of i)-lvi) in the manufacture of a medicament for treating or preventing a prolactin-related disorder in an individual.

lxxx) Use of a compound according to any one of i)-lvi) in the manufacture of a medicament for treating or preventing a neurocognitive disorder in an individual.

lxxxi) Use of a compound according to any one of i)-lvi) in the manufacture of a medicament for treating or preventing a trauma- or stressor-related disorder; a disruptive, impulse-control, or conduct disorder; or a sleep-wake disorder in an individual.

lxxxii) Use of a compound according to any one of i)-lvi) in the manufacture of a medicament for treating or preventing a substance-related disorder, an addictive disorder, or a behavioral disorder in an individual.

lxxxiii) Use of a compound according to any one of i)-lvi) in the manufacture of a medicament for treating or preventing hypofrontality in an individual.

lxxxiv) Use of a compound according to any one of i)-lvi) in the manufacture of a medicament for treating or preventing an abnormality in the tuberoinfundibular pathway, mesolimbic pathway, mesocortical pathway, or nigrostriatal pathway in an individual.

lxxxv) Use of a compound according to any one of i)-lvi) in the manufacture of a medicament for increasing activity in the striatum in an individual.

lxxxvi) Use of a compound according to any one of i)-lvi) in the manufacture of a medicament for improving cortical function in an individual.

lxxxvii) Use of a compound according to any one of i)-lvi) in the manufacture of a medicament for improving neurocognitive function in an individual.

lxxxviii) A compound according to any one of i)-lvi); a pharmaceutical product according to lvii); or a pharmaceutical composition according to lviii); for use in a method of treatment of the human or animal body by therapy.

lxxxix) A compound according to any one of i)-lvi); a pharmaceutical product according to lvii); or a pharmaceutical composition according to lviii); for use in a method for treating or preventing a GPR52-mediated disorder in an individual.

xc) A compound according to any one of i)-lvi); a pharmaceutical product according to lvii); or a pharmaceutical composition according to lviii); for use in a method for treating or preventing an extrapyramidal or movement disorder in an individual.

xci) A compound according to any one of i)-lvi); a pharmaceutical product according to lvii); or a pharmaceutical composition according to lviii); for use in a method for treating or preventing a psychotic disorder in an individual.

xcii) A compound according to any one of i)-lvi); a pharmaceutical product according to lvii); or a pharmaceutical composition according to lviii); for use in a method for treating or preventing a mood disorder, a depressive disorder, or a bipolar or related disorder in an individual.

xciii) A compound according to any one of i)-lvi); a pharmaceutical product according to lvii); or a pharmaceutical composition according to lviii); for use in a method for treating or preventing attention deficit disorder (ADHD), anxiety disorder, obsessive-compulsive disorder (OCD), or autism spectrum disorder in an individual.

xciv) A compound according to any one of i)-lvi); a pharmaceutical product according to lvii); or a pharmaceutical composition according to lviii); for use in a method for treating or preventing a prolactin-related disorder in an individual.

xcv) A compound according to any one of i)-lvi); a pharmaceutical product according to lvii); or a pharmaceutical composition according to lviii); for use in a method for treating or preventing a neurocognitive disorder in an individual.

xcvi) A compound according to any one of i)-lvi); a pharmaceutical product according to lvii); or a pharmaceutical composition according to lviii); for use in a method for treating or preventing a trauma- or stressor-related disorder; a disruptive, impulse-control, or conduct disorder; or a sleep-wake disorder in an individual.

xcvii) A compound according to any one of i)-lvi); a pharmaceutical product according to lvii); or a pharmaceutical composition according to lviii); for use in a method for treating or preventing a substance-related disorder, an addictive disorder, or a behavioral disorder in an individual.

xcviii) A compound according to any one of i)-lvi); a pharmaceutical product according to lvii); or a pharmaceutical composition according to lviii); for use in a method for treating or preventing hypofrontality in an individual.

xcix) A compound according to any one of i)-lvi); a pharmaceutical product according to lvii); or a pharmaceutical composition according to lviii); for use in a method for treating or preventing an abnormality in the tuberoinfundibular pathway, mesolimbic pathway, mesocortical pathway, or nigrostriatal pathway in an individual.

c) A compound according to any one of i)-lvi); a pharmaceutical product according to lvii); or a pharmaceutical composition according to lviii); for use in a method for increasing activity in the striatum in an individual.

ci) A compound according to any one of i)-lvi); a pharmaceutical product according to lvii); or a pharmaceutical composition according to lviii); for use in a method for improving cortical function in an individual.

cii) A compound according to any one of i)-lvi); a pharmaceutical product according to lvii); or a pharmaceutical composition according to lviii); for use in a method for improving neurocognitive function in an individual.

ciii) The method according to lx); a use according to lxxiv); or a compound according to lxxxix); wherein the GPR52-mediated disorder is selected from: Huntington's disease, schizophrenia, bipolar disorder, attention deficit hyperactivity disorder (ADHD), and Tourette's syndrome.

civ) The method according to lxi); a use according to lxxv); or a compound according to xc); wherein the extrapyramidal or movement disorder is selected from: akathisia, associated movements, athetosis, ataxia, ballismus, hemiballismus, chorea, Huntington's disease, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, Tourette's syndrome, tremor, and Wilson's disease.

cv) The method according to lxi); a use according to lxxv); or a compound according to xc); wherein the extrapyramidal or movement disorder is a motor disorder.

cvi) The method according to cv); a use according to cv); or a compound according to cv); wherein the motor disorder is selected from: developmental coordination disorder, stereotypic movement disorder, and Tic disorder.

cvii) The method according to lxi); a use according to lxxv); or a compound according to xc); wherein the extrapyramidal or movement disorder is a hyperkinetic movement disorder.

cviii) The method according to cvii); a use according to cvii); or a compound according to cvii); wherein the hyperkinetic movement disorder is selected from: Huntington's disease, Wilson's disease, restless leg syndrome, a post-stroke effect, and dentatorubral-pallidoluysian atrophy.

cix) The method according to lxi); a use according to lxxv); or a compound according to xc); wherein treating or preventing an extrapyramidal or movement disorder comprises treating or preventing extrapyramidal syndrome.

cx) The method according to lxii); a use according to lxxvi); or a compound according to xci); wherein the psychotic disorder is selected from: schizotypal personality disorder, delusional disorder, brief psychotic disorder, schizophreniform disorder, schizophrenia, schizoaffective disorder, and substance- or medication-induced psychotic disorder.

cxi) The method according to lxii); a use according to lxxvi); or a compound according to xci); wherein treating or preventing a psychotic disorder comprises treating or preventing a positive symptom of schizophrenia.

cxii) The method according to cxi); a use according to cxi); or a compound according to cxi); wherein the positive symptom is selected from: delusions, hallucinations, disorganized thinking, and grossly disorganized or abnormal motor behavior.

cxiii) The method according to lxii); a use according to lxxvi); or a compound according to xci); wherein treating or preventing a psychotic disorder comprises treating or preventing a negative symptom of schizophrenia.

cxiv) The method according to cxiii); a use according to cxiii); or a compound according to cxiii); wherein the negative symptom is selected from: diminished emotional expression, avolition, alogia, anhedonia, and asociality.

cxv) The method according to lxii); a use according to lxxvi); or a compound according to xci); wherein the psychotic disorder comprises a schizophrenia spectrum domain selected from: delusions, hallucinations, disorganized thinking, grossly disorganized or abnormal motor behavior, and negative symptoms.

cxvi) The method according to lxii); a use according to lxxvi); or a compound according to xci); wherein the psychotic disorder is characterized by catatonia.

cxvii) The method according to lxiii); a use according to lxxvii); or a compound according to xcii); wherein the depressive disorder is major depressive disorder.

cxviii) The method according to lxiii); a use according to lxxvii); or a compound according to xcii); wherein the bipolar or related disorder is selected from: bipolar I disorder, bipolar II disorder, cyclothymic disorder, substance- or medication-induced bipolar and related disorders, and bipolar and related disorders due to another medical condition.

cxix) The method according to lxiv); a use according to lxxviii); or a compound according to xciii); wherein the anxiety disorder is selected from: separation anxiety disorder, selective mutism, specific phobia, social anxiety disorder, panic disorder, agoraphobia, generalized anxiety disorder, substance- or medication-induced anxiety disorder, and anxiety disorder due to another medical condition.

cxx) The method according to lxv); a use according to lxxix); or a compound according to xciv); wherein the prolactin-related disorder is hyperprolactinemia.

cxxi) The method according to lxvi); a use according to lxxx); or a compound according to xcv); wherein the neurocognitive disorder is selected from: delirium, major neurocognitive disorder, and minor neurocognitive disorder.

cxxii) The method according to lxvi); a use according to lxxx); or a compound according to xcv); wherein the neurocognitive disorder is selected from: amnesia, dementia, and delirium.

cxxiii) The method according to lxvii); a use according to lxxxi); or a compound according to xcvi); wherein the trauma- or stressor-related disorder is posttraumatic stress disorder (PTSD).

cxxiv) The method according to lxviii); a use according to lxxxii); or a compound according to xcvii); wherein the substance is selected from: alcohol, caffeine, *cannabis*, a hallucinogen, an inhalant, an opioid, a sedative, a hypnotic, an anxiolytic, a stimulant, and tobacco.

cxxv) The method according to lxix); a use according to lxxxiii); or a compound according to xcviii); wherein the hypofrontality is associated with at least one disorder selected from: schizophrenia, attention deficit hyperactivity disorder (ADHD), bipolar disorder, and major depressive disorder.

cxxvi) The method according to lxxii); a use according to lxxxvi); or a compound according to ci); wherein the cortical function is selected from: executive function, attention, and memory.

cxxvii) The method according to lxxiii); a use according to lxxxvii); or a compound according to cii); wherein the neurocognitive function is at least one domain selected from: complex attention, executive function, learning and memory, language, perceptual-motor, and social cognition.

We claim:

1. A compound selected from compounds of Formula (Ia) and pharmaceutically acceptable salts, and N-oxides thereof:

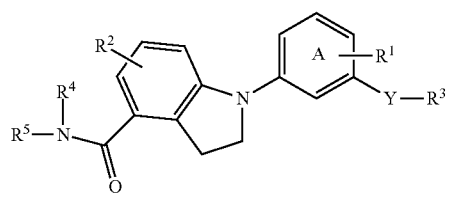

(Ia)

wherein:
Y is selected from: —CH$_2$—, —O—, and —S—;
Ring A is pyridinediyl or pyrazine-2,6-diyl;
R$^1$ is H or C$_1$-C$_6$ alkyl;
R$^2$ is H or halogen;
R$^3$ is aryl or heteroaryl, wherein each ring is optionally substituted with one or more groups selected independently from: C$_1$-C$_6$ acyl, C$_1$-C$_6$ acyloxy, C$_1$-C$_6$ alkoxy, C$_1$-C$_6$ alkylcarboxamide, C$_1$-C$_6$ alkyl, cyano, C$_1$-C$_6$ haloalkoxy, C$_1$-C$_6$ haloalkyl, halogen, hydroxyl, and hydroxy-C$_1$-C$_6$-alkyl; and said C$_1$-C$_6$ alkyl is optionally substituted with one or more groups selected independently from: C$_1$-C$_6$ alkylamino, C$_2$-C$_6$ dialkylamino, and oxo;
R$^4$ is H; and
R$^5$ is selected from: H, C$_1$-C$_6$ alkyl, heteroaryl, heteroaryl-C$_1$-C$_6$ alkyl, heterocyclyl, and heterocyclyl-C$_1$-C$_6$ alkyl; and each group is optionally substituted with one or more groups selected independently from: C$_1$-C$_6$ alkoxy, C$_1$-C$_6$ alkylcarboxamide, C$_1$-C$_6$ alkyl, cyano, C$_1$-C$_6$ alkylamino, C$_2$-C$_6$ dialkylamino, C$_1$-C$_6$ haloalkyl, halogen, hydroxyl, hydroxy-C$_1$-C$_6$-alkoxy, hydroxy-C$_1$-C$_6$-alkyl, and oxo.

2. The compound according to claim 1, or an N-oxide or a pharmaceutically acceptable salt thereof, wherein Y is —CH$_2$—.

3. The compound according to claim 2, or an N-oxide or a pharmaceutically acceptable salt thereof, wherein Ring A is

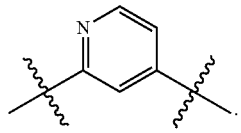 [SMILES: *c1ccnc(*)c1]

4. The compound according to claim 2, or an N-oxide or pharmaceutically acceptable salt thereof, wherein Ring A is:

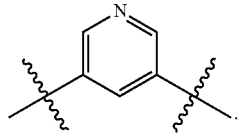 [SMILES: *c1cncc(*)c1]

5. The compound according to claim 2, or an N-oxide or a pharmaceutically acceptable salt thereof, wherein Ring A is:

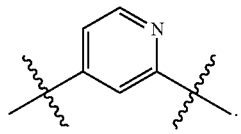 [SMILES: *c1ccnc(*)c1]

6. The compound according to claim 2, or an N-oxide or a pharmaceutically acceptable salt thereof, wherein Ring A is:

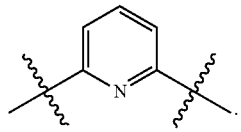 [SMILES: *c1cccc(*)n1]

7. The compound according to claim 2, or an N-oxide or a pharmaceutically acceptable salt thereof, wherein Ring A is pyrazine-2,6-diyl of the formula:

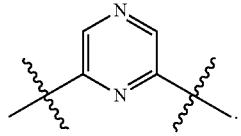 [SMILES: *c1cncc(*)n1]

8. The compound according to claim 2, or an N-oxide or a pharmaceutically acceptable salt thereof, wherein R$^1$ is H or methyl.

9. The compound according to claim 8, or an N-oxide or a pharmaceutically acceptable salt thereof, wherein R$^1$ is H.

10. The compound according to claim 8, or an N-oxide or a pharmaceutically acceptable salt thereof, wherein R$^2$ is H or fluoro.

11. The compound according to claim 10, or an N-oxide or a pharmaceutically acceptable salt thereof, wherein R$^2$ is H.

12. The compound according to claim 10, or an N-oxide or a pharmaceutically acceptable salt thereof, wherein R³ is phenyl optionally substituted with one or more groups selected independently from: acetoxy, acetyl, chloro, cyano, (dimethylamino)methyl, ethoxy, fluoro, hydroxy, hydroxymethyl, methoxy, methyl, methylcarbamoyl, trifluoromethoxy, and trifluoromethyl.

13. The compound according to claim 12, or an N-oxide or a pharmaceutically acceptable salt thereof, wherein R³ is selected from: 3-((dimethylamino)methyl)phenyl, 3-(trifluoromethoxy)phenyl, 3-(trifluoromethyl)phenyl, 3,4,5-trifluorophenyl, 3,4-difluorophenyl, 3,5-difluoro-4-methoxyphenyl, 3,5-difluorophenyl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, and 4-methoxy-3-methylphenyl.

14. The compound according to claim 12, or an N-oxide or a pharmaceutically acceptable salt thereof, wherein R⁵ is selected from: H, (oxetan-3-yl)methyl, 1H-pyrazol-4-yl, 1-hydroxybutan-2-yl, 2-(1H-imidazol-1-yl)ethyl, 2-(1H-imidazol-5-yl)ethyl, 2-(imidazolidin-1-yl)ethyl, 2-(pyridin-2-yl)ethyl, 2-(pyridin-3-yl)ethyl, 2-(pyridin-4-yl)ethyl, 2-(pyrrolidin-1-yl)ethyl, 2-hydroxypropyl, 3-hydroxypropan-2-yl, 3-hydroxypropyl, ethyl, 2-hydroxyethyl, methyl, piperidin-3-yl, piperidin-4-yl, propan-2-yl, propyl, pyridin-4-yl, pyrrolidin-3-yl, and tetrahydrofuran-3-yl; and each group is optionally substituted with one or more groups selected independently from: 2-hydroxyethoxy, 2-hydroxyethyl, acetamido, cyano, dimethylamino, fluoro, hydroxy, hydroxymethyl, methoxy, methyl, methylamino, oxo, and trifluoromethyl.

15. The compound according to claim 14, or an N-oxide or a pharmaceutically acceptable salt thereof, wherein R⁵ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

16. The compound according to claim 1, according to Formula (Im):

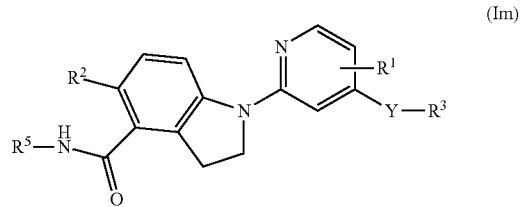

(Im)

or an N-oxide or a pharmaceutically acceptable salt thereof, wherein:

Y is selected from: —CH₂—, —O—, and —S—;

R¹ is H or methyl;

R² is H or fluoro;

R³ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl; and R⁵ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

17. The compound according to claim 1, according to Formula (Io):

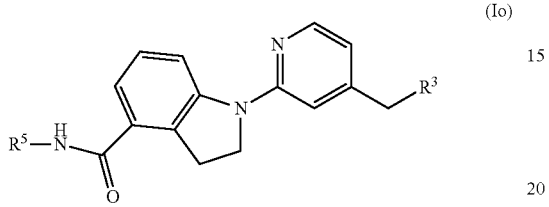

(Io)

or an N-oxide or a pharmaceutically acceptable salt thereof, wherein:

$R^3$ is selected from: 1H-indol-4-yl, 2-(trifluoromethyl)pyridin-4-yl, 2,3-dihydrobenzofuran-5-yl, 2-chloropyrimidin-5-yl, 2-methoxypyrimidin-5-yl, 3-((dimethylamino)methyl)phenyl, 3-(trifluoromethoxy)phenyl, 3-(trifluoromethyl)phenyl, 3,4,5-trifluorophenyl, 3,4-difluorophenyl, 3,4-dihydro-2H-benzo[b][1,4]dioxepin-7-yl, 3,5-difluoro-4-methoxyphenyl, 3,5-difluorophenyl, 3,5-dimethylisoxazol-4-yl, 3-acetoxyphenyl, 3-acetyl-4-fluorophenyl, 3-acetylphenyl, 3-chloro-4-fluorophenyl, 3-chloro-4-methoxyphenyl, 3-chloro-5-fluorophenyl, 3-chloro-5-methoxyphenyl, 3-cyano-4-fluorophenyl, 3-cyano-5-fluorophenyl, 3-fluoro-4-(hydroxymethyl)phenyl, 3-fluoro-4-hydroxyphenyl, 3-fluoro-4-methoxyphenyl, 3-fluoro-5-(trifluoromethyl)phenyl, 3-fluoro-5-methoxyphenyl, 3-methoxyphenyl, 4-acetyl-3-fluorophenyl, 4-acetylphenyl, 4-chloro-3-fluorophenyl, 4-chloro-3-methoxyphenyl, 4-cyano-3-fluorophenyl, 4-ethoxy-3-fluorophenyl, 4-fluoro-3-(hydroxymethyl)phenyl, 4-fluoro-3-(methylcarbamoyl)phenyl, 4-fluoro-3-(trifluoromethyl)phenyl, 4-fluoro-3-hydroxyphenyl, 4-fluoro-3-methoxyphenyl, 4-methoxy-3-(trifluoromethyl)phenyl, 4-methoxy-3-methylphenyl, 5-(trifluoromethyl)pyridin-3-yl, 5,6-difluoropyridin-3-yl, 5-chloro-6-fluoropyridin-3-yl, 5-chloro-6-methoxypyridin-3-yl, 5-chloropyridin-3-yl, 5-fluoro-6-methoxypyridin-3-yl, 6-(trifluoromethyl)pyridin-2-yl, 6-cyanopyridin-3-yl, 6-fluoro-5-methylpyridin-3-yl, 6-methoxypyridin-3-yl, benzo[d][1,3]dioxol-5-yl, benzofuran-2-yl, benzofuran-5-yl, furan-2-yl, furan-3-yl, quinolin-3-yl, and quinolin-5-yl; and $R^5$ is selected from: H, (2R,3S)-1,3-dihydroxybutan-2-yl, (3-(hydroxymethyl)oxetan-3-yl)methyl, (dimethylamino)ethyl, (R)-2,3-dihydroxypropyl, (R)-2-fluoro-3-hydroxypropyl, (R)-2-hydroxy-2-(pyridin-3-yl)ethyl, (R)-2-hydroxy-3-methoxypropyl, (R)-2-hydroxypropyl, (R)-2-oxopyrrolidin-3-yl, (R)-2-oxotetrahydrofuran-3-yl, (S)-2,3-dihydroxypropyl, (S)-2-fluoro-3-hydroxypropyl, (S)-2-hydroxy-2-(pyridin-3-yl)ethyl, (S)-2-hydroxy-3-methoxypropyl, (S)-2-hydroxypropyl, (S)-2-oxopyrrolidin-3-yl, (S)-2-oxotetrahydrofuran-3-yl, (S)-3,3,3-trifluoro-2-hydroxypropyl, (S)-3-fluoro-2-hydroxypropyl, (S)-tetrahydrofuran-3-yl, 1-(2-hydroxyethyl)-1H-pyrazol-4-yl, 1-(2-hydroxyethyl)piperidin-4-yl, 1,3-dihydroxypropan-2-yl, 1,3-dimethoxypropan-2-yl, 1-methyl-1H-pyrazol-4-yl, 1-methylpiperidin-4-yl, 2-(1H-imidazol-1-yl)ethyl, 2-(1H-imidazol-5-yl)ethyl, 2-(2-hydroxyethoxy)ethyl, 2-(2-oxoimidazolidin-1-yl)ethyl, 2-(2-oxopyrrolidin-1-yl)ethyl, 2-(pyrrolidin-1-yl)ethyl, 2-acetamidoethyl, 2-cyanoethyl, 2-fluoroethyl, 2-hydroxy-2-(pyridin-2-yl)ethyl, 2-hydroxy-2-(pyridin-4-yl)ethyl, 2-hydroxyethyl, 2-morpholinoethyl, 3-(dimethylamino)-2-hydroxypropyl, 3-(methylamino)-3-oxopropyl, 3-hydroxypropyl, 6-oxopiperidin-3-yl, cyanomethyl, methyl, and pyridin-4-yl.

18. The compound according to claim 1, according to Formula (Iq):

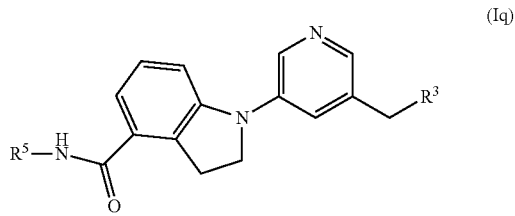

(Iq)

or an N-oxide or a pharmaceutically acceptable salt thereof, wherein:

$R^3$ is phenyl optionally substituted with trifluoromethyl; and $R^5$ is selected from: H, methyl, ethyl, and tetrahydrofuranyl; and ethyl is optionally substituted with hydroxyl.

19. The compound according to claim 1, according to Formula (Is):

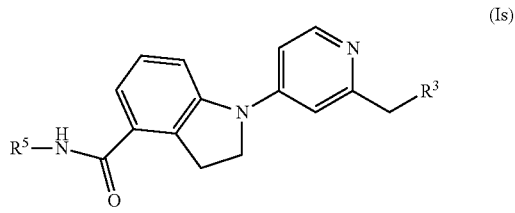

(Is)

or an N-oxide or a pharmaceutically acceptable salt thereof, wherein:

$R^3$ is phenyl is optionally substituted with one or more groups selected independently from: acetyl, methoxy, trifluoromethyl, chloro, and fluoro; and $R^5$ is selected from: H, ethyl, pyrrolidinyl, and tetrahydrofuranyl; and ethyl and pyrrolidinyl are each optionally substituted with one or more groups selected independently from: methoxy, fluoro, hydroxyl, and oxo.

20. The compound according to claim 1, according to Formula (Iu):

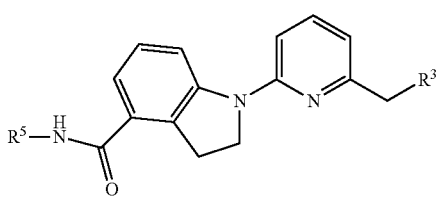

or an N-oxide or a pharmaceutically acceptable salt thereof, wherein:
$R^3$ is phenyl optionally substituted with trifluoromethyl; and
$R^5$ is selected from: H and tetrahydrofuranyl.

21. The compound according to claim 1, according to Formula (Iw):

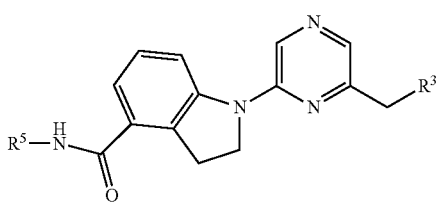

or an N-oxide or a pharmaceutically acceptable salt thereof, wherein:
$R^3$ is phenyl optionally substituted with trifluoromethyl; and
$R^5$ is selected from: H and ethyl; and ethyl is optionally substituted with hydroxyl.

22. The compound according to claim 1, selected from the group consisting of:
1-(6-(3-(Trifluoromethyl)benzyl)pyridin-2-yl)indoline-4-carboxamide;
(S)—N-(Tetrahydrofuran-3-yl)-1-(6-(3-(trifluoromethyl)benzyl)pyridin-2-yl)indoline-4-carboxamide;
(S)—N-(Tetrahydrofuran-3-yl)-1-(2-(3-(trifluoromethyl)benzyl)pyridin-4-yl)indoline-4-carboxamide;
(S)—N-(Tetrahydrofuran-3-yl)-1-(4-(3-(trifluoromethyl)benzyl)pyridin-2-yl)indoline-4-carboxamide;
1-(4-(3-(Trifluoromethyl)benzyl)pyridin-2-yl)indoline-4-carboxamide;
1-(2-(3-(Trifluoromethyl)benzyl)pyridin-4-yl)indoline-4-carboxamide;
(S)—N-(Tetrahydrofuran-3-yl)-1-(5-(3-(trifluoromethyl)benzyl)pyridin-3-yl)indoline-4-carboxamide;
1-(5-(3-(Trifluoromethyl)benzyl)pyridin-3-yl)indoline-4-carboxamide;
N-Methyl-1-(5-(3-(trifluoromethyl)benzyl)pyridin-3-yl)indoline-4-carboxamide;
N-(2-Hydroxyethyl)-1-(5-(3-(trifluoromethyl)benzyl)pyridin-3-yl)indoline-4-carboxamide;
(S)-3-(4-(Tetrahydrofuran-3-ylcarbamoyl)indolin-1-yl)-5-(3-(trifluoromethyl)benzyl)pyridine 1-oxide;
3-(4-Carbamoylindolin-1-yl)-5-(3-(trifluoromethyl)benzyl)pyridine 1-oxide;
N-(2-Hydroxyethyl)-1-(4-(3-(trifluoromethyl)benzyl)pyridin-2-yl)indoline-4-carboxamide;
1-(4-(3,5-Difluorobenzyl)pyridin-2-yl)-N-(2-hydroxyethyl)indoline-4-carboxamide;
1-(4-(3,5-Difluorobenzyl)pyridin-2-yl)indoline-4-carboxamide;
1-(4-(3,5-Difluorobenzyl)pyridin-2-yl)-N-methylindoline-4-carboxamide;
1-(6-Methyl-4-(3-(trifluoromethyl)benzyl)pyridin-2-yl)indoline-4-carboxamide;
N-Methyl-1-(6-methyl-4-(3-(trifluoromethyl)benzyl)pyridin-2-yl)indoline-4-carboxamide;
(S)-1-(4-(3,5-Difluorobenzyl)pyridin-2-yl)-N-(tetrahydrofuran-3-yl)indoline-4-carboxamide;
N-(2-Cyanoethyl)-1-(4-(3-(trifluoromethyl)benzyl)pyridin-2-yl)indoline-4-carboxamide;
(R)—N-(2,3-Dihydroxypropyl)-1-(4-(3-(trifluoromethyl)benzyl)pyridin-2-yl)indoline-4-carboxamide;
(S)—N-(2,3-Dihydroxypropyl)-1-(4-(3-(trifluoromethyl)benzyl)pyridin-2-yl)indoline-4-carboxamide;
1-(4-(3-Fluoro-5-(trifluoromethyl)phenoxy)pyridin-2-yl)-N-(2-hydroxyethyl)indoline-4-carboxamide;
1-(4-(3-Fluoro-5-(trifluoromethyl)phenoxy)pyridin-2-yl)indoline-4-carboxamide;
N-(3-Hydroxypropyl)-1-(4-(3-(trifluoromethyl)benzyl)pyridin-2-yl)indoline-4-carboxamide;
(R)—N-(2-Hydroxypropyl)-1-(4-(3-(trifluoromethyl)benzyl)pyridin-2-yl)indoline-4-carboxamide;
N-(Cyanomethyl)-1-(4-(3-(trifluoromethyl)benzyl)pyridin-2-yl)indoline-4-carboxamide;
1-(4-(3-Fluoro-5-(trifluoromethyl)benzyl)pyridin-2-yl)-N-(2-hydroxyethyl)indoline-4-carboxamide;
N-(2-Hydroxyethyl)-1-(4-(3-(trifluoromethyl)phenyl)pyridin-2-yl)indoline-4-carboxamide;
1-(4-(3-(Trifluoromethyl)phenylthio)pyridin-2-yl)indoline-4-carboxamide;
(S)—N-(2,3-Dihydroxypropyl)-1-(4-(3-fluoro-5-(trifluoromethyl)benzyl)pyridin-2-yl)indoline-4-carboxamide;
(R)—N-(2,3-Dihydroxypropyl)-1-(4-(3-fluoro-5-(trifluoromethyl)benzyl)pyridin-2-yl)indoline-4-carboxamide;
1-(4-(3-Fluoro-5-(trifluoromethyl)benzyl)pyridin-2-yl)indoline-4-carboxamide;
N-(2-(Dimethylamino)ethyl)-1-(4-(3-fluoro-5-(trifluoromethyl)benzyl)pyridin-2-yl)indoline-4-carboxamide;
N-(1,3-Dihydroxypropan-2-yl)-1-(4-(3-fluoro-5-(trifluoromethyl)benzyl)pyridin-2-yl)indoline-4-carboxamide;
N-(2-(Dimethylamino)ethyl)-1-(4-(3-(trifluoromethyl)benzyl)pyridin-2-yl)indoline-4-carboxamide;
N-(1,3-Dihydroxypropan-2-yl)-1-(4-(3-(trifluoromethyl)benzyl)pyridin-2-yl)indoline-4-carboxamide;
N-(2-Hydroxyethyl)-1-(6-(3-(trifluoromethyl)benzyl)pyrazin-2-yl)indoline-4-carboxamide;
1-(6-(3-(Trifluoromethyl)benzyl)pyrazin-2-yl)indoline-4-carboxamide;
N-(2-Hydroxyethyl)-1-(4-((6-(trifluoromethyl)pyridin-2-yl)methyl)pyridin-2-yl)indoline-4-carboxamide;
1-(4-((6-(Trifluoromethyl)pyridin-2-yl)methyl)pyridin-2-yl)indoline-4-carboxamide;
1-(4-(3-Chloro-5-fluorobenzyl)pyridin-2-yl)indoline-4-carboxamide;
1-(4-(3-Chloro-5-fluorobenzyl)pyridin-2-yl)-N-(2-hydroxyethyl)indoline-4-carboxamide;
1-(4-(3-Chloro-5-fluorobenzyl)pyridin-2-yl)-N-(2-(dimethylamino)ethyl)indoline-4-carboxamide;
1-(4-(3-Chloro-5-fluorobenzyl)pyridin-2-yl)-N-(pyridin-4-yl)indoline-4-carboxamide;
1-(4-((5-Chloropyridin-3-yl)methyl)pyridin-2-yl)indoline-4-carboxamide;

1-(4-((5-(Trifluoromethyl)pyridin-3-yl)methyl)pyridin-2-yl)indoline-4-carboxamide;
N-(2-Hydroxyethyl)-1-(4-((5-(trifluoromethyl)pyridin-3-yl)methyl)pyridin-2-yl)indoline-4-carboxamide;
1-(4-((5,6-Difluoropyridin-3-yl)methyl)pyridin-2-yl)indoline-4-carboxamide;
1-(4-((6-Fluoro-5-methylpyridin-3-yl)methyl)pyridin-2-yl)indoline-4-carboxamide;
1-(4-((2-(Trifluoromethyl)pyridin-4-yl)methyl)pyridin-2-yl)indoline-4-carboxamide;
1-(4-((5-Chloro-6-fluoropyridin-3-yl)methyl)pyridin-2-yl)indoline-4-carboxamide;
N-(1-Methylpiperidin-4-yl)-1-(4-(3-(trifluoromethyl)benzyl)pyridin-2-yl)indoline-4-carboxamide;
1-(4-(3-Fluoro-4-methoxybenzyl)pyridin-2-yl)indoline-4-carboxamide;
1-(4-(4-Acetylbenzyl)pyridin-2-yl)indoline-4-carboxamide;
1-(4-(4-Methoxy-3-(trifluoromethyl)benzyl)pyridin-2-yl)indoline-4-carboxamide;
1-(4-(4-Chloro-3-fluorobenzyl)pyridin-2-yl)indoline-4-carboxamide;
1-(4-(3-Chloro-4-fluorobenzyl)pyridin-2-yl)indoline-4-carboxamide;
1-(4-(4-Fluoro-3-(methylcarbamoyl)benzyl)pyridin-2-yl)indoline-4-carboxamide;
1-(4-(3-Cyano-4-fluorobenzyl)pyridin-2-yl)indoline-4-carboxamide;
1-(4-(4-Fluoro-3-(trifluoromethyl)benzyl)pyridin-2-yl)indoline-4-carboxamide;
1-(4-(3-Acetyl-4-fluorobenzyl)pyridin-2-yl)indoline-4-carboxamide;
1-(4-(4-Fluoro-3-(hydroxymethyl)benzyl)pyridin-2-yl)indoline-4-carboxamide;
1-(4-(3-(Trifluoromethoxy)benzyl)pyridin-2-yl)indoline-4-carboxamide;
1-(4-(3,4,5-Trifluorobenzyl)pyridin-2-yl)indoline-4-carboxamide;
1-(4-((2,3-Dihydrobenzofuran-5-yl)methyl)pyridin-2-yl)indoline-4-carboxamide;
1-(4-(4-Fluoro-3-methoxybenzyl)pyridin-2-yl)indoline-4-carboxamide;
1-(4-(3-Cyano-5-fluorobenzyl)pyridin-2-yl)indoline-4-carboxamide;
1-(4-(3-Fluoro-4-methoxybenzyl)pyridin-2-yl)-N-(2-hydroxyethyl)indoline-4-carboxamide;
1-(4-(3-Chloro-4-fluorobenzyl)pyridin-2-yl)-N-(2-hydroxyethyl)indoline-4-carboxamide;
1-(4-(3-Fluoro-5-methoxybenzyl)pyridin-2-yl)indoline-4-carboxamide;
1-(4-((2-Methoxypyrimidin-5-yl)methyl)pyridin-2-yl)indoline-4-carboxamide;
1-(4-((2-Chloropyrimidin-5-yl)methyl)pyridin-2-yl)indoline-4-carboxamide;
1-(4-(4-Fluoro-3-methoxybenzyl)pyridin-2-yl)-N-(2-hydroxyethyl)indoline-4-carboxamide;
1-(4-(4-Fluoro-3-(trifluoromethyl)benzyl)pyridin-2-yl)-N-(2-hydroxyethyl)indoline-4-carboxamide;
1-(4-((2,3-Dihydrobenzofuran-5-yl)methyl)pyridin-2-yl)-N-(2-hydroxyethyl)indoline-4-carboxamide;
1-(4-(3-Acetyl-4-fluorobenzyl)pyridin-2-yl)-N-(2-hydroxyethyl)indoline-4-carboxamide;
1-(4-(3-Acetylbenzyl)pyridin-2-yl)indoline-4-carboxamide;
1-(4-((2,3-Dihydrobenzofuran-5-yl)methyl)pyridin-2-yl)-N-(1-(2-hydroxyethyl)piperidin-4-yl)indoline-4-carboxamide;
1-(4-(3-Acetyl-4-fluorobenzyl)pyridin-2-yl)-N-(1-(2-hydroxyethyl)piperidin-4-yl)indoline-4-carboxamide;
1-(4-(3-((Dimethylamino)methyl)benzyl)pyridin-2-yl)indoline-4-carboxamide;
1-(4-(4-Acetyl-3-fluorobenzyl)pyridin-2-yl)indoline-4-carboxamide;
1-(4-((5-Fluoro-6-methoxypyridin-3-yl)methyl)pyridin-2-yl)indoline-4-carboxamide;
1-(4-((5-Chloro-6-methoxypyridin-3-yl)methyl)pyridin-2-yl)indoline-4-carboxamide;
1-(4-((6-Methoxypyridin-3-yl)methyl)pyridin-2-yl)indoline-4-carboxamide;
1-(4-((6-Cyanopyridin-3-yl)methyl)pyridin-2-yl)indoline-4-carboxamide;
1-(4-(3-Fluoro-4-(hydroxymethyl)benzyl)pyridin-2-yl)indoline-4-carboxamide;
1-(4-(4-Cyano-3-fluorobenzyl)pyridin-2-yl)indoline-4-carboxamide;
N-(1-(2-Hydroxyethyl)piperidin-4-yl)-1-(4-(3-(trifluoromethyl)benzyl)pyridin-2-yl)indoline-4-carboxamide;
1-(4-(3-Chloro-5-fluorobenzyl)pyridin-2-yl)-N-(1-(2-hydroxyethyl)piperidin-4-yl)indoline-4-carboxamide;
1-(4-(3-Fluoro-4-methoxybenzyl)pyridin-2-yl)-N-(1-(2-hydroxyethyl)piperidin-4-yl)indoline-4-carboxamide;
N-(2-Hydroxyethyl)-1-(4-(3,4,5-trifluorobenzyl)pyridin-2-yl)indoline-4-carboxamide;
N-(1-(2-Hydroxyethyl)piperidin-4-yl)-1-(4-(3,4,5-trifluorobenzyl)pyridin-2-yl)indoline-4-carboxamide;
N-(2-Morpholinoethyl)-1-(4-(3-(trifluoromethyl)benzyl)pyridin-2-yl)indoline-4-carboxamide;
N-(2-(Pyrrolidin-1-yl)ethyl)-1-(4-(3-(trifluoromethyl)benzyl)pyridin-2-yl)indoline-4-carboxamide;
1-(4-((3,4-Dihydro-2H-benzo[b][1,4]dioxepin-7-yl)methyl)pyridin-2-yl)indoline-4-carboxamide;
1-(4-(3-Fluoro-4-hydroxybenzyl)pyridin-2-yl)indoline-4-carboxamide;
1-(4-(3-Methoxybenzyl)pyridin-2-yl)indoline-4-carboxamide;
1-(4-(4-Methoxy-3-methylbenzyl)pyridin-2-yl)indoline-4-carboxamide;
1-(4-(3-Chloro-4-methoxybenzyl)pyridin-2-yl)indoline-4-carboxamide;
1-(4-(Benzo[d][1,3]dioxol-5-ylmethyl)pyridin-2-yl)indoline-4-carboxamide;
3-((2-(4-Carbamoylindolin-1-yl)pyridin-4-yl)methyl)phenyl acetate;
1-(4-(Furan-2-ylmethyl)pyridin-2-yl)indoline-4-carboxamide;
1-(4-((3,5-Dimethylisoxazol-4-yl)methyl)pyridin-2-yl)indoline-4-carboxamide;
1-(4-(Furan-3-ylmethyl)pyridin-2-yl)indoline-4-carboxamide;
1-(4-(Benzofuran-5-ylmethyl)pyridin-2-yl)indoline-4-carboxamide;
1-(4-(3-Chloro-5-methoxybenzyl)pyridin-2-yl)indoline-4-carboxamide;
5-Fluoro-N-(2-hydroxyethyl)-1-(4-(3-(trifluoromethyl)benzyl)pyridin-2-yl)indoline-4-carboxamide;
5-Fluoro-N-(1-(2-hydroxyethyl)piperidin-4-yl)-1-(4-(3-(trifluoromethyl)benzyl)pyridin-2-yl)indoline-4-carboxamide;
1-(4-(4-Ethoxy-3-fluorobenzyl)pyridin-2-yl)indoline-4-carboxamide;
1-(4-(Quinolin-3-ylmethyl)pyridin-2-yl)indoline-4-carboxamide;
1-(4-(Quinolin-5-ylmethyl)pyridin-2-yl)indoline-4-carboxamide;

N-(1,3-Dihydroxypropan-2-yl)-1-(4-(3,4,5-trifluorobenzyl)pyridin-2-yl)indoline-4-carboxamide;
1-(4-(4-Fluoro-3-hydroxybenzyl)pyridin-2-yl)indoline-4-carboxamide;
1-(4-(4-Chloro-3-methoxybenzyl)pyridin-2-yl)indoline-4-carboxamide;
1-(4-(3,4-Difluorobenzyl)pyridin-2-yl)indoline-4-carboxamide;
N-(1-Methyl-1H-pyrazol-4-yl)-1-(4-(3,4,5-trifluorobenzyl)pyridin-2-yl)indoline-4-carboxamide;
N-(1-(2-Hydroxyethyl)-1H-pyrazol-4-yl)-1-(4-(3,4,5-trifluorobenzyl)pyridin-2-yl)indoline-4-carboxamide;
1-(4-(Benzofuran-2-ylmethyl)pyridin-2-yl)indoline-4-carboxamide;
1-(4-((1H-Indol-4-yl)methyl)pyridin-2-yl)indoline-4-carboxamide;
1-(4-(3,5-Difluoro-4-methoxybenzyl)pyridin-2-yl)indoline-4-carboxamide;
5-Fluoro-1-(4-(3-(trifluoromethyl)benzyl)pyridin-2-yl)indoline-4-carboxamide;
(R)—N-(2,3-Dihydroxypropyl)-1-(4-(3,4,5-trifluorobenzyl)pyridin-2-yl)indoline-4-carboxamide;
(S)—N-(2,3-dihydroxypropyl)-1-(4-(3,4,5-trifluorobenzyl)pyridin-2-yl)indoline-4-carboxamide;
N-(2-Hydroxy-2-(pyridin-2-yl)ethyl)-1-(4-(3,4,5-trifluorobenzyl)pyridin-2-yl)indoline-4-carboxamide;
N-(2-Hydroxy-2-(pyridin-3-yl)ethyl)-1-(4-(3,4,5-trifluorobenzyl)pyridin-2-yl)indoline-4-carboxamide;
N-(2-Hydroxy-2-(pyridin-4-yl)ethyl)-1-(4-(3,4,5-trifluorobenzyl)pyridin-2-yl)indoline-4-carboxamide;
N-(6-Oxopiperidin-3-yl)-1-(4-(3,4,5-trifluorobenzyl)pyridin-2-yl)indoline-4-carboxamide;
N-(2-Acetamidoethyl)-1-(4-(3,4,5-trifluorobenzyl)pyridin-2-yl)indoline-4-carboxamide;
N-(2-Hydroxy-3-methoxypropyl)-1-(4-(3,4,5-trifluorobenzyl)pyridin-2-yl)indoline-4-carboxamide;
N-(1,3-Dimethoxypropan-2-yl)-1-(4-(3,4,5-trifluorobenzyl)pyridin-2-yl)indoline-4-carboxamide;
N-(2-(2-Oxopyrrolidin-1-yl)ethyl)-1-(4-(3,4,5-trifluorobenzyl)pyridin-2-yl)indoline-4-carboxamide;
N-(2-(2-Oxoimidazolidin-1-yl)ethyl)-1-(4-(3,4,5-trifluorobenzyl)pyridin-2-yl)indoline-4-carboxamide;
N-((2R,3S)-1,3-Dihydroxybutan-2-yl)-1-(4-(3,4,5-trifluorobenzyl)pyridin-2-yl)indoline-4-carboxamide;
(R)—N-(2-Oxotetrahydrofuran-3-yl)-1-(4-(3,4,5-trifluorobenzyl)pyridin-2-yl)indoline-4-carboxamide;
(S)—N-(2-Oxotetrahydrofuran-3-yl)-1-(4-(3,4,5-trifluorobenzyl)pyridin-2-yl)indoline-4-carboxamide;
(R)—N-(2-Hydroxy-3-methoxypropyl)-1-(4-(3,4,5-trifluorobenzyl)pyridin-2-yl)indoline-4-carboxamide;
(S)—N-(2-Hydroxy-3-methoxypropyl)-1-(4-(3,4,5-trifluorobenzyl)pyridin-2-yl)indoline-4-carboxamide;
N-(2-(1H-Imidazol-1-yl)ethyl)-1-(4-(3,4,5-trifluorobenzyl)pyridin-2-yl)indoline-4-carboxamide;
5-Fluoro-N-(2-hydroxyethyl)-1-(4-(3,4,5-trifluorobenzyl)pyridin-2-yl)indoline-4-carboxamide;
N-(1,3-Dihydroxypropan-2-yl)-5-fluoro-1-(4-(3,4,5-trifluorobenzyl)pyridin-2-yl)indoline-4-carboxamide;
(R)—N-(2,3-Dihydroxypropyl)-5-fluoro-1-(4-(3,4,5-trifluorobenzyl)pyridin-2-yl)indoline-4-carboxamide;
5-Fluoro-N-(2-hydroxy-2-(pyridin-3-yl)ethyl)-1-(4-(3,4,5-trifluorobenzyl)pyridin-2-yl)indoline-4-carboxamide;
(R)-5-Fluoro-N-(2-hydroxy-3-methoxypropyl)-1-(4-(3,4,5-trifluorobenzyl)pyridin-2-yl)indoline-4-carboxamide;
N-(2-Acetamidoethyl)-5-fluoro-1-(4-(3,4,5-trifluorobenzyl)pyridin-2-yl)indoline-4-carboxamide;
(R)-5-Fluoro-N-(2-oxopyrrolidin-3-yl)-1-(4-(3,4,5-trifluorobenzyl)pyridin-2-yl)indoline-4-carboxamide;
(S)-5-Fluoro-N-(2-oxopyrrolidin-3-yl)-1-(4-(3,4,5-trifluorobenzyl)pyridin-2-yl)indoline-4-carboxamide;
(R)—N-(2-Hydroxy-2-(pyridin-3-yl)ethyl)-1-(4-(3,4,5-trifluorobenzyl)pyridin-2-yl)indoline-4-carboxamide;
(S)—N-(2-Hydroxy-2-(pyridin-3-yl)ethyl)-1-(4-(3,4,5-trifluorobenzyl)pyridin-2-yl)indoline-4-carboxamide;
(S)-5-Fluoro-N-(2-hydroxy-3-methoxypropyl)-1-(4-(3,4,5-trifluorobenzyl)pyridin-2-yl)indoline-4-carboxamide;
(R)—N-(2-Oxopyrrolidin-3-yl)-1-(4-(3,4,5-trifluorobenzyl)pyridin-2-yl)indoline-4-carboxamide;
(S)—N-(2-Oxopyrrolidin-3-yl)-1-(4-(3,4,5-trifluorobenzyl)pyridin-2-yl)indoline-4-carboxamide;
N-(2-(1H-Imidazol-5-yl)ethyl)-1-(4-(3,4,5-trifluorobenzyl)pyridin-2-yl)indoline-4-carboxamide;
N-((3-(Hydroxymethyl)oxetan-3-yl)methyl)-1-(4-(3,4,5-trifluorobenzyl)pyridin-2-yl)indoline-4-carboxamide;
5-Fluoro-N-((3-(hydroxymethyl)oxetan-3-yl)methyl)-1-(4-(3,4,5-trifluorobenzyl)pyridin-2-yl)indoline-4-carboxamide;
(S)-1-(4-(3-Fluoro-4-methoxybenzyl)pyridin-2-yl)-N-(2-hydroxy-3-methoxypropyl)indoline-4-carboxamide;
(S)-1-(4-(3-Fluoro-4-methoxybenzyl)pyridin-2-yl)-N-(2-oxopyrrolidin-3-yl)indoline-4-carboxamide;
N-(3-(Dimethylamino)-2-hydroxypropyl)-1-(4-(3,4,5-trifluorobenzyl)pyridin-2-yl)indoline-4-carboxamide;
N-(3-Hydroxypropyl)-1-(4-(3,4,5-trifluorobenzyl)pyridin-2-yl)indoline-4-carboxamide;
(S)—N-(3,3,3-Trifluoro-2-hydroxypropyl)-1-(4-(3,4,5-trifluorobenzyl)pyridin-2-yl)indoline-4-carboxamide;
N-(2-Fluoroethyl)-1-(4-(3,4,5-trifluorobenzyl)pyridin-2-yl)indoline-4-carboxamide;
5-Fluoro-1-(4-(3-fluoro-4-methoxybenzyl)pyridin-2-yl)-N-(2-hydroxyethyl)indoline-4-carboxamide;
5-Fluoro-1-(4-(3-fluoro-4-methoxybenzyl)pyridin-2-yl)-N-(2-fluoroethyl)indoline-4-carboxamide;
N-(2-Acetamidoethyl)-5-fluoro-1-(4-(3-fluoro-4-methoxybenzyl)pyridin-2-yl)indoline-4-carboxamide;
N-(3-Fluoro-2-hydroxypropyl)-1-(4-(3,4,5-trifluorobenzyl)pyridin-2-yl)indoline-4-carboxamide;
(R)—N-(2-Fluoro-3-hydroxypropyl)-1-(4-(3,4,5-trifluorobenzyl)pyridin-2-yl)indoline-4-carboxamide;
(R)-5-Fluoro-N-(2-fluoro-3-hydroxypropyl)-1-(4-(3-fluoro-4-methoxybenzyl)pyridin-2-yl)indoline-4-carboxamide;
(S)-1-(4-(3-Chloro-5-fluorobenzyl)pyridin-2-yl)-N-(2-hydroxy-3-methoxypropyl)indoline-4-carboxamide;
N-(2-Hydroxyethyl)-1-(3-methyl-4-(3-(trifluoromethyl)benzyl)pyridin-2-yl)indoline-4-carboxamide;
1-(4-(3-Chloro-5-fluorobenzyl)pyridin-2-yl)-N-(3-fluoro-2-hydroxypropyl)indoline-4-carboxamide;
(S)-1-(4-(3-Chloro-5-fluorobenzyl)pyridin-2-yl)-N-(2-oxopyrrolidin-3-yl)indoline-4-carboxamide;
N-(3-(Methylamino)-3-oxopropyl)-1-(4-(3,4,5-trifluorobenzyl)pyridin-2-yl)indoline-4-carboxamide;
(R)-1-(4-(3-Chloro-5-fluorobenzyl)pyridin-2-yl)-N-(2-fluoro-3-hydroxypropyl)indoline-4-carboxamide;
1-(4-(Benzofuran-5-ylmethyl)pyridin-2-yl)-N-(2-hydroxyethyl)indoline-4-carboxamide;
(S)-1-(4-(Benzofuran-5-ylmethyl)pyridin-2-yl)-N-(2-oxopyrrolidin-3-yl)indoline-4-carboxamide;
(R)-1-(4-(Benzofuran-5-ylmethyl)pyridin-2-yl)-N-(2-fluoro-3-hydroxypropyl)indoline-4-carboxamide;

1-(4-(Benzofuran-5-ylmethyl)pyridin-2-yl)-N-(3-fluoro-2-hydroxypropyl)indoline-4-carboxamide;
(S)-1-(4-(Benzofuran-5-ylmethyl)pyridin-2-yl)-N-(2-hydroxy-3-methoxypropyl)indoline-4-carboxamide;
(R)—N-(2-Hydroxypropyl)-1-(4-(3,4,5-trifluorobenzyl)pyridin-2-yl)indoline-4-carboxamide;
(S)—N-(2-Hydroxypropyl)-1-(4-(3,4,5-trifluorobenzyl)pyridin-2-yl)indoline-4-carboxamide;
(S)—N-(2-Fluoro-3-hydroxypropyl)-1-(4-(3,4,5-trifluorobenzyl)pyridin-2-yl)indoline-4-carboxamide;
(S)-1-(4-(Benzofuran-5-ylmethyl)pyridin-2-yl)-N-(2-fluoro-3-hydroxypropyl)indoline-4-carboxamide;
(S)—N-(3-Fluoro-2-hydroxypropyl)-1-(4-(3,4,5-trifluorobenzyl)pyridin-2-yl)indoline-4-carboxamide;
N-(2-Hydroxyethyl)-1-(2-(3-(trifluoromethyl)benzyl)pyridin-4-yl)indoline-4-carboxamide;
1-(2-(3-Acetylbenzyl)pyridin-4-yl)-N-(2-hydroxyethyl)indoline-4-carboxamide;
N-(2-Hydroxyethyl)-1-(2-(3,4,5-trifluorobenzyl)pyridin-4-yl)indoline-4-carboxamide;
1-(2-(3-Chloro-5-fluorobenzyl)pyridin-4-yl)-N-(2-hydroxyethyl)indoline-4-carboxamide;
1-(2-(4-Fluoro-3-(trifluoromethyl)benzyl)pyridin-4-yl)-N-(2-hydroxyethyl)indoline-4-carboxamide;
(S)—N-(2-Hydroxy-3-methoxypropyl)-1-(2-(3,4,5-trifluorobenzyl)pyridin-4-yl)indoline-4-carboxamide;
N-(2-Fluoroethyl)-1-(2-(3,4,5-trifluorobenzyl)pyridin-4-yl)indoline-4-carboxamide;
(R)—N-(2-Hydroxy-3-methoxypropyl)-1-(2-(3,4,5-trifluorobenzyl)pyridin-4-yl)indoline-4-carboxamide;
N-(3-Fluoro-2-hydroxypropyl)-1-(2-(3,4,5-trifluorobenzyl)pyridin-4-yl)indoline-4-carboxamide;
(R)—N-(2-Fluoro-3-hydroxypropyl)-1-(2-(3,4,5-trifluorobenzyl)pyridin-4-yl)indoline-4-carboxamide;
(S)—N-(2-Oxopyrrolidin-3-yl)-1-(2-(3,4,5-trifluorobenzyl)pyridin-4-yl)indoline-4-carboxamide;
(R)—N-(2-Hydroxypropyl)-1-(2-(3,4,5-trifluorobenzyl)pyridin-4-yl)indoline-4-carboxamide;
(S)—N-(2-Hydroxypropyl)-1-(2-(3,4,5-trifluorobenzyl)pyridin-4-yl)indoline-4-carboxamide;
(R)—N-(3-fluoro-2-hydroxypropyl)-1-(4-(3-fluoro-4-methoxybenzyl)pyridin-2-yl)indoline-4-carboxamide;
(S)—N-(3-fluoro-2-hydroxypropyl)-1-(4-(3-fluoro-4-methoxybenzyl)pyridin-2-yl)indoline-4-carboxamide;
(S)-1-(4-(benzofuran-5-ylmethyl)pyridin-2-yl)-N-(3-fluoro-2-hydroxypropyl)indoline-4-carboxamide;
(R)-1-(4-(benzofuran-5-ylmethyl)pyridin-2-yl)-N-(3-fluoro-2-hydroxypropyl)indoline-4-carboxamide;
(R)—N-(3-fluoro-2-hydroxypropyl)-1-(4-(3,4,5-trifluorobenzyl)pyridin-2-yl)indoline-4-carboxamide;
(R)—N-(2-fluoro-3-hydroxypropyl)-1-(4-(3-fluoro-4-methoxybenzyl)pyridin-2-yl)indoline-4-carboxamide;
1-(4-(3-fluoro-4-methoxybenzyl)pyridin-2-yl)-N-(2-fluoroethyl)indoline-4-carboxamide;
1-(4-(3-fluoro-4-methoxybenzyl)pyridin-2-yl)-N-((3-(hydroxymethyl)oxetan-3-yl)methyl)indoline-4-carboxamide;
1-(4-(3-fluoro-4-methoxybenzyl)pyridin-2-yl)-N-(2-(2-hydroxyethoxy)ethyl)indoline-4-carboxamide;
N-(2-(2-hydroxyethoxy)ethyl)-1-(4-(3,4,5-trifluorobenzyl)pyridin-2-yl)indoline-4-carboxamide;
1-(4-(benzofuran-5-ylmethyl)pyridin-2-yl)-N-(2-(2-hydroxyethoxy)ethyl)indoline-4-carboxamide; and
1-(4-(benzofuran-5-ylmethyl)pyridin-2-yl)-N-(2-fluoroethyl)indoline-4-carboxamide;
or a pharmaceutically acceptable salt thereof.

23. A pharmaceutical composition comprising a compound according to claim 1, or an N oxide or a pharmaceutically acceptable salt thereof, and a pharmaceutically acceptable carrier.

24. A method for preparing a pharmaceutical composition comprising the step of admixing a compound according to claim 1, or an N-oxide or a pharmaceutically acceptable salt thereof, and a pharmaceutically acceptable carrier.

25. A method for therapeutically treating a GPR52-mediated disorder in an individual, comprising administering to said individual in need thereof, a therapeutically effective amount of a compound according to claim 1, or a pharmaceutically acceptable salt thereof.

26. The method according to claim 25, wherein the disorder is selected from the group consisting of: an extrapyramidal or movement disorder; a psychotic disorder; a mood disorder, a depressive disorder, or a bipolar or related disorder; attention deficit disorder (ADHD), anxiety disorder, obsessive-compulsive disorder (OCD), or autism spectrum disorder; a prolactin-related disorder; a neurocognitive disorder; a trauma- or stressor-related disorder; a disruptive, impulse-control, or conduct disorder; a sleep-wake disorder; a substance-related disorder, an addictive disorder, or a behavioral disorder; hypofrontality; an abnormality in the tuberoinfundibular pathway, mesolimbic pathway, mesocortical pathway, or nigrostriatal pathway; increasing activity in the striatum; a cortical function disorder; and neurocognitive function disorder.

27. The method according to claim 26, wherein the GPR52-mediated disorder is selected from: Huntington's disease, schizophrenia, bipolar disorder, attention deficit hyperactivity disorder (ADHD), Tourette's syndrome, akathisia, associated movements, athetosis, ataxia, ballismus, hemiballismus, chorea, choreoathetosis, dyskinesia, tardive dyskinesia, neuroleptic-induced dyskinesia, myoclonus, mirror movement disorder, paroxysmal kinesigenic dyskinesia, restless legs syndrome, spasms, stereotypic movement disorder, sterotypy, Tic disorder, tremor, Wilson's disease, a motor disorder, a hyperkinetic movement disorder, an extrapyramidal syndrome, schizotypal personality disorder, delusional disorder, brief psychotic disorder, schizophreniform disorder, schizophrenia, schizoaffective disorder, and substance- or medication-induced psychotic disorder, delusions, hallucinations, disorganized thinking, grossly disorganized or abnormal motor behavior, negative symptoms, catatonia, major depressive disorder, bipolar I disorder, bipolar II disorder, cyclothymic disorder, substance- or medication-induced bipolar and related disorders, bipolar and related disorders due to another medical condition, separation anxiety disorder, selective mutism, specific phobia, social anxiety disorder, panic disorder, agoraphobia, generalized anxiety disorder, substance- or medication-induced anxiety disorder, anxiety disorder due to another medical condition, hyperprolactinemia, delirium, major neurocognitive disorder, minor neurocognitive disorder, amnesia, dementia, delirium, posttraumatic stress disorder (PTSD), a substance-relate disorder, wherein the substance is selected from: alcohol, caffeine, *cannabis*, a hallucinogen, an inhalant, an opioid, a sedative, a hypnotic, an anxiolytic, a stimulant, and tobacco; a cortical function disorder selected from: executive function, attention, and memory; and a neurocognitive function disorder selected from: complex attention, executive function, learning and memory, language, perceptual-motor, and social cognition.

28. The compound according to claim 1, wherein the compound is of the formula:

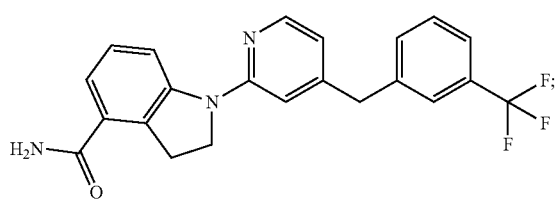 [SMILES: NC(=O)c1cccc2c1CCN2c1cc(Cc2cccc(C(F)(F)F)c2)ccn1]

or a pharmaceutically acceptable salt thereof.

29. The compound according to claim 1, wherein the compound is of the formula:

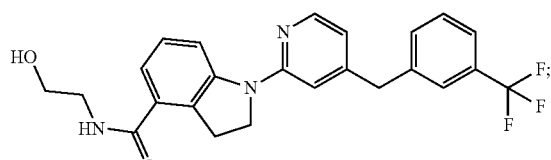

or a pharmaceutically acceptable salt thereof.

30. The compound according to claim 1, wherein the compound is of the formula:

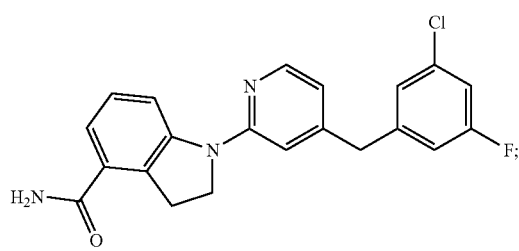 [SMILES: NC(=O)c1cccc2c1CCN2c1cc(Cc2cc(F)cc(Cl)c2)ccn1]

or a pharmaceutically acceptable salt thereof.

31. The compound according to claim 1, wherein the compound is of the formula:

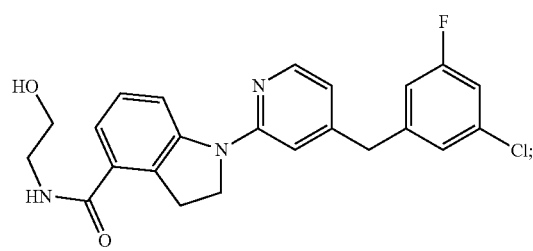 [SMILES: O=C(NCCO)c1cccc2c1CCN2c1cc(Cc2cc(F)cc(Cl)c2)ccn1]

or a pharmaceutically acceptable salt thereof.

32. The compound according to claim 1, wherein the compound is of the formula:

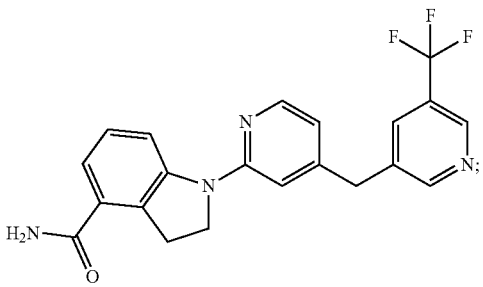 [SMILES: NC(=O)c1cccc2c1CCN2c1cc(Cc2cncc(C(F)(F)F)c2)ccn1]

or a pharmaceutically acceptable salt thereof.

33. The compound according to claim 1, wherein the compound is of the formula:

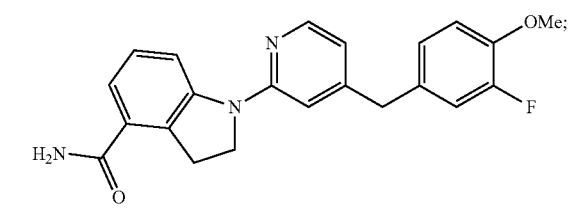 [SMILES: COc1ccc(Cc2ccnc(N3CCc4c(C(N)=O)cccc43)c2)cc1F]

or a pharmaceutically acceptable salt thereof.

34. The compound according to claim 1, wherein the compound is of the formula:

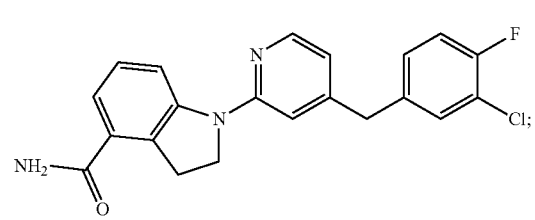 [SMILES: NC(=O)c1cccc2c1CCN2c1cc(Cc2ccc(F)c(Cl)c2)ccn1]

or a pharmaceutically acceptable salt thereof.

35. The compound according to claim 1, wherein the compound is of the formula:

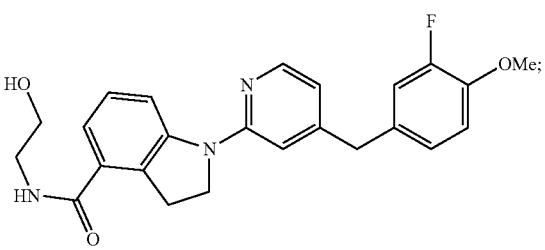 [SMILES: COc1ccc(Cc2ccnc(N3CCc4c(C(=O)NCCO)cccc43)c2)cc1F]

or a pharmaceutically acceptable salt thereof.

36. The compound according to claim 1, wherein the compound is of the formula:

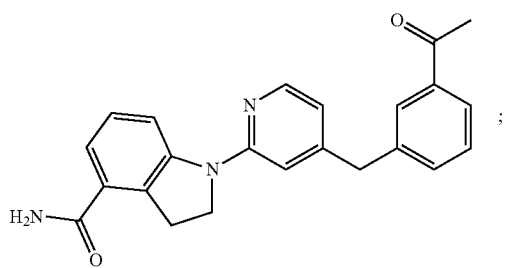 [SMILES: CC(=O)c1cccc(Cc2ccnc(N3CCc4c(C(N)=O)cccc43)c2)c1]

or a pharmaceutically acceptable salt thereof.

37. The compound according to claim 1, wherein the compound is of the formula:

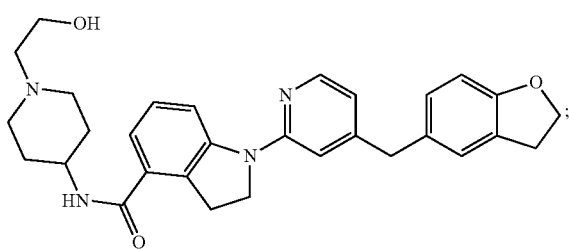 [SMILES: O=C(NC1CCN(CCO)CC1)c1cccc2c1CCN2c1cc(Cc2ccc3c(c2)CCO3)ccn1]

or a pharmaceutically acceptable salt thereof.

38. The compound according to claim 1, wherein the compound is of the formula:

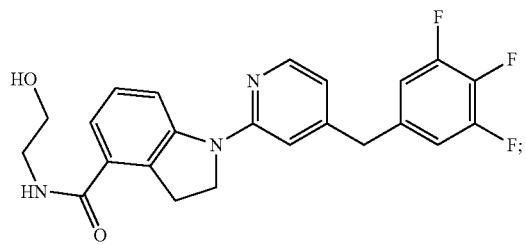 [SMILES: O=C(NCCO)c1cccc2c1CCN2c1cc(Cc2cc(F)c(F)c(F)c2)ccn1]

or a pharmaceutically acceptable salt thereof.

39. The compound according to claim 1, wherein the compound is of the formula:

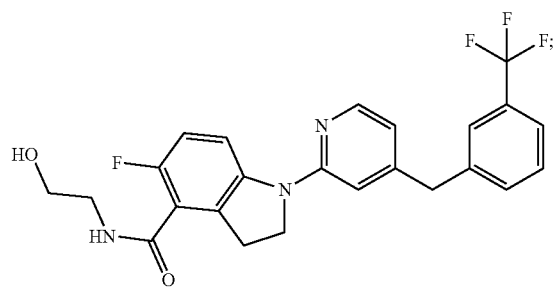 [SMILES: O=C(NCCO)c1c(F)ccc2c1CCN2c1cc(Cc2cccc(C(F)(F)F)c2)ccn1]

or a pharmaceutically acceptable salt thereof.

40. The compound according to claim 1, wherein the compound is of the formula:

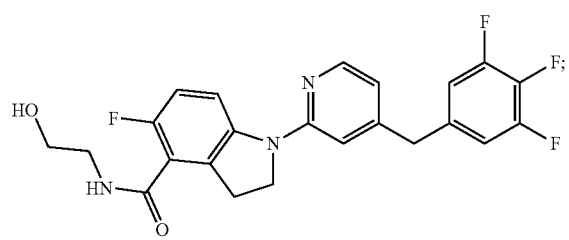 [SMILES: O=C(NCCO)c1c(F)ccc2c1CCN2c1cc(Cc2cc(F)c(F)c(F)c2)ccn1]

or a pharmaceutically acceptable salt thereof.

41. The compound according to claim 1, wherein the compound is of the formula:

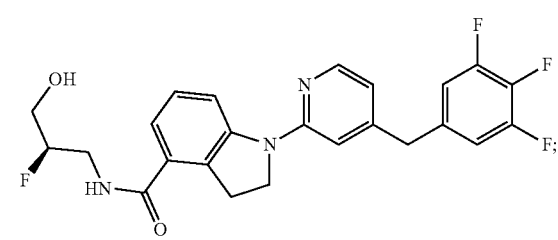 [SMILES: O=C(NC[C@@H](F)CO)c1cccc2c1CCN2c1cc(Cc2cc(F)c(F)c(F)c2)ccn1]

or a pharmaceutically acceptable salt thereof.

* * * * *